(12) United States Patent
Ley et al.

(10) Patent No.: US 7,078,383 B2
(45) Date of Patent: *Jul. 18, 2006

(54) ITI-D1 KUNITZ DOMAIN MUTANTS AS HNE INHIBITORS

(75) Inventors: Arthur C Ley, Newton, MA (US); Sonia K Guterman, Belmont, MA (US); William Markland, Milford, MA (US); Rachel B Kent, Boxborough, MA (US); Bruce L Roberts, Milford, MA (US); Robert C Ladner, Ijamsville, MD (US)

(73) Assignee: Dyax Corp., Cambridge, MA (US)

( * ) Notice: Subject to any disclaimer, the term of this patent is extended or adjusted under 35 U.S.C. 154(b) by 598 days.

This patent is subject to a terminal disclaimer.

(21) Appl. No.: 10/038,722

(22) Filed: Jan. 8, 2002

(65) Prior Publication Data

US 2003/0175919 A1 Sep. 18, 2003

Related U.S. Application Data

(63) Continuation of application No. 08/849,406, filed as application No. PCT/US95/16349 on Dec. 15, 1995, now abandoned, which is a continuation-in-part of application No. 08/358,160, filed on Dec. 16, 1994, now Pat. No. 5,663,143, which is a continuation-in-part of application No. 08/133,031, filed on Oct. 13, 1993, now abandoned.

(51) Int. Cl.
*A61K 38/55* (2006.01)
*C07N 14/81* (2006.01)
*C12N 15/15* (2006.01)

(52) U.S. Cl. .................. 514/12; 530/300; 530/350; 435/69.2; 435/69.7; 514/2

(58) Field of Classification Search .................. 514/2; 530/300, 350; 435/69.2, 69.7, 252.3
See application file for complete search history.

(56) References Cited

U.S. PATENT DOCUMENTS

| | | | | |
|---|---|---|---|---|
| 5,118,668 A | * | 6/1992 | Auerswald et al. | 514/12 |
| 5,223,409 A | * | 6/1993 | Ladner et al. | 435/69.7 |
| 5,403,484 A | * | 4/1995 | Ladner et al. | 435/235.1 |
| 5,407,915 A | * | 4/1995 | Fritz et al. | 514/12 |
| 5,541,288 A | * | 7/1996 | Nakano et al. | 530/324 |
| 5,571,698 A | * | 11/1996 | Ladner et al. | 435/69.7 |
| 5,663,143 A | * | 9/1997 | Ley et al. | 514/12 |
| 5,837,500 A | * | 11/1998 | Ladner et al. | 435/69.7 |

FOREIGN PATENT DOCUMENTS

| | | | |
|---|---|---|---|
| EP | 0 401 508 A3 | * | 12/1990 |
| EP | 0 486 001 A1 | * | 5/1992 |
| WO | WO 92/15605 A2 | * | 9/1992 |
| WO | WO 96/20278 A2 | * | 7/1996 |

OTHER PUBLICATIONS

Travis et al., 1991, "Potential problems in designing elastase inhibitors for therapy", Am. Rev. Respir. Dis., vol. 143, pp. 1412-1315.*

Roberts et al., 1992, "Protease inhibitor display M13 phage: selection of high-affinity neutrophil elastase inhibitors", vol. 121, pp. 9-15.*

Rogerts et al., 1992, "Directed evolution of a protein: Selection of potent neutrophil elastase inhibitor displayed on M13 fusion phage", Proc. Nat'l Acad. Sci., USA, vol. 89, pp. 2429-2433.*

Nii et al., 1994, "Design of variants of the second domain of urinary trypsin inhibitor (R-020) with increased Factor Xa inhibitory activity", Journal of Biochemistry, vol. 115, No. 6, pp. 1107-1112.*

Sinha et al. Conversion of the Alzheimer's beta-Amyloid Precursor Protein (APP) Kunitz Domain into a Potent Human Neutrophil Elastase Inhibitor. J Biol. Chem. (1991) 266(31):21011-21013.*

Roberts et al. Protease inhibitor display M13 phage: selection of high-affinity neutrophil elastase inhibitors. Gene (1992) 121:9-15.*

Travis et al. Potential problems in designing elastase inhibitors for therapy. Am. Rev. Respir. Dis. (1991) 143:1412-1415.*

Roberts et al. Directed evolution of a protein: Selection of potent neutrophil elastase inhibitor displayed on M13 fusion phage. Proc. Natl. Acad. Sci. (1992) 89:2429-2433.*

Albrecht, et al., *Elastase Inhibition by the Inter-αTrypsin Inhibitor and Derived Inhibitors of Man and Cattle*, Hoppe-Seyler's Z. Physiol. Chem., vol. 364, pp. 1703-1708, Dec. 1983.

Albrecht, et al., *Kunitz-Type Proteinase Inhibitors Derived by Limited Proteolysis of the Inter-α-Trypsin Inhibitor, IX$^{[1-8]}$*, Hoppe-Seyler's Z. Physiol. Chem., vol. 364, pp. 1697-1702, Dec. 1983.

Beckmann, et al, *Preparation of chemically 'mutated' aprotinin homologues by semisynthesis P1 substitutions change inhibitory specificity*, Eur. J. Biochem., vol. 176, pp. 675-682, 1988.

(Continued)

*Primary Examiner*—Kathleen Kerr
*Assistant Examiner*—William W. Moore
(74) *Attorney, Agent, or Firm*—Wolf, Greenfield & Sacks, P.C.

(57) ABSTRACT

Mutants of Kunitz domain 1 (ITI-D1) of human inter-α-trypsin inhibitor (ITI), are useful as inhibitors of human neutrophil elastase. Mutants characterized by one or more of the following substitutions (numbered to correspond to bovine pancreatic trypsin inhibitor, the archetypal Kunitz domain) are of particular interest: (a) Val15 or Ile15, (b) Ala16, (c) Phe18, (d) Pro19, (e) Arg1, (f) Pro2, and/or (g) Phe4.

10 Claims, No Drawings

OTHER PUBLICATIONS

Blow, et al., *A Model for the Association of Bovine Pancreatic Trypsin Inhibitor with Chymotrypsin and Trypsin*, J. Mol. Biol., vol. 69, pp. 137-144, 1972.

Brinkmann, et al., *Design of an Aprotinin Variant with Inhibitory Activity against Chymotrypsin and Cathepsin G by Recombinant DNA Technology*, Biol. Chem. Hoppe-Seyler, vol. 371, suppl., pp. 43-52, May 1990.

Cantor, et al., *Elastin and Elastases in Lung Disease*, Elastin and Elastases, vol. II, pp. 159-168, 1989.

Chen, et al., *Identification of a Factor in Fetal Bovine Serum That Stabilizes the Cumulus Extracellular Matrix*, The Journal of Biological Chemistry, vol. 267, No. 17, pp. 12380-12386, Jun. 15, 1992.

Diarra-Mehrpour, et al., *Structural analysis of the human inter-α-trypsin inhibitor light-chain gene*, Eur. J. Biochem., vol. 191, pp. 131-139, 1990.

Dufton, Mark J., *Proteinase inhibitors and dendrotoxins*, Eur. J. Biochem., vol. 153, pp. 647-654, 1985.

Enghild, et al., *Chondroitin 4-Sulfate Covalently Cross-links the Chains of the Human Blood Protein Pre-α-inhibitor*, The Journal of Biological Chemistry, vol. 266, No. 2, pp. 747-751, Jan. 15, 1991.

Enghild, et al., *Presence of the Protein-Glycosaminoglycan-Protein Covalent Cross-link in the Inter-α-inhibitor-related Proteinase Inhibitor Heavy Chain 2/bikunin*, The Journal of Biological Chemistry, vol. 268, No. 12, pp. 8711-8716, 1993.

Engleberg, et al., *DNA Sequence of mip, a Legionella pneumophila Gene Associated with Macrophage Infectivity*, Infection and Immunity, vol. 57, No. 4, pp. 1263-1270, Apr. 1989.

Escribano, et al., *Location and characterization of the three carbohydrate prosthetic groups of human protein HC*, FEBS Letters, vol. 266, No. 1,2, pp. 167-170, Jun. 1990.

Escribano, et al., *The Protein HC Chromophore Is Liked to the Cysteine Residue at Position 34 of the Polypeptide Chain by a Reduction-resistant Bond and Causes the Charge Heterogeneity of Protein HC*, The Journal of Biological Chemistry, vol. 266, No. 24, pp. 15758-15763, Aug. 25, 1991.

Gebhard, et al., *Inter-α-trypsin inhibitor and its close relatives*, Barrett and Salvesen (Eds.) Proteinase Inhibitors, chapter 11, pp. 388-401, 1986.

Girard, et al., *Functional significance of the Kunitz-type inhibitory domains of lipoprotein-associated coagulation inhibitor*, Letters to Nature, vol. 338, pp. 518-520, Apr. 6, 1989.

Goldstein, et al., *Lysosomal Enzymes from Polymorphonuclear Leukocytes and Proteinase Inhibitors in Patients with Cystic Fibrosis*, Am. Rev. Respir. Dis., vol. 134, pp. 49-56, 1986.

Heidtmann, et al., *Human $\alpha_1$-proteinase inhibitor*, Barrett and Salvesen (Eds.) Proteinase Inhibitors, chapter 14, pp. 441-456, 1986.

Hochstrasser, et al., *Kunitz-Type Proteinase Inhibitors Derived by Limited Proteolysis of the Inter-α-Trypsin Inhibitor, V$^{[1-4]}$*, Hoppe-Seyler's Z. Physiol. Chem., vol. 362, pp. 1357-1362, Oct. 1981.

Hochstrasser, et al., *Kunitz-Type Proteinase Inhibitors Derived by Limited Proteolysis of the Inter-α-Trypsin Inhibitor, VII$^{[1-6]}$*, Hoppe-Seyler's Z. Physiol. Chem., vol. 364, pp. 1679-1687, Dec. 1983.

Hochstrasser, et al., *Kunitz-Type Proteinase Inhibitors Derived by Limited Proteolysis of the Inter-α-Trypsin Inhibitor, VIII$^{[1-7]}$*, Hoppe-Seyler's Z. Physiol. Chem., vol. 364, pp. 1689-1696, Dec. 1983.

Hochstrasser, et al., *Kunitz-Type Proteinase Inhibitors Derived by Limited Proteolysis of the Inter-α-Trypsin Inhibitor, X$^{[1]}$*, Biol. Chem., vol. 366, pp. 473-478, May 1985.

Hynes, et al., *X-ray Crystal Structure of the Protease Inhibitor Domain of Alzheimer's Amyloid β-Protein Precursor*, Biochemistry, vol. 29, pp. 10018-10022, 1990.

Kaumeyer, et al., *The mRNA for a proteinase inhibitor related to the HI-30 domain of inter-α-trypsin inhibitor also encodes α-1-microglobulin (protein HC)*, Nucleic Acids Research, vol. 14, No. 20, pp. 7839-7850, 1986.

Laskowski, et al., *Protein Inhibitors of Proteinases*, Ann. Rev. Biochem., vol. 49, pp. 593-626, 1980.

Lindqvist, et al., *Bovine $\alpha_1$-microglobulin/bikuni. Isolation and characterization of liver cDNA and urinary $\alpha_1$-microglobulin*, Biochimica et Biophysica Acta, vol. 1306, pp. 98-106, 1996.

Lopez, et al., *Human protein HC displays variability in its carboxyl-terminal amino acid*, FEBS Letters, vol. 144, No. 2, pp. 349-353-, Aug. 1982.

McElvaney, et al., *Aerosol α1-antitrypsin treatment for cystic fibrosis*, The Lancet, vol. 337, pp. 392-394, Feb. 16, 1991.

Morelle, et al., *Chondroitin sulphate covalently cross-links the three polypeptide chains of inter-α-trypsin inhibitor*, Eur. J. Biochem., vol. 221, pp. 881-888, 1994.

Morii, et al., *The Reactive Site of Human Inter-α-Trypsin Inhibitor is in the Amino-Terminal Half of the Protein*, Biol. Chem. Hoppe-Seyler, vol. 366, pp. 19-21, Jan. 1985.

Nakao, et al., *sc-39026, A Specific Human Neutrophil Elastase Inhibitor*, Biochemical and Biophysical Research Communications, vol. 147, No. 2, pp. 666-674, Sep. 15, 1987.

ØDum, Lars, *Inter-α-Trypsin Inhibitor: A Plasma Proteinase Inhibitor with a Unique Chemical Structure*, Int. J. Biochem, vol. 22, No. 9, pp. 925-930, 1990.

Otin, et al., *The Complete Amino Acid Sequence of Human Complex-Forming Glycoprotein Heterogeneous in Charge (Protein HC) from One Individual*, Archives of Biochemistry and Biophysics, vol. 228, No. 2, pp. 544-554, Feb. 1, 1984.

Reisinger, et al., *Human Inter-α-Trypsin Inhibitor: Localization of the Kunitz-Type Domains in the N-terminal Part of the Molecule and their Release by a Trypsin-Like Proteinase*, Biol. Chemistry Hoppe-Seyler, vol. 366, pp. 479-483, May 1985.

Salier, Jean-Philippe, *Inter-α-trypsin inhibitor: emergence of a family within the Kunitz-type protease inhibitor superfamily*, TIBS, vol. 15, pp. 435-439, Nov. 1990.

Selloum, et al., *The Effect of the Glycosaminoglycan Chain Removal on some Properties of the Human Urinary Trypsin Inhibitor*, Biol. Chem. Hoppe-Seyler, vol. 368, pp. 47-55, Jan. 1987.

Sinha, et al., *Conversion of the Alzheimer's β-Amyloid Precursor Protein (APP) Kunitz Domain into a Potent Human Neutrophil Elastase Inhibitor*, The Journal of Biological Chemistry, vol. 266, No. 31, pp. 21011-21013, Nov. 5, 1991.

Snider, et al., *Putative Role of Neutrophil Elastase in the Pathogenesis of Emphysema*, Annals New York Academy of Sciences, vol. 624, pp. 45-59, 1991.

Swaim, et al., *Modification of the tandem reactive centres of human inter-α-trypsin inhibitor with butanedione and cis-*

*dichlorodiammineplatinum (II)*, Biochem. J., vol. 254, pp. 171-178, 1988.

Takagi, et al., *Complete Amino Acid Sequence of Human $\alpha_1$-Microglobulin*, Biochemical and Biophysical Research Communications, vol. 98, No. 4, pp. 997-1001, Feb. 27, 1981.

Traboni, et al., *Sequence of a full length cDNA coding for human protein HC ($\alpha$ 1microglobulin)*, Nucleic Acids Research, vol. 14, No. 15, p. 6340, Aug. 1986.

Tschesche, et al., *Semisynthetic engineering of proteinase inhibitor homologues*, Biochimica et Biophysica Acta, vol. 913, pp. 97-101, 1987.

Vetr, et al., *Structure of the Human $\alpha$1-Microglobulin-Bikunin Gene*, Biol. Chem. Hoppe-Seyler, vol. 371, pp. 1185-1196, Dec. 1990.

Weiss, Stephen J., *Tissue Destruction by Neutrophils*, The New England Journal of Medicine, vol. 320, No. 6, pp. 365-376, Feb. 9, 1989.

Wun, et al., *Cloning and Characterization of a cDNA Coding for the Lipoprotein-associated Coagulation Inhibitor Shows That It Consists of Three Tandem Kunitz-type Inhibitory Domains*, The Journal of Biological Chemistry, vol. 263, No. 13, pp. 6001-6004, May 5, 1988.

Xu, et al., *The Crystal Structure of Bikunin from the Inter-$\alpha$-Inhibitor Complex: A Serine Protease Inhibitor with Two Kunitz Domains*, J. Mol. Biol., vol. 276, pp. 955-966, 1998.

Gebhard, et al., *Structure of Inter-$\alpha$-Inhibitor (Inter-$\alpha$-Trypsin Inhibitor) and Pre-$\alpha$-Inhibitor: Current State and Proposition of a New Terminology*, Biol. Chem. Hoppe-Seyler, vol. 371, Suppl., pp. 13-22, May 1990.

\* cited by examiner

SEQUENCE LISTING

<160> NUMBER OF SEQ ID NOS: 143

<210> SEQ ID NO 1
<211> LENGTH: 276
<212> TYPE: DNA
<213> ORGANISM: Artificial Sequence
<220> FEATURE:
<223> OTHER INFORMATION: IIIsp::bpti::matureIII (initial fragment)

<400> SEQUENCE: 1

```
gtgaaaaaat tattattcgc aattcctta gttgttcctt tctattctgg cgcccgtccg      60
gatttctgtc tcgagccacc atacactggg ccctgcaaag cgcgcatcat ccgctatttc    120
tacaatgcta aagcaggcct gtgccagacc tttgtatacg gtggttgccg tgctaagcgt    180
aacaacttta atcggccga agattgcatg cgtacctgcg gtggcgccgc tgaaactgtt    240
gaaagttgtt tagcaaaacc ccatacagaa aattca                              276
```

<210> SEQ ID NO 2
<211> LENGTH: 92
<212> TYPE: PRT
<213> ORGANISM: Artificial Sequence
<220> FEATURE:
<223> OTHER INFORMATION: IIIsp::bpti::matureIII (initial fragment)

<400> SEQUENCE: 2

```
Met Lys Lys Leu Leu Phe Ala Ile Pro Leu Val Val Pro Phe Tyr Ser
1               5                   10                  15

Gly Ala Arg Pro Asp Phe Cys Leu Glu Pro Pro Tyr Thr Gly Pro Cys
```

```
                20                  25                  30
Lys Ala Arg Ile Ile Arg Tyr Phe Tyr Asn Ala Lys Gly Leu Cys
        35                  40                  45

Gln Thr Phe Val Tyr Gly Gly Cys Arg Ala Lys Arg Asn Asn Phe Lys
    50                  55                  60

Ser Ala Glu Asp Cys Met Arg Thr Cys Gly Gly Ala Ala Glu Thr Val
65                  70                  75                  80

Glu Ser Cys Leu Ala Lys Pro His Thr Glu Asn Ser
                85                  90
```

```
<210> SEQ ID NO 3
<211> LENGTH: 285
<212> TYPE: DNA
<213> ORGANISM: Artificial Sequence
<220> FEATURE:
<223> OTHER INFORMATION: IIIsp::itiD1::mature III fusion gene

<400> SEQUENCE: 3
gtgaaaaaat tattattcgc aattccttta gttgttcctt tctattctgg cgccaaagaa      60
gactcttgcc agctgggcta ctcggccggt ccctgcatgg gaatgaccag caggtatttc     120
tataatggta catccatggc ctgtgagact ttccagtacg gcggctgcat gggcaacggt     180
aacaacttcg tcacagaaaa ggagtgtctg cagacctgcc gaactgtggg cgccgctgaa     240
actgttgaaa gttgtttagc aaaaccccat acagaaaatt cattt                     285
```

```
<210> SEQ ID NO 4
<211> LENGTH: 95
<212> TYPE: PRT
<213> ORGANISM: Artificial Sequence
<220> FEATURE:
<223> OTHER INFORMATION: IIIsp::itiD1::mature III fusion gene

<400> SEQUENCE: 4

Met Lys Lys Leu Leu Phe Ala Ile Pro Leu Val Val Pro Phe Tyr Ser
1               5                   10                  15

Gly Ala Lys Glu Asp Ser Cys Gln Leu Gly Tyr Ser Ala Gly Pro Cys
                20                  25                  30

Met Gly Met Thr Ser Arg Tyr Phe Tyr Asn Gly Thr Ser Met Ala Cys
        35                  40                  45

Glu Thr Phe Gln Tyr Gly Gly Cys Met Gly Asn Gly Asn Asn Phe Val
    50                  55                  60

Thr Glu Lys Glu Cys Leu Gln Thr Cys Arg Thr Val Gly Ala Ala Glu
65                  70                  75                  80

Thr Val Glu Ser Cys Leu Ala Lys Pro His Thr Glu Asn Ser Phe
                85                  90                  95
```

```
<210> SEQ ID NO 5
<211> LENGTH: 58
<212> TYPE: PRT
<213> ORGANISM: Artificial Sequence
<220> FEATURE:
<223> OTHER INFORMATION: Consensus Kunitz domain

<400> SEQUENCE: 5

Arg Pro Asp Phe Cys Leu Leu Pro Ala Glu Thr Gly Pro Cys Arg Ala
1               5                   10                  15

Met Ile Pro Arg Phe Tyr Tyr Asn Ala Lys Ser Gly Lys Cys Glu Pro
                20                  25                  30

Phe Ile Tyr Gly Gly Cys Gly Gly Asn Ala Asn Asn Phe Lys Thr Glu
```

```
                35                  40                  45
Glu Glu Cys Arg Arg Thr Cys Gly Gly Ala
 50                  55

<210> SEQ ID NO 6
<211> LENGTH: 58
<212> TYPE: PRT
<213> ORGANISM: Bos Taurus

<400> SEQUENCE: 6

Arg Pro Asp Phe Cys Leu Glu Pro Pro Tyr Thr Gly Pro Cys Lys Ala
 1               5                  10                  15

Arg Ile Ile Arg Tyr Phe Tyr Asn Ala Lys Ala Gly Leu Cys Gln Thr
                20                  25                  30

Phe Val Tyr Gly Gly Cys Arg Ala Lys Arg Asn Asn Phe Lys Ser Ala
                35                  40                  45

Glu Asp Cys Met Arg Thr Cys Gly Gly Ala
 50                  55

<210> SEQ ID NO 7
<211> LENGTH: 58
<212> TYPE: PRT
<213> ORGANISM: Artificial Sequence
<220> FEATURE:
<223> OTHER INFORMATION: Epi-HNE-1

<400> SEQUENCE: 7

Arg Pro Asp Phe Cys Leu Glu Pro Pro Tyr Thr Gly Pro Cys Ile Ala
 1               5                  10                  15

Phe Phe Pro Arg Tyr Phe Tyr Asn Ala Lys Ala Gly Leu Cys Gln Thr
                20                  25                  30

Phe Val Tyr Gly Gly Cys Met Gly Asn Gly Asn Asn Phe Lys Ser Ala
                35                  40                  45

Glu Asp Cys Met Arg Thr Cys Gly Gly Ala
 50                  55

<210> SEQ ID NO 8
<211> LENGTH: 62
<212> TYPE: PRT
<213> ORGANISM: Artificial Sequence
<220> FEATURE:
<223> OTHER INFORMATION: Epi-HNE-2

<400> SEQUENCE: 8

Glu Ala Glu Ala Arg Pro Asp Phe Cys Leu Glu Pro Pro Tyr Thr Gly
 1               5                  10                  15

Pro Cys Ile Ala Phe Phe Pro Arg Tyr Phe Tyr Asn Ala Lys Ala Gly
                20                  25                  30

Leu Cys Gln Thr Phe Val Tyr Gly Gly Cys Met Gly Asn Gly Asn Asn
                35                  40                  45

Phe Lys Ser Ala Glu Asp Cys Met Arg Thr Cys Gly Gly Ala
 50                  55                  60

<210> SEQ ID NO 9
<211> LENGTH: 58
<212> TYPE: PRT
<213> ORGANISM: Artificial Sequence
<220> FEATURE:
<223> OTHER INFORMATION: EpiNE7

<400> SEQUENCE: 9
```

```
Arg Pro Asp Phe Cys Leu Glu Pro Pro Tyr Thr Gly Pro Cys Val Ala
1               5                   10                  15

Met Phe Pro Arg Tyr Phe Tyr Asn Ala Lys Ala Gly Leu Cys Gln Thr
            20                  25                  30

Phe Val Tyr Gly Gly Cys Met Gly Asn Gly Asn Asn Phe Lys Ser Ala
        35                  40                  45

Glu Asp Cys Met Arg Thr Cys Gly Gly Ala
    50                  55
```

<210> SEQ ID NO 10
<211> LENGTH: 58
<212> TYPE: PRT
<213> ORGANISM: Artificial Sequence
<220> FEATURE:
<223> OTHER INFORMATION: EpiNE3

<400> SEQUENCE: 10

```
Arg Pro Asp Phe Cys Leu Glu Pro Pro Tyr Thr Gly Pro Cys Val Gly
1               5                   10                  15

Phe Phe Ser Arg Tyr Phe Tyr Asn Ala Lys Ala Gly Leu Cys Gln Thr
            20                  25                  30

Phe Val Tyr Gly Gly Cys Met Gly Asn Gly Asn Asn Phe Lys Ser Ala
        35                  40                  45

Glu Asp Cys Met Arg Thr Cys Gly Gly Ala
    50                  55
```

<210> SEQ ID NO 11
<211> LENGTH: 58
<212> TYPE: PRT
<213> ORGANISM: Artificial Sequence
<220> FEATURE:
<223> OTHER INFORMATION: EpiNE6

<400> SEQUENCE: 11

```
Arg Pro Asp Phe Cys Leu Glu Pro Pro Tyr Thr Gly Pro Cys Val Gly
1               5                   10                  15

Phe Phe Gln Arg Tyr Phe Tyr Asn Ala Lys Ala Gly Leu Cys Gln Thr
            20                  25                  30

Phe Val Tyr Gly Gly Cys Met Gly Asn Gly Asn Asn Phe Lys Ser Ala
        35                  40                  45

Glu Asp Cys Met Arg Thr Cys Gly Gly Ala
    50                  55
```

<210> SEQ ID NO 12
<211> LENGTH: 58
<212> TYPE: PRT
<213> ORGANISM: Artificial Sequence
<220> FEATURE:
<223> OTHER INFORMATION: EpiNE4

<400> SEQUENCE: 12

```
Arg Pro Asp Phe Cys Leu Glu Pro Pro Tyr Thr Gly Pro Cys Val Ala
1               5                   10                  15

Ile Phe Pro Arg Tyr Phe Tyr Asn Ala Lys Ala Gly Leu Cys Gln Thr
            20                  25                  30

Phe Val Tyr Gly Gly Cys Met Gly Asn Gly Asn Asn Phe Lys Ser Ala
        35                  40                  45

Glu Asp Cys Met Arg Thr Cys Gly Gly Ala
    50                  55
```

```
<210> SEQ ID NO 13
<211> LENGTH: 58
<212> TYPE: PRT
<213> ORGANISM: Artificial Sequence
<220> FEATURE:
<223> OTHER INFORMATION: EpiNE8

<400> SEQUENCE: 13

Arg Pro Asp Phe Cys Leu Glu Pro Pro Tyr Thr Gly Pro Cys Val Ala
1               5                   10                  15

Phe Phe Lys Arg Ser Phe Tyr Asn Ala Lys Ala Gly Leu Cys Gln Thr
            20                  25                  30

Phe Val Tyr Gly Gly Cys Met Gly Asn Gly Asn Asn Phe Lys Ser Ala
        35                  40                  45

Glu Asp Cys Met Arg Thr Cys Gly Gly Ala
    50                  55

<210> SEQ ID NO 14
<211> LENGTH: 58
<212> TYPE: PRT
<213> ORGANISM: Artificial Sequence
<220> FEATURE:
<223> OTHER INFORMATION: EpiNE5

<400> SEQUENCE: 14

Arg Pro Asp Phe Cys Leu Glu Pro Pro Tyr Thr Gly Pro Cys Ile Ala
1               5                   10                  15

Phe Phe Gln Arg Tyr Phe Tyr Asn Ala Lys Ala Gly Leu Cys Gln Thr
            20                  25                  30

Phe Val Tyr Gly Gly Cys Met Gly Asn Gly Asn Asn Phe Lys Ser Ala
        35                  40                  45

Glu Asp Cys Met Arg Thr Cys Gly Gly Ala
    50                  55

<210> SEQ ID NO 15
<211> LENGTH: 58
<212> TYPE: PRT
<213> ORGANISM: Artificial Sequence
<220> FEATURE:
<223> OTHER INFORMATION: EpiNE2

<400> SEQUENCE: 15

Arg Pro Asp Phe Cys Leu Glu Pro Pro Tyr Thr Gly Pro Cys Ile Ala
1               5                   10                  15

Leu Phe Lys Arg Tyr Phe Tyr Asn Ala Lys Ala Gly Leu Cys Gln Thr
            20                  25                  30

Phe Val Tyr Gly Gly Cys Met Gly Asn Gly Asn Asn Phe Lys Ser Ala
        35                  40                  45

Glu Asp Cys Met Arg Thr Cys Gly Gly Ala
    50                  55

<210> SEQ ID NO 16
<211> LENGTH: 58
<212> TYPE: PRT
<213> ORGANISM: Homo sapiens

<400> SEQUENCE: 16

Lys Glu Asp Ser Cys Gln Leu Gly Tyr Ser Ala Gly Pro Cys Met Gly
1               5                   10                  15

Met Thr Ser Arg Tyr Phe Tyr Asn Gly Thr Ser Met Ala Cys Glu Thr
            20                  25                  30
```

```
Phe Gln Tyr Gly Gly Cys Met Gly Asn Gly Asn Asn Phe Val Thr Glu
        35                  40                  45

Lys Asp Cys Leu Gln Thr Cys Arg Thr Val
    50                  55

<210> SEQ ID NO 17
<211> LENGTH: 58
<212> TYPE: PRT
<213> ORGANISM: Artificial Sequence
<220> FEATURE:
<223> OTHER INFORMATION: BITI-E7-141

<400> SEQUENCE: 17

Arg Pro Asp Phe Cys Gln Leu Gly Tyr Ser Ala Gly Pro Cys Val Ala
1               5                   10                  15

Met Phe Pro Arg Tyr Phe Tyr Asn Gly Thr Ser Met Ala Cys Gln Thr
            20                  25                  30

Phe Val Tyr Gly Gly Cys Met Gly Asn Gly Asn Asn Phe Val Thr Glu
        35                  40                  45

Lys Asp Cys Leu Gln Thr Cys Arg Gly Ala
    50                  55

<210> SEQ ID NO 18
<211> LENGTH: 58
<212> TYPE: PRT
<213> ORGANISM: Artificial Sequence
<220> FEATURE:
<223> OTHER INFORMATION: MUTT26A

<400> SEQUENCE: 18

Arg Pro Asp Phe Cys Gln Leu Gly Tyr Ser Ala Gly Pro Cys Val Ala
1               5                   10                  15

Met Phe Pro Arg Tyr Phe Tyr Asn Gly Ala Ser Met Ala Cys Gln Thr
            20                  25                  30

Phe Val Tyr Gly Gly Cys Met Gly Asn Gly Asn Asn Phe Val Thr Glu
        35                  40                  45

Lys Asp Cys Leu Gln Thr Cys Arg Gly Ala
    50                  55

<210> SEQ ID NO 19
<211> LENGTH: 58
<212> TYPE: PRT
<213> ORGANISM: Artificial Sequence
<220> FEATURE:
<223> OTHER INFORMATION: MUTQE

<400> SEQUENCE: 19

Arg Pro Asp Phe Cys Gln Leu Gly Tyr Ser Ala Gly Pro Cys Val Ala
1               5                   10                  15

Met Phe Pro Arg Tyr Phe Tyr Asn Gly Thr Ser Met Ala Cys Glu Thr
            20                  25                  30

Phe Val Tyr Gly Gly Cys Met Gly Asn Gly Asn Asn Phe Val Thr Glu
        35                  40                  45

Lys Asp Cys Leu Gln Thr Cys Arg Gly Ala
    50                  55

<210> SEQ ID NO 20
<211> LENGTH: 58
<212> TYPE: PRT
<213> ORGANISM: Artificial Sequence
<220> FEATURE:
<223> OTHER INFORMATION: MUT1619
```

<400> SEQUENCE: 20

Arg Pro Asp Phe Cys Gln Leu Gly Tyr Ser Ala Gly Pro Cys Val Gly
1               5                   10                  15

Met Phe Ser Arg Tyr Phe Tyr Asn Gly Thr Ser Met Ala Cys Gln Thr
            20                  25                  30

Phe Val Tyr Gly Gly Cys Met Gly Asn Gly Asn Asn Phe Val Thr Glu
        35                  40                  45

Lys Asp Cys Leu Gln Thr Cys Arg Gly Ala
    50                  55

<210> SEQ ID NO 21
<211> LENGTH: 58
<212> TYPE: PRT
<213> ORGANISM: Artificial Sequence
<220> FEATURE:
<223> OTHER INFORMATION: ITI-D1E7

<400> SEQUENCE: 21

Lys Glu Asp Ser Cys Gln Leu Gly Tyr Ser Ala Gly Pro Cys Val Ala
1               5                   10                  15

Met Phe Pro Arg Tyr Phe Tyr Asn Gly Thr Ser Met Ala Cys Glu Thr
            20                  25                  30

Phe Gln Tyr Gly Gly Cys Met Gly Asn Gly Asn Asn Phe Val Thr Glu
        35                  40                  45

Lys Asp Cys Leu Gln Thr Cys Arg Gly Ala
    50                  55

<210> SEQ ID NO 22
<211> LENGTH: 58
<212> TYPE: PRT
<213> ORGANISM: Artificial Sequence
<220> FEATURE:
<223> OTHER INFORMATION: AMINO1

<400> SEQUENCE: 22

Lys Glu Asp Phe Cys Gln Leu Gly Tyr Ser Ala Gly Pro Cys Val Ala
1               5                   10                  15

Met Phe Pro Arg Tyr Phe Tyr Asn Gly Thr Ser Met Ala Cys Glu Thr
            20                  25                  30

Phe Gln Tyr Gly Gly Cys Met Gly Asn Gly Asn Asn Phe Val Thr Glu
        35                  40                  45

Lys Asp Cys Leu Gln Thr Cys Arg Gly Ala
    50                  55

<210> SEQ ID NO 23
<211> LENGTH: 58
<212> TYPE: PRT
<213> ORGANISM: Artificial Sequence
<220> FEATURE:
<223> OTHER INFORMATION: AMINO2

<400> SEQUENCE: 23

Lys Pro Asp Ser Cys Gln Leu Gly Tyr Ser Ala Gly Pro Cys Val Ala
1               5                   10                  15

Met Phe Pro Arg Tyr Phe Tyr Asn Gly Thr Ser Met Ala Cys Glu Thr
            20                  25                  30

Phe Gln Tyr Gly Gly Cys Met Gly Asn Gly Asn Asn Phe Val Thr Glu
        35                  40                  45

Lys Asp Cys Leu Gln Thr Cys Arg Gly Ala

<210> SEQ ID NO 24
<211> LENGTH: 58
<212> TYPE: PRT
<213> ORGANISM: Artificial Sequence
<220> FEATURE:
<223> OTHER INFORMATION: MUTP1

<400> SEQUENCE: 24

Arg Pro Asp Phe Cys Gln Leu Gly Tyr Ser Ala Gly Pro Cys Ile Gly
1               5                   10                  15

Met Phe Ser Arg Tyr Phe Tyr Asn Gly Thr Ser Met Ala Cys Glu Thr
            20                  25                  30

Phe Gln Tyr Gly Gly Cys Met Gly Asn Gly Asn Asn Phe Val Thr Glu
        35                  40                  45

Lys Asp Cys Leu Gln Thr Cys Arg Gly Ala
    50                  55

<210> SEQ ID NO 25
<211> LENGTH: 58
<212> TYPE: PRT
<213> ORGANISM: Homo sapiens

<400> SEQUENCE: 25

Thr Val Ala Ala Cys Asn Leu Pro Ile Val Arg Gly Pro Cys Arg Ala
1               5                   10                  15

Phe Ile Gln Leu Trp Ala Phe Asp Ala Val Lys Gly Lys Cys Val Leu
            20                  25                  30

Phe Pro Tyr Gly Gly Cys Gln Gly Asn Gly Asn Lys Phe Tyr Ser Glu
        35                  40                  45

Lys Glu Cys Arg Glu Tyr Cys Gly Val Pro
    50                  55

<210> SEQ ID NO 26
<211> LENGTH: 56
<212> TYPE: PRT
<213> ORGANISM: Artificial Sequence
<220> FEATURE:
<223> OTHER INFORMATION: Epi-HNE-3

<400> SEQUENCE: 26

Ala Ala Cys Asn Leu Pro Ile Val Arg Gly Pro Cys Ile Ala Phe Phe
1               5                   10                  15

Pro Arg Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro
    50                  55

<210> SEQ ID NO 27
<211> LENGTH: 56
<212> TYPE: PRT
<213> ORGANISM: Artificial Sequence
<220> FEATURE:
<223> OTHER INFORMATION: Epi-HNE-4

<400> SEQUENCE: 27

Glu Ala Cys Asn Leu Pro Ile Val Arg Gly Pro Cys Ile Ala Phe Phe
1               5                   10                  15

```
Pro Arg Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
            35                  40                  45

Cys Arg Glu Tyr Cys Gly Val Pro
 50                  55

<210> SEQ ID NO 28
<211> LENGTH: 58
<212> TYPE: PRT
<213> ORGANISM: Homo sapiens

<400> SEQUENCE: 28

Val Arg Glu Val Cys Ser Glu Gln Ala Glu Thr Gly Pro Cys Arg Ala
 1               5                  10                  15

Met Ile Ser Arg Trp Tyr Phe Asp Val Thr Glu Gly Lys Cys Ala Pro
            20                  25                  30

Phe Phe Tyr Gly Gly Cys Gly Asn Arg Asn Asn Phe Asp Thr Glu
            35                  40                  45

Glu Tyr Cys Met Ala Val Cys Gly Ser Ala
 50                  55

<210> SEQ ID NO 29
<211> LENGTH: 58
<212> TYPE: PRT
<213> ORGANISM: Artificial Sequence
<220> FEATURE:
<223> OTHER INFORMATION: DPI.1.1

<400> SEQUENCE: 29

Val Arg Glu Val Cys Ser Glu Gln Ala Tyr Thr Gly Pro Cys Ile Ala
 1               5                  10                  15

Phe Phe Pro Arg Tyr Tyr Phe Asp Val Thr Glu Gly Lys Cys Gln Thr
            20                  25                  30

Phe Val Tyr Gly Gly Cys Met Gly Asn Gly Asn Asn Phe Asp Thr Glu
            35                  40                  45

Glu Tyr Cys Met Ala Val Cys Gly Ser Ala
 50                  55

<210> SEQ ID NO 30
<211> LENGTH: 58
<212> TYPE: PRT
<213> ORGANISM: Artificial Sequence
<220> FEATURE:
<223> OTHER INFORMATION: DPI.1.2

<400> SEQUENCE: 30

Val Arg Glu Val Cys Ser Glu Gln Ala Glu Thr Gly Pro Cys Ile Ala
 1               5                  10                  15

Met Phe Ser Arg Trp Tyr Phe Asp Val Thr Glu Gly Lys Cys Ala Pro
            20                  25                  30

Phe Val Tyr Gly Gly Cys Gly Gly Asn Arg Asn Asn Phe Asp Thr Glu
            35                  40                  45

Glu Tyr Cys Met Ala Val Cys Gly Ser Ala
 50                  55

<210> SEQ ID NO 31
<211> LENGTH: 58
<212> TYPE: PRT
<213> ORGANISM: Artificial Sequence
<220> FEATURE:
```

-continued

```
<223> OTHER INFORMATION: DPI.1.3

<400> SEQUENCE: 31

Val Arg Glu Val Cys Ser Glu Gln Ala Glu Thr Gly Pro Cys Ile Ala
1               5                   10                  15

Phe Phe Ser Arg Trp Tyr Phe Asp Val Thr Glu Gly Lys Cys Ala Thr
            20                  25                  30

Phe Val Tyr Gly Gly Cys Met Gly Asn Arg Asn Asn Phe Asp Thr Glu
        35                  40                  45

Glu Tyr Cys Met Ala Val Cys Gly Ser Ala
    50                  55

<210> SEQ ID NO 32
<211> LENGTH: 58
<212> TYPE: PRT
<213> ORGANISM: Homo sapiens

<400> SEQUENCE: 32

Asn Ala Glu Ile Cys Leu Leu Pro Leu Asp Tyr Gly Pro Cys Arg Ala
1               5                   10                  15

Leu Leu Leu Arg Tyr Tyr Asp Arg Tyr Thr Gln Ser Cys Arg Gln
            20                  25                  30

Phe Leu Tyr Gly Gly Cys Glu Gly Asn Ala Asn Asn Phe Tyr Thr Trp
        35                  40                  45

Glu Ala Cys Asp Asp Ala Cys Trp Arg Ile
    50                  55

<210> SEQ ID NO 33
<211> LENGTH: 58
<212> TYPE: PRT
<213> ORGANISM: Artificial Sequence
<220> FEATURE:
<223> OTHER INFORMATION: DPI.2.1

<400> SEQUENCE: 33

Asn Ala Glu Ile Cys Leu Leu Pro Leu Tyr Thr Gly Pro Cys Ile Ala
1               5                   10                  15

Phe Phe Pro Arg Tyr Tyr Asp Arg Tyr Thr Gln Ser Cys Gln Thr
            20                  25                  30

Phe Val Tyr Gly Gly Cys Met Gly Asn Ala Asn Asn Phe Tyr Thr Trp
        35                  40                  45

Glu Ala Cys Asp Asp Ala Cys Trp Arg Ile
    50                  55

<210> SEQ ID NO 34
<211> LENGTH: 58
<212> TYPE: PRT
<213> ORGANISM: Artificial Sequence
<220> FEATURE:
<223> OTHER INFORMATION: DPI.2.2

<400> SEQUENCE: 34

Asn Ala Glu Ile Cys Leu Leu Pro Leu Asp Tyr Gly Pro Cys Ile Ala
1               5                   10                  15

Leu Phe Leu Arg Tyr Tyr Asp Arg Tyr Thr Gln Ser Cys Arg Gln
            20                  25                  30

Phe Val Tyr Gly Gly Cys Glu Gly Asn Ala Asn Asn Phe Tyr Thr Trp
        35                  40                  45

Glu Ala Cys Asp Asp Ala Cys Trp Arg Ile
    50                  55
```

<210> SEQ ID NO 35
<211> LENGTH: 58
<212> TYPE: PRT
<213> ORGANISM: Artificial Sequence
<220> FEATURE:
<223> OTHER INFORMATION: DPI.2.3

<400> SEQUENCE: 35

```
Asn Ala Glu Ile Cys Leu Leu Pro Leu Asp Thr Gly Pro Cys Ile Ala
 1               5                  10                  15

Phe Phe Leu Arg Tyr Tyr Tyr Asp Arg Tyr Thr Gln Ser Cys Gln Thr
            20                  25                  30

Phe Val Tyr Gly Gly Cys Met Gly Asn Ala Asn Asn Phe Tyr Thr Trp
        35                  40                  45

Glu Ala Cys Asp Asp Ala Cys Trp Arg Ile
    50                  55
```

<210> SEQ ID NO 36
<211> LENGTH: 61
<212> TYPE: PRT
<213> ORGANISM: Homo sapiens

<400> SEQUENCE: 36

```
Val Pro Lys Val Cys Arg Leu Gln Val Ser Val Asp Asp Gln Cys Glu
 1               5                  10                  15

Gly Ser Thr Glu Lys Tyr Phe Phe Asn Leu Ser Ser Met Thr Cys Glu
            20                  25                  30

Lys Phe Phe Ser Gly Gly Cys His Arg Asn Arg Ile Glu Asn Arg Phe
        35                  40                  45

Pro Asp Glu Ala Thr Cys Met Gly Phe Cys Ala Pro Lys
    50                  55                  60
```

<210> SEQ ID NO 37
<211> LENGTH: 58
<212> TYPE: PRT
<213> ORGANISM: Artificial Sequence
<220> FEATURE:
<223> OTHER INFORMATION: DPI.3.1

<400> SEQUENCE: 37

```
Val Pro Lys Val Cys Arg Leu Gln Val Val Arg Gly Pro Cys Ile Ala
 1               5                  10                  15

Phe Phe Pro Arg Trp Phe Phe Asn Leu Ser Ser Met Thr Cys Val Leu
            20                  25                  30

Phe Pro Tyr Gly Gly Cys Gln Gly Asn Gly Asn Arg Phe Pro Asp Glu
        35                  40                  45

Ala Thr Cys Met Gly Phe Cys Ala Pro Lys
    50                  55
```

<210> SEQ ID NO 38
<211> LENGTH: 61
<212> TYPE: PRT
<213> ORGANISM: Artificial Sequence
<220> FEATURE:
<223> OTHER INFORMATION: DPI.3.2

<400> SEQUENCE: 38

```
Val Pro Lys Val Cys Arg Leu Gln Val Ser Val Asp Asp Gln Cys Ile
 1               5                  10                  15

Gly Ser Phe Glu Lys Tyr Phe Phe Asn Leu Ala Ser Met Thr Cys Glu
```

```
            20                  25                  30
Thr Phe Val Ser Gly Gly Cys His Arg Asn Arg Ile Glu Asn Arg Phe
        35                  40                  45

Pro Asp Glu Ala Thr Cys Met Gly Phe Cys Ala Pro Lys
    50                  55                  60

<210> SEQ ID NO 39
<211> LENGTH: 58
<212> TYPE: PRT
<213> ORGANISM: Artificial Sequence
<220> FEATURE:
<223> OTHER INFORMATION: DPI.3.3

<400> SEQUENCE: 39

Val Pro Lys Val Cys Arg Leu Gln Val Val Ala Gly Pro Cys Ile Gly
1               5                   10                  15

Phe Phe Lys Arg Tyr Phe Phe Ala Leu Ser Ser Met Thr Cys Glu Thr
            20                  25                  30

Phe Val Ser Gly Gly Cys His Arg Asn Arg Asn Arg Phe Pro Asp Glu
        35                  40                  45

Ala Thr Cys Met Gly Phe Cys Ala Pro Lys
    50                  55

<210> SEQ ID NO 40
<211> LENGTH: 58
<212> TYPE: PRT
<213> ORGANISM: Homo sapiens

<400> SEQUENCE: 40

Ile Pro Ser Phe Cys Tyr Ser Pro Lys Asp Glu Gly Leu Cys Ser Ala
1               5                   10                  15

Asn Val Thr Arg Tyr Tyr Phe Asn Pro Arg Tyr Arg Thr Cys Asp Ala
            20                  25                  30

Phe Thr Tyr Thr Gly Cys Gly Gly Asn Asp Asn Asn Phe Val Ser Arg
        35                  40                  45

Glu Asp Cys Lys Arg Ala Cys Ala Lys Ala
    50                  55

<210> SEQ ID NO 41
<211> LENGTH: 58
<212> TYPE: PRT
<213> ORGANISM: Artificial Sequence
<220> FEATURE:
<223> OTHER INFORMATION: DPI.4.1

<400> SEQUENCE: 41

Ile Pro Ser Phe Cys Tyr Ser Pro Lys Ser Ala Gly Pro Cys Val Ala
1               5                   10                  15

Met Phe Pro Arg Tyr Tyr Phe Asn Pro Arg Tyr Arg Thr Cys Glu Thr
            20                  25                  30

Phe Val Tyr Gly Gly Cys Met Gly Asn Gly Asn Asn Phe Val Ser Arg
        35                  40                  45

Glu Asp Cys Lys Arg Ala Cys Ala Lys Ala
    50                  55

<210> SEQ ID NO 42
<211> LENGTH: 58
<212> TYPE: PRT
<213> ORGANISM: Artificial Sequence
<220> FEATURE:
<223> OTHER INFORMATION: DPI.4.2
```

```
<400> SEQUENCE: 42

Ile Pro Ser Phe Cys Tyr Ser Pro Lys Asp Glu Gly Leu Cys Ile Ala
1               5                   10                  15

Phe Phe Thr Arg Tyr Tyr Phe Asn Pro Arg Tyr Arg Thr Cys Asp Ala
            20                  25                  30

Phe Thr Tyr Thr Gly Cys Gly Gly Asn Asp Asn Asn Phe Val Ser Arg
            35                  40                  45

Glu Asp Cys Lys Arg Ala Cys Ala Lys Ala
        50                  55

<210> SEQ ID NO 43
<211> LENGTH: 58
<212> TYPE: PRT
<213> ORGANISM: Artificial Sequence
<220> FEATURE:
<223> OTHER INFORMATION: DPI.4.3

<400> SEQUENCE: 43

Ile Pro Ser Phe Cys Tyr Ser Pro Lys Asp Thr Gly Pro Cys Ile Ala
1               5                   10                  15

Phe Phe Thr Arg Tyr Tyr Phe Asn Pro Arg Tyr Arg Thr Cys Asp Thr
            20                  25                  30

Phe Val Tyr Gly Gly Cys Gly Gly Asn Asp Asn Asn Phe Val Ser Arg
            35                  40                  45

Glu Asp Cys Lys Arg Ala Cys Ala Lys Ala
        50                  55

<210> SEQ ID NO 44
<211> LENGTH: 58
<212> TYPE: PRT
<213> ORGANISM: Homo sapiens

<400> SEQUENCE: 44

Met His Ser Phe Cys Ala Phe Lys Ala Asp Asp Gly Pro Cys Lys Ala
1               5                   10                  15

Ile Met Lys Arg Phe Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
        50                  55

<210> SEQ ID NO 45
<211> LENGTH: 58
<212> TYPE: PRT
<213> ORGANISM: Artificial Sequence
<220> FEATURE:
<223> OTHER INFORMATION: DPI.5.1

<400> SEQUENCE: 45

Met His Ser Phe Cys Ala Phe Lys Ala Ser Ala Gly Pro Cys Val Ala
1               5                   10                  15

Met Phe Pro Arg Tyr Phe Phe Asn Ile Phe Thr Arg Gln Cys Glu Thr
            20                  25                  30

Phe Val Tyr Gly Gly Cys Met Gly Asn Gly Asn Arg Phe Glu Ser Leu
            35                  40                  45

Glu Glu Cys Lys Lys Met Cys Thr Arg Asp
        50                  55
```

<210> SEQ ID NO 46
<211> LENGTH: 58
<212> TYPE: PRT
<213> ORGANISM: Artificial Sequence
<220> FEATURE:
<223> OTHER INFORMATION: DPI.5.2

<400> SEQUENCE: 46

Met His Ser Phe Cys Ala Phe Lys Ala Asp Asp Gly Pro Cys Ile Ala
1               5                   10                  15

Ile Phe Lys Arg Phe Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55

<210> SEQ ID NO 47
<211> LENGTH: 58
<212> TYPE: PRT
<213> ORGANISM: Artificial Sequence
<220> FEATURE:
<223> OTHER INFORMATION: DPI.5.3

<400> SEQUENCE: 47

Met His Ser Phe Cys Ala Phe Lys Ala Tyr Thr Gly Pro Cys Ile Ala
1               5                   10                  15

Phe Phe Lys Arg Phe Phe Phe Asn Ile Phe Thr Arg Gln Cys Glu Thr
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55

<210> SEQ ID NO 48
<211> LENGTH: 58
<212> TYPE: PRT
<213> ORGANISM: Homo sapiens

<400> SEQUENCE: 48

Lys Pro Asp Phe Cys Phe Leu Glu Glu Asp Pro Gly Ile Cys Arg Gly
1               5                   10                  15

Tyr Ile Thr Arg Tyr Phe Tyr Asn Asn Gln Thr Lys Gln Cys Glu Arg
            20                  25                  30

Phe Lys Tyr Gly Gly Cys Leu Gly Asn Met Asn Asn Phe Glu Thr Leu
        35                  40                  45

Glu Glu Cys Lys Asn Ile Cys Glu Asp Gly
    50                  55

<210> SEQ ID NO 49
<211> LENGTH: 58
<212> TYPE: PRT
<213> ORGANISM: Artificial Sequence
<220> FEATURE:
<223> OTHER INFORMATION: DPI.6.1

<400> SEQUENCE: 49

Lys Pro Asp Phe Cys Phe Leu Glu Glu Ser Ala Gly Pro Cys Val Ala
1               5                   10                  15

Met Phe Pro Arg Tyr Phe Tyr Asn Asn Gln Thr Lys Gln Cys Glu Thr
            20                  25                  30

Phe Val Tyr Gly Gly Cys Met Gly Asn Gly Asn Phe Glu Thr Leu
            35                  40                  45

Glu Glu Cys Lys Asn Ile Cys Glu Asp Gly
        50                  55

<210> SEQ ID NO 50
<211> LENGTH: 58
<212> TYPE: PRT
<213> ORGANISM: Artificial Sequence
<220> FEATURE:
<223> OTHER INFORMATION: DPI.6.2

<400> SEQUENCE: 50

Lys Pro Asp Phe Cys Phe Leu Glu Glu Asp Pro Gly Ile Cys Val Gly
1               5                   10                  15

Tyr Phe Thr Arg Tyr Phe Tyr Asn Asn Gln Thr Lys Gln Cys Glu Arg
            20                  25                  30

Phe Lys Tyr Gly Gly Cys Leu Gly Asn Met Asn Asn Phe Glu Thr Leu
            35                  40                  45

Glu Glu Cys Lys Asn Ile Cys Glu Asp Gly
        50                  55

<210> SEQ ID NO 51
<211> LENGTH: 58
<212> TYPE: PRT
<213> ORGANISM: Artificial Sequence
<220> FEATURE:
<223> OTHER INFORMATION: DPI.6.3

<400> SEQUENCE: 51

Lys Pro Asp Phe Cys Phe Leu Glu Glu Asp Pro Gly Ile Cys Val Gly
1               5                   10                  15

Phe Phe Thr Arg Tyr Phe Tyr Asn Asn Gln Thr Lys Gln Cys Glu Arg
            20                  25                  30

Phe Val Tyr Gly Gly Cys Leu Gly Asn Met Asn Asn Phe Glu Thr Leu
            35                  40                  45

Glu Glu Cys Lys Asn Ile Cys Glu Asp Gly
        50                  55

<210> SEQ ID NO 52
<211> LENGTH: 58
<212> TYPE: PRT
<213> ORGANISM: Artificial Sequence
<220> FEATURE:
<223> OTHER INFORMATION: DPI.6.4

<400> SEQUENCE: 52

Lys Pro Asp Phe Cys Phe Leu Glu Glu Asp Pro Gly Ile Cys Val Gly
1               5                   10                  15

Phe Phe Thr Arg Tyr Phe Tyr Asn Ala Gln Thr Lys Gln Cys Glu Arg
            20                  25                  30

Phe Val Tyr Gly Gly Cys Leu Gly Asn Met Asn Asn Phe Glu Thr Leu
            35                  40                  45

Glu Glu Cys Lys Asn Ile Cys Glu Asp Gly
        50                  55

<210> SEQ ID NO 53
<211> LENGTH: 58
<212> TYPE: PRT
<213> ORGANISM: Artificial Sequence
<220> FEATURE:

-continued

<223> OTHER INFORMATION: DPI.6.5

<400> SEQUENCE: 53

Lys Pro Asp Phe Cys Phe Leu Glu Glu Asp Pro Gly Pro Cys Val Gly
1               5                   10                  15

Phe Phe Gln Arg Tyr Phe Tyr Asn Ala Gln Thr Lys Gln Cys Glu Arg
            20                  25                  30

Phe Val Tyr Gly Gly Cys Gln Gly Asn Met Asn Asn Phe Glu Thr Leu
        35                  40                  45

Glu Glu Cys Lys Asn Ile Cys Glu Asp Gly
    50                  55

<210> SEQ ID NO 54
<211> LENGTH: 58
<212> TYPE: PRT
<213> ORGANISM: Artificial Sequence
<220> FEATURE:
<223> OTHER INFORMATION: DPI.6.6

<400> SEQUENCE: 54

Lys Pro Asp Phe Cys Phe Leu Glu Glu Asp Pro Gly Pro Cys Val Gly
1               5                   10                  15

Phe Phe Thr Arg Tyr Phe Tyr Asn Asn Gln Thr Lys Gln Cys Glu Arg
            20                  25                  30

Phe Val Tyr Gly Gly Cys Gln Gly Asn Met Asn Asn Phe Glu Thr Leu
        35                  40                  45

Glu Glu Cys Lys Asn Ile Cys Glu Asp Gly
    50                  55

<210> SEQ ID NO 55
<211> LENGTH: 58
<212> TYPE: PRT
<213> ORGANISM: Artificial Sequence
<220> FEATURE:
<223> OTHER INFORMATION: DPI.6.7

<400> SEQUENCE: 55

Lys Pro Asp Phe Cys Phe Leu Glu Glu Asp Pro Gly Pro Cys Ile Gly
1               5                   10                  15

Phe Phe Pro Arg Tyr Phe Tyr Asn Asn Gln Thr Lys Gln Cys Glu Arg
            20                  25                  30

Phe Val Tyr Gly Gly Cys Gln Gly Asn Met Asn Asn Phe Glu Thr Leu
        35                  40                  45

Glu Glu Cys Lys Asn Ile Cys Glu Asp Gly
    50                  55

<210> SEQ ID NO 56
<211> LENGTH: 58
<212> TYPE: PRT
<213> ORGANISM: Homo sapiens

<400> SEQUENCE: 56

Gly Pro Ser Trp Cys Leu Thr Pro Ala Asp Arg Gly Leu Cys Arg Ala
1               5                   10                  15

Asn Glu Asn Arg Phe Tyr Tyr Asn Ser Val Ile Gly Lys Cys Arg Pro
            20                  25                  30

Phe Lys Tyr Ser Gly Cys Gly Gly Asn Glu Asn Asn Phe Thr Ser Lys
        35                  40                  45

Gln Glu Cys Leu Arg Ala Cys Lys Lys Gly
    50                  55

```
<210> SEQ ID NO 57
<211> LENGTH: 58
<212> TYPE: PRT
<213> ORGANISM: Artificial Sequence
<220> FEATURE:
<223> OTHER INFORMATION: DPI.7.1

<400> SEQUENCE: 57

Gly Pro Ser Trp Cys Leu Thr Pro Ala Val Arg Gly Pro Cys Ile Ala
1               5                   10                  15

Phe Phe Pro Arg Trp Tyr Tyr Asn Ser Val Ile Gly Lys Cys Val Leu
            20                  25                  30

Phe Pro Tyr Gly Gly Cys Gln Gly Asn Gly Asn Asn Phe Thr Ser Lys
        35                  40                  45

Gln Glu Cys Leu Arg Ala Cys Lys Lys Gly
    50                  55

<210> SEQ ID NO 58
<211> LENGTH: 58
<212> TYPE: PRT
<213> ORGANISM: Artificial Sequence
<220> FEATURE:
<223> OTHER INFORMATION: DPI.7.2

<400> SEQUENCE: 58

Gly Pro Ser Trp Cys Leu Thr Pro Ala Asp Arg Gly Leu Cys Val Ala
1               5                   10                  15

Asn Phe Asn Arg Phe Tyr Tyr Asn Ser Val Ile Gly Lys Cys Arg Pro
            20                  25                  30

Phe Lys Tyr Ser Gly Cys Gly Asn Glu Asn Asn Phe Thr Ser Lys
        35                  40                  45

Gln Glu Cys Leu Arg Ala Cys Lys Lys Gly
    50                  55

<210> SEQ ID NO 59
<211> LENGTH: 58
<212> TYPE: PRT
<213> ORGANISM: Artificial Sequence
<220> FEATURE:
<223> OTHER INFORMATION: DPI.7.3

<400> SEQUENCE: 59

Gly Pro Ser Trp Cys Leu Thr Pro Ala Asp Arg Gly Leu Cys Val Ala
1               5                   10                  15

Phe Phe Asn Arg Phe Tyr Tyr Asn Ser Val Ile Gly Lys Cys Arg Pro
            20                  25                  30

Phe Lys Tyr Ser Gly Cys Gly Gly Asn Glu Asn Asn Phe Lys Ser Lys
        35                  40                  45

Gln Glu Cys Leu Arg Ala Cys Lys Lys Gly
    50                  55

<210> SEQ ID NO 60
<211> LENGTH: 58
<212> TYPE: PRT
<213> ORGANISM: Artificial Sequence
<220> FEATURE:
<223> OTHER INFORMATION: DPI.7.4

<400> SEQUENCE: 60

Gly Pro Ser Trp Cys Leu Thr Pro Ala Val Arg Gly Pro Cys Val Ala
1               5                   10                  15
```

```
Phe Phe Asn Arg Phe Tyr Tyr Asn Ser Val Ile Gly Lys Cys Arg Pro
            20                  25                  30

Phe Lys Tyr Gly Gly Cys Gly Gly Asn Glu Asn Asn Phe Lys Ser Lys
        35                  40                  45

Gln Glu Cys Leu Arg Ala Cys Lys Lys Gly
    50                  55

<210> SEQ ID NO 61
<211> LENGTH: 58
<212> TYPE: PRT
<213> ORGANISM: Artificial Sequence
<220> FEATURE:
<223> OTHER INFORMATION: DPI.7.5

<400> SEQUENCE: 61

Gly Pro Ser Trp Cys Leu Thr Pro Ala Asp Arg Gly Pro Cys Ile Ala
1               5                   10                  15

Phe Phe Pro Arg Trp Tyr Tyr Asn Ser Val Ile Gly Lys Cys Gln Thr
            20                  25                  30

Phe Val Tyr Gly Gly Cys Gly Gly Asn Glu Asn Asn Phe Ala Ser Lys
        35                  40                  45

Gln Glu Cys Leu Arg Ala Cys Lys Lys Gly
    50                  55

<210> SEQ ID NO 62
<211> LENGTH: 58
<212> TYPE: PRT
<213> ORGANISM: Homo sapiens

<400> SEQUENCE: 62

Glu Thr Asp Ile Cys Lys Leu Pro Lys Asp Glu Gly Thr Cys Arg Asp
1               5                   10                  15

Phe Ile Leu Lys Trp Tyr Tyr Asp Pro Asn Thr Lys Ser Cys Ala Arg
            20                  25                  30

Phe Trp Tyr Gly Gly Cys Gly Gly Asn Glu Asn Lys Phe Gly Ser Gln
        35                  40                  45

Lys Glu Cys Glu Lys Val Cys Ala Pro Val
    50                  55

<210> SEQ ID NO 63
<211> LENGTH: 58
<212> TYPE: PRT
<213> ORGANISM: Artificial Sequence
<220> FEATURE:
<223> OTHER INFORMATION: DPI.8.1

<400> SEQUENCE: 63

Glu Thr Asp Ile Cys Lys Leu Pro Lys Val Arg Gly Pro Cys Ile Ala
1               5                   10                  15

Phe Phe Pro Arg Trp Tyr Tyr Asp Pro Asn Thr Lys Ser Cys Val Leu
            20                  25                  30

Phe Pro Tyr Gly Gly Cys Gln Gly Asn Gly Asn Lys Phe Gly Ser Gln
        35                  40                  45

Lys Glu Cys Glu Lys Val Cys Ala Pro Val
    50                  55

<210> SEQ ID NO 64
<211> LENGTH: 58
<212> TYPE: PRT
<213> ORGANISM: Artificial Sequence
```

```
<220> FEATURE:
<223> OTHER INFORMATION: DPI.8.2

<400> SEQUENCE: 64
```

Glu Thr Asp Ile Cys Lys Leu Pro Lys Asp Glu Gly Thr Cys Ile Ala
1               5                   10                  15

Phe Phe Leu Lys Trp Tyr Tyr Asp Pro Asn Thr Lys Ser Cys Ala Arg
                20                  25                  30

Phe Val Tyr Gly Gly Cys Gly Gly Asn Glu Asn Lys Phe Gly Ser Gln
            35                  40                  45

Lys Glu Cys Glu Lys Val Cys Ala Pro Val
    50                  55

```
<210> SEQ ID NO 65
<211> LENGTH: 58
<212> TYPE: PRT
<213> ORGANISM: Artificial Sequence
<220> FEATURE:
<223> OTHER INFORMATION: DPI.8.3

<400> SEQUENCE: 65
```

Glu Thr Asp Ile Cys Lys Leu Pro Lys Asp Glu Gly Pro Cys Ile Ala
1               5                   10                  15

Phe Phe Leu Arg Trp Tyr Tyr Asp Pro Asn Thr Lys Ser Cys Ala Arg
                20                  25                  30

Phe Val Tyr Gly Gly Cys Gly Gly Asn Glu Asn Lys Phe Gly Ser Gln
            35                  40                  45

Lys Glu Cys Glu Lys Val Cys Ala Pro Val
    50                  55

```
<210> SEQ ID NO 66
<211> LENGTH: 58
<212> TYPE: PRT
<213> ORGANISM: Homo sapiens

<400> SEQUENCE: 66
```

Leu Pro Asn Val Cys Ala Phe Pro Met Glu Lys Gly Pro Cys Gln Thr
1               5                   10                  15

Tyr Met Thr Arg Trp Phe Phe Asn Phe Glu Thr Gly Glu Cys Glu Leu
                20                  25                  30

Phe Ala Tyr Gly Gly Cys Gly Gly Asn Ser Asn Asn Phe Leu Arg Lys
            35                  40                  45

Glu Lys Cys Glu Lys Phe Cys Lys Phe Thr
    50                  55

```
<210> SEQ ID NO 67
<211> LENGTH: 58
<212> TYPE: PRT
<213> ORGANISM: Artificial Sequence
<220> FEATURE:
<223> OTHER INFORMATION: DPI.9.1

<400> SEQUENCE: 67
```

Leu Pro Asn Val Cys Ala Phe Pro Met Val Arg Gly Pro Cys Ile Ala
1               5                   10                  15

Phe Phe Pro Arg Trp Phe Phe Asn Phe Glu Thr Gly Glu Cys Val Leu
                20                  25                  30

Phe Val Tyr Gly Gly Cys Gln Gly Asn Gly Asn Asn Phe Leu Arg Lys
            35                  40                  45

Glu Lys Cys Glu Lys Phe Cys Lys Phe Thr

<210> SEQ ID NO 68
<211> LENGTH: 58
<212> TYPE: PRT
<213> ORGANISM: Artificial Sequence
<220> FEATURE:
<223> OTHER INFORMATION: DPI.9.2

<400> SEQUENCE: 68

Leu Pro Asn Val Cys Ala Phe Pro Met Glu Lys Gly Pro Cys Ile Ala
1               5                   10                  15

Tyr Phe Thr Arg Trp Phe Phe Asn Phe Glu Thr Gly Glu Cys Glu Leu
            20                  25                  30

Phe Ala Tyr Gly Gly Cys Gly Gly Asn Ser Asn Asn Phe Leu Arg Lys
        35                  40                  45

Glu Lys Cys Glu Lys Phe Cys Lys Phe Thr
    50                  55

<210> SEQ ID NO 69
<211> LENGTH: 58
<212> TYPE: PRT
<213> ORGANISM: Artificial Sequence
<220> FEATURE:
<223> OTHER INFORMATION: DPI.9.3

<400> SEQUENCE: 69

Leu Pro Asn Val Cys Ala Phe Pro Met Glu Lys Gly Pro Cys Ile Ala
1               5                   10                  15

Tyr Phe Pro Arg Trp Phe Phe Asn Phe Glu Thr Gly Glu Cys Val Leu
            20                  25                  30

Phe Val Tyr Gly Gly Cys Gly Gly Asn Ser Asn Asn Phe Leu Arg Lys
        35                  40                  45

Glu Lys Cys Glu Lys Phe Cys Lys Phe Thr
    50                  55

<210> SEQ ID NO 70
<211> LENGTH: 8157
<212> TYPE: DNA
<213> ORGANISM: Artificial Sequence
<220> FEATURE:
<223> OTHER INFORMATION: Plasmid pHIL-D2

<400> SEQUENCE: 70
agatcgcggc cgcgatctaa catccaaaga cgaaaggttg aatgaaacct ttttgccatc    60
cgacatccac aggtccattc tcacacataa gtgccaaacg caacaggagg ggatacacta   120
gcagcagacc gttgcaaacg caggacctcc actcctcttc tcctcaacac ccactttgc    180 catcgaaaaa ccagcccagt tattgggctt gattggagct cgctcattcc aattccttct   240
attaggctac taacaccatg actttattag cctgtctatc ctggcccccc tggcgaggtc   300
atgtttgttt atttccgaat gcaacaagct ccgcattaca cccgaacatc actccagatg   360
agggctttct gagtgtgggg tcaaatagtt tcatgttccc aaatggccca aaactgacag   420
tttaaacgct gtcttggaac ctaatatgac aaaagcgtga tctcatccaa gatgaactaa   480
gtttggttcg ttgaaatgct aacggccagt tggtcaaaaa gaaacttcca aaagtcgcca   540
taccgtttgt cttgtttggt attgattgac gaatgctcaa aaataatctc attaatgctt   600
agcgcagtct ctctatcgct tctgaacccg gtggcacctg tgccgaaacg caaatgggga   660
aacaacccgc ttttttggatg attatgcatt gtcctccaca ttgtatgctt ccaagattct   720

```
ggtgggaata ctgctgatag cctaacgttc atgatcaaaa tttaactgtt ctaacccta      780
cttgacaggc aatatataaa cagaaggaag ctgccctgtc ttaaacccttt tttttttatca    840
tcattattag cttactttca taattgcgac tggttccaat tgacaagctt ttgattttaa      900
cgactttttaa cgacaacttg agaagatcaa aaaacaacta attattcgaa acgaggaatt    960
cgccttagac atgactgttc ctcagttcaa gttgggcatt acgagaagac cggtcttgct     1020
agattctaat caagaggatg tcagaatgcc atttgcctga gagatgcagg cttcattttt    1080
gatacttttt tatttgtaac ctatatagta taggatttt tttgtcattt tgtttcttct     1140
cgtacgagct tgctcctgat cagcctatct cgcagctgat gaatatcttg tggtaggggt    1200
ttgggaaaat cattcgagtt tgatgttttt cttggtattt cccactcctc ttcagagtac    1260
agaagattaa gtgagaagtt cgtttgtgca agcttatcga taagctttaa tgcggtagtt    1320
tatcacagtt aaattgctaa cgcagtcagg caccgtgtat gaaatctaac aatgcgctca    1380
tcgtcatcct cggcaccgtc accctggatg ctgtaggcat aggcttggtt atgccggtac    1440
tgccgggcct cttgcgggat atcgtccatt ccgacagcat cgccagtcac tatgcgtgc    1500
tgctagcgct atatgcgttg atgcaatttc tatgcgcacc cgttctcgga gcactgtccg    1560
accgctttgg ccgccgccca gtcctgctcg cttcgctact tggagccact atcgactacg    1620
cgatcatggc gaccacaccc gtcctgtgga tctatcgaat ctaaatgtaa gttaaaatct    1680
ctaaataatt aaataagtcc cagtttctcc atacgaacct taacagcatt gcggtgagca    1740
tctagacctt caacagcagc cagatccatc actgcttggc caatatgttt cagtccctca    1800
ggagttacgt cttgtgaagt gatgaacttc tggaaggttg cagtgttaac tccgctgtat    1860
tgacgggcat atccgtacgt tggcaaagtg tggttggtac cggaggagta atctccacaa    1920
ctctctggag agtaggcacc aacaaacaca gatccagcgt gttgtacttg atcaacataa    1980
gaagaagcat tctcgatttg caggatcaag tgttcaggag cgtactgatt ggacatttcc    2040
aaagcctgct cgtaggttgc aaccgatagg gttgtagagt gtgcaataca cttgcgtaca    2100
atttcaaccc ttggcaactg cacagcttgg ttgtgaacag catcttcaat tctggcaagc    2160
tccttgtctg tcatatcgac agccaacaga atcacctggg aatcaatacc atgttcagct    2220
tgagcagaag gtctgaggca acgaaatctg gatcagcgta tttatcagca ataactagaa    2280
cttcagaagg cccagcaggc atgtcaatac tacacagggc tgatgtgtca ttttgaacca    2340
tcatcttggc agcagtaacg aactggtttc ctggaccaaa tattttgtca cacttaggaa    2400
cagtttctgt tccgtaagcc atagcagcta ctgcctgggc gcctcctgct agcacgatac    2460
acttagcacc aaccttgtgg gcaacgtaga tgacttctgg ggtaagggta ccatccttct    2520
taggtggaga tgcaaaaaca atttctttgc aaccagcaac tttggcagga acacccagca    2580
tcagggaagt ggaaggcaga attgcggttc caccaggaat atagaggcca actttctcaa    2640
taggtcttgc aaaacgagag cagactacac cagggcaagt ctcaacttgc aacgtctccg    2700
ttagttgagc ttcatggaat ttcctgacgt tatctataga gagatcaatg gctctcttaa    2760
cgttatctgg caattgcata agttcctctg ggaaaggagc ttctaacaca ggtgtcttca    2820
aagcgactcc atcaaacttg gcagttagtt ctaaaagggc tttgtcacca ttttgacgaa    2880
cattgtcgac aattggtttg actaattcca taatctgttc cgttttctgg ataggacgac    2940
gaagggcatc ttcaatttct tgtgaggagg cctagaaaac gtcaattttg cacaattcaa    3000
tacgaccttc agaagggact tctttaggtt tggattcttc tttaggttgt tccttggtgt    3060
```

```
atcctggctt ggcatctcct ttccttctag tgacctttag ggacttcata tccaggtttc   3120
tctccacctc gtccaacgtc acaccgtact tggcacatct aactaatgca aaataaaata   3180
agtcagcaca ttcccaggct atatcttcct tggatttagc ttctgcaagt tcatcagctt   3240
cctccctaat tttagcgttc aacaaaactt cgtcgtcaaa taaccgtttg gtataagaac   3300
cttctggagc attgctctta cgatcccaca aggtgcttcc atggctctaa gacccttga    3360 ttggccaaaa caggaagtgc gttccaagtg acagaaacca cacctgtttt gttcaaccac   3420
aaatttcaag cagtctccat cacaatccaa ttcgataccc agcaactttt gagttcgtcc   3480
agatgtagca cctttatacc acaaaccgtg acgacgagat tggtagactc cagtttgtgt   3540
ccttatagcc tccggaatag acttttttgga cgagtacacc aggcccaacg agtaattaga   3600
agagtcagcc accaaagtag tgaatagacc atcggggcgg tcagtagtca aagacgccaa   3660
caaaatttca ctgacaggga acttttgac atcttcagaa agttcgtatt cagtagtcaa    3720
ttgccgagca tcaataatgg ggattatacc agaagcaaca gtggaagtca catctaccaa   3780
ctttgcggtc tcagaaaaag cataaacagt tctactaccg ccattagtga aacttttcaa   3840
atcgcccagt gggagaagaaa aaggcacagc gatactagca ttagcgggca aggatgcaac   3900
tttatcaacc agggtcctat agataaccct agcgcctggg atcatccttt ggacaactct   3960
ttctgccaaa tctaggtcca aaatcacttc attgatacca ttatacggat gactcaactt   4020
gcacattaac ttgaagctca gtcgattgag tgaacttgat caggttgtgc agctggtcag   4080
cagcatdagg aaaacacggct tttcctacca aactcaagga attatcaaac tctgcaacac   4140
ttgcgtatgc aggtagcaag ggaaatgtca tacttgaagt cggacagtga gtgtagtctt   4200
gagaaattct gaagccgtat tttatattatc agtgagtcag tcatcaggag atcctctacg   4260
ccggacgcat cgtggccggc atcaccggcg ccacaggtgc ggttgctggc gcctatatcg   4320
ccgacatcac cgatggggaa gatcgggctc gccacttcgg gctcatgagc gcttgtttcg   4380
gcgtgggtat ggtggcaggc cccgtggccg ggggactgtt gggcgccatc tccttgcatg   4440
caccattcct tgcggcggcg gtgctcaacg gcctcaacct actactgggc tgcttcctaa   4500
tgcaggagtc gcataaggga gagcgtcgag tatctatgat tggaagtatg ggaatggtga   4560
tacccgcatt cttcagtgtc ttgaggtctc ctatcagatt atgcccaact aaagcaaccg   4620
gaggaggaga tttcatggta aatttctctg acttttggtc atcagtagac tcgaactgtg   4680
agactatctc ggttatgaca gcagaaatgt ccttcttgga gacagtaaat gaagtcccac   4740
caataaagaa atccttgtta tcaggaacaa acttcttgtt tcgaacttttt tcggtgcctt   4800 gaactataaa atgtagagtg gatatgtcgg gtaggaatgg agcgggcaaa tgcttacctt   4860
ctggaccttc aagaggtatg tagggtttgt agatactgat gccaacttca gtgacaacgt   4920
tgctatttcg ttcaaaccat tccgaatcca gagaaatcaa agttgtttgt ctactattga   4980
tccaagccag tgcggtcttg aaactgacaa tagtgtgctc gtgttttgag gtcatctttg   5040
tatgaataaa tctagtcttt gatctaaata atcttgacga gccaaggcga taaatacccca   5100 aatctaaaac tcttttaaaa cgttaaaagg acaagtatgt ctgcctgtat taaaccccaa   5160
atcagctcgt agtctgatcc tcatcaactt gaggggcact atcttgtttt agagaaattt   5220
gcggagatgc gatatcgaga aaaggtacg ctgattttaa acgtgaaatt tatctcaaga   5280
tcgcggccgc gatctcgaat aataactgtt attttttcagt gttcccgatc tgcgtctatt   5340
tcacaatacc aacatgagtc agcttatcga tgataagctg tcaaacatga gaattaattc   5400
gatgataagc tgtcaaacat gagaaatctt gaagacgaaa gggcctcgtg atacgcctat   5460
```

```
ttttataggt taatgtcatg ataataatgg tttcttagac gtcaggtggc acttttcggg      5520
gaaatgtgcg cggaacccct atttgtttat ttttctaaat acattcaaat atgtatccgc      5580
tcatgagaca ataaccctga taaatgcttc aataatattg aaaaggaag agtatgagta       5640 ttcaacattt ccgtgtcgcc cttattccct tttttgcggc attttgcctt cctgttttg      5700 ctcacccaga aacgctggtg aaagtaaaag atgctgaaga tcagttgggt gcacgagtgg      5760
gttacatcga actggatctc aacagcggta agatccttga gagttttcgc cccgaagaac     5820
gttttccaat gatgagcact tttaaagttc tgctatgtgg cgcggtatta tcccgtgttg     5880
acgccgggca agagcaactc ggtcgccgca tacactattc tcagaatgac ttggttgagt    5940
actcaccagt cacagaaaag catcttacgg atggcatgac agtaagagaa ttatgcagtg   6000
ctgccataac catgagtgat aacactgcgg ccaacttact tctgacaacg atcggaggac  6060
cgaaggagct aaccgctttt ttgcacaaca tgggggatca tgtaactcgc cttgatcgtt  6120
gggaaccgga gctgaatgaa gccataccaa acgacgagcg tgacaccacg atgcctgcag  6180
caatggcaac aacgttgcgc aaactattaa ctggcgaact acttactcta gcttcccggc  6240
aacaattaat agactggatg gaggcggata aagttgcagg accacttctg cgctcggccc  6300
ttccggctgg ctggtttatt gctgataaat ctggagccgg tgagcgtggg tctcgcggta   6360
tcattgcagc actggggcca gatggtaagc cctcccgtat cgtagttatc tacacgacgg  6420
ggagtcaggc aactatggat gaacgaaata gacagatcgc tgagataggt gcctcactga  6480
ttaagcattg gtaactgtca gaccaagttt actcatatat actttagatt gatttaaatt   6540
gtaaacgtta atattttgtt aaaattcgcg ttaattttt gttaaatcag ctcatttttt     6600
aaccataggc cgaaatcgg caaatccct tataaatcaa agaatagac cgagataggg      6660 ttgagtgttg ttccagtttg gaacaagagt ccactattaa agaacgtgga ctccaacgtc  6720
aaagggcgaa aaaccgtcta tcagggcgat ggcccactac gtgaaccatc accctaatca  6780
agttttttgg ggtcgaggtg ccgtaaagca ctaaatcgga acccctaaagg gagcccccga  6840 tttagagctt gacggggaaa gccggcgaac gtggcgagaa aggaagggaa gaaagcgaaa  6900
ggagcgggcg ctagggcgct ggcaagtgta gcggtcacgc tgcgcgtaac caccacccc   6960 gccgcgctta atgcgccgct acaggcgcg taaaaggatc taggtgaaga tccttttga    7020 taatctcatg accaaaatcc cttaacgtga gttttcgttc cactgagcgt cagacccgt   7080 agaaaagatc aaaggatctt cttgagatcc ttttttctg cgcgtaatct gctgcttgca   7140
aacaaaaaaa ccaccgctac cagcggtggt ttgtttgccg gatcaagagc taccaactct  7200
ttttccgaag gtaactggct tcagcagagc gcagatacca aatactgtcc ttctagtgta  7260
gccgtagtta ggccaccact tcaagaactc tgtagcaccg cctacatacc tcgctctgct  7320
aatcctgtta ccagtggctg ctgccagtgg cgataagtcg tgtcttaccg ggttggactc  7380
aagacgatag ttaccggata aggcgcagcg gtcgggctga acgggggtt cgtgcacaca  7440 gcccagcttg gagcgaacga cctacaccga actgagatac ctacagcgtg agcattgaga  7500
aagcgccacg cttcccgaag ggagaaaggc ggacaggtat ccggtaagcg gcagggtcgg  7560
aacaggagag cgcacgaggg agcttccagg gggaaacgcc tggtatcttt atagtcctgt  7620
cgggtttcgc cacctctgac ttgagcgtcg attttttgtga tgctcgtcag gggggcggag   7680
cctatggaaa aacgccagca acgcggcctt tttacggttc ctggcctttt gctggccttt  7740
tgctcacatg ttctttcctg cgttatcccc tgattctgtg ataaccgta ttaccgcctt   7800
```

```
tgagtgagct gataccgctc gccgcagccg aacgaccgag cgcagcgagt cagtgagcga    7860
ggaagcggaa gagcgcctga tgcggtattt tctccttacg catctgtgcg gtatttcaca    7920
ccgcatatgg tgcactctca gtacaatctg ctctgatgcc gcatagttaa gccagtatac    7980
actccgctat cgctacgtga ctgggtcatg gctgcgcccc gacacccgcc aacacccgct    8040
gacgcgccct gacgggcttg tctgctcccg gcatccgctt acagacaagc tgtgaccgtc    8100
tccgggagct gcatgtgtca gaggttttca ccgtcatcac cgaaacgcgc gaggcag      8157
```

<210> SEQ ID NO 71
<211> LENGTH: 8584
<212> TYPE: DNA
<213> ORGANISM: Artificial Sequence
<220> FEATURE:
<223> OTHER INFORMATION: Plasmid pHIL-D2 (MFalphaPrePro::EPI-HNE-3)

<400> SEQUENCE: 71

```
agatcgcggc cgcgatctaa catccaaaga cgaaaggttg aatgaaacct ttttgccatc      60
cgacatccac aggtccattc tcacacataa gtgccaaacg caacaggagg ggatacacta    120
gcagcagacc gttgcaaacg caggacctcc actcctcttc tcctcaacac ccacttttgc    180
catcgaaaaa ccagcccagt tattgggctt gattggagct cgctcattcc aattccttct    240
attaggctac taacaccatg actttattag cctgtctatc ctggcccccc tggcgaggtc    300
atgtttgttt atttccgaat gcaacaagct ccgcattaca cccgaacatc actccagatg    360
agggctttct gagtgtgggg tcaaatagtt tcatgttccc aaatggccca aaactgacag    420
tttaaacgct gtcttggaac ctaatatgac aaaagcgtga tctcatccaa gatgaactaa    480
gtttggttcg ttgaaatgct aacggccagt tggtcaaaaa gaaacttcca aaagtcgcca    540
taccgtttgt cttgtttggt attgattgac gaatgctcaa aaataatctc attaatgctt    600
agcgcagtct ctctatcgct tctgaacccg gtggcacctg tgccgaaacg caaatgggga    660
aacaacccgc tttttggatg attatgcatt gtcctccaca ttgtatgctt ccaagattct    720
ggtgggaata ctgctgatag cctaacgttc atgatcaaaa tttaactgtt ctaaccccta    780
cttgacaggc aatatataaa cagaaggaag ctgccctgtc ttaaaccttt tttttttatca    840
tcattattag cttactttca taattgcgac tggttccaat tgacaagctt ttgattttaa    900
cgacttttaa cgacaacttg agaagatcaa aaaacaacta attattcgaa acgatgagat    960
tcccatctat cttcactgct gttttgttcg ctgcttcctc tgctttggct gctccagtta   1020
acaccactac tgaagacgag actgctcaaa ttcctgctga ggctgtcatc ggttactctg   1080
acttggaagg tgacttcgac gtcgctgttt tgccattctc taactctact aacaacggtt   1140
tgttgttcat caacactacc atcgcttcta tcgctgctaa ggaggaaggt gtttccttgg   1200
acaagagagc tgcttgtaac ttgccaatcg tcagaggtcc atgcattgct ttcttcccaa   1260
gatgggcttt cgacgctgtt aagggtaagt gcgtcttgtt cccatacggt ggttgtcaag   1320
gtaacggtaa caagttctac tctgagaagg agtgtagaga gtactgtggt gttccatagt   1380
aagaattcgc cttagacatg actgttcctc agttcaagtt gggcattacg agaagaccgg   1440
tcttgctaga ttctaatcaa gaggatgtca gaatgccatt tgcctgagag atgcaggctt   1500
catttttgat actttttat ttgtaaccta tatagtatag gatttttttt gtcattttgt   1560
ttcttctcgt acgagcttgc tcctgatcag cctatctcgc agctgatgaa tatcttgtgg   1620
taggggtttg ggaaaatcat tcgagtttga tgttttttctt ggtatttccc actcctcttc   1680
agagtacaga agattaagtg agaagttcgt ttgtgcaagc ttatcgataa gctttaatgc   1740
```

```
ggtagtttat cacagttaaa ttgctaacgc agtcaggcac cgtgtatgaa atctaacaat    1800
gcgctcatcg tcatcctcgg caccgtcacc ctggatgctg taggcatagg cttggttatg    1860
ccggtactgc cgggcctctt gcgggatatc gtccattccg acagcatcgc cagtcactat    1920
ggcgtgctgc tagcgctata tgcgttgatg caatttctat gcgcacccgt tctcggagca    1980
ctgtccgacc gctttggccg ccgcccagtc ctgctcgctt cgctacttgg agccactatc    2040
gactacgcga tcatggcgac cacacccgtc ctgtggatct atcgaatcta aatgtaagtt    2100
aaaatctcta ataattaaa taagtcccag tttctccata cgaaccttaa cagcattgcg    2160
gtgagcatct agaccttcaa cagcagccag atccatcact gcttggccaa tatgtttcag    2220
tccctcagga gttacgtctt gtgaagtgat gaacttctgg aaggttgcag tgttaactcc    2280
gctgtattga cggcatatc cgtacgttgg caaagtgtgg ttggtaccgg aggagtaatc    2340
tccacaactc tctggagagt aggcaccaac aaacacagat ccagcgtgtt gtacttgatc    2400
aacataagaa gaagcattct cgatttgcag gatcaagtgt tcaggagcgt actgattgga    2460
catttccaaa gcctgctcgt aggttgcaac cgataggggtt gtagagtgtg caatacactt    2520
gcgtacaatt tcaaccctttg gcaactgcac agcttggttg tgaacagcat cttcaattct    2580
ggcaagctcc ttgtctgtca tatcgacagc aacagaatc acctgggaat caataccatg    2640
ttcagcttga gcagaaggtc tgaggcaacg aaatctggat cagcgtattt atcagcaata    2700
actagaactt cagaaggccc agcaggcatg tcaatactac acagggctga tgtgtcattt    2760
tgaaccatca tcttggcagc agtaacgaac tggtttcctg gaccaaatat tttgtcacac    2820
ttaggaacag tttctgttcc gtaagccata gcagctactg cctgggcgcc tcctgctagc    2880
acgatacact tagcaccaac cttgtgggca acgtagatga cttctggggt aagggtacca    2940
tccttcttag gtggagatgc aaaaacaatt tctttgcaac cagcaacttt ggcaggaaca    3000
cccagcatca gggaagtgga aggcagaatt gcggttccac caggaatata gaggccaact    3060
ttctcaatag gtcttgcaaa acgagagcag actacaccag ggcaagtctc aacttgcaac    3120
gtctccgtta gttgagcttc atggaatttc ctgacgttat ctatagagag atcaatggct    3180
ctcttaacgt tatctggcaa ttgcataagt tcctctggga aggagcttc taacacaggt    3240
gtcttcaaag cgactccatc aaacttggca gttagttcta aaaggctttt gtcaccattt    3300
tgacgaacat tgtcgacaat tggtttgact aattccataa tctgttccgt tttctggata    3360
ggacgacgaa gggcatcttc aatttcttgt gaggaggcct tagaaacgtc aattttgcac    3420
aattcaatac gaccttcaga agggacttct ttaggtttgg attcttcttt aggttgttcc    3480
ttggtgtatc ctggcttggc atctcctttc cttctagtga cctttaggga cttcatatcc    3540
aggtttctct ccacctcgtc caacgtcaca ccgtacttgg cacatctaac taatgcaaaa    3600
taaaataagt cagcacattc ccaggctata tcttccttgg atttagcttc tgcaagttca    3660
tcagcttcct ccctaatttt agcgttcaac aaaacttcgt cgtcaaataa ccgtttggta    3720
taagaacctt ctggagcatt gctcttacga tcccacaagg tgcttccatg gctctaagac    3780
cctttgattg gccaaaacag gaagtgcgtt ccaagtgaca gaaaccaaca cctgtttgtt    3840
caaccacaaa tttcaagcag tctccatcac aatccaattc gatcccagc aacttttgag    3900
ttcgtccaga tgtagcacct ttataccaca aaccgtgacg acgagattgg tagactccag    3960
tttgtgtcct tatagcctcc ggaatagact ttttggacga gtacaccagg cccaacgagt    4020
aattagaaga gtcagccacc aaagtagtga atagaccatc ggggcggtca gtagtcaaag    4080
```

```
acgccaacaa aatttcactg acagggaact ttttgacatc ttcagaaagt tcgtattcag    4140
tagtcaattg ccgagcatca ataatgggga ttataccaga agcaacagtg gaagtcacat    4200
ctaccaactt tgcggtctca gaaaaagcat aaacagttct actaccgcca ttagtgaaac    4260
ttttcaaatc gcccagtgga gaagaaaaag gcacagcgat actagcatta gcgggcaagg    4320
atgcaacttt atcaaccagg gtcctataga taacccctagc gcctgggatc atcctttgga    4380
caactctttc tgccaaatct aggtccaaaa tcacttcatt gataccatta tacggatgac    4440
tcaacttgca cattaacttg aagctcagtc gattgagtga acttgatcag gttgtgcagc    4500
tggtcagcag catagggaaa cacggctttt cctaccaaac tcaaggaatt atcaaactct    4560
gcaacacttg cgtatgcagg tagcaaggga aatgtcatac ttgaagtcgg acagtgagtg    4620
tagtcttgag aaattctgaa gccgtatttt tattatcagt gagtcagtca tcaggagatc    4680
ctctacgccg gacgcatcgt ggccggcatc accggcgcca caggtgcggt tgctggcgcc    4740
tatatcgccg acatcaccga tggggaagat cgggctcgcc acttcgggct catgagcgct    4800
tgtttcggcg tgggtatggt ggcaggcccc gtggccgggg gactgttggg cgccatctcc    4860
ttgcatgcac cattccttgc ggcggcggtg ctcaacggcc tcaacctact actgggctgc    4920
ttcctaatgc aggagtcgca taagggagag cgtcgagtat ctatgattgg aagtatggga    4980
atggtgatac ccgcattctt cagtgtcttg aggtctccta tcagattatg cccaactaaa    5040
gcaaccggag gaggagattt catggtaaat ttctctgact tttggtcatc agtagactcg    5100
aactgtgaga ctatctcggt tatgacagca gaaatgtcct tcttggagac agtaaatgaa    5160
gtcccaccaa taaagaaatc cttgttatca ggaacaaact tcttgtttcg aacttttttcg   5220 gtgccttgaa ctataaaatg tagagtggat atgtcgggta ggaatggagc gggcaaatgc    5280
ttaccttctg gaccttcaag aggtatgtag ggtttgtaga tactgatgcc aacttcagtg    5340
acaacgttgc tatttcgttc aaaccattcc gaatccagag aaatcaaagt tgtttgtcta    5400
ctattgatcc aagccagtgc ggtcttgaaa ctgacaatag tgtgctcgtg ttttgaggtc    5460
atctttgtat gaataaatct agtctttgat ctaaataatc ttgacgagcc aaggcgataa    5520 atcccaaat ctaaaactct tttaaaacgt taaaaggaca agtatgtctg cctgtattaa      5580
accccaaatc agctcgtagt ctgatcctca tcaacttgag gggcactatc ttgttttaga    5640
gaaatttgcg gagatgcgat atcgagaaaa aggtacgctg attttaaacg tgaaatttat    5700
ctcaagatcg cggccgcgat ctcgaataat aactgttatt tttcagtgtt cccgatctgc    5760
gtctatttca caataccaac atgagtcagc ttatcgtgata aagctgtca aacatgagaa    5820 ttaattcgat gataagctgt caaacatgag aaatcttgaa gacgaaaggg cctcgtgata    5880
cgcctatttt tataggttaa tgtcatgata ataatggttt cttagacgtc aggtggcact    5940
tttcggggaa atgtgcgcgg aacccctatt tgtttatttt tctaaataca ttcaaatatg    6000
tatccgctca tgagacaata accctgataa atgcttcaat aatattgaaa aaggaagagt    6060
atgagtattc aacatttccg tgtcgccctt attcccttt ttgcggcatt ttgccttcct      6120 gttttgctc acccagaaac gctggtgaaa gtaaaagatg ctgaagatca gttgggtgca     6180
cgagtgggtt acatcgaact ggatctcaac agcggtaaga tccttgagag ttttcgcccc    6240
gaagaacgtt ttccaatgat gagcactttt aaagttctgc tatgtggcgc ggtattatcc    6300
cgtgttgacg ccgggcaaga gcaactcggt cgccgcatac actattctca gaatgacttg    6360
gttgagtact caccagtcac agaaaagcat cttacggatg gcatgacagt aagagaatta    6420
tgcagtgctg ccataaccat gagtgataac actgcggcca acttacttct gacaacgatc    6480
```

```
ggaggaccga aggagctaac cgcttttttg cacaacatgg gggatcatgt aactcgcctt      6540
gatcgttggg aaccggagct gaatgaagcc ataccaaacg acgagcgtga caccacgatg      6600
cctgcagcaa tggcaacaac gttgcgcaaa ctattaactg gcgaactact tactctagct      6660
tcccggcaac aattaataga ctggatggag gcggataaag ttgcaggacc acttctgcgc      6720
tcggcccttc cggctggctg gtttattgct gataaatctg gagccggtga gcgtgggtct      6780
cgcggtatca ttgcagcact ggggccagat ggtaagccct cccgtatcgt agttatctac      6840
acgacgggga gtcaggcaac tatggatgaa cgaaatagac agatcgctga gataggtgcc      6900
tcactgatta agcattggta actgtcagac caagtttact catatatact ttagattgat      6960
ttaaattgta aacgttaata ttttgttaaa attcgcgtta aattttttgtt aaatcagctc      7020 attttttaac caataggccg aaatcggcaa aatcccttat aaatcaaaag aatagaccga      7080 gataggttg agtgttgttc cagtttggaa caagagtcca ctattaaaga acgtggactc      7140
caacgtcaaa gggcgaaaaa ccgtctatca gggcgatggc ccactacgtg aaccatcacc      7200
ctaatcaagt tttttggggt cgaggtgccg taaagcacta atcggaaccc ctaaagggag      7260
cccccgattt agagcttgac ggggaaagcc ggcgaacgtg gcgagaaagg aagggaagaa      7320
agcgaaagga gcgggcgcta gggcgctggc aagtgtagcg gtcacgctgc gcgtaaccac      7380
cacacccgcc gcgcttaatg cgccgctaca gggcgcgtaa aaggatctag gtgaagatcc      7440
tttttgataa tctcatgacc aaaatccctt aacgtgagtt ttcgttccac tgagcgtcag      7500
accccgtaga aaagatcaaa ggatcttctt gagatccttt ttttctgcgc gtaatctgct      7560
gcttgcaaac aaaaaaacca ccgctaccag cggtggtttg tttgccggat caagagctac      7620
caactctttt tccgaaggta actggcttca gcagagcgca gataccaaat actgtccttc      7680
tagtgtagcc gtagttaggc caccacttca agaactctgt agcaccgcct acatacctcg      7740
ctctgctaat cctgttacca gtggctgctg ccagtggcga taagtcgtgt cttaccgggt      7800
tggactcaag acgatagtta ccggataagg cgcagcggtc gggctgaacg gggggttcgt      7860
gcacacagcc cagcttggag cgaacgacct acaccgaact gagatacccta cagcgtgagc      7920 attgagaaag cgccacgctt cccgaaggga gaaaggcgga caggtatccg gtaagcggca      7980
gggtcggaac aggagagcgc acgagggagc ttccaggggg aaacgcctgg tatctttata      8040
gtcctgtcgg gtttcgccac ctctgacttg agcgtcgatt tttgtgatgc tcgtcagggg      8100
ggcggagcct atgaaaaaac gccagcaacg cggccttttt acggttcctg gccttttgct      8160
ggccttttgc tcacatgttc tttcctgcgt tatcccctga ttctgtggat aaccgtatta      8220
ccgcctttga gtgagctgat accgctcgcc gcagccgaac gaccgagcgc agcgagtcag      8280
tgagcgagga agcggaagag cgcctgatgc ggtattttct ccttacgcat ctgtgcggta      8340
tttcacaccg catatggtgc actctcagta caatctgctc tgatgccgca tagttaagcc      8400
agtatacact ccgctatcgc tacgtgactg ggtcatggct gcgccccgac acccgccaac      8460
acccgctgac gcgccctgac gggcttgtct gctcccggca tccgcttaca gacaagctgt      8520
gaccgtctcc gggagctgca tgtgtcagag gttttcaccg tcatcaccga aacgcgcgag      8580
gcag                                                                  8584
```

<210> SEQ ID NO 72
<211> LENGTH: 141
<212> TYPE: PRT
<213> ORGANISM: Artificial Sequence
<220> FEATURE:

-continued

<223> OTHER INFORMATION: Plasmid pHIL-D2 (MFalphaPrePro::EPI-HNE-3)

<400> SEQUENCE: 72

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Ala Ala Cys Asn Leu Pro Ile Val Arg Gly Pro
                85                  90                  95

Cys Ile Ala Phe Phe Pro Arg Trp Ala Phe Asp Ala Val Lys Gly Lys
            100                 105                 110

Cys Val Leu Phe Pro Tyr Gly Gly Cys Gln Gly Asn Gly Asn Lys Phe
        115                 120                 125

Tyr Ser Glu Lys Glu Cys Arg Glu Tyr Cys Gly Val Pro
    130                 135                 140
```

<210> SEQ ID NO 73
<211> LENGTH: 444
<212> TYPE: DNA
<213> ORGANISM: Artificial Sequence
<220> FEATURE:
<223> OTHER INFORMATION: BstBI-AatII-EcoRI cassette for expression of Epi-HNE-4

<400> SEQUENCE: 73

```
ttcgaaacga tgagattccc atctatcttc actgctgttt tgttcgctgc ttcctctgct      60
ttggctgctc cagttaacac cactactgaa gacgagactg ctcaaattcc tgctgaggct    120
gtcatcggtt actctgactt ggaaggtgac ttcgacgtcg ctgttttgcc attctctaac    180
tctactaaca acggtttgtt gttcatcaac actaccatcg cttctatcgc tgctaaggag    240
gaaggtgttt ccttggacaa gagagaggct tgtaacttgc caatcgtcag aggtccatgc    300
attgctttct cccaagatg gctttcgac gctgttaagg gtaagtgcgt cttgttccca     360
tacggtggtt gtcaaggtaa cggtaacaag ttctactctg agaaggagtg tagagagtac    420
tgtggtgttc catagtaaga attc                                           444
```

<210> SEQ ID NO 74
<211> LENGTH: 141
<212> TYPE: PRT
<213> ORGANISM: Artificial Sequence
<220> FEATURE:
<223> OTHER INFORMATION: BstBI-AatII-EcoRI cassette for expression of Epi-HNE-4

<400> SEQUENCE: 74

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
```

```
            50                  55                  60
Phe Ile Asn Thr Thr Ile Ala Ser Ile Ala Ala Lys Glu Glu Gly Val
 65                  70                  75                  80

Ser Leu Asp Lys Arg Glu Ala Cys Asn Leu Pro Ile Val Arg Gly Pro
                 85                  90                  95

Cys Ile Ala Phe Phe Pro Arg Trp Ala Phe Asp Ala Val Lys Gly Lys
                100                 105                 110

Cys Val Leu Phe Pro Tyr Gly Cys Gln Gly Asn Gly Asn Lys Phe
            115                 120                 125

Tyr Ser Glu Lys Glu Cys Arg Glu Tyr Cys Gly Val Pro
        130                 135                 140

<210> SEQ ID NO 75
<211> LENGTH: 8590
<212> TYPE: DNA
<213> ORGANISM: Artificial Sequence
<220> FEATURE:
<223> OTHER INFORMATION: pD2pick (MFalphaPrePro::EPI-NHE-3) circular
      dsDNA

<400> SEQUENCE: 75
agatcgcggc cgcgatctaa catccaaaga cgaaaggttg aatgaaacct ttttgccatc      60
cgacatccac aggtccattc tcacacataa gtgccaaacg caacaggagg ggatacacta    120
gcagcagacc gttgcaaacg caggacctcc actcctcttc tcctcaacac ccacttttgc    180
catcgaaaaa ccagcccagt tattgggctt gattggagct cgctcattcc aattccttct    240
attaggctac taacaccatg actttattag cctgtctatc ctggcccccc tggcgaggtc    300
atgtttgttt atttccgaat gcaacaagct ccgcattaca cccgaacatc actccagatg    360
agggctttct gagtgtgggg tcaaatagtt tcatgttccc aaatggccca aaactgacag    420
tttaaacgct gtcttggaac ctaatatgac aaaagcgtga tctcatccaa gatgaactaa    480
gtttggttcg ttgaaatgct aacggccagt tggtcaaaaa gaaacttcca aaagtcgcca    540
taccgtttgt cttgtttggt attgattgac gaatgctcaa aaataatctc attaatgctt    600
agcgcagtct ctctatcgct tctgaacccg gtggcacctg tgccgaaacg caaatgggga    660
aacaacccgc tttttggatg attatgcatt gtcctccaca ttgtatgctt ccaagattct    720
ggtgggaata ctgctgatag cctaacgttc atgatcaaaa tttaactgtt ctaaccccta    780
cttgacaggc aatatataaa cagaaggaag ctgccctgtc ttaaaccttt ttttttatca    840
tcattattag cttactttca taattgcgac tggttccaat tgacaagctt ttgattttaa    900
cgacttttaa cgacaacttg agaagatcaa aaaacaacta attattcgaa acgatgagat    960
tcccatctat cttcactgct gttttgttcg ctgcttcctc tgctttggct gctccagtta  1020
acaccactac tgaagacgag actgctcaaa ttcctgctga ggctgtcatc ggttactctg  1080
acttggaagg tgacttcgac gtcgctgttt tgccattctc taactctact aacaacggtt  1140
tgttgttcat caacactacc atcgcttcta tcgctgctaa ggaggaaggt gtttccttgg  1200
acaagagagc tgcttgtaac ttgccaatcg tcagaggtcc atgcattgct tcttccccaa  1260
gatgggcttt cgacgctgtt aagggtaagt gcgtcttgtt cccatacggt ggttgtcaag  1320
gtaacggtaa caagttctac tctgagaagg agtgtagaga gtactgtggt gttccatagt  1380
aagaattcgc cttagacatg actgttcctc agttcaagtt gggcattacg agaagaccgg  1440
tcttgctaga ttctaatcaa gaggatgtca gaatgccatt tgcctgagag atgcaggctt  1500
cattttgat acttttttat ttgtaaccta tatagtatag gatttttttt gtcatttgt   1560
```

-continued

```
ttcttctcgt acgagcttgc tcctgatcag cctatctcgc agctgatgaa tatcttgtgg    1620
tagggctttg ggaaaatcat tcgagtttga tgttttcctt ggtatttccc actcctcttc    1680
agagtacaga agattaagtg agaagttcgt ttgtgcaagc ttatcgataa gctttaatgc    1740
ggtagtttat cacagttaaa ttgctaacgc agtcaggcac cgtgtatgaa atctaacaat    1800
gcgctcatcg tcatcctcgg caccgtcacc ctggatgctg taggcatagg cttggttatg    1860
ccggtactgc cgggcctctt gcgggatatc gtccattccg acagcatcgc cagtcactat    1920
ggcgtgctgc tagcgctata tgcgttgatg caatttctat gcgcacccgt tctcggagca    1980
ctgtccgacc gctttggccg ccgcccagtc ctgctcgctt cgctacttgg agccactatc    2040
gactacgcga tcatggcgac cacacccgtc ctgtggatct atcgaatcta atgtaagtt    2100
aaaatctcta ataattaaa taagtcccag tttctccata cgaaccttaa cagcattgcg    2160
gtgagcatct agaccttcaa cagcagccag atccatcact gcttggccaa tatgtttcag    2220
tccctcagga gttacgtctt gtgaagtgat gaacttctgg aaggttgcag tgttaactcc    2280
gctgtattga cggcatatc cgtacgttgg caaagtgtgg ttggtaccgg aggagtaatc    2340
tccacaactc tctggagagt aggcaccaac aaacacagat ccagcgtgtt gtacttgatc    2400
aacataagaa gaagcattct cgatttgcag gatcaagtgt tcaggagcgt actgattgga    2460
catttccaaa gcctgctcgt aggttgcaac cgatagggtt gtagagtgtg caatacactt    2520
gcgtacaatt tcaacccttg gcaactgcac agcttggttg tgaacagcat cttcaattct    2580
ggcaagctcc ttgtctgtca tatcgacagc caacagaatc acctgggaat caataccatg    2640
ttcagcttga gcagaaggtc tgaggcaacg aaatctggat cagcgtattt atcagcaata    2700
actagaactt cagaaggccc agcaggcatg tcaatactac acagggctga tgtgtcattt    2760
tgaaccatca tcttggcagc agtaacgaac tggtttcctg gaccaaatat tttgtcacac    2820
ttaggaacag tttctgttcc gtaagccata gcagctactg cctgggcgcc tcctgctagc    2880
acgatacact tagcaccaac cttgtgggca acgtagatga cttctggggt aagggtacca    2940
tccttcttag gtgagatgc aaaaacaatt tctttgcaac cagcaacttt ggcaggaaca    3000
cccagcatca gggaagtgga aggcagaatt gcggttccac caggaatata gaggccaact    3060
ttctcaatag gtcttgcaaa acgagagcag actacaccag ggcaagtctc aacttgcaac    3120
gtctccgtta gttgagcttc atggaatttc ctgacgttat ctatagagag atcaatggct    3180
ctcttaacgt tatctggcaa ttgcataagt tcctctggga aggagcttc taacacaggt    3240
gtcttcaaag cgactccatc aaacttggca gttagttcta aaagggcttt gtcaccattt    3300
tgacgaacat tgtcgacaat tggtttgact aattccataa tctgttccgt tttctggata    3360
ggacgacgaa gggcatcttc aatttcttgt gaggaggcct tagaaacgtc aatttttgcac    3420
aattcaatac gaccttcaga agggacttct ttaggtttgg attcttcttt aggttgttcc    3480
ttggtgtatc ctggcttggc atctccttc cttctagtga cctttaggga cttcatatcc    3540
aggtttctct ccacctcgtc caacgtcaca ccgtacttgg cacatctaac taatgcaaaa    3600
taaaataagt cagcacattc ccaggctata tcttccttgg atttagcttc tgcaagttca    3660
tcagcttcct ccctaatttt agcgttcaac aaaacttcgt cgtcaaataa ccgtttggta    3720
taagaacctt ctgctgagcatt gctcttacga tcccacaagg tgcttccatg gctctaagac    3780
cctttgattg gccaaaacag gaagtgcgtt ccaagtgaca gaaaccaaca cctgtttgtt    3840
caaccacaaa tttcaagcag tctccatcac aatccaattc gatacccagc aacttttgag    3900
```

```
ttcgtccaga tgtagcacct ttataccaca aaccgtgacg acgagattgg tagactccag    3960
tttgtgtcct tatagcctcc ggaatagact ttttggacga gtacaccagg cccaacgagt    4020
aattagaaga gtcagccacc aaagtagtga atagaccatc ggggcggtca gtagtcaaag    4080
acgccaacaa aatttcactg acagggaact ttttgacatc ttcagaaagt tcgtattcag    4140
tagtcaattg ccgagcatca ataatgggga ttataccaga agcaacagtg gaagtcacat    4200
ctaccaactt tgcggtctca gaaaaagcat aaacagttct actaccgcca ttagtgaaac    4260
ttttcaaatc gcccagtgga gaagaaaaag gcacagcgat actagcatta gcgggcaagg    4320
atgcaacttt atcaaccagg gtcctataga taaccctagc gcctgggatc atcctttgga    4380
caactctttc tgccaaatct aggtccaaaa tcacttcatt gataccatta tacggatgac    4440
tcaacttgca cattaacttg aagctcagtc gattgagtga acttgatcag gttgtgcagc    4500
tggtcagcag catagggaaa cacggctttt cctaccaaac tcaaggaatt atcaaactct    4560
gcaacacttg cgtatgcagg tagcaaggga aatgtcatac ttgaagtcgg acagtgagtg    4620
tagtcttgag aaattctgaa gccgtatttt tattatcagt gagtcagtca tcaggagatc    4680
ctctacgccg gacgcatcgt ggccggcatc accggcgcca caggtgcggt tgctggcgcc    4740
tatatcgccg acatcaccga tggggaagat cgggctcgcc acttcgggct catgagcgct    4800
tgtttcggcg tgggtatggt ggcaggcccc gtggccgggg gactgttggg cgccatctcc    4860
ttgcatgcac cattccttgc ggcggcggtg ctcaacggcc tcaacctact actgggctgc    4920
ttcctaatgc aggagtcgca taaggggagg cgtcgagtat ctatgattgg aagtatggga    4980
atggtgatac ccgcattctt cagtgtcttg aggtctccta tcagattatg cccaactaaa    5040
gcaaccggag gaggagattt catggtaaat ttctctgact tttggtcatc agtagactcg    5100
aactgtgaga ctatctcggt tatgacagca gaaatgtcct tcttggagac agtaaatgaa    5160 gtccccaccaa taaagaaatc cttgttatca ggaacaaact tcttgtttcg cgaacttttt    5220
cggtgccttg aactataaaa tgtagagtgg atatgtcggg taggaatgga gcgggcaaat    5280
gcttaccttc tggaccttca agaggtatgt agggtttgta gatactgatg ccaacttcag    5340
tgacaacgtt gctatttcgt tcaaaccatt ccgaatccag agaaatcaaa gttgtttgtc    5400
tactattgat ccaagccagt gcggtcttga aactgacaat agtgtgctcg tgttttgagg    5460
tcatctttgt atgaataaat ctagtctttg atctaaataa tcttgacgag ccaaggcgat    5520
aaatacccaa atctaaaact cttttaaaac gttaaaagga caagtatgtc tgcctgtatt    5580
aaaccccaaa tcagctcgta gtctgatcct catcaacttg aggggcacta tcttgtttta    5640
gagaaatttg cggagatgcg atatcgagaa aaagtacgc tgattttaaa cgtgaaattt    5700
atctcaagat cgcggccgcg atctcgaata ataactgtta ttttcagtg ttcccgatct    5760 gcgtctattt cacaatacca acatgagtca gcttatcgat gataagctgt caaacatgag    5820
aattaattcg atgataagct gtcaaacatg agaaatcttg aagacgaaag ggcctcgtga    5880
tacgcctatt tttataggtt aatgtcatga taataatggt ttcttagacg tacgtcaggt    5940
ggcacttttc ggggaaatgt gcgcggaacc cctatttgtt tatttttcta aatacattca    6000
aatatgtatc cgctcatgag acaataaccc tgataaatgc ttcaataata ttgaaaaagg    6060
aagagtatga gtattcaaca tttccgtgtc gcccttattc ccttttttgc ggcattttgc    6120
cttcctgttt ttgctcaccc agaaacgctg gtgaaagtaa agatgctga agatcagttg    6180 ggtgcacgag tgggttacat cgaactggat ctcaacagcg gtaagatcct tgagagtttt    6240
cgccccgaag aacgttttcc aatgatgagc acttttaaag ttctgctatg tggcgcggta    6300
```

-continued

```
ttatcccgtg ttgacgccgg gcaagagcaa ctcggtcgcc gcatacacta ttctcagaat     6360
gacttggttg agtactcacc agtcacagaa aagcatctta cggatggcat gacagtaaga     6420
gaattatgca gtgctgccat aaccatgagt gataacactg cggccaactt acttctgaca     6480
acgatcggag gaccgaagga gctaaccgct tttttgcaca acatggggga tcatgtaact     6540
cgccttgatc gttgggaacc ggagctgaat gaagccatac caaacgacga gcgtgacacc     6600
acgatgcctg cagcaatggc aacaacgttg cgcaaactat taactggcga actacttact     6660
ctagcttccc ggcaacaatt aatagactgg atggaggcgg ataaagttgc aggaccactt     6720
ctgcgctcgg cccttccggc tggctggttt attgctgata atctggagc cggtgagcgt     6780 gggtctcgcg gtatcattgc agcactgggg ccagatggta agccctcccg tatcgtagtt     6840
atctacacga cggggagtca ggcaactatg gatgaacgaa atagacagat cgctgagata     6900
ggtgcctcac tgattaagca ttggtaactg tcagaccaag tttactcata tactttag      6960 attgatttaa attgtaaacg ttaatatttt gttaaaattc gcgttaaatt tttgttaaat     7020
cagctcattt tttaaccaat aggccgaaat cggcaaaatc ccttataaat caaaagaata     7080
gaccgagata gggttgagtg ttgttccagt ttggaacaag agtccactat taaagaacgt     7140
ggactccaac gtcaaagggc gaaaaaccgt ctatcagggc gatggcccac tacgtgaacc     7200
atcaccctaa tcaagttttt tggggtcgag gtgccgtaaa gcactaaatc ggaaccctaa     7260
agggagcccc cgatttagag cttgacgggg aaagccggcg aacgtggcga aaaggaagg     7320 gaagaaagcg aaaggagcgg gcgctagggc gctggcaagt gtagcggtca cgctgcgcgt     7380
aaccaccaca cccgccgcgc ttaatgcgcc gctacagggc gcgtaaaagg atctaggtga     7440 agatccttt tgataatctc atgaccaaaa tcccttaacg tgagttttcg ttccactgag     7500
cgtcagaccc cgtagaaaag atcaaaggat cttcttgaga tcctttttt ctgcgcgtaa     7560 tctgctgctt gcaaacaaaa aaaccaccgc taccagcggt ggtttgtttg ccggatcaag     7620
agctaccaac tctttttccg aaggtaactg gcttcagcag agcgcagata ccaaatactg     7680
tccttctagt gtagccgtag ttaggccacc acttcaagaa ctctgtagca ccgcctacat     7740
acctcgctct gctaatcctg ttaccagtgg ctgctgccag tggcgataag tcgtgtctta     7800
ccgggttgga ctcaagacga tagttaccgg ataaggcgca gcggtcgggc tgaacgggg     7860 gttcgtgcac acagcccagc ttggagcgaa cgacctacac cgaactgaga tacctacagc     7920
gtgagcattg agaaagcgcc acgcttcccg aagggagaaa ggcggacagg tatccggtaa     7980
gcggcagggt cggaacagga gagcgcacga gggagcttcc agggggaaac gcctggtatc     8040
tttatagtcc tgtcgggttt cgccacctct gacttgagcg tcgatttttg tgatgctcgt     8100
caggggggcg gagcctatgg aaaaacgcca gcaacgcggc cttttacgg ttcctggcct     8160 tttgctggcc ttttgctcac atgttctttc ctgcgttatc ccctgattct gtggataacc     8220
gtattaccgc ctttgagtga gctgataccg ctcgccgcag ccgaacgacc gagcgcagcg     8280
agtcagtgag cgaggaagcg gaagagcgcc tgatgcggta ttttctcctt acgcatctgt     8340
gcggtatttc acaccgcata tggtgcactc tcagtacaat ctgctctgat gccgcatagt     8400
taagccagta tacactccgc tatcgctacg tgactgggtc atggctgcgc ccgacaccc      8460 gccaacaccc gctgacgcgc cctgacgggc ttgtctgctc ccggcatccg cttacagaca     8520
agctgtgacc gtctccggga gctgcatgtg tcagaggttt tcaccgtcat caccgaaacg     8580
cgcgaggcag                                                           8590
```

```
<210> SEQ ID NO 76
<211> LENGTH: 141
<212> TYPE: PRT
<213> ORGANISM: Artificial Sequence
<220> FEATURE:
<223> OTHER INFORMATION: EPI-HNE-3 fusion protein

<400> SEQUENCE: 76
```

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Lys Glu Glu Gly Val
65                  70                  75                  80

Ser Leu Asp Lys Arg Ala Ala Cys Asn Leu Pro Ile Val Arg Gly Pro
                85                  90                  95

Cys Ile Ala Phe Phe Pro Arg Trp Ala Phe Asp Ala Val Lys Gly Lys
            100                 105                 110

Cys Val Leu Phe Pro Tyr Gly Gly Cys Gln Gly Asn Gly Asn Lys Phe
        115                 120                 125

Tyr Ser Glu Lys Glu Cys Arg Glu Tyr Cys Gly Val Pro
    130                 135                 140

```
<210> SEQ ID NO 77
<211> LENGTH: 147
<212> TYPE: PRT
<213> ORGANISM: Homo sapiens

<400> SEQUENCE: 77
```

Ala Val Leu Pro Gln Glu Glu Gly Ser Gly Gly Gly Gln Leu Val
1               5                   10                  15

Thr Glu Val Thr Lys Lys Glu Asp Ser Cys Gln Leu Gly Tyr Ser Ala
            20                  25                  30

Gly Pro Cys Met Gly Met Thr Ser Arg Tyr Phe Tyr Asn Gly Thr Ser
        35                  40                  45

Met Ala Cys Glu Thr Phe Gln Tyr Gly Gly Cys Met Gly Asn Gly Asn
    50                  55                  60

Asn Phe Val Thr Glu Lys Glu Cys Leu Gln Thr Cys Arg Thr Val Ala
65                  70                  75                  80

Ala Cys Asn Leu Pro Ile Val Arg Gly Pro Cys Arg Ala Phe Ile Gln
                85                  90                  95

Leu Trp Ala Phe Asp Ala Val Lys Gly Lys Cys Val Leu Phe Pro Tyr
            100                 105                 110

Gly Gly Cys Gln Gly Asn Gly Asn Lys Phe Tyr Ser Glu Lys Glu Cys
        115                 120                 125

Arg Glu Tyr Cys Gly Val Pro Gly Asp Gly Asp Glu Glu Leu Leu Arg
    130                 135                 140

Phe Ser Asn
145

```
<210> SEQ ID NO 78
<211> LENGTH: 249
<212> TYPE: DNA
```

-continued

<213> ORGANISM: Artificial Sequence
<220> FEATURE:
<223> OTHER INFORMATION: M13_III_signal::Human_LACI-D2::mature_M13_III

<400> SEQUENCE: 78

```
atgaagaagc ttctcttcgc cattcctctg gtggtaccttt tctattccgg cgccaagcct    60
gacttctgct tcctcgagga ggatcccggg atttgccgcg gttatattac gcgttatttc   120
tataataacc agactaagca atgtgagcgg ttcaagtatg tggttgcct aggtaatatg    180 aacaacttcg agactctaga agagtgtaag aacatatgtg aggatggtgg tgctgagact   240
gttgagtct                                                            249
```

<210> SEQ ID NO 79
<211> LENGTH: 83
<212> TYPE: PRT
<213> ORGANISM: Artificial Sequence
<220> FEATURE:
<223> OTHER INFORMATION: LACI-D2 fusion protein

<400> SEQUENCE: 79

```
Met Lys Lys Leu Leu Phe Ala Ile Pro Leu Val Val Pro Phe Tyr Ser
 1               5                  10                  15

Gly Ala Lys Pro Asp Phe Cys Phe Leu Glu Glu Asp Pro Gly Ile Cys
             20                  25                  30

Arg Gly Tyr Ile Thr Arg Tyr Phe Tyr Asn Asn Gln Thr Lys Gln Cys
         35                  40                  45

Glu Arg Phe Lys Tyr Gly Gly Cys Leu Gly Asn Met Asn Asn Phe Glu
     50                  55                  60

Thr Leu Glu Glu Cys Lys Asn Ile Cys Glu Asp Gly Gly Ala Glu Thr
 65                  70                  75                  80

Val Glu Ser
```

<210> SEQ ID NO 80
<211> LENGTH: 189
<212> TYPE: DNA
<213> ORGANISM: Artificial Sequence
<220> FEATURE:
<223> OTHER INFORMATION: laci-d1 with cloning sites

<400> SEQUENCE: 80

```
gcggccgaga tgcattcctt ctgcgctttc aaagctgatg acggtccgtg taaagctatc    60
atgaaacgtt tcttcttcaa catttttcacg cgtcagtgcg aggaattcat ttacggtggt   120
tgtgaaggta accagaaccg gttcgaatct ctagaggaat gtaagaagat gtgcactcgt   180
gacggcgcc                                                            189
```

<210> SEQ ID NO 81
<211> LENGTH: 63
<212> TYPE: PRT
<213> ORGANISM: Artificial Sequence
<220> FEATURE:
<223> OTHER INFORMATION: laci-d1 with linkers

<400> SEQUENCE: 81

```
Ala Ala Glu Met His Ser Phe Cys Ala Phe Lys Ala Asp Asp Gly Pro
 1               5                  10                  15

Cys Lys Ala Ile Met Lys Arg Phe Phe Phe Asn Ile Phe Thr Arg Gln
             20                  25                  30

Cys Glu Glu Phe Ile Tyr Gly Gly Cys Glu Gly Asn Gln Asn Arg Phe
         35                  40                  45
```

Glu Ser Leu Glu Glu Cys Lys Lys Met Cys Thr Arg Asp Gly Ala
 50                  55                  60

<210> SEQ ID NO 82
<211> LENGTH: 189
<212> TYPE: DNA
<213> ORGANISM: Artificial sequence
<220> FEATURE:
<223> OTHER INFORMATION: LACI-D1 hNE library
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (38)..(38)
<223> OTHER INFORMATION: n is a or g
<220> FEATURE:
<221> NAME/KEY: misc_feature
<222> LOCATION: (40)..(40)
<223> OTHER INFORMATION: n is a or g
<220> FEATURE:
<221> NAME/KEY: misc_feature
<222> LOCATION: (41)..(41)
<223> OTHER INFORMATION: n is a, c or g
<220> FEATURE:
<221> NAME/KEY: misc_feature
<222> LOCATION: (42)..(42)
<223> OTHER INFORMATION: n is c or g
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (52)..(52)
<223> OTHER INFORMATION: n is a or g
<220> FEATURE:
<221> NAME/KEY: misc_feature
<222> LOCATION: (56)..(56)
<223> OTHER INFORMATION: n is c or g
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (64)..(64)
<223> OTHER INFORMATION: n is a or c
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (66)..(66)
<223> OTHER INFORMATION: n is c or g
<220> FEATURE:
<221> NAME/KEY: misc_feature
<222> LOCATION: (71)..(71)
<223> OTHER INFORMATION: n is a, g or t
<220> FEATURE:
<221> NAME/KEY: misc_feature
<222> LOCATION: (72)..(72)
<223> OTHER INFORMATION: n is c or g
<220> FEATURE:
<221> NAME/KEY: misc_feature
<222> LOCATION: (100)..(100)
<223> OTHER INFORMATION: n is c or g
<220> FEATURE:
<221> NAME/KEY: misc_feature
<222> LOCATION: (101)..(101)
<223> OTHER INFORMATION: n is a or t
<220> FEATURE:
<221> NAME/KEY: misc_feature
<222> LOCATION: (103)..(103)
<223> OTHER INFORMATION: n is a, c or g -continued

```
<220> FEATURE:
<221> NAME/KEY: misc_feature
<222> LOCATION: (104)..(104)
<223> OTHER INFORMATION: n is a, c or t
<220> FEATURE:
<221> NAME/KEY: misc_feature
<222> LOCATION: (109)..(109)
<223> OTHER INFORMATION: n is a, c or g
<220> FEATURE:
<221> NAME/KEY: misc_feature
<222> LOCATION: (110)..(110)
<223> OTHER INFORMATION: n is a, c or t
<220> FEATURE:
<221> NAME/KEY: misc_feature
<222> LOCATION: (124)..(124)
<223> OTHER INFORMATION: n is a, c or g
<220> FEATURE:
<221> NAME/KEY: misc_feature
<222> LOCATION: (125)..(125)
<223> OTHER INFORMATION: n is a, c or t
<220> FEATURE:
<221> NAME/KEY: misc_feature
<222> LOCATION: (128)..(128)
<223> OTHER INFORMATION: n is c or g
<220> FEATURE:
<221> NAME/KEY: misc_feature
<222> LOCATION: (133)..(133)
<223> OTHER INFORMATION: n is c or g
<220> FEATURE:
<221> NAME/KEY: misc_feature
<222> LOCATION: (134)..(134)
<223> OTHER INFORMATION: n is a or g

<400> SEQUENCE: 82
gcggccgaga tgcattcctt ctgcgctttc aaagctnntn nnggtcnttg tnttgntntc      60
ttcnnncgtt nnttcttcaa cattttcacg cgtcagtgcn ngnnattcnn atacggtggt    120 tgtnggnta acnngaaccg gttcgaatct ctagaggaat gtaagaagat gtgcactcgt    180
gacggcgcc                                                            189

<210> SEQ ID NO 83
<211> LENGTH: 63
<212> TYPE: PRT
<213> ORGANISM: Artificial Sequence
<220> FEATURE:
<223> OTHER INFORMATION: LACI-D1 hNE library
<220> FEATURE:
<221> NAME/KEY: misc_feature
<222> LOCATION: (13)..(13)
<223> OTHER INFORMATION: Xaa is Cys, Arg, Ser, Gly, Tyr, His, Asp or Asn
<220> FEATURE:
<221> NAME/KEY: misc_feature
<222> LOCATION: (14)..(14)
<223> OTHER INFORMATION: Xaa is Thr, Asn, Lys, Arg, Ser, Ala, Glu, Gly
      or Asp
<220> FEATURE:
<221> NAME/KEY: misc_feature
<222> LOCATION: (16)..(16)
<223> OTHER INFORMATION: Xaa is His, Arg, Pro or Leu
<220> FEATURE:
<221> NAME/KEY: misc_feature
<222> LOCATION: (18)..(18)
<223> OTHER INFORMATION: Xaa is Val or Ile
<220> FEATURE:
<221> NAME/KEY: misc_feature
<222> LOCATION: (19)..(19)
<223> OTHER INFORMATION: Xaa is Ala or Gly
<220> FEATURE:
<221> NAME/KEY: misc_feature
<222> LOCATION: (20)..(20)
<223> OTHER INFORMATION: Xaa is Phe, Leu, Ile or Val
<220> FEATURE:
<221> NAME/KEY: misc_feature
<222> LOCATION: (22)..(22)
<223> OTHER INFORMATION: Xaa is Ser, Thr, Asn, Ile, Met, Gln, His, Leu,
```

```
        Pro, Lys or Arg
<220> FEATURE:
<221> NAME/KEY: misc_feature
<222> LOCATION: (24)..(24)
<223> OTHER INFORMATION: Xaa is Cys, Tyr, Trp, Phe or Leu
<220> FEATURE:
<221> NAME/KEY: misc_feature
<222> LOCATION: (34)..(34)
<223> OTHER INFORMATION: Xaa is Leu, Gln, Glu or Val
<220> FEATURE:
<221> NAME/KEY: misc_feature
<222> LOCATION: (35)..(35)
<223> OTHER INFORMATION: Xaa is Gln, Leu, Pro, Thr, Lys, Val, Ile, Glu
        or Ala
<220> FEATURE:
<221> NAME/KEY: misc_feature
<222> LOCATION: (37)..(37)
<223> OTHER INFORMATION: Xaa is Gln, Leu, Pro, Thr, Lys, Val, Glu, Ile
        or Ala
<220> FEATURE:
<221> NAME/KEY: misc_feature
<222> LOCATION: (42)..(42)
<223> OTHER INFORMATION: Xaa is Gln, Leu, Pro, Thr, Lys, Val, Met, Glu
        or Ala
<220> FEATURE:
<221> NAME/KEY: misc_feature
<222> LOCATION: (43)..(43)
<223> OTHER INFORMATION: Xaa is Gly or Ala
<220> FEATURE:
<221> NAME/KEY: misc_feature
<222> LOCATION: (45)..(45)
<223> OTHER INFORMATION: Xaa is Glu, Gly, Gln or Arg

<400> SEQUENCE: 83

Ala Ala Glu Met His Ser Phe Cys Ala Phe Lys Ala Xaa Xaa Gly Xaa
1               5                   10                  15

Cys Xaa Xaa Xaa Phe Xaa Arg Xaa Phe Phe Asn Ile Phe Thr Arg Gln
            20                  25                  30

Cys Xaa Xaa Phe Xaa Tyr Gly Gly Cys Xaa Xaa Asn Xaa Asn Arg Phe
        35                  40                  45

Glu Ser Leu Glu Glu Cys Lys Lys Met Cys Thr Arg Asp Gly Ala
    50                  55                  60

<210> SEQ ID NO 84
<211> LENGTH: 201
<212> TYPE: DNA
<213> ORGANISM: Artificial sequence
<220> FEATURE:
<223> OTHER INFORMATION: LACI-D2 hNE library
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (35)..(35)
<223> OTHER INFORMATION: n is a or g
<220> FEATURE:
<221> NAME/KEY: misc_feature
<222> LOCATION: (37)..(38)
<223> OTHER INFORMATION: n is a, c or g
<220> FEATURE:
<221> NAME/KEY: misc_feature
<222> LOCATION: (39)..(39)
<223> OTHER INFORMATION: n is c or g
<220> FEATURE:
<221> NAME/KEY: misc_feature
<222> LOCATION: (43)..(43)
<223> OTHER INFORMATION: n is a or c
<220> FEATURE:
<221> NAME/KEY: misc_feature
<222> LOCATION: (44)..(44)
<223> OTHER INFORMATION: n is a, c, g, or t
<220> FEATURE:
```

-continued

```
<221> NAME/KEY: misc_feature
<222> LOCATION: (49)..(49)
<223> OTHER INFORMATION: n is a or g
<220> FEATURE:
<221> NAME/KEY: misc_feature
<222> LOCATION: (53)..(53)
<223> OTHER INFORMATION: n is c or g
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (56)..(56)
<223> OTHER INFORMATION: n is a or t
<220> FEATURE:
<221> NAME/KEY: misc_feature
<222> LOCATION: (61)..(61)
<223> OTHER INFORMATION: n is a or c
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (63)..(63)
<223> OTHER INFORMATION: n is c or g
<220> FEATURE:
<221> NAME/KEY: misc_feature
<222> LOCATION: (68)..(68)
<223> OTHER INFORMATION: n is a, g or t
<220> FEATURE:
<221> NAME/KEY: misc_feature
<222> LOCATION: (69)..(69)
<223> OTHER INFORMATION: n is c or g
<220> FEATURE:
<221> NAME/KEY: misc_feature
<222> LOCATION: (97)..(97)
<223> OTHER INFORMATION: n is c or g
<220> FEATURE:
<221> NAME/KEY: misc_feature
<222> LOCATION: (98)..(98)
<223> OTHER INFORMATION: n is a or t
<220> FEATURE:
<221> NAME/KEY: misc_feature
<222> LOCATION: (100)..(100)
<223> OTHER INFORMATION: n is a, c or g
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, or g
<220> FEATURE:
<221> NAME/KEY: misc_feature
<222> LOCATION: (107)..(107)
<223> OTHER INFORMATION: n is a, c, or t
<220> FEATURE:
<221> NAME/KEY: misc_feature
<222> LOCATION: (121)..(121)
<223> OTHER INFORMATION: n is a, c, or g
<220> FEATURE:
<221> NAME/KEY: misc_feature
<222> LOCATION: (122)..(122)
<223> OTHER INFORMATION: n is a, c, or t
<220> FEATURE:
<221> NAME/KEY: misc_feature
<222> LOCATION: (125)..(125)
<223> OTHER INFORMATION: n is c or g
<220> FEATURE:
<221> NAME/KEY: misc_feature
<222> LOCATION: (130)..(130)
<223> OTHER INFORMATION: n is a, c or g
<220> FEATURE:
<221> NAME/KEY: misc_feature
<222> LOCATION: (131)..(131)
<223> OTHER INFORMATION: n is c, g or t
```

```
<400> SEQUENCE: 84
ggcgccaagc ctgacttctg cttcctcgag gagnntnnng ggnnttgcnt tgntnntttt      60
nnncgttnnt tctataataa ccaggctaag caatgtnngn nattcnnata tggtggttgc     120
nnggntaatn ngaacaactt cgagactcta gaagagtgta agaacatatg tgaggatggt     180
ggtgctgaga ctgttgagtc t                                              201
```

<210> SEQ ID NO 85
<211> LENGTH: 67
<212> TYPE: PRT
<213> ORGANISM: Artificial Sequence
<220> FEATURE:
<223> OTHER INFORMATION: LACI-D2 hNE library
<220> FEATURE:
<221> NAME/KEY: misc_feature
<222> LOCATION: (12)..(12)
<223> OTHER INFORMATION: Xaa is Cys, Arg, Ser, Gly, Tyr, His, Asp or Asn
<220> FEATURE:
<221> NAME/KEY: misc_feature
<222> LOCATION: (13)..(13)
<223> OTHER INFORMATION: Xaa is Pro, His, Thr, Asn, Lys, Arg, Ser, Ala,
      Glu, Gly, Asp or Gln
<220> FEATURE:
<221> NAME/KEY: misc_feature
<222> LOCATION: (15)..(15)
<223> OTHER INFORMATION: Xaa is His, Arg, Pro, Leu, Asn, Ser, Ile or Thr
<220> FEATURE:
<221> NAME/KEY: misc_feature
<222> LOCATION: (17)..(17)
<223> OTHER INFORMATION: Xaa is Val or Ile
<220> FEATURE:
<221> NAME/KEY: misc_feature
<222> LOCATION: (18)..(18)
<223> OTHER INFORMATION: Xaa is Gly or Ala
<220> FEATURE:
<221> NAME/KEY: misc_feature
<222> LOCATION: (19)..(19)
<223> OTHER INFORMATION: Xaa is Phe, Leu, Ile, Val, Tyr, His, Asn or Asp
<220> FEATURE:
<221> NAME/KEY: misc_feature
<222> LOCATION: (21)..(21)
<223> OTHER INFORMATION: Xaa is Ile, Asn, Gln, Met, Leu, His, Lys, Pro,
      Thr or Arg
<220> FEATURE:
<221> NAME/KEY: misc_feature
<222> LOCATION: (23)..(23)
<223> OTHER INFORMATION: Xaa is Cys, Phe, Leu, Tyr or Trp
<220> FEATURE:
<221> NAME/KEY: misc_feature
<222> LOCATION: (33)..(33)
<223> OTHER INFORMATION: Xaa is Leu, Gln, Glu or Val
<220> FEATURE:
<221> NAME/KEY: misc_feature
<222> LOCATION: (34)..(34)
<223> OTHER INFORMATION: Xaa is Gln, Gly, Leu, Pro, Thr, Lys, Val, Ile,
      Glu, Ala or Arg
<220> FEATURE:
<221> NAME/KEY: misc_feature
<222> LOCATION: (36)..(36)
<223> OTHER INFORMATION: Xaa is Gln, Leu, Pro, Thr, Val, Glu, Ile, Ala
      or Lys
<220> FEATURE:
<221> NAME/KEY: misc_feature
<222> LOCATION: (41)..(41)
<223> OTHER INFORMATION: Xaa is Gln, Pro, Thr, Lys, Val, Met, Glu, Ala
      or Leu
<220> FEATURE:
<221> NAME/KEY: misc_feature
<222> LOCATION: (42)..(42)
<223> OTHER INFORMATION: Xaa is Gly or Ala
<220> FEATURE:
<221> NAME/KEY: misc_feature
<222> LOCATION: (44)..(44)
<223> OTHER INFORMATION: Xaa is Arg, Gly, Lys, Glu, Leu, Gln, Met or Val -continued

<400> SEQUENCE: 85

Gly Ala Lys Pro Asp Phe Cys Phe Leu Glu Xaa Xaa Gly Xaa Cys
1               5                   10                  15

Xaa Xaa Xaa Phe Xaa Arg Xaa Phe Tyr Asn Asn Gln Ala Lys Gln Cys
            20                  25                  30

Xaa Xaa Phe Xaa Tyr Gly Gly Cys Xaa Xaa Asn Xaa Asn Asn Phe Glu
        35                  40                  45

Thr Leu Glu Glu Cys Lys Asn Ile Cys Glu Asp Gly Gly Ala Glu Thr
    50                  55                  60

Val Glu Ser
65

<210> SEQ ID NO 86
<211> LENGTH: 51
<212> TYPE: PRT
<213> ORGANISM: Artificial Sequence
<220> FEATURE:
<223> OTHER INFORMATION: definition of aprotonin-like Kunitz domain
      (p. 11)
<220> FEATURE:
<221> NAME/KEY: misc_feature
<222> LOCATION: (2)..(7)
<223> OTHER INFORMATION: Xaa is any amino acid
<220> FEATURE:
<221> NAME/KEY: misc_feature
<222> LOCATION: (9)..(9)
<223> OTHER INFORMATION: Xaa is any amino acid
<220> FEATURE:
<221> NAME/KEY: misc_feature
<222> LOCATION: (11)..(18)
<223> OTHER INFORMATION: Xaa is any amino acid
<220> FEATURE:
<221> NAME/KEY: misc_feature
<222> LOCATION: (19)..(19)
<223> OTHER INFORMATION: Xaa is any Tyr or Phe
<220> FEATURE:
<221> NAME/KEY: misc_feature
<222> LOCATION: (20)..(25)
<223> OTHER INFORMATION: Xaa is any amino acid
<220> FEATURE:
<221> NAME/KEY: misc_feature
<222> LOCATION: (27)..(28)
<223> OTHER INFORMATION: Xaa is any amino acid
<220> FEATURE:
<221> NAME/KEY: misc_feature
<222> LOCATION: (30)..(30)
<223> OTHER INFORMATION: Xaa is any amino acid
<220> FEATURE:
<221> NAME/KEY: misc_feature
<222> LOCATION: (31)..(31)
<223> OTHER INFORMATION: Xaa is Tyr, Trp or Phe
<220> FEATURE:
<221> NAME/KEY: misc_feature
<222> LOCATION: (32)..(32)
<223> OTHER INFORMATION: Xaa is any amino acid
<220> FEATURE:
<221> NAME/KEY: misc_feature
<222> LOCATION: (35)..(38)
<223> OTHER INFORMATION: Xaa is any amino acid
<220> FEATURE:
<221> NAME/KEY: misc_feature
<222> LOCATION: (39)..(39)
<223> OTHER INFORMATION: Xaa is Asn or Gly
<220> FEATURE:
<221> NAME/KEY: misc_feature
<222> LOCATION: (40)..(40)
<223> OTHER INFORMATION: Xaa is any amino acid
<220> FEATURE:
<221> NAME/KEY: misc_feature
<222> LOCATION: (41)..(41)
<223> OTHER INFORMATION: Xaa is Phe or Tyr
<220> FEATURE:

```
<221> NAME/KEY: misc_feature
<222> LOCATION: (42)..(46)
<223> OTHER INFORMATION: Xaa is any amino acid
<220> FEATURE:
<221> NAME/KEY: misc_feature
<222> LOCATION: (48)..(50)
<223> OTHER INFORMATION: Xaa is any amino acid

<400> SEQUENCE: 86

Cys Xaa Xaa Xaa Xaa Xaa Gly Xaa Cys Xaa Xaa Xaa Xaa Xaa
 1               5                  10                  15

Xaa Xaa Xaa Xaa Xaa Xaa Xaa Xaa Cys Xaa Xaa Phe Xaa Xaa Xaa
             20                  25                  30

Gly Cys Xaa Xaa Xaa Xaa Xaa Xaa Xaa Xaa Xaa Xaa Cys Xaa
         35                  40                  45

Xaa Xaa Cys
     50

<210> SEQ ID NO 87
<211> LENGTH: 58
<212> TYPE: PRT
<213> ORGANISM: Bos Taurus

<400> SEQUENCE: 87

Arg Pro Asp Phe Cys Leu Glu Pro Pro Tyr Thr Gly Pro Cys Lys Ala
 1               5                  10                  15

Arg Ile Ile Arg Tyr Phe Tyr Asn Ala Lys Ala Gly Leu Cys Gln Thr
             20                  25                  30

Phe Val Tyr Gly Gly Cys Arg Ala Lys Arg Asn Asn Phe Lys Ser Ala
         35                  40                  45

Glu Asp Cys Met Arg Thr Cys Gly Gly Ala
     50                  55

<210> SEQ ID NO 88
<211> LENGTH: 58
<212> TYPE: PRT
<213> ORGANISM: Artificial Sequence
<220> FEATURE:
<223> OTHER INFORMATION: Engineered B-PTI from MARK87

<400> SEQUENCE: 88

Arg Pro Asp Phe Cys Leu Glu Pro Pro Tyr Thr Gly Pro Thr Lys Ala
 1               5                  10                  15

Arg Ile Ile Arg Tyr Phe Tyr Asn Ala Lys Ala Gly Leu Cys Gln Thr
             20                  25                  30

Phe Val Tyr Gly Gly Thr Arg Ala Lys Arg Asn Asn Phe Lys Ser Ala
         35                  40                  45

Glu Asp Cys Met Arg Thr Cys Gly Gly Ala
     50                  55

<210> SEQ ID NO 89
<211> LENGTH: 58
<212> TYPE: PRT
<213> ORGANISM: Artificial Sequence
<220> FEATURE:
<223> OTHER INFORMATION: Engineered B-PTI from MARK87

<400> SEQUENCE: 89

Arg Pro Asp Phe Cys Leu Glu Pro Pro Tyr Thr Gly Pro Ala Lys Ala
 1               5                  10                  15

Arg Ile Ile Arg Tyr Phe Tyr Asn Ala Lys Ala Gly Leu Cys Gln Thr
             20                  25                  30
```

```
Phe Val Tyr Gly Gly Ala Arg Ala Lys Arg Asn Asn Phe Lys Ser Ala
            35                  40                  45

Glu Asp Cys Met Arg Thr Cys Gly Gly Ala
 50                  55

<210> SEQ ID NO 90
<211> LENGTH: 67
<212> TYPE: PRT
<213> ORGANISM: Bos taurus (Bovine Colostrum)

<400> SEQUENCE: 90

Phe Gln Thr Pro Pro Asp Leu Cys Gln Leu Pro Gln Ala Arg Gly Pro
  1               5                  10                  15

Cys Lys Ala Ala Leu Leu Arg Tyr Phe Tyr Asn Ser Thr Ser Asn Ala
             20                  25                  30

Cys Glu Pro Phe Thr Tyr Gly Gly Cys Gln Gly Asn Asn Asn Asn Phe
             35                  40                  45

Glu Thr Thr Glu Met Cys Leu Arg Ile Cys Glu Pro Pro Gln Gln Thr
 50                  55                  60

Asp Lys Ser
 65

<210> SEQ ID NO 91
<211> LENGTH: 60
<212> TYPE: PRT
<213> ORGANISM: Bos Taurus (Bovine serum)

<400> SEQUENCE: 91

Thr Glu Arg Pro Asp Phe Cys Leu Glu Pro Pro Tyr Thr Gly Pro Cys
  1               5                  10                  15

Lys Ala Ala Met Ile Arg Tyr Phe Tyr Asn Ala Lys Ala Gly Phe Cys
             20                  25                  30

Glu Thr Phe Val Tyr Gly Gly Cys Arg Ala Lys Ser Asn Asn Phe Lys
             35                  40                  45

Ser Ala Glu Asp Cys Met Arg Thr Cys Gly Gly Ala
 50                  55                  60

<210> SEQ ID NO 92
<211> LENGTH: 58
<212> TYPE: PRT
<213> ORGANISM: Artificial Sequence
<220> FEATURE:
<223> OTHER INFORMATION: Semisynthetic BPTI, TSCH87

<400> SEQUENCE: 92

Arg Pro Asp Phe Cys Leu Glu Pro Pro Tyr Thr Gly Pro Cys Val Ala
  1               5                  10                  15

Arg Ile Ile Arg Tyr Phe Tyr Asn Ala Lys Ala Gly Leu Cys Gln Thr
             20                  25                  30

Phe Val Tyr Gly Gly Cys Arg Ala Lys Arg Asn Asn Phe Lys Ser Ala
             35                  40                  45

Glu Asp Cys Met Arg Thr Cys Gly Gly Ala
 50                  55

<210> SEQ ID NO 93
<211> LENGTH: 58
<212> TYPE: PRT
<213> ORGANISM: Artificial Sequence
<220> FEATURE:
<223> OTHER INFORMATION: Semisynthetic BPTI, TSCH87
```

```
<400> SEQUENCE: 93

Arg Pro Asp Phe Cys Leu Glu Pro Pro Tyr Thr Gly Pro Cys Gly Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 94
<211> LENGTH: 58
<212> TYPE: PRT
<213> ORGANISM: Artificial Sequence
<220> FEATURE:
<223> OTHER INFORMATION: Semisynthetic BPTI, TSCH87

<400> SEQUENCE: 94

Arg Pro Asp Phe Cys Leu Glu Pro Pro Tyr Thr Gly Pro Cys Ala Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 95
<211> LENGTH: 58
<212> TYPE: PRT
<213> ORGANISM: Artificial Sequence
<220> FEATURE:
<223> OTHER INFORMATION: Semisynthetic BPTI, TSCH87

<400> SEQUENCE: 95

Arg Pro Asp Phe Cys Leu Glu Pro Pro Tyr Thr Gly Pro Cys Leu Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 96
<211> LENGTH: 58
<212> TYPE: PRT
<213> ORGANISM: Artificial Sequence
<220> FEATURE:
<223> OTHER INFORMATION: Semisynthetic BPTI, TSCH87

<400> SEQUENCE: 96

Arg Pro Asp Phe Cys Leu Glu Pro Pro Tyr Thr Gly Pro Cys Ile Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
```

<210> SEQ ID NO 97
<211> LENGTH: 58
<212> TYPE: PRT
<213> ORGANISM: Artificial Sequence
<220> FEATURE:
<223> OTHER INFORMATION: Engineered BPTI, AUER87

<400> SEQUENCE: 97

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Glu Arg Thr Cys Gly Gly Ala
    50                  55

<210> SEQ ID NO 98
<211> LENGTH: 60
<212> TYPE: PRT
<213> ORGANISM: Dendroaspis polylepis polylepis (Black mamba venom I)

<400> SEQUENCE: 98

Gln Pro Leu Arg Lys Leu Cys Ile Leu His Arg Asn Pro Gly Arg Cys
1               5                   10                  15

Tyr Gln Lys Ile Pro Ala Phe Tyr Tyr Asn Gln Lys Lys Lys Gln Cys
            20                  25                  30

Glu Gly Phe Thr Trp Ser Gly Cys Gly Gly Asn Ser Asn Arg Phe Lys
        35                  40                  45

Thr Ile Glu Glu Cys Arg Arg Thr Cys Ile Arg Lys
    50                  55                  60

<210> SEQ ID NO 99
<211> LENGTH: 57
<212> TYPE: PRT
<213> ORGANISM: Dendroaspis polylepis polylepis (Black mamba venom K)

<400> SEQUENCE: 99

Ala Ala Lys Tyr Cys Lys Leu Pro Leu Arg Ile Gly Pro Cys Lys Arg
1               5                   10                  15

Lys Ile Pro Ser Phe Tyr Tyr Lys Trp Lys Ala Lys Gln Cys Leu Pro
            20                  25                  30

Phe Asp Tyr Ser Gly Cys Gly Gly Asn Ala Asn Arg Phe Lys Thr Ile
        35                  40                  45

Glu Glu Cys Arg Arg Thr Cys Val Gly
    50                  55

<210> SEQ ID NO 100
<211> LENGTH: 57
<212> TYPE: PRT
<213> ORGANISM: Hemachatus hemachates

<400> SEQUENCE: 100

Arg Pro Asp Phe Cys Glu Leu Pro Ala Glu Thr Gly Leu Cys Lys Ala
1               5                   10                  15

Tyr Ile Arg Ser Phe His Tyr Asn Leu Ala Ala Gln Gln Cys Leu Gln
            20                  25                  30

Phe Ile Tyr Gly Gly Cys Gly Gly Asn Ala Asn Arg Phe Lys Thr Ile

Asp Glu Cys Arg Arg Thr Cys Val Gly
    50                  55

<210> SEQ ID NO 101
<211> LENGTH: 57
<212> TYPE: PRT
<213> ORGANISM: Naja nivea

<400> SEQUENCE: 101

Arg Pro Arg Phe Cys Glu Leu Pro Ala Glu Thr Gly Leu Cys Lys Ala
1               5                   10                  15

Arg Ile Arg Ser Phe His Tyr Asn Arg Ala Ala Gln Cys Leu Glu
            20                  25                  30

Phe Ile Tyr Gly Gly Cys Gly Asn Ala Asn Arg Phe Lys Thr Ile
            35                  40                  45

Asp Glu Cys His Arg Thr Cys Val Gly
    50                  55

<210> SEQ ID NO 102
<211> LENGTH: 60
<212> TYPE: PRT
<213> ORGANISM: Vipera russelli

<400> SEQUENCE: 102

His Asp Arg Pro Thr Phe Cys Asn Leu Pro Pro Glu Ser Gly Arg Cys
1               5                   10                  15

Arg Gly His Ile Arg Arg Ile Tyr Tyr Asn Leu Glu Ser Asn Lys Cys
            20                  25                  30

Lys Val Phe Phe Tyr Gly Gly Cys Gly Gly Asn Ala Asn Asn Phe Glu
            35                  40                  45

Thr Arg Asp Glu Cys Arg Glu Thr Cys Gly Gly Lys
    50                  55                  60

<210> SEQ ID NO 103
<211> LENGTH: 64
<212> TYPE: PRT
<213> ORGANISM: Caretta sp. (Red sea turtle egg white)
<220> FEATURE:
<221> NAME/KEY: misc_feature
<222> LOCATION: (1)..(1)
<223> OTHER INFORMATION: Xaa is Glu or Gln

<400> SEQUENCE: 103

Xaa Gly Asp Lys Arg Asp Ile Cys Arg Leu Pro Pro Glu Gln Gly Pro
1               5                   10                  15

Cys Lys Gly Arg Leu Pro Arg Tyr Phe Tyr Asn Pro Ala Ser Arg Met
            20                  25                  30

Cys Glu Ser Phe Ile Tyr Gly Gly Cys Lys Gly Asn Lys Asn Asn Phe
            35                  40                  45

Lys Thr Lys Ala Glu Cys Val Arg Ala Cys Arg Pro Pro Glu Arg Pro
    50                  55                  60

<210> SEQ ID NO 104
<211> LENGTH: 58
<212> TYPE: PRT
<213> ORGANISM: Helix pomania
<220> FEATURE:
<221> NAME/KEY: misc_feature
<222> LOCATION: (1)..(1)
<223> OTHER INFORMATION: Xaa is Glu or Gln -continued

```
<400> SEQUENCE: 104

Xaa Gly Arg Pro Ser Phe Cys Asn Leu Pro Ala Glu Thr Gly Pro Cys
1               5                   10                  15

Lys Ala Ser Ile Arg Gln Tyr Tyr Asn Ser Lys Ser Gly Gly Cys
            20                  25                  30

Gln Gln Phe Ile Tyr Gly Gly Cys Arg Gly Asn Gln Asn Arg Phe Asp
        35                  40                  45

Thr Thr Gln Gln Cys Gln Gly Val Cys Val
        50                  55

<210> SEQ ID NO 105
<211> LENGTH: 57
<212> TYPE: PRT
<213> ORGANISM: Dendroaspis angusticeps (Eastern green mamba C13 S1 C3
      toxin)

<400> SEQUENCE: 105

Ala Ala Lys Tyr Cys Lys Leu Pro Val Arg Tyr Gly Pro Cys Lys Lys
1               5                   10                  15

Lys Phe Pro Ser Phe Tyr Tyr Asn Trp Lys Ala Lys Gln Cys Leu Pro
            20                  25                  30

Phe Asn Tyr Ser Gly Cys Gly Gly Asn Ala Asn Arg Phe Lys Thr Ile
        35                  40                  45

Glu Glu Cys Arg Arg Thr Cys Val Gly
        50                  55

<210> SEQ ID NO 106
<211> LENGTH: 59
<212> TYPE: PRT
<213> ORGANISM: Dendroaspis angusticeps (Eastern green mamba C13 S2 C3
      toxin)
<220> FEATURE:
<221> NAME/KEY: misc_feature
<222> LOCATION: (1)..(1)
<223> OTHER INFORMATION: Xaa is Glu or Gln

<400> SEQUENCE: 106

Xaa Pro Arg Arg Lys Leu Cys Ile Leu His Arg Asn Pro Gly Arg Cys
1               5                   10                  15

Tyr Asp Lys Ile Pro Ala Phe Tyr Tyr Asn Gln Lys Lys Lys Gln Cys
            20                  25                  30

Glu Arg Phe Asp Trp Ser Gly Cys Gly Gly Asn Ser Asn Arg Phe Lys
        35                  40                  45

Thr Ile Glu Glu Cys Arg Arg Thr Cys Ile Gly
        50                  55

<210> SEQ ID NO 107
<211> LENGTH: 57
<212> TYPE: PRT
<213> ORGANISM: Dendroaspis polylepis polylepis (Black mamba B toxin)

<400> SEQUENCE: 107

Arg Pro Tyr Ala Cys Glu Leu Ile Val Ala Ala Gly Pro Cys Met Phe
1               5                   10                  15

Phe Ile Ser Ala Phe Tyr Tyr Ser Lys Gly Ala Asn Lys Cys Tyr Pro
            20                  25                  30

Phe Thr Tyr Ser Gly Cys Arg Gly Asn Ala Asn Arg Phe Lys Thr Ile
        35                  40                  45

Glu Glu Cys Arg Arg Thr Cys Val Val
        50                  55
```

<210> SEQ ID NO 108
<211> LENGTH: 59
<212> TYPE: PRT
<213> ORGANISM: Dendroaspis polylepis polylepis (Black mamba E toxin)

<400> SEQUENCE: 108

Leu Gln His Arg Thr Phe Cys Lys Leu Pro Ala Glu Pro Gly Pro Cys
1               5                   10                  15

Lys Ala Ser Ile Pro Ala Phe Tyr Tyr Asn Trp Ala Ala Lys Lys Cys
                20                  25                  30

Gln Leu Phe His Tyr Gly Gly Cys Lys Gly Asn Ala Asn Arg Phe Ser
            35                  40                  45

Thr Ile Glu Lys Cys Arg His Ala Cys Val Gly
        50                  55

<210> SEQ ID NO 109
<211> LENGTH: 61
<212> TYPE: PRT
<213> ORGANISM: Vipera ammodytes TI toxin
<220> FEATURE:
<221> NAME/KEY: misc_feature
<222> LOCATION: (1)..(1)
<223> OTHER INFORMATION: Xaa is Glu or Gln

<400> SEQUENCE: 109

Xaa Asp His Pro Lys Phe Cys Tyr Leu Pro Ala Asp Pro Gly Arg Cys
1               5                   10                  15

Lys Ala His Ile Pro Arg Phe Tyr Tyr Asp Ser Ala Ser Asn Lys Cys
                20                  25                  30

Asn Lys Phe Ile Tyr Gly Gly Cys Pro Gly Asn Ala Asn Asn Phe Lys
            35                  40                  45

Thr Trp Asp Glu Cys Arg Gln Thr Cys Gly Ala Ser Ala
        50                  55                  60

<210> SEQ ID NO 110
<211> LENGTH: 62
<212> TYPE: PRT
<213> ORGANISM: Vipera ammodytes CTI toxin

<400> SEQUENCE: 110

Arg Asp Arg Pro Lys Phe Cys Tyr Leu Pro Ala Asp Pro Gly Arg Cys
1               5                   10                  15

Leu Ala Tyr Met Pro Arg Phe Tyr Tyr Asn Pro Ala Ser Asn Lys Cys
                20                  25                  30

Glu Lys Phe Ile Tyr Gly Gly Cys Arg Gly Asn Ala Asn Asn Phe Lys
            35                  40                  45

Thr Trp Asp Glu Cys Arg His Thr Cys Val Ala Ser Gly Ile
        50                  55                  60

<210> SEQ ID NO 111
<211> LENGTH: 62
<212> TYPE: PRT
<213> ORGANISM: Bungarus fasciatus VIII B toxin

<400> SEQUENCE: 111

Lys Asn Arg Pro Thr Phe Cys Asn Leu Leu Pro Glu Thr Gly Arg Cys
1               5                   10                  15

Asn Ala Leu Ile Pro Ala Phe Tyr Tyr Asn Ser His Leu His Lys Cys
                20                  25                  30

```
Gln Lys Phe Asn Tyr Gly Gly Cys Gly Gly Asn Ala Asn Asn Phe Lys
        35                  40                  45

Thr Ile Asp Glu Cys Gln Arg Thr Cys Ala Ala Lys Tyr Gly
 50                  55                  60
```

<210> SEQ ID NO 112
<211> LENGTH: 59
<212> TYPE: PRT
<213> ORGANISM: Anemonia sulcata

<400> SEQUENCE: 112

```
Ile Asn Gly Asp Cys Glu Leu Pro Lys Val Val Gly Pro Cys Arg Ala
  1               5                  10                  15

Arg Phe Pro Arg Tyr Tyr Tyr Asn Ser Ser Lys Arg Cys Glu Lys
             20                  25                  30

Phe Ile Tyr Gly Gly Cys Gly Gly Asn Ala Asn Asn Phe His Thr Leu
         35                  40                  45

Glu Glu Cys Glu Lys Val Cys Gly Val Arg Ser
 50                  55
```

<210> SEQ ID NO 113
<211> LENGTH: 56
<212> TYPE: PRT
<213> ORGANISM: Homo sapiens

<400> SEQUENCE: 113

```
Lys Glu Asp Ser Cys Gln Leu Gly Tyr Ser Ala Gly Pro Cys Met Gly
  1               5                  10                  15

Met Thr Ser Arg Tyr Phe Tyr Asn Gly Thr Ser Met Ala Cys Glu Thr
             20                  25                  30

Phe Gln Tyr Gly Gly Cys Met Gly Asn Gly Asn Asn Phe Val Thr Glu
         35                  40                  45

Lys Glu Cys Leu Gln Thr Cys Arg
 50                  55
```

<210> SEQ ID NO 114
<211> LENGTH: 61
<212> TYPE: PRT
<213> ORGANISM: Homo sapiens

<400> SEQUENCE: 114

```
Thr Val Ala Ala Cys Asn Leu Pro Val Ile Arg Gly Pro Cys Arg Ala
  1               5                  10                  15

Phe Ile Gln Leu Trp Ala Phe Asp Ala Val Lys Gly Lys Cys Val Leu
             20                  25                  30

Phe Pro Tyr Gly Gly Cys Gln Gly Asn Gly Asn Lys Phe Tyr Ser Glu
         35                  40                  45

Lys Glu Cys Arg Glu Tyr Cys Gly Val Pro Gly Asp Glu
 50                  55                  60
```

<210> SEQ ID NO 115
<211> LENGTH: 60
<212> TYPE: PRT
<213> ORGANISM: Bungarus multicinctus (beta bungarotoxin B1)

<400> SEQUENCE: 115

```
Arg Gln Arg His Arg Asp Cys Asp Lys Pro Pro Asp Lys Gly Asn Cys
  1               5                  10                  15

Gly Pro Val Arg Ala Phe Tyr Tyr Asp Thr Arg Leu Lys Thr Cys Lys
             20                  25                  30
```

```
Ala Phe Gln Tyr Arg Gly Cys Asp Gly Asp His Gly Asn Phe Lys Thr
            35                  40                  45

Glu Thr Leu Cys Arg Cys Glu Cys Leu Val Tyr Pro
 50                  55                  60

<210> SEQ ID NO 116
<211> LENGTH: 60
<212> TYPE: PRT
<213> ORGANISM: Bungarus multicinctus (beta bungarotoxin B2)

<400> SEQUENCE: 116

Arg Lys Arg His Pro Asp Cys Asp Lys Pro Pro Asp Thr Lys Ile Cys
 1               5                  10                  15

Gln Thr Val Arg Ala Phe Tyr Tyr Lys Pro Ser Ala Lys Arg Cys Val
            20                  25                  30

Gln Phe Arg Tyr Gly Gly Cys Asp Gly Asp His Gly Asn Phe Lys Ser
            35                  40                  45

Asp His Leu Cys Arg Cys Glu Cys Glu Leu Tyr Arg
 50                  55                  60

<210> SEQ ID NO 117
<211> LENGTH: 58
<212> TYPE: PRT
<213> ORGANISM: Bos taurus

<400> SEQUENCE: 117

Arg Pro Asp Phe Cys Leu Glu Pro Pro Tyr Thr Gly Pro Cys Lys Ala
 1               5                  10                  15

Lys Met Ile Arg Tyr Phe Tyr Asn Ala Lys Ala Gly Phe Cys Glu Thr
            20                  25                  30

Phe Val Tyr Gly Gly Cys Lys Ala Lys Ser Asn Asn Phe Arg Ser Ala
            35                  40                  45

Glu Asp Cys Met Arg Thr Cys Gly Gly Ala
 50                  55

<210> SEQ ID NO 118
<211> LENGTH: 61
<212> TYPE: PRT
<213> ORGANISM: Tachypleus tridentatus

<400> SEQUENCE: 118

Thr Glu Arg Gly Phe Leu Asp Cys Thr Ser Pro Pro Val Thr Gly Pro
 1               5                  10                  15

Cys Arg Ala Gly Phe Lys Arg Tyr Asn Tyr Asn Thr Arg Thr Lys Gln
            20                  25                  30

Cys Glu Pro Phe Lys Tyr Gly Gly Cys Lys Gly Asn Gly Asn Arg Tyr
            35                  40                  45

Lys Ser Glu Gln Asp Cys Leu Asp Ala Cys Ser Gly Phe
 50                  55                  60

<210> SEQ ID NO 119
<211> LENGTH: 63
<212> TYPE: PRT
<213> ORGANISM: Bombyx mori

<400> SEQUENCE: 119

Asp Glu Pro Thr Thr Asp Leu Pro Ile Cys Glu Gln Ala Phe Gly Asp
 1               5                  10                  15

Ala Gly Leu Cys Phe Gly Tyr Met Lys Leu Tyr Ser Tyr Asn Gln Glu
```

```
                     20                  25                  30
Thr Lys Asn Cys Glu Glu Phe Ile Tyr Gly Gly Cys Gln Gly Asn Asp
             35                  40                  45

Asn Arg Phe Ser Thr Leu Ala Glu Cys Glu Gln Lys Cys Ile Asn
         50                  55                  60

<210> SEQ ID NO 120
<211> LENGTH: 56
<212> TYPE: PRT
<213> ORGANISM: Bos taurus

<400> SEQUENCE: 120

Lys Ala Asp Ser Cys Gln Leu Asp Tyr Ser Gln Gly Pro Cys Leu Gly
1               5                   10                  15

Leu Phe Lys Arg Tyr Phe Tyr Asn Gly Thr Ser Met Ala Cys Glu Thr
             20                  25                  30

Phe Leu Tyr Gly Gly Cys Met Gly Asn Leu Asn Asn Phe Leu Ser Gln
         35                  40                  45

Lys Glu Cys Leu Gln Thr Cys Arg
     50                  55

<210> SEQ ID NO 121
<211> LENGTH: 61
<212> TYPE: PRT
<213> ORGANISM: Bos taurus

<400> SEQUENCE: 121

Thr Val Glu Ala Cys Asn Leu Pro Ile Val Gln Gly Pro Cys Arg Ala
1               5                   10                  15

Phe Ile Gln Leu Trp Ala Phe Asp Ala Val Lys Gly Lys Cys Val Arg
             20                  25                  30

Phe Ser Tyr Gly Gly Cys Lys Gly Asn Gly Asn Lys Phe Tyr Ser Gln
         35                  40                  45

Lys Glu Cys Lys Glu Tyr Cys Gly Ile Pro Gly Glu Ala
     50                  55                  60

<210> SEQ ID NO 122
<211> LENGTH: 58
<212> TYPE: PRT
<213> ORGANISM: Artificial Sequence
<220> FEATURE:
<223> OTHER INFORMATION: Engineered BPTI (KR15, ME52)

<400> SEQUENCE: 122

Arg Pro Asp Phe Cys Leu Glu Pro Pro Tyr Thr Gly Pro Cys Arg Ala
1               5                   10                  15

Arg Ile Ile Arg Tyr Phe Tyr Asn Ala Lys Ala Gly Leu Cys Gln Thr
             20                  25                  30

Phe Val Tyr Gly Gly Cys Arg Ala Lys Arg Asn Asn Phe Lys Ser Ala
         35                  40                  45

Glu Asp Cys Glu Arg Thr Cys Gly Gly Ala
     50                  55

<210> SEQ ID NO 123
<211> LENGTH: 59
<212> TYPE: PRT
<213> ORGANISM: Artificial Sequence
<220> FEATURE:
<223> OTHER INFORMATION: Isoaprotinin G-1
<220> FEATURE:
<221> NAME/KEY: misc_feature
```

```
<222> LOCATION: (1)..(1)
<223> OTHER INFORMATION: Xaa is Glu or Gln

<400> SEQUENCE: 123

Xaa Arg Pro Asp Phe Cys Leu Glu Pro Pro Tyr Thr Gly Pro Cys Lys
1               5                   10                  15

Ala Arg Met Ile Arg Tyr Phe Tyr Asn Ala Lys Ala Gly Leu Cys Gln
            20                  25                  30

Pro Phe Val Tyr Gly Gly Cys Arg Ala Lys Ser Asn Asn Phe Lys Ser
        35                  40                  45

Ala Glu Asp Cys Met Arg Thr Cys Gly Gly Ala
    50                  55

<210> SEQ ID NO 124
<211> LENGTH: 58
<212> TYPE: PRT
<213> ORGANISM: Artificial Sequence
<220> FEATURE:
<223> OTHER INFORMATION: Isoaprotinin 2

<400> SEQUENCE: 124

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Pro
            20                  25                  30

Phe Val Tyr Gly Gly Cys Arg Ala Lys Arg Asn Asn Phe Lys Ser Ser
        35                  40                  45

Glu Asp Cys Met Arg Thr Cys Gly Gly Ala
    50                  55

<210> SEQ ID NO 125
<211> LENGTH: 58
<212> TYPE: PRT
<213> ORGANISM: Artificial Sequence
<220> FEATURE:
<223> OTHER INFORMATION: Isoaprotinin G-2

<400> SEQUENCE: 125

Arg Pro Asp Phe Cys Leu Glu Pro Pro Tyr Thr Gly Pro Cys Lys Ala
1               5                   10                  15

Arg Met Ile Arg Tyr Phe Tyr Asn Ala Lys Ala Gly Leu Cys Gln Pro
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 126
<211> LENGTH: 58
<212> TYPE: PRT
<213> ORGANISM: Artificial Sequence
<220> FEATURE:
<223> OTHER INFORMATION: Isoaprotinin 1

<400> SEQUENCE: 126

Arg Pro Asp Phe Cys Leu Glu Pro Pro Tyr Thr Gly Pro Cys Lys Ala
1               5                   10                  15

Lys Met Ile Arg Tyr Phe Tyr Asn Ala Lys Ala Gly Phe Cys Glu Thr
            20                  25                  30

Phe Val Tyr Gly Gly Cys Lys Ala Lys Ser Asn Asn Phe Arg Ser Ala
        35                  40                  45
```

```
Glu Asp Cys Met Arg Thr Cys Gly Gly Ala
    50                  55

<210> SEQ ID NO 127
<211> LENGTH: 11
<212> TYPE: DNA
<213> ORGANISM: Artificial Sequence
<220> FEATURE:
<223> OTHER INFORMATION: PfMI restriction site
<220> FEATURE:
<221> NAME/KEY: misc_feature
<222> LOCATION: (4)..(8)
<223> OTHER INFORMATION: n is a, c, g or t

<400> SEQUENCE: 127
ccannnnntg g                                                         11

<210> SEQ ID NO 128
<211> LENGTH: 15
<212> TYPE: DNA
<213> ORGANISM: Artificial Sequence
<220> FEATURE:
<223> OTHER INFORMATION: XcmI restriction site
<220> FEATURE:
<221> NAME/KEY: misc_feature
<222> LOCATION: (4)..(12)
<223> OTHER INFORMATION: n is a, c, g or t

<400> SEQUENCE: 128
ccannnnnnn nntgg                                                     15

<210> SEQ ID NO 129
<211> LENGTH: 9
<212> TYPE: PRT
<213> ORGANISM: Artificial Sequence
<220> FEATURE:
<223> OTHER INFORMATION: amino acids 13-21 of EpiNE alpha

<400> SEQUENCE: 129

Pro Cys Val Ala Met Phe Gln Arg Tyr
1               5

<210> SEQ ID NO 130
<211> LENGTH: 6
<212> TYPE: PRT
<213> ORGANISM: Artificial Sequence
<220> FEATURE:
<223> OTHER INFORMATION: amino acids 15-20 of EpiNE-7

<400> SEQUENCE: 130

Val Ala Met Phe Pro Arg
1               5

<210> SEQ ID NO 131
<211> LENGTH: 4
<212> TYPE: PRT
<213> ORGANISM: Artificial Sequence
<220> FEATURE:
<223> OTHER INFORMATION: amino acids 35-38 of HNE

<400> SEQUENCE: 131

Tyr Gly Gly Cys
1

<210> SEQ ID NO 132
<211> LENGTH: 9
<212> TYPE: PRT
```

```
<213> ORGANISM: Artificial Sequence
<220> FEATURE:
<223> OTHER INFORMATION: amino acids 13-21 of BPTI

<400> SEQUENCE: 132

Pro Cys Lys Ala Arg Ile Ile Arg Tyr
1               5

<210> SEQ ID NO 133
<211> LENGTH: 9
<212> TYPE: PRT
<213> ORGANISM: Artificial Sequence
<220> FEATURE:
<223> OTHER INFORMATION: amino acids 13-21 of EpiNE3

<400> SEQUENCE: 133

Pro Cys Val Gly Phe Phe Ser Arg Tyr
1               5

<210> SEQ ID NO 134
<211> LENGTH: 9
<212> TYPE: PRT
<213> ORGANISM: Artificial Sequence
<220> FEATURE:
<223> OTHER INFORMATION: amino acids 13-21 of EpiNE6

<400> SEQUENCE: 134

Pro Cys Val Gly Phe Phe Gln Arg Tyr
1               5

<210> SEQ ID NO 135
<211> LENGTH: 9
<212> TYPE: PRT
<213> ORGANISM: Artificial Sequence
<220> FEATURE:
<223> OTHER INFORMATION: amino acids 13-21 of EpiNE7

<400> SEQUENCE: 135

Pro Cys Val Ala Met Phe Pro Arg Tyr
1               5

<210> SEQ ID NO 136
<211> LENGTH: 9
<212> TYPE: PRT
<213> ORGANISM: Artificial Sequence
<220> FEATURE:
<223> OTHER INFORMATION: amino acids 13-21 of EpiNE4

<400> SEQUENCE: 136

Pro Cys Val Ala Ile Phe Pro Arg Tyr
1               5

<210> SEQ ID NO 137
<211> LENGTH: 9
<212> TYPE: PRT
<213> ORGANISM: Artificial Sequence
<220> FEATURE:
<223> OTHER INFORMATION: amino acids 13-21 of EpiNE8

<400> SEQUENCE: 137

Pro Cys Val Ala Ile Phe Lys Arg Ser
1               5

<210> SEQ ID NO 138
<211> LENGTH: 9
<212> TYPE: PRT
<213> ORGANISM: Artificial Sequence
```

-continued

<220> FEATURE:
<223> OTHER INFORMATION: amino acids 13-21 of EpiNE1

<400> SEQUENCE: 138

Pro Cys Ile Ala Phe Phe Pro Arg Tyr
1               5

<210> SEQ ID NO 139
<211> LENGTH: 9
<212> TYPE: PRT
<213> ORGANISM: Artificial Sequence
<220> FEATURE:
<223> OTHER INFORMATION: amino acids 13-21 of EpiNE5

<400> SEQUENCE: 139

Pro Cys Ile Ala Phe Phe Gln Arg Tyr
1               5

<210> SEQ ID NO 140
<211> LENGTH: 9
<212> TYPE: PRT
<213> ORGANISM: Artificial Sequence
<220> FEATURE:
<223> OTHER INFORMATION: amino acids 13-21 of EpiNE2

<400> SEQUENCE: 140

Pro Cys Ile Ala Leu Phe Lys Arg Tyr
1               5

<210> SEQ ID NO 141
<211> LENGTH: 58
<212> TYPE: PRT
<213> ORGANISM: Artificial sequence
<220> FEATURE:
<223> OTHER INFORMATION: BITI

<400> SEQUENCE: 141

Arg Pro Asp Phe Cys Gln Leu Gly Tyr Ser Ala Gly Pro Cys Met Gly
1               5                   10                  15

Met Thr Ser Arg Tyr Phe Tyr Asn Gly Thr Ser Met Ala Cys Glu Thr
            20                  25                  30

Phe Gln Tyr Gly Gly Cys Met Gly Asn Gly Asn Asn Phe Val Thr Glu
        35                  40                  45

Lys Asp Cys Leu Gln Thr Cys Arg Gly Ala
    50                  55

<210> SEQ ID NO 142
<211> LENGTH: 58
<212> TYPE: PRT
<213> ORGANISM: Artificial sequence
<220> FEATURE:
<223> OTHER INFORMATION: BITI-E7

<400> SEQUENCE: 142

Arg Pro Asp Phe Cys Gln Leu Gly Tyr Ser Ala Gly Pro Cys Val Ala
1               5                   10                  15

Met Phe Pro Arg Tyr Phe Tyr Asn Gly Thr Ser Met Ala Cys Glu Thr
            20                  25                  30

Phe Gln Tyr Gly Gly Cys Met Gly Asn Gly Asn Asn Phe Val Thr Glu
        35                  40                  45

Lys Asp Cys Leu Gln Thr Cys Arg Gly Ala
    50                  55

```
<210> SEQ ID NO 143
<211> LENGTH: 58
<212> TYPE: PRT
<213> ORGANISM: Artificial sequence
<220> FEATURE:
<223> OTHER INFORMATION: BITI-E7-1222

<400> SEQUENCE: 143

Arg Pro Asp Phe Cys Gln Leu Gly Tyr Ser Thr Gly Pro Cys Val Ala
1               5                   10                  15

Met Phe Pro Arg Tyr Phe Tyr Asn Gly Thr Ser Met Ala Cys Glu Thr
            20                  25                  30

Phe Gln Tyr Gly Gly Cys Met Gly Asn Gly Asn Asn Phe Val Thr Glu
        35                  40                  45

Lys Asp Cys Leu Gln Thr Cys Arg Gly Ala
    50                  55
```

ITI-D1 KUNITZ DOMAIN MUTANTS AS HNE INHIBITORS

CROSS-REFERENCE TO RELATED APPLICATIONS

This application is a continuation of Ser. No. 08/849,406 filed Jul. 21, 1999, now abandoned, which is a National Stage of International Application PCT/US95/16349 filed Dec. 15, 1995, which is a continuation-in-part of application Ser. No. 08/358,160 Issued U.S. Pat. No. 5,663,143, filed Dec. 16, 1994, which is a continuation-in-part of application Ser. No. 08/133,031 filed Oct. 13, 1993 (abandoned), the entire disclosures of which are incorporated herein by reference.

The following applications are incorporated herein by reference. Application Ser. No. 08/133,031, filed Oct. 13, 1993 (abandoned), which is the National Stage of International application number PCT/US92/01501, filed Feb. 28, 1992, which is a divisional of application Ser. No. 07/664,989, Issued U.S. Pat. No. 5,223,409, filed Mar. 1,1991, which is a continuation-in-part of application Ser. No. 07/240,160, filed Sep. 2, 1988 (abandoned).

All of the foregoing applications, whether or not §120 benefit is claimed, are hereby incorporated by reference.

The following related and commonly-owned applications are also incorporated by reference:

Robert Charles Ladner, Sonia Kosow Guterman, Rachel Baribault Kent, and Arthur Charles Ley are named as joint inventors on U.S. Ser. No. 07/293,980, filed Jan. 8, 1989, and entitled GENERATION AND SELECTION OF NOVEL DNA-BINDING PROTEINS AND POLYPEPTIDES. This application has been assigned to Protein Engineering Corporation.

Robert Charles Ladner, Sonia Kosow Guterman, and Bruce Lindsay Roberts are named as a joint inventors on a U.S. Ser. No. 07/470,651 filed Jan. 26, 1990 (now abandoned), entitled "PRODUCTION OF NOVEL SEQUENCE-SPECIFIC DNA-ALTERING ENZYMES", likewise assigned to Protein Engineering Corp.

Ladner, Guterman, Kent, Ley, and Markland, Ser. No. 07/558,011 is also assigned to Protein Engineering Corporation.

Ladner filed an application on May 17, 1991, Ser. No. 07/715,934 that is hereby incorporated by reference.

BACKGROUND OF THE INVENTION

Field of the Invention

This invention relates to novel proteins that inhibit human neutrophil elastase (hNE). A large fraction of the sequence of each of these proteins is identical to a known human protein which has very little or no inhibitory activity with respect to hNE.

Information Disclosure Statement 1. hNE, its Natural Inhibitors, and Pathologies Human Neutrophil Elastase (hNE, also known as Human Leukocyte Elastase (hLE); EC 3.4.21.11) is a 29 Kd protease with a wide spectrum of activity against extracellular matrix components (CAMP82, CAMP88, MCWH89). The enzyme is one of the major neutral proteases of the azurophil granules of polymorphonuclear leucocytes and is involved in the elimination of pathogens and in connective tissue restructuring (TRAV88). In cases of hereditary reduction of the circulating α-1-protease inhibitor (API, formerly known as α1 antitrypsin), the principal systemic physiological inhibitor of hNE (HEID86), or the inactivation of API by oxidation ("smoker's emphysema"), extensive destruction of lung tissue may result from uncontrolled elastolytic activity of hNE (CANT89). Several human respiratory disorders, including cystic fibrosis and emphysema, are characterized by an increased neutrophil burden on the epithelial surface of the lungs (SNID91, MCEL91, GOLD86) and hNE release by neutrophils is implicated in the progress of these disorders (MCEL91, WEIS89). A preliminary study of aerosol administration of API to cystic fibrosis patients indicates that such treatment can be effective both in prevention of respiratory tissue damage and in augmentation of host antimicrobial defenses (MCEL91).

API presents some practical problems to large-scale routine use as a pulmonary anti-elastolytic agent. These include the relatively large size of the molecule (394 residues, 51 k Dalton), the lack of intramolecular stabilizing disulfide bridges, and specific post translational modifications of the protein by glycosylation at three sites. Perhaps of even greater importance is the sensitivity of API to oxidation, such as those released by activated neutrophils. Hence a small stable nontoxic highly efficacious inhibitor of hNE would be of great therapeutic value.

2. Proteinaceous Serine Protease Inhibitors. A large number of proteins act as serine protease inhibitors by serving as a highly specific, limited proteolysis substrate for their target enzymes. In many cases, the reactive site peptide bond ("scissile bond") is encompassed in at least one disulfide loop, which insures that during conversion of virgin to modified inhibitor the two peptide chains cannot dissociate.

A special nomenclature has evolved for describing the active site of the inhibitor. Starting at the residue on the amino side of the scissile bond, and moving away from the bond, residues are named P1, P2, P3, etc. (SCHE67). Residues that follow the scissile bond are called P1', P2', P3', etc. It has been found that the main chain of protein inhibitors having very different overall structure are highly similar in the region between P3 and P3' with especially high similarity for P2, $P_1$ and P1' (LASK80 and works cited therein). It is generally accepted that each serine protease has sites S1, S2, etc. that receive the side groups of residues P1, P2, etc. of the substrate or inhibitor and sites S1', S2', etc. that receive the side groups of P1', P2', etc. of the substrate or inhibitor (SCHE67). It is the interactions between the S sites and the P side groups that give the protease specificity with respect to substrates and the inhibitors specificity with respect to proteases.

The serine protease inhibitors have been grouped into families according to both sequence similarity and the topological relationship of their active site and disulfide loops. The families include the bovine pancreatic trypsin inhibitor (Kunitz), pancreatic secretory trypsin inhibitor (Kazal), the Bowman-Birk inhibitor, and soybean trypsin inhibitor (Kunitz) families. Some inhibitors have several reactive sites on a single polypeptide chains, and these distinct domains may have different sequences, specificities, and even topologies.

One of the more unusual characteristics of these inhibitors is their ability to retain some form of inhibitory activity even after replacement of the P1 residue. It has further been found that substituting amino acids in the $P_5$ to $P_5'$ region, and more particularly the P3 to P3' region, can greatly influence the specificity of an inhibitor. LASK80 suggested that among the BPTI (Kunitz) family, inhibitors with P1 Lys and Arg tend to inhibit trypsin, those with P1=Tyr, Phe, Trp, Leu and Met tend to inhibit chymotrypsin, and those with P1=Ala or Ser are likely to inhibit elastase. Among the Kazal inhibitors, they continue, inhibitors with P1=Leu or Met are strong inhibitors of elastase, and in the Bowman-Kirk family elastase is inhibited with P1 Ala, but not with P1 Leu.

"Kunitz" Domain Proteinase Inhibitors. Bovine pancreatic trypsin inhibitor (BPTI, a.k.a. aprotonin) is a 58 a.a. serine proteinase inhibitor of the BPTI (Kunitz) domain (KuDom) family. Under the tradename TRASYLOL, it is used for countering the effects of trypsin released during pancreatitis. Not only is its 58 amino acid sequence known, the 3D structure of BPTI has been determined at high resolution by X-ray diffraction (HUBE77, MARQ83, WLOD84, WLOD87a, WLOD87b), neutron diffraction (WLOD84), and by NMR (WAGN87). One of the X-ray structures is deposited in the Brookhaven Protein Data Bank as "6PTI" [sic]. The 3D structure of various BPTI homologues (EIGE90, HYNE90) are also known. At least sixty homologues have been reported; the sequences of 39 homologues are given in Table 5. The known human homologues include domains of Lipoprotein Associated Coagulation Inhibitor (LACI) (WUNT88, GIRA89), Inter-α-Trypsin Inhibitor (ALBR83a, ALBR83b, DIAR90, ENGH89, TRIB86, GEBH86, GEBH90, KAUM86, ODOM90, SALI90), and the Alzheimer beta-Amyloid Precursor Protein. Circularized BPTI and circularly permuted BPTI have binding properties similar to BPTI (GOLD83). Some proteins homologous to BPTI have more or fewer residues at either terminus.

In BPTI, the P1 residue is at position 15. Tschesche et al. (TSCH87) reported on the binding of several BPTI P1 derivatives to various proteases:

| Dissociation constants for BPTI P1 derivatives, Molar. | | | | |
|---|---|---|---|---|
| Residue #15 P1 | Trypsin (bovine pancreas) | Chymotrypsin (bovine pancreas) | Elastase (porcine pancreas) | Elastase (human leukocytes) |
| lysine | $6.0 \cdot 10^{-14}$ | $9.0 \cdot 10^{-9}$ | – | $3.5 \cdot 10^{-6}$ (WT) |
| glycine | – | – | + | $7.0 \cdot 10^{-9}$ |
| alanine | + | – | $2.8 \cdot 10^{-8}$ | $2.5 \cdot 10^{-9}$ |
| valine | – | – | $5.7 \cdot 10^{-8}$ | $1.1 \cdot 10^{-10}$ |
| leucine | – | – | $1.9 \cdot 10^{-8}$ | $2.9 \cdot 10^{-9}$ |

From the report of Tschesche et al. we infer that molecular pairs marked "+" have $K_d s \geq 3.5 \cdot 10^{-6}$ M and that molecular pairs marked "–" have $K_d s >> 3.5 \cdot 10^{-6}$ M. It is apparent that wild-type BPTI has only modest affinity for hNE, however, mutants of BPTI with higher affinity are known. While not shown in the Table, BPTI does not significantly bind hCG. However, Brinkmann and Tschesche (BRIN90) made a triple mutant of BPTI (viz. K15F, R17F, M52E) that has a $K_i$ with respect to hCG of $5.0 \times 10^{-7}$ M.

3. ITI Domain 1 and ITI Domain 2 as an Initial Protein Binding Domains (IPBD)

Many mammalian species have a protein in their plasma that can be identified, by sequence homology and similarity of physical and chemical properties, as inter-α-trypsin inhibitor (ITI), a large ($M_r$ ca 240,000) circulating protease inhibitor (for recent reviews see ODOM90, SALI90, GEBH90, GEBH86). The sequence of human ITI is shown in Table 28. The intact inhibitor is a glycoprotein and is currently believed to consist of three glycosylated subunits that interact through a strong glycosaminoglycan linkage (ODOM90, SALI90, ENGH89, SELL87). The anti-trypsin activity of ITI is located on the smallest subunit (ITI light chain, unglycosylated $M_r$ ca 15,000) which is identical in amino acid sequence to an acid stable inhibitor found in urine (UTI) and serum (STI) (GEBH86, GEBH90). The amino-acid sequence of the ITI light chain is shown in Table 28. The mature light chain consists of a 21 residue N-terminal sequence, glycosylated at $Ser_{10}$, followed by two tandem Kunitz-type domains the first of which is glycosylated at $Asn_{45}$ (ODOM90). In the human protein, the second Kunitz-type domain has been shown to inhibit trypsin, chymotrypsin, and plasmin (ALBR83a, ALBR83b, SELL87, SWAI88). The first domain lacks these activities but has been reported to inhibit leukocyte elastase (≈1 µM>$K_i$>1 nM) (ALBR83a,b, ODOM90). cDNA encoding the ITI light chain also codes for α-1-microglobulin (TRAB86, KAUM86, DIAR90); the proteins are separated post-translationally by proteolysis.

The two Kunitz domains of the ITI light chain (ITI-D1 and ITI-D2) possesses a number of characteristics that make them useful as Initial Potential Binding Domains (IPBDs). ITI-D1 comprises at least residues 26 to 76 of the UTI sequence shown in FIG. 1 of GEBH86. The Kunitz domain could be thought of as comprising residues from as early as residue 22 to as far as residue 79. Residues 22 through 79 constitute a 58-amino-acid domain having the same length as bovine pancreatic trypsin inhibitor (BPTI) and having the cysteines aligned. ITI-D2 comprises at least residues 82 through 132; residues as early as 78 and as later as 135 could be included to give domains closer to the classical 58-amino-acid length. As the space between the last cysteine of ITI-D1 (residue 76 of ITI light chain) and the first cysteine of ITI-D2 (residue 82 of ITI light chain) is only 5 residues, one can not assign 58 amino acids to each domain without some overlap. Unless otherwise stated, herein, we have taken the second domain to begin at residue 78 of the ITI light chain. Each of the domains are highly homologous to both BPTI and the EpiNE series of proteins described in U.S. Pat. No. 5,223,409. Although x-ray structures of the isolated domains ITI-D1 and ITI-D2 are not available, crystallographic studies of the related Kunitz-type domain isolated from the Alzheimer's amyloid β-protein (AAβP) precursor show that this polypeptide assumes a 3D structure almost identical to that of BPTI (HYNE90).

The three-dimensional structure of α-dendrotoxin from green mamba venom has been determined (SKAR92) and the structure is highly similar to that of BPTI. The author states, "Although the main-chain fold of α-DTX is similar to that of homologous bovine pancreatic trypsin inhibitor (BPTI), there are significant differences involving segments of the polypeptide chain close to the 'antiprotease site' of BPTI. Comparison of the structure of α-DTX with the existing models of BPTI and its complexes with trypsin and kallikrein reveals structural differences that explain the inability of α-DTX to inhibit trypsin and chymotrypsin."

The structure of the black mamba K venom has been determined by NMR spectroscopy and has a 3D structure that is highly similar to that of BPTI despite 32 amino-acid sequence differences between residues 5 and 55 (the first and last cysteines)(BERN93). "The solution structure of Toxin K is very similar to the solution structure of the basic pancreatic trypsin inhibitor (BPTI) and the X-ray crystal structure of the α-dendrotoxin from Dendroaspis angusticeps (α-DTX), with r.m.s.d. values of 1.31 Å and 0.92 Å, respectively, for the backbone atoms of residues 2 to 56. Some local structural differences between Toxin K and BPTI are directly related to the fact that intermolecular interactions with two of the four internal molecules of hydration water in BPTI are replaced by intramolecular hydrogen bonds in Toxin K." Thus, it is likely that the solution 3D structure of either of the isolated ITI-D1 domain or of the isolated ITI-D2 domain will be highly similar to the structures of BPTI, AAβP, and black mamba K venom. In this case, the advantages described previously for use of BPTI as an IPBD apply to ITI-D1 and to ITI-D2. ITI-D1 and ITI-D2 provide additional advantages as an IPBD for the development of specific anti-elastase inhibitory activity. First, the ITI-D1 domain has been reported to inhibit both leukocyte elastase (ALBR83a,b, ODOM90) and Cathepsin-G (SWAI88, ODOM90); activities which BPTI lacks. Second, ITI-D1 lacks affinity for the related serine proteases trypsin, chymotrypsin, and plasmin (ALBR83a,b, SWAI88), an advantage for the development of specificity in inhibition. ITI-D2 has the advantage of not being glycosylated. Additionally, ITI-D1 and ITI-D2 are human-derived polypeptides so that derivatives are anticipated to show minimal antigenicity in clinical applications.

4. Secretion of Heteroloqous Proteins from *Pichia pastoris*

Others have produced a number of proteins in the yeast *Pichia pastoris*. For example, Vedvick et al. (VEDV91) and Wagner et al. (WAGN92) produced aprotinin from the alcohol oxidase promoter with induction by methanol as a secreted protein in the culture medium (CM) at ≈1 mg/mL. Gregg et al. (GREG93) have reviewed production of a number of proteins in *P. pastoris*. Table 1 of GREG93 shows proteins that have been produced in *P. pastoris* and the yields.

5. Recombinant Production of Kunitz Domains:

Aprotinin has been made via recombinant-DNA technology (AUER87, AUER88, AUER89, AUER90, BRIN90, BRIN91, ALTM91).

6. Construction Methods:

Unless otherwise stated, genetic constructions and other manipulations are carries out by standard methods, such as found in standard references (e.g. AUSU87 and SAMB89).

No admission is made that any cited reference is prior art or pertinent prior art, and the dates given are those appearing on the reference and may not be identical to the actual publication date. The descriptions of the teachings of any cited reference are based on our present reading thereof, and we reserve the right to revise the description if an error comes to our attention, and to challenge whether the description accurately reflects the actual work reported. We reserve the right to challenge the interpretation of cited works, particularly in light of new or contradictory evidence.

SUMMARY OF THE INVENTION

The present invention describes a series of small potent proteinaceous inhibitors of human neutrophil elastase (hNE). One group of inhibitors is derived from a Kunitz-type inhibitory domain found in a protein of human origin, namely, the light chain of human Inter-α-trypsin inhibitor (ITI) which contains domains designated ITI-D1 and ITI-D2. The present invention discloses variants of ITI-D1 and ITI-D2 that have very high affinity for hNE. The present invention comprises modifications to the ITI-D2 sequence that facilitate its production in the yeast *Pichia pastoris* and that are highly potent inhibitors of hNE. The invention also relates to methods of transferring segments of sequence from one Kunitz domain to another and to methods of production.

The invention is presented as a series of examples that describe design, production, and testing of actual inhibitors and additional examples describing how other inhibitors could be discovered. The invention relates to proteins that inhibit human neutrophil elastase (hNE) with high affinity.

| NOMENCLATURE and ABBREVIATIONS | |
|---|---|
| Term | Meaning |
| x::y | Fusion of gene x to gene y in frame. |
| X::Y | Fusion protein expressed from x::y fusion gene. |
| μM | Micromolar, $10^{-6}$ molar. |
| nM | Nanomolar, $10^{-9}$ molar. |
| pM | Picomolar, $10^{-12}$ molar. |
| Single-letter amino-acid codes: | | | |
| A: Ala | C: Cys | D: Asp | E: Glu |
| F: Phe | G: Gly | H: His | I: Ile |
| K: Lys | L: Leu | M: Met | N: Asn |
| P: Pro | Q: Gln | R: Arg | S: Ser |
| T: Thr | V: Val | W: Trp | Y: Tyr |

DETAILED DESCRIPTION OF THE PREFERRED EMBODIMENTS OF THE INVENTION

A protein sequence can be called an "aprotinin-like Kunitz domain" if it contains a sequence that when aligned to minimize mismatches, can be aligned, with four or fewer mismatches, to the pattern: Cys-(Xaa)$_6$-Gly-Xaa-Cys-(Xaa)$_8$-[Tyr|Phe]-(Xaa)$_6$-Cys-(Xaa)$_2$-Phe-Xaa-[Tyr|Trp|Phe]-Xaa-Gly-Cys-(Xaa)$_4$-[Asn|Gly]-Xaa-[Phe|Tyr]-(Xaa)$_5$-Cys-(Xaa)$_3$-Cys (SEQ ID NO:86), where bracketed amino acids separated by a | symbol are alternative amino acids for a single position. For example, [Tyr|Phe] indicates that at that position, the amino acid may be either Tyr or Phe. The symbol Xaa denotes that at that position, any amino acid may be used. For the above test, an insertion or deletion counts as one mismatch.

In aprotinin, the cysteines are numbered 5, 14, 30, 38, 51, and 55 and are joined by disulfides 5-to-55, 14-to-38, and 30-to-51. Residue 15 is called the P1 residue (SCHE67); residues toward the amino terminus are called P2 (residue 14), P3 (residue 13), etc. Residue 16 is called P1', 17 is P2', 18 is P3', etc.

There are many homologues of aprotonin, which differ from it at one or more positions but retain the fundamental structure defined above. For a given list of homologues, it is possible to tabulate the frequency of occurrence of each amino acid at each ambiguous position. (The sequence having the most prevalent amino acid at each ambiguous position is listed as "Consensus Kunitz Domain" in Table 10).

A "human aprotonin-like Kunitz domain" is an aprotonin-like Kunitz domain which is found in nature in a human protein. Human aprotinin-like Kunitz domains include, but are not limited to, ITI-D1, ITI-D2, App-I, TFPI2-D1, TFPI2-D2, TFPI2-D3, LACI-D1, LACI-D2, LACI-D3, A3 collagen, and the HKI B9 domain. In this list, D1, D2, etc., denote the first, second, etc. domain of the indicated multidomain protein.

"Weak", "Moderate", "Strong" and "Very Strong" binding to and inhibition of hNE are defined in accordance with Table 8. Preferably, the proteins of the present invention have a Ki of less than 1000 pM (i.e., are "strong" inhibitors), more preferably less than 50 pM, most preferably less than 10 pM (i.e., are "very strong" inhibitors).

For purposes of the present invention, an aprotonin-like Kunitz domain may be divided into ten segments, based on the consensus sequence and the location of the catalytic site. Using the amino acid numbering scheme of aprotonin, these segments are as follows (see Table 10):

1: 1–4 (residues before first Cys)
2: 5–9 (first Cys and subsequent residues before P6)
3: 10–13 (P6 to P3)
4: 14 (second Cys; P2)
5: 15–21 (P1, and P1' to P6')
6: 22–30 (after P6 and up to and incl. third Cys.)
7: 31–36 (after third Cys and up to consensus Gly-Cys)
8: 37–38 (consensus Gly-Cys)
9: 39–42 (residues after Gly-Cys and before consensus [Asn|Gly]
10: 43–55 (up to last Cys)(also includes residues after last Cys, if any)

It will be appreciated that in those aprotonin-like Kunitz domains that differ from aprotonin by one or more amino acid insertions or deletions, or which have a different number of amino acids before the first cysteine or after the last cysteine, the actual amino acid position may differ from that given above. It is applicant's intent that these domains be numbered so as to correspond to the aligned aprotonin sequence, e.g., the first cysteine of the domain is numbered amino acid 5, for the purpose of segment identification. Note that segment 1, while a part of aprotonin, is not a part of the formal definition of an aprotonin-like Kunitz domain, and therefore it is not required that the proteins of the present invention include a sequence corresponding to segment 1. Similarly, part of segment 10 (after the last Cys) is not a required part of the domain.

A "humanized inhibitor" is one in which at least one of segments 3, 5, 7 and 9 differs by at least one nonconservative modification from the most similar (based on amino acid identities) human aprotonin-like Kunitz domain, at least one of segments 2, 6, and 10 (considered up to the last Cys) is identical, or differs only by conservative modifications, from said most similar human aprotonin-like Kunitz domain, and which is not-identical to any naturally occurring nonhuman aprotonin-like Kunitz domain. (Note that segment 1 is ignored in making this determination since it is outside the sequence used to define a domain, and segments 4 and 8 are ignored because they are required by the definition of an aprotonin-like Kunitz domain.)

The proteins of the present invention are preferably humanized strong or very strong hNE inhibitors. It should be noted that the human aprotonin-like Kunitz domains thus far identified are merely weak hNE inhibitors.

For the purpose of the appended claims, an aprotonin-like Kunitz domain is "substantially homologous" to a reference domain if, over the critical region (aprotonin residues 5–55) set forth above, it is at least at least 50% identical in amino acid sequence to the corresponding sequence of or within the reference domain, and all divergences take the form of conservative and/or semi-conservative modifications.

Proteins of the present invention include those comprising a Kunitz domain that is substantially homologous to the reference proteins EPI-HNE-3, EPI-HNE-4, DPI.1.1, DPI.1.2, DPI.1.3, DPI.2.1, DPI.2.2, DPI.2.3, DPI.3.1, DPI.3.2, DPI.3.3, DPI.4.1, DPI.4.2, DPI.4.3, DPI.5.1, DPI.5.2, DPI.5.3, DPI.6.1, DPI.6.2, DPI.6.3, DPI.6.4, DPI.6.5, DPI.6.6, DPI.6.7, DPI.7.1, DPI.7.2, DPI.7.3, DPI.7.4, DPI.7.5, DPI.8.1, DPI.8.2, DPI.8.3, DPI.9.1, DPI.9.2, or DPI.9.3, as defined in Table 10. Homologues of EPI-HNE-3 and EPI-HNE-4 are especially preferred.

Preferably, the hNE-binding domains of the proteins of the present invention are at least 80% identical, more preferably, at least 90% identical, in amino acid sequence to the corresponding reference sequence. Most preferably, the number of mismatches is zero, one, two, three, four or five. Desirably, the hNE-binding domains diverge from the reference domain solely by one or more conservative modifications.

"Conservative modifications" are defined as:
a) conservative substitutions of amino acids as hereafter defined, and
b) single or multiple insertions or deletions of amino acids at the termini, at interdomain boundaries, in loops or in other segments of relatively high mobility (as indicated, for example, by high temperature factors or lack of resolution in X-ray diffraction, neutron diffraction, or NMR). Preferably, except at the termini, no more than about five amino acids are inserted or deleted at a particular locus, and the modifications are outside regions known to contain binding sites important to activity.

"Conservative substitutions" are herein defined as exchanges within on of the following five groups:
I. Small aliphatic, nonpolar or slightly polar residues: [Ala, Ser, Thr, (Pro, Gly)],
II. Acidic amino acids and their amides: [Asp, Glu, Asn, Gln],
III. Polar, positively charged residues: [His, Lys, Arg],
IV. Aliphatic nonpolar residues: [Met, Leu, Ile, Val, (Cys)], and
V. Large, aromatic residues: [Phe, Tyr, Trp]

Residues Pro, Gly, and Cys are parenthesized because they have special conformational roles. Cys often participates in disulfide bonds; when not so doing, it is highly hydrophobic. Gly imparts flexibility to the chain; it is often described as a "helix breaker" although many a helices contain Gly. Pro imparts rigidity to the chain and is also described as a "helix breaker". Although Pro is most often found in turns, Pro is also found in helices and sheets. These residues may be essential at certain positions and substitutable elsewhere.

"Semi-Conservative Modifications" are defined herein as transpositions of adjacent amino acids (or their conservative replacements), and semi-conservative substitutions. "Semi-conservative substitutions" are defined to be exchanges between two of groups (I)–(V) above which are limited either to the supergroup consisting of (I), (II), and (III) or to the supergroup consisting of (IV) and (V). For the purpose of this definition, however, glycine and alanine are considered to be members of both supergroups.

"Non-conservative modifications" are modifications which are neither conservative nor semi-conservative.

Preferred proteins of the present invention are further characterized by one of more of the preferred, highly preferred, or most preferred mutations set forth in Table 41.

Preferably, the proteins of the present invention have hNE-inhibitory domains which are not only substantially homologous to a reference domain, but also qualify as humanized inhibitors.

Claim 1 of PCT/US92/01501 refers to proteins denoted EpiNEalpha, EpiNE1, EpiNE2, EpiNE3, EpiNE4, EpiNE5, EpiNE6, EpiNE7, and EpiNE8. Claim 3 refers to proteins denoted ITI-E7, BITI-E7, BITI-E&-1222, AMINO1, AMINO2, MUTP1, BITI-E7-141, MUTT26A, MUTQE, and MUT1619. (With the exception of EpiNEalpha, the sequences of all of these domains appears in Table 10.) Claims 4–6 related to inhibitors which are homologous to, but not identical with, the aforementioned inhibitors. These homologous inhibitors could differ from the lead inhibitors by one or more class A substitutions (claim 4), one or more class A or B substitutions (claim 5), or one or more class A, B or C substitutions (claim 6). Class A, B and C substitutions were defined in Table 65 of PCT/US92/01501. For convenience, Table 65 has been duplicated in this specification (Table 9).

The meaning of classes A, B and C were as follows: A, no major effect expected if molecular charge stays in range −1 to +1; B, major effects not expected, but more likely than with A; and C, residue in binding interface, any change must be tested. Each residue position was assigned an A, B, C or X rating; X meant no substitution allowed. At the non-X positions, allowed substitutions were noted.

In one series of embodiments, the present invention is directed to HNE inhibitors as disclosed in Ser. No. 08/133,031 (previously incorporated by reference), which is the U.S. national stage of PCT/US92/01501.

The invention disclosed in Ser. No. 08/133,031 relates to muteins of BPTI, ITI-D1 and other Kunitz domain-type inhibitors which have a high affinity for elastase. Some of the described inhibitors are derived from BPTI and some from ITI-D1. However, hybrids of the identified muteins and other Kunitz domain-type inhibitors could be constructed.

For the purpose of simultaneously assessing the affinity of a large number of different BPTI and ITI-D1 muteins, DNA sequences encoding the BPTI or ITI-D1 was incorporated into the genome of the bacteriophage M13. The KuDom is displayed on the surface of M13 as an amino-terminal fusion with the gene III coat protein. Alterations in the KuDom amino acid sequence were introduced. Each pure population of phage displaying a particular KuDom was characterized with regard to its interactions with immobilized hNE or hCG. Based on comparison to the pH elution profiles of phage displaying other KuDoms of known affinities for the particular protease, mutant KuDoms having high affinity for the target proteases were identified. Subsequently, the sequences of these mutant KuDoms were determined (typically by sequencing the corresponding DNA sequence).

Certain aprotonin-like protease inhibitors were shown to have a high affinity for HNE ($\approx 10^{12}$/M). These 58 amino acid polypeptides were biologically selected from a library of aprotinin mutants produced through synthetic diversity. Positions P1, P1', P2', P3', and P4' were varied. At P1, only VAL and ILE were selected, although LEU, PHE, and MET were allowed by the synthetic conditions. At P1', ALA and GLY were allowed and both were found in proteins having high affinity. (While not explored in the library, many Kazal family inhibitors of serine proteases have glutamic or aspartic acid at P1'.) All selected proteins contained either PHE or MET at P2'; LEU, ILE, and VAL, which are amino acids with branched aliphatic side groups, were in the library but apparently hinder binding to HNE. Surprisingly, position P3' of all proteins selected for high affinity for HNE have phenylalanine. No one had suggested that P3' was a crucial position for determining specificity relative to HNE. At P4', SER, PRO, THR, LYS, and GLN were allowed; all of these except THR were observed. PRO and SER are found in the derivatives having the highest affinity.

In Ser. No. 08/133,031, Table 61 showed the variability of 39 naturally-occurring Kunitz domains. All these proteins have 51 residues in the region $C_5$ through $C_{55}$; the total number of residues varies due to the proteins having more or fewer residues at the termini. Table 62 list the names of the proteins that are included in Table 61. Table 64 cites works where these sequences are recorded. Table 63 shows a histogram of how many loci show a particular variability vs. the variability. "Core" refers to residues from 5 to 55 that show greater sequence and structural similarity than do residues outside the core.

At ten positions a single amino-acid type is observed in all 42 cases, these are $C_5$, $G_{12}$, $C_{14}$, $C_{30}$, $F_{33}$, $G_{37}$, $C_{38}$, $N_{43}$, $C_{51}$, and $C_{55}$. Although there are reports that each of these positions may be substituted without complete loss of structure, only $G_{12}$, $C_{14}$, $G_{37}$, and $C_{38}$ are close enough to the binding interface to offer any incentive to make changes. $G_{12}$ is in a conformation that only glycine can attain; this residue is best left as is. Marks et al. (MARK87) replaced both $C_{14}$ and $C_{38}$ with either two alanines or two threonines. The $C_{14}/C_{38}$ cystine bridge that Marks et al. removed is the one very close to the scissile bond in BPTI; surprisingly, both mutant molecules functioned as trypsin inhibitors. Both BPTI(C14A,C38A) and BPTI(C14T,C38T) are stable and inhibit trypsin. Altering these residues might give rise to a useful inhibitor that retains a useful stability, and the phage-display of a variegated population is the best way to obtain and test mutants that embody alterations at either 14 or 38. Only if the $C_{14}/C_{38}$ disulfide is removed, would the strict conservation of G37 be removed.

At seven positions (viz. 23, 35, 36, 40, 41, 45, and 47) only two amino-acid types have been found. At position 23 only Y and F are observed; the para position of the phenyl ring is solvent accessible and far from the binding site. Changes here are likely to exert subtle influences on binding and are not a high priority for variegation. Similarly, 35 has only the aromatic residues Y and W; phenylalanine would probably function well here. At 36, glycine predominates while serine is also seen. Other amino acids, especially {N, D, A, R}, should be allowed and would likely affect binding properties. Position 40 has only G or A; structural models suggest that other amino acids would be tolerated, particularly those in the set {S, D, N, E, K, R, L, M, Q, and T}. Position 40 is close enough to the binding site that alteration here might affect binding. At 41, only N, and K have been seen, but any amino acid, other than proline, should be allowed. The side group is exposed, so hydrophilic side groups are preferred, especially {D, S, T, E, R, Q, and A}. This residue is far enough from the binding site that changes here are not expected to have big effects on binding. At 45, F is highly preferred, but Y is observed once. As one edge of the phenyl ring is exposed, substitution of other aromatics (W or H) is likely to make molecules of similar structure, though it is difficult to predict how the stability will be affected. Aliphatics such as leucine or methionine (not having branched $C_\beta$s) might also work here. At 47, only S and T have been seen, but other amino acids, especially {N, D, G, and A}, should give stable proteins.

At one position (44), only three amino-acid types have been observed. Here, asparagine predominates and may form internal hydrogen bonds. Other amino acids should be allowed, excepting perhaps proline.

At the remaining 40 positions, four or more amino acids have been observed; at 28 positions, eight or more amino-acid types are seen. Position 25 exhibits 13 different types and 5 positions (1, 6, 17, 26, and 34) exhibit 12 types. Proline (the most rigid amino acid) has been observed at fourteen positions: 1, 2, 8, 9, 11, 13, 19, 25, 32, 34, 39, 49, 57, and 58. The $\phi,\psi$ angles of BPTI (CREI84, Table 6-3, p. 222) indicate that proline should be allowed at positions 1, 2, 3, 7, 8, 9, 11, 13, 16, 19, 23, 25, 26, 32, 35, 36, 40, 43, 48, 49, 50, 52, 53, 54, 56, and 58. Proline occurs at four positions (34, 39, 57, and 58) where the BPTI $\phi,\psi$ angles indicate that it should be unacceptable. We conclude that the main chain rearranges locally in these cases.

Based on these data and excluding the six cysteines, we judge that the KuDom structure will allow those substitutions shown in Table 9. The class indicates whether the substitutions: A) are very likely to give a stable protein having substantially the same binding to hNE, hCG, or some other serine protease as the parental sequence, B) are likely to give similar binding as the parent, or C) are likely to give a protein retaining the KuDom structure, but which are likely to affect the binding. Mutants in class C must be tested for affinity, which is relatively easy using a display-phage system, such as the one set forth in W0/02809. The affinity of hNE and hCG inhibitors is most sensitive to substitutions at positions 15, 16, 17, 18, 34, 39, 19, 13, 11, 20, 36 of BPTI, if the inhibitor is a mutant of ITI-D1, these positions must be converted to their ITI-D1 equivalents by aligning the cysteines in BPTI and ITI-D1.

Wild-type BPTI is not a good inhibitor of hNE. BPTI with a single K15L mutation exhibits a moderate affinity for HNE ($K_d$=2.9·10$^{-9}$ M) (BECK88b). However, the amino terminal Kunitz domain (BI-8e) of the light chain of bovine inter-α-trypsin inhibitor has been generated by proteolysis and shown to be a potent inhibitor of HNE ($K_d$=4.4·10$^{-11}$ M) (ALBR83).

It has been proposed that the P1 residue is the primary determinant of the specificity and potency of BPTI-like molecules (SINH91, BECK88b, LASK80 and works cited therein). Although both BI-8e and BPTI(K15L) feature LEU at their respective P1 positions, there is a 66 fold difference in the affinities of these molecules for HNE. We therefore hypothesized that other structural features must contribute to the affinity of BPTI-like molecules for HNE.

A comparison of the structures of BI-8e and BPTI(K15L) reveals the presence of three positively charged residues at positions 39, 41, and 42 of BPTI which are absent in BI-8e. These hydrophilic and highly charged residues of BPTI are displayed on a loop which underlies the loop containing the P1 residue and is connected to it via a disulfide bridge. Residues within the underlying loop (in particular residue 39) participate in the interaction of BPTI with the surface of trypsin (BLOW72) and may contribute significantly to the tenacious binding of BPTI to trypsin. These hydrophilic residues might, however, hamper the docking of BPTI variants with HNE. Supporting this hypothesis, BI-8e displays a high affinity for HNE and contains no charged residues in residues 39–42. Hence, residues 39 through 42 of wild type BPTI were replaced with the corresponding residues (MGNG) of the human homologue of BI-8e. As we anticipated, a BPTI(K15L) derivative containing the MGNG 39–42 substitution exhibited a higher affinity for HNE than did the single substitution mutant BPTI(K15L). Mutants of BPTI with Met at position 39 are known, but positions 40–42 were not mutated simultaneously.

Tables 12 and 13 present the sequences of additional novel BPTI mutants with high affinity for hNE. We believe these mutants to have an affinity for hNE which is about an order of magnitude higher than that of BPTI (K15V, R17L). All of these mutants contain, besides the active site mutations shown in the Tables, the MGNG mutation at positions 39–42.

Although BPTI has been used in humans with very few adverse effects, a KuDom having much higher similarity to a human KuDom poses much less risk of causing an immune response. Thus, we transferred the active site changes found in EpiNE7 into the first KuDom of inter-α-trypsin inhibitor. For the purpose of this application, the numbering of the nucleic acid sequence for the ITI light chain gene is that of TRAB86 and that of the amino acid sequence is the one shown for UTI in FIG. 1 of GEBH86. The necessary coding sequence for ITI-DI is the 168 bases between positions 750 and 917 in the cDNA sequence presented in TRAB86. The amino acid sequence of human ITI-D1 is 56 amino acids long, extending from Lys-22 to Arg-77 of the complete ITI light chain sequence. The P1 site of ITI-DI is Met-36. Tables 21–22 present certain ITI mutants; note that the residues are numbered according to the homologus Kunitz domain of BPTI, i.e., with the P1 residue numbered 15. It should be noted that it is probably acceptable to truncate the amino-terminal of ITI-D1, at least up to the first residue homologous with BPTI.

The EpiNE7-inspired mutation (BPTI 15–19 region) of ITI-D1 significantly enhanced its affinity for hNE. We also discovered that mutation of a different part of the molecule (BPTI 1–4 region) provided a similar increase in affinity. When these two mutational patterns were combined, a synergistic increase in affinity was observed. Further mutations in nearby amino acids (BPTI 26, 31, 34) led to additional improvements in affinity.

The elastase-binding muteins of ITI-DI envisioned herein preferably differ from the wild-type domain at one or more of the following positions (numbered per BPTI): 1, 2, 4, 15, 16, 18, 19, 31 and 34. More preferably, they exhibit one or more of the following mutations: Lys1->Arg; Glu2->Pro; Ser4->Phe*; Met15->Val*, Ile; Gly16->Ala; THr18->Phe*; Ser19->Pro; Thr26->ALa; Glu31->Gln; Gln34->Val*. Introduction of one or more of the starred mutations is especially desirable, and, in one preferred embodiment, at least all of the starred mutations are present.

In a second series of embodiments, the present invention relates to Kunitz-type domains which inhibit HNE, but excludes those domains corresponding exactly to the lead domains of claims 1 and 3 of PCT/US92/01501. Preferably, such domains also differ from these lead domains by one or more mutations which are not class A substitutions, more preferably, not class A or B substitutions, and still more preferably, not class A, B or C substitutions, as defined in Table 9. Desirably, such domains are each more similar to one of the aforementioned reference proteins than to any of the lead proteins set forth in PCT/US92/01501.

The examples contain numerous examples of amino-acid sequences accompanied by DNA sequences that encode them. It is to be understood that the invention is not limited to the particular DNA sequence shown.

EXAMPLE 1

Expression and Display of BPTI, ITI-D1, and other Kunitz Domains

Table 6 shows a display gene that encodes: 1) the M13 III signal peptide, 2) BPTI, and 3) the first few amino-acids of mature M13 III protein. Phage have been made in which this gene is the only iii-like gene so that all copies of III expressed are expected to be modified at the amino terminus of the mature protein. Substitutions in the BPTI domain can be made in the cassettes delimited by the AccIII, XhoI, PflMI, ApaI, BssHII, StuI, XcaI, EspI, SphI, or NarI (same recognition as KasI) sites. Table 10 gives amino-acid sequences of a number of Kunitz domains, some of which inhibit hNE. Each of the hNE-inhibiting sequences shown in Table 10 can be expressed as an intact hNE-binding protein or can be incorporated into a larger protein as a domain. Proteins that comprise a substantial part of one of the hNE-inhibiting sequences found in Table 10 are expected to exhibit hNE-inhibitory activity. This is particularly true if the sequence beginning with the first cysteine and continuing through the last cysteine is retained.

ITI domain 1 is a Kunitz domain as discussed below. The ability of display phage to be retained on matrices that display hNE is related to the affinity of the particular Kunitz domain (or other protein) displayed on the phage. Expression of the ITI domain 1::iii fusion gene and display of the fusion protein on the surface of phage were demonstrated by Western analysis and phage titer neutralization experiments. The infectivity of ITI-D1-display phage was blocked by up to 99% by antibodies that bind ITI while wild-type phage were unaffected.

Table 7 gives the sequence of a fusion gene comprising: a) the signal sequence of M13 III, b) ITI-D1, and c) the initial part of mature III of M13. The displayed ITI-D1 domain can be altered by standard methods including: i) oligonucleotide-directed mutagenesis of single-stranded phage DNA, and ii) cassette mutagenesis of RF DNA using the restriction sites (BglI, EagI, NcoI, StyI, PstI, and KasI (two sites)) designed into the gene.

EXAMPLE 2

Fractionation of MA-ITI-D1 Phase Bound to Agarose-Immobilized Protease Beads

To test if phage displaying the ITI-D1::III fusion protein interact strongly with the proteases human neutrophil elastase (hNE), aliquots of display phage were incubated with agarose-immobilized hNE beads ("hNE beads"). The beads were washed and bound phage eluted by pH fractionation as described in U.S. Pat. No. 5,223,409. The pHs used in the step gradient were 7.0, 6.0, 5.5, 5.0, 4.5, 4.0, 3.5, 3.0, 2.5, and 2.0. Following elution and neutralization, the various input, wash, and pH elution fractions were titered. Phage displaying ITI-D1 were compared to phage that display EpiNE-7.

The results of several fractionations are shown in Table 14 (EpiNE-7 or MA-ITI-D1 phage bound to hNE beads). The pH elution profiles obtained using the control display phage (EpiNE-7) were similar previous profiles (U.S. Pat. No. 5,223,409). About 0.3% of the EpiNE-7 display phage applied to the hNE beads eluted during the fractionation procedure and the elution profile had a maximum for elution at about pH 4.0.

The MA-ITI-D1 phage show no evidence of great affinity for hNE beads. The pH elution profiles for MA-ITI-D1 phage bound to hNE beads show essentially monotonic decreases in phage recovered with decreasing pH. Further, the total fractions of the phage applied to the beads that were recovered during the fractionation procedures were quite low: 0.002%.

Published values of $K_i$ for inhibition neutrophil elastase by the intact, large ($M_r$=240,000) ITI protein range between 60 and 150 nM (SWAI88, ODOM90). Our own measurements of pH fraction of display phage bound to hNE beads show that phage displaying proteins with low affinity (>1 µM) for hNE are not bound by the beads while phage displaying proteins with greater affinity (nM) bind to the beads and are eluted at about pH 5. If the first Kunitz-type domain of the ITI light chain is entirely responsible for the inhibitory activity of ITI against hNE, and if this domain is correctly displayed on the MA-ITI-D1 phage, then it appears that the minimum affinity of an inhibitor for hNE that allows binding and fractionation of display phage on hNE beads is between 50 and 100 nM.

EXAMPLE 3

Alteration of the P1 Region of ITI-D1

We assume that ITI-D1 and EpiNE-7 have the same 3D configuration in solution as BPTI. Although EpiNE-7 and ITI-D1 are identical at positions 13, 17, 20, 32, and 39, they differ greatly in their affinities for hNE. To improve the affinity of ITI-D1 for hNE, the EpiNE-7 sequence $\underline{Val}_{15}$-$\underline{Ala}_{16}$-Met$_{17}$-$\underline{Phe}_{18}$-$\underline{Pro}_{19}$-Arg$_{20}$ SEQ ID NO. 130 (bold, underscored amino acids are alterations) was incorporated into the ITI-D1 sequence by cassette mutagenesis between the EagI and StyI/NcoI sites shown in Table 7. Phage isolates containing the ITI-D1::III fusion gene with the EpiNE-7 changes around the P1 position are called MA-ITI-D1E7.

EXAMPLE 4

Fractionation of MA-ITI-D1E7 Phage

To test if ITI-D1E7-display phage bind hNE beads, pH elution profiles were measured. Aliquots of EpiNE-7, MA-ITI-D1, and MA-ITI-D1E7 display phage were incubated with hNE beads for three hours at room temperature (RT). The beads were washed and phage were eluted as described in U.S. Pat. No. 5,223,409, except that only three pH elutions were performed. These data are in Table 16. The pH elution profile of EpiNE-7 display phage is as described. MA-ITI-D1E7 phage show a broad elution maximum around pH 5. The total fraction of MA-ITI-D1E7 phage obtained on pH elution from hNE beads was about 40-fold less than that obtained using EpiNE-7 display phage.

EXAMPLE 5

Preparation of BITI-E7 Phage

Possible reasons for MA-ITI-D1E7 phage having lower affinity for hNE than do MA-EpiNE7 phage include: a) incorrect cleavage of the IIIsignal::ITI-D1E7::matureIII fusion protein, b) inappropriate negative charge on the ITI-D1E7 domain, c) conformational or dynamic changes in the Kunitz backbone caused by substitutions such as Phe$_4$ to Ser$_4$, and d) non-optimal amino acids in the ITI-D1E7:hNE interface, such as $Q_{34}$ or $A_{11}$.

To investigate the first three possibilities, we substituted the first four amino acids of EpiNE7 for the first four amino acids of ITI-D1E7. This substitution should provide a peptide that can be cleaved by signal peptidase-I in the same manner as is the IIIsignal::EpiNE7::matureIII fusion. Furthermore, Phe$_4$ of BPTI is part of the hydrophobic core of the protein; replacement with serine may alter the stability or dynamic character of ITI-D1E7 unfavorably. ITI-D1E7 has a negatively charged Glu at position 2 while EpiNE7 has Pro. We introduced the three changes at the amino terminus of the ITI-D1E7 protein (K1R, E2P, and S4F) by oligonucleotide-directed mutagenesis to produce BITI-E7; phage that display BITI-E7 are called MA-BITI-E7.

We compared the properties of the ITI-III fusion proteins displayed by phage MA-ITI-D1 and MA-BITI using Western analysis as described previously and found no significant differences in apparent size or relative abundance of the fusion proteins produced by either display phage strain. Thus, there are no large differences in the processed forms of either fusion protein displayed on the phage. By extension, there are also no large differences in the processed forms of the gene III fusion proteins displayed by MA-ITI-D1E7 and MA-EpiNE7. Large changes in protein conformation due to altered processing are therefore not likely to be responsible for the great differences in binding to hNE-beads shown by MA-ITI-D1E7 and MA-EpiNE7 display phage.

We characterized the binding properties to hNE-beads of MA-BITI and MA-BITI-E7 display phage using the extended pH fractionation procedure described in U.S. Pat. No. 5,223,409. The results are in Table 17. The pH elution profiles for MA-BITI and MA-BITI-E7 show significant differences from the profiles exhibited by MA-ITI-D1 and MA-ITI-D1E7. In both cases, the alterations at the putative amino terminus of the displayed fusion protein produce a several-fold increase in the fraction of the input display phage eluted from the hNE-beads.

The binding capacity of hNE-beads for display phage varies among preparations of beads and with age for each individual preparation of beads. Thus, it is difficult to directly compare absolute yields of phage from elutions performed at different times. For example, the fraction of MA-EpiNE7 display phage recovered from hNE-beads varies two-fold among the experiments shown in Tables 14, 16, and 17. However, the shapes of the pH elution profiles are similar. It is possible to correct somewhat for variations in binding capacity of hNE-beads by normalizing display phage yields to the total yield of MA-EpiNE7 phage recovered from the beads in a concurrent elution. When the data shown in Tables 14, 16, and 17 are so normalized, the recoveries of display phage, relative to recovered MA-EpiNE7, are shown in Table 3.

TABLE 3

Recovery of Display phage

| Display Phage strain | Normalized fraction of input |
| --- | --- |
| MA-ITI-D1 | 0.0067 |
| MA-BITI | 0.018 |
| MA-ITI-D1E7 | 0.027 |
| MA-BITI-E7 | 0.13 |

Thus, the changes in the amino terminal sequence of the displayed protein produce a three- to five-fold increase in the fraction of display phage eluted from hNE-beads.

In addition to increased binding, the changes introduced into MA-BITI-E7 produce phage that elute from hNE-beads at a lower pH than do the parental MA-ITI-D1E7 phage. While the parental display phage elute with a broad pH maximum centered around pH 5.0, the pH elution profile for MA-BITI-E7 display phage has a pH maximum at around pH 4.75 to pH 4.5.

The pH elution maximum of the MA-BITI-E7 display phage is between the maxima exhibited by the BPTI(K15L) and BPTI(K15V, R17L) display phage (pH 4.75 and pH 4.5 to pH 4.0, respectively) described in U.S. Pat. No. 5,223, 409. From the pH maximum exhibited by the display phage we predict that the BITI-E7 protein free in solution may have an affinity for hNE in the 100 pM range. This would represent an approximately ten-fold increase in affinity for hNE over that estimated above for ITI-D1E7.

As was described above, Western analysis of phage proteins show that there are no large changes in gene III fusion proteins upon alteration of the amino terminal sequence. Thus, it is unlikely that the changes in affinity of display phage for hNE-beads can be attributed to large-scale alterations in protein folding resulting from altered ("correct") processing of the fusion protein in the amino terminal mutants. The improvements in binding may in part be due to: 1) the decrease in the net negative charge (−1 to 0) on the protein arising from the Glu to Pro change at position 2, or 2) increased protein stability resulting from the Ser to Phe substitution at residue 4 in the hydrophobic core of the protein, or 3) the combined effects of both substitutions.

EXAMPLE 6

Production and Properties of MA-BITI-E7-1222 and MA-BITI-E7-141

Within the presumed Kunitz:hNE interface, BITI-E7 and EpiNE7 differ at only two positions: 11 and 34. In EpiNE7 these residues are Thr and Val, respectively. In BITI-E7 they are Ala and Gln. In addition BITI-E7 has Glu at 31 while EpiNE7 has Gln. This negative charge may influence binding although the residue is not directly in the interface. We used oligonucleotide-directed mutagenesis to investigate the effects of substitutions at positions 11, 31 and 34 on the protease:inhibitor interaction.

ITI-D1 derivative BITI-E7-1222 is BITI-E7 with the alteration A11T. ITI-D1 derivative BITI-E7-141 is BITI-E7 with the alterations E31Q and Q34V; phage that display the presence of these proteins are MA-BITI-E7-1222 and MA-BITI-E7-141. We determined the binding properties to hNE-beads of MA-BITI-E7-1222 and MA-BITI-E7-141 display phage using the extended pH fractionation protocol described previously. The results are in Tables 18 (for MA-BITI-E7 and MA-BITI-E7-1222) and 19 (for MA-EpiNE7 and MA-BITI-E7-141). The pH elution profiles for the MA-BITI-E7 and MA-BITI-E7-1222 phage are almost identical. Both phage strains exhibit pH elution profiles with identical maxima (between pH 5.0 and pH 4.5) as well as the same total fraction of input phage eluted from the hNE-beads (0.03%). Thus, the T11A substitution in the displayed ITI-D1 derivative has no appreciable effect on the binding to hNE-beads.

In contrast, the changes at positions 31 and 34 strongly affect the hNE-binding properties of the display phage. The elution profile pH maximum of MA-BITI-E7-141 phage is shifted to lower pH relative to the parental MA-BITI-E7 phage. Further, the position of the maximum (between pH 4.5 and pH 4.0) is identical to that exhibited by MA-EpiNE7 phage in this experiment. Finally, the MA-BITI-E7-141 phage show a ten-fold increase, relative to the parental MA-BITI-E7, in the total fraction of input phage eluted from hNE-beads (0.3% vs 0.03%). The total fraction of MA-BITI-E7-141 phage eluted from the hNE-beads is nearly twice that of MA-EpiNE7 phage.

The above results show that binding by MA-BITI-E7-141 display phage to hNE-beads is comparable to that of MA-EpiNE7 phage. If the two proteins (EpiNE7 and BITI-E7-141) in solution have similar affinities for hNE, then the affinity of the BITI-E7-141 protein for hNE is on the order of 1 pM. Such an affinity is approximately 100-fold greater than that estimated above for the parental protein (BITI-E7) and is $10^5$ to $10^6$ times as great as the affinity for hNE reported for the intact ITI protein.

EXAMPLE 7

Mutagenesis of BITI-E7-141

BITI-E7-141 differs from ITI-D1 at nine positions (1, 2, 4, 15, 16, 18, 19, 31, and 34). To obtain the protein having the fewest changes from ITI-D1 while retaining high specific affinity for hNE, we have investigated the effects of reversing the changes at positions 1, 2, 4, 16, 19, 31, and 34. The derivatives of BITI-E7-141 that were tested are MUT1619, MUTP1, and MUTT26A. The derivatives of BITI that were tested are AMINO1 and AMINO2. The derivative of BITI-E7 that was tested is MUTQE. All of these sequences are shown in Table 10. MUT1619 restores the ITI-D1 residues $Ala_{16}$ and $Ser_{19}$. The sequence designated "MUTP1" asserts the amino acids $I_{15}$, $G_{16}$, $S_{19}$ in the context of BITI-E7-141. It is likely that $M_{17}$ and $F_{18}$ are optimal for high affinity hNE binding. $G_{16}$ and $S_{19}$ occurred frequently in the high affinity hNE-binding BPTI-variants obtained from fractionation of a library of BPTI-variants against hNE (ROBE92). Three changes at the putative amino terminus of the displayed ITI-D1 domain were introduced to produce the MA-BITI series of phage. AMINO1 carries the sequence $K_1$–$E_2$ while $AMINO_2$ carries $K_1$–$S_4$. Other amino acids in the amino-terminal region of these sequences are as in ITI-D1. MUTQE is derived from BITI-E7-141 by the alteration Q31E (reasseting the ITI-D1 w.t. residue). Finally, the mutagenic oligonucleotide MUTT26A is intended to remove a potential site of N-linked glycosylation, $N_{24}$-$G_{25}$-$T_{26}$. In the intact ITI molecule isolated from human serum, the light chain polypeptide is glycosylated at this site ($N_{45}$, ODOM90). It is likely that $N_{24}$ will be glycosylated if the BITI-E7-141 protein is produced via eukaryotic expression. Such glycosylation may render the protein immunogenic when used for long-term treatment. The MUTT26A contains the alteration T26A and removes the potential glycosylation site with minimal changes in the overall chemical properties of the residue at that position. In addition, an Ala residue is frequently found in other BPTI homologues at position 26 (see Table 34 of U.S. Pat. No. 5,223,409). Mutagenesis was performed on ssDNA of MA-BITI-E7-141 phage.

EXAMPLE 8 hNE-Binding Properties of Mutagenized MA-BITI-E7-141 Display Phage

Table 20 shows pH elution data for various display phage eluted from hNE-beads. Total pfu applied to the beads are in column two. The fractions of this input pfu recovered in each pH fraction of the abbreviated pH elution protocol (pH 7.0, pH 3.5, and pH 2.0) are in the next three columns. For data obtained using the extended pH elution protocol, the pH 3.5 listing represents the sum of the fractions of input recovered in the pH 6.0, pH 5.5, pH 5.0, pH 4.5, pH 4.0, and pH 3.5 elution samples. The pH 2.0 listing is the sum of the fractions of input obtained from the pH 3.0, pH 2.5, and pH 2.0 elution samples. The total fraction of input pfu obtained throughout the pH elution protocol is in the sixth column. The final column of the table lists the total fraction of input pfu recovered, normalized to the value obtained for MA-BITI-E7-141 phage.

Two factors must be considered when making comparisons among the data shown in Table 20. The first is that due to the kinetic nature of phage release from hNE-beads and the longer time involved in the extended pH elution protocol, the fraction of input pfu recovered in the pH 3.5 fraction will be enriched at the expense of the pH 2.0 fraction in the extended protocol relative to those values obtained in the abbreviated protocol. The magnitude of this effect can be seen by comparing the results obtained when MA-BITI-E7-141 display phage were eluted from hNE-beads using the two protocols. The second factor is that, for the range of input pfu listed in Table 20, the input pfu influences recovery. The greater the input pfu, the greater the total fraction of the input recovered in the elution. This effect is apparent when input pfu differ by more than a factor of about 3 to 4. The effect can lead to an overestimate of affinity of display phage for hNE-beads when data from phage applied at higher titers is compared with that from phage applied at lower titers.

With these caveats in mind, we can interpret the data in Table 20. The effects of the mutations introduced into MA-BITI-E7-141 display phage ("parental") on binding of display phage to hNE-beads can be grouped into three categories: those changes that have little or no measurable effects, those that have moderate (2- to 3-fold) effects, and those that have large (>5-fold) effects.

The MUTT26A and MUTQE changes appear to have little effect on the binding of display phage to hNE-beads. In terms of total pfu recovered, the display phage containing these alterations bind as well as the parental to hNE-beads. Indeed, the pH elution profiles obtained for the parental and the MUTT26A display phage from the extended pH elution protocol are indistinguishable. The binding of the MUTTQE display phage appears to be slightly reduced relative to the parental and, in light of the applied pfu, it is likely that this binding is somewhat overestimated.

The sequence alterations introduced via the MUTP1 and MUT1619 oligonucleotides appear to reduce display phage binding to hNE-beads about 2- to 3-fold. In light of the input titers and the distributions of pfu recovered among the various elution fractions, it is likely that 1) both of these display phage have lower affinities for hNE-beads than do MA-EpiNE7 display phage, and 2) the MUT1619 display phage have a greater affinity for hNE-beads than do the MUTP1 display phage.

The sequence alterations at the amino terminus of BITI-E7-14 appear to reduce binding by the display phage to hNE-beads at least ten fold. The AMINO2 changes are likely to reduce display phage binding to a substantially greater extent than do the AMINO1 changes.

On the basis of the above interpretations of the data in Table 20, we can conclude that:

1.) The substitution of ALA for THR at position 26 in ITI-D1 and its derivatives has no effect on the interaction of the inhibitor with hNE. Thus, the possibility of glycosylation at $Asn_{24}$ of an inhibitor protein produced in eukaryotic cell culture can be avoided with no reduction in affinity for hNE.

2.) The increase in affinity of display phage for hNE-beads from the changes E31Q and Q34V results primarily from the Val substitution at 34.

3.) All three changes at the amino terminal region of ITI-D1 (positions 1,2, and 4) influence display phage binding to hNE-beads to varying extents. The S4F alteration seems to have about the same effect as does E2P. The change at position 1 appears to have only a small effect.

4.) The changes in the region around the P1 residue in BITI-E7-141 (position 15) influence display phage binding to hNE. The changes A16G and P19S appear to reduce the affinity of the inhibitor somewhat (perhaps 3-fold). The substitution of I15V further reduces binding.

BITI-E7-141 differs from ITI-D1 at nine positions. From the discussion above, it appears likely that a high affinity hNE-inhibitor based on ITI-D1 could be constructed that would differ from the ITI-D1 sequence at only five or six positions. These differences would be: Pro at position 2, Phe at position 4, Val at position 15, Phe at position 18, Val at position 34, and Ala at position 26. If glycosylation of $Asn_{24}$ is not a concern Thr could be retained at 26.

Summary: Estimated Affinities of Isolated ITI-D1 Derivatives for hNE

On the basis of display phage binding to and elution from hNE beads, it is possible to estimate affinities for hNE that various derivatives of ITI-D1 may display free in solution. These estimates are summarized in Table 8.

hNE Inhibitors Derived from ITI Domain 2

In addition to hNE inhibitors derived from ITI-D1, the present invention comprises hNE inhibitors derived from ITI-D2. These inhibitors have been produced in *Pichia pastoris* in good yield. EPI-HNE-4 inhibits human neutrophil elastase with a $K_D \approx 5$ pM.

Purification and Properties of EPI-HNE Proteins

I. EPI-HNE Proteins.

EXAMPLE 9

Amino-Acid Sequences of EPI-HNE-3 and EPI-HNE-4

Table 10 gives amino acid sequences of four human-neutrophil-elastase (hNE) inhibitor proteins: EPI-HNE-1 which is (identical to EpiNE1), EPI-HNE-2, EPI-HNE-3, and EPI-HNE-4. These proteins have been derived from the parental Kunitz-type domains shown. Each of the proteins is shown aligned to the parental domain using the six cysteine residues (shaded) characteristic of the Kunitz-type domain. Residues within the inhibitor proteins that differ from those in the parental protein are in upper case. Entire proteins having the sequences EPI-HNE-1, EPI-HNE-2, EPI-HNE-3, and EPI-HNE-4 (Table 10) have been produced. Larger proteins that comprise one of the hNE-inhibiting sequences are expected to have potent hNE-inhibitory activity; EPI-HNE-1, EPI-HNE-2, EPI-HNE-3, and EPI-HNE-4 are particularly preferred. It is expected that proteins that comprise a significant part of one of the hNE-inhibiting sequences found in Table 10 (particularly if the sequence starting at or before the first cysteine and continuing through or beyond the last cysteine is retained) will exhibit potent hNE-inhibitory activity.

The hNE-inhibitors EPI-HNE-1 and EPI-HNE-2 are derived from the bovine protein BPTI (aprotinin). Within the Kunitz-type domain, these two inhibitors differ from BPTI at the same eight positions: K15I, R17F, I18F, I19P, R39M, A40G, K41N, and R42G. In addition, EPI-HNE-2 differs from both BPTI and EPI-HNE-1 in the presence of four additional residues (EAEA) present at the amino terminus. These residues were added to facilitate secretion of the protein in *Pichia pastoris*.

EPI-HNE-3 is derived from the second Kunitz domain of the light chain of the human inter-α-trypsin inhibitor protein (ITI-D2). The amino acid sequence of EPI-HNE-3 differs from that of ITI-D2(3–58) at only four positions: R15I, I18F, Q19P and L20R. EPI-HNE-4 differs from EPI-HNE-3 by the substitution A3E (the amino-terminal residue) which both facilitates secretion of the protein in *P. pastoris* and improves the $K_D$ for hNE. Table 30 gives some physical properties of the hNE inhibitor proteins. All four proteins are small, high-affinity ($K_i$=2 to 6 pM), fast-acting ($k_{on}$=4 to $11 \times 10^6$ $M^{-1}s^{-1}$) inhibitors of hNE.

II. Production of the hNE-Inhibitors EPI-HNE-2, EPI-HNE-3, and EPI-HNE-4.

EXAMPLE 10

*Pichia pastoris* Production System

Transformed strains of *Pichia pastoris* were used to express the various EPI-HNE proteins derived from BPTI and ITI-D2. Protein expression cassettes are cloned into the plasmid pHIL-D2 using the BstBI and EcoRI sites (Table 111). The DNA sequence of pHIL-D2 is given in Table 250. The cloned gene is under transcriptional control of *P. pastoris* upstream (labeled "aox1 5'") aox1 gene promoter and regulatory sequences (dark shaded region) and downstream polyadenylation and transcription termination sequences (second cross-hatched region, labeled "aox1 3'"). *P. pastoris* GS115 is a mutant strain containing a non-functional histidinol dehydrogenase (his4) gene. The his4 gene contained on plasmid pHIL-D2 and its derivatives can be used to complement the histidine deficiency in the host strain. Linearization of plasmid pHIL-D2 at the indicated SacI site directs plasmid incorporation into the host genome at the aox1 locus by homologous recombination during transformation. Strains of *P. pastoris* containing integrated copies of the expression plasmid will express protein genes under control of the aox1 promoter when the promoter is activated by growth in the presence of methanol as the sole carbon source.

We have used this high density *Pichia pastoris* production system to produce proteins by secretion into the cell culture medium. Expression plasmids were constructed by ligating synthetic DNA sequences encoding the *S. cerevisiae* mating factor α prepro peptide fused directly to the amino terminus of the desired hNE inhibitor into the plasmid pHIL-D2 using the BstBI and the EcoRI sites shown. Table 24 gives the DNA sequence of a BstBI-to-EcoRI insert that converts pHIL-D2 into pHIL-D2(MFα-PrePro::EPI-HNE-3). In this construction, the fusion protein is placed under control of the upstream inducible *P. pastoris* aox1 gene promoter and the downstream aox5 gene transcription termination and polyadenylation sequences. Expression plasmids were linearized by SacI digestion and the linear DNA was incorporated by homologous recombination into the genome of the *P. pastoris* strain GS115 by spheroplast transformation. Regenerated spheroplasts were selected for growth in the absence of added histidine, replated, and individual isolates were screened for methanol utilization phenotype (mut⁺), secretion levels, and gene dose (estimated via Southern hybridization experiments). High level secretion stains were selected for production of hNE inhibitors: PEY-33 for production of EPI-HNE-2 and PEY-43 for production of EPI-HNE-3. In both of these strains, we estimate that four copies of the expression plasmid are integrated as a tandem array into the aox1 gene locus.

To facilitate alteration of the Kunitz-domain encoding segment of pHIL-D2 derived plasmids, we removed two restriction sites given in Table 11: the BstBI at 4780 and the AatII site at 5498. Thus, the Kunitz-domain encoding segment is bounded by unique AatII and EcoRI sites. The new plasmids are called pD2pick("insert") where "insert" defines the domain encoded under control of the aox1 promoter.

Table 26 gives the DNA sequence of pD2pick(MFα::EPI-HNE-3). Table 27 gives a list of restriction sites in pD2pick (MFα::EPI-HNE-3).

EPI-HNE-4 is encoded by pD2pick(MFαPrePro::EPI-HNE-4) which differs from pHIL-D2 in that: 1) the AatII/EcoRI segment of the sequence given in Table 24 is replaced by the segment shown in Table 25 and 2) the changes in the restriction sites discussed above have been made. Strain PEY-53 is *P. pastoris* GS115 transformed with pD2pick (MFα::EPI-HNE-4).

EXAMPLE 11

Protein Production

To produce the proteins, *P. pastoris* strains were grown in mixed-feed fermentations similar to the procedure described by Digan et al. (DIGA89). Although others have reported production of Kunitz domains in *P. pastoris*, it is well known that many secretion systems involve proteases. Thus, it is not automatic that an altered Kunitz domain having a high potency in inhibiting hNE could be secreted from *P. pastoris* because the new inhibitor might inhibit some key enzyme in the secretion pathway. Nevertheless, we have found that *P. pastoris* can secrete hNE inhibitors in high yield.

Briefly, cultures were first grown in batch mode with glycerol as the carbon source. Following exhaustion of glycerol, the culture was grown for about four hours in glycerol-limited feed mode to further increase cell mass and to derepress the aoxl promoter. In the final production phase, the culture was grown in methanol-limited feed mode. During this phase, the aox1 promoter is fully active and protein is secreted into the CM.

Table 34 and Table 35 give the kinetics of cell growth (estimated as $A_{600}$) and protein secretion (mg/l) for cultures of PEY-33 and PEY-43 during the methanol-limited feed portions of the relevant fermentations. Concentrations of the inhibitor proteins in the fermentation cultures were determined from in vitro assays of hNE inhibition by diluted aliquots of cell-free culture media obtained at the times indicated. Despite similarities in gene dose, fermentation conditions, cell densities, and secretion kinetics, the final concentrations of inhibitor proteins secreted by the two strains differ by nearly an order of magnitude. The final concentration of EPI-HNE-2 in the PEY-33 fermentation CM was 720 mg/l. The final concentration of EPI-HNE-3 in the PEY-43 fermentation CM was 85 mg/l. The differences in final secreted protein concentrations may result from idiosyncratic differences in the efficiencies with which the yeast synthesis and processing systems interact with the different protein sequences.

Strain PEY-33 secreted EPI-HNE-2 protein into the CM as a single molecular species which amino acid composition and N-terminal sequencing reveled to be the correctly-processed Kunitz domain with the sequence shown in Table 29. The major molecular species produced by PEY-43 cultures was the properly-processed EPI-HNE-3 protein. However, this strain also secreted a small amount (about 15% to 20% of the total EPI-HNE-3) of incorrectly-processed material. This material proved to be a mixture of proteins with amino terminal extensions (primarily nine or seven residues in length) arising from incorrect cleavage of the MF α PrePro leader peptide from the mature Kunitz domain. The correctly processed protein was purified substantially free of these contaminants as described below.

III. Purification of the hNE-Inhibitors EPI-HNE-2 and EPI-HNE-3.

The proteins can be readily purified from fermenter CM by standard biochemical techniques. The specific purification procedure varies with the specific properties of each protein as described below.

EXAMPLE 12

Purification of EPI-HNE-2

Table 31 gives particulars of the purification of EPI-HNE-2, lot 1. The PEY-33 fermenter culture was harvested by centrifugation at 8000×g for 15 min and the cell pellet was discarded. The 3.3 liter supernatant fraction was microfiltered used a Minitan Ultrafiltration System (Millipore Corporation, Bedford, Mass.) equipped with four 0.2μ filter packets.

The filtrate obtained from the microfiltration step was used in two subsequent ultrafiltration steps. First, two 30K ultrafiltrations were performed on the 0.2μ microfiltrate using the Minitan apparatus equipped with eight 30,000 NMWL polysulfone filter plates (#PLTK0MP04, Millipore Corporation, Bedford, Mass.). The retentate solution from the first 30K ultrafiltration was diluted with 10 mM NaCitrate, pH=3.5, and subjected to a second 30K ultrafiltration. The two 30K ultrafiltrates were combined to give a final volume of 5 liters containing about 1.4 gram of EPI-HNE-2 protein (estimated from hNE-inhibition measurements).

The 30K ultrafiltrate was concentrated with change of buffer in the second ultrafiltration step using the Minitan apparatus equipped with eight 5,000 NMWL filter plates (#PLCC0MP04, Millipore Corporation, Bedford, Mass.). At two times during the 5K ultrafiltration, the retentate solution was diluted from about 300 ml to 1.5 liters with 10 mM NaCitrate, pH=3.5. The final 5K ultrafiltration retentate (Ca. 200 ml) was diluted to a final volume of 1000 ml with 10 mM NaCitrate, pH-3.5.

EPI-HNE-2 protein was obtained from the 5K ultrafiltration retentate solution by ammonium sulfate precipitation at RT. 100 ml of 0.25 M ammonium acetate, pH=3.2, (1/10 volume) was added to the 5K ultrafiltration retentate, followed by one final volume (1.1 liter) of 3 M ammonium sulfate. Following a 30 minute incubation at RT, precipitated material was pelleted by centrifugation at 10,000×g for 45 minutes. The supernatant solution was removed, the pellet was dissolved in water in a final volume of 400 ml, and the ammonium sulfate precipitation was repeated using the ratios described above. The pellet from the second ammonium sulfate precipitation was dissolved in 50 mM sodium acetate, pH=3.5 at a final volume of 300 ml.

Residual ammonium sulfate was removed from the EPI-HNE-2 preparation by ion exchange chromatography. The solution from the ammonium sulfate precipitation step was applied to a strong cation-exchange column (50 ml bed volume Macroprep 50S) (Bio-Rad Laboratories, Inc, Hercules, Calif.) previously equilibrated with 10 mM NaCitrate, pH=3.5. After loading, the column was washed with 300 ml of 10 mM NaCitrate, pH=3.5. EPI-HNE-2 was then batch-eluted from the column with 300 ml of 50 mM NH$_4$OAc, pH=6.2. Fractions containing EPI-HNE-2 activity were pooled and the resulting solution was lyophilized. The dried protein powder was dissolved in 50 ml dH$_2$O and the solution was passed through a 0.2μ filter (#4192, Gelman Sciences, Ann Arbor, Mich.). The concentration of the active inhibitor in the final stock solution was determined to be 2 mM (13.5 mg/ml). This stock solution (EPI-HNE-2, Lot 1)

has been stored as 1 ml aliquots at 4° C. and −70° C. for more than 11 months with no loss in activity.

Table 31 summarizes the yields and relative purity of EPI-HNE-2 at various steps in the purification procedure. The overall yield of the purification procedure was about 30%. The major source of loss was retention of material in the retentate fractions of the 0.2μ microfiltration and 30 k ultrafiltration steps.

EXAMPLE 13

Purification of EPI-HNE-3

Purification of EPI-HNE-3, lot 1, is set out in Table 32. The PEY-43 fermenter culture was harvested by centrifugation at 8,000×g for 15 min and the cell pellet was discarded. The supernatant solution (3100 ml) was microfiltered through 0.2μ Minitan packets (4 packets). After the concentration, a diafiltration of the retentate was performed so that the final filtrate volume from the 0.2μ filtration was 3300 ml.

EPI-HNE-3 protein and other medium components were found to precipitate from solution when the fermenter CM was concentrated. For this reason, the 5 k ultrafiltration step was not performed.

Properly processed EPI-HNE-3 was purified substantially free of mis-processed forms and other fermenter culture components by ion exchange chromatography. A 30 ml bed volume strong cation ion exchange column (Macroprep 50S) was equilibrated with 10 mM NaCitrate pH=3.5. The 30K ultrafiltration filtrate was applied to the column and binding of EPI-HNE-3 to the column was confirmed by demonstrating the complete loss of inhibitor activity in the column flow through. The column was then washed with 300 ml of 10 mM NaCitrate, pH=3.5.

To remove EPI-HNE-3 from the column, we sequentially eluted it with 300 ml volumes of the following solutions:

100 mM ammonium acetate, pH=3.5
50 mM ammonium acetate, pH=4.8
50 mM ammonium acetate, pH=6.0
50 mM ammonium acetate, pH=6.0, 0.1 M NaCl
50 mM ammonium acetate, pH=6.0, 0.2 M NaCl
50 mM ammonium acetate, pH=6.0, 0.3 M NaCl
50 mM ammonium acetate, pH=6.0, 0.4 M NaCl
50 mN Tris/Cl pH=8.0, 1.0 NaCl The majority of the EPI-HNE-3 eluted in two 50 mM ammonium acetate, pH=6.0 fractions. The 0.1 M NaCl fraction contained about 19% of the input EPI-HNE-3 activity (28 mg of 159 mg input) and essentially all of the mis-processed forms of EPI-HNE-3. The 0.2M NaCl fraction contained about 72% (114 mg) of the input EPI-HNE-3 and was almost completely free of the higher molecular weight mis-processed forms and other UV-absorbing contaminants. The fractions from the 50 mM ammonium acetate, pH=6.0, 0.2 M NaCl elution having the highest concentrations of EPI-HNE-3 were combined (95 mg).

An ammonium sulfate precipitation was performed on the 0.2 M NaCl, pH=6.0 ion exchange column eluate. 800 ml of 3 M ammonium sulfate was added to 160 ml of eluate solution (final ammonium sulfate concentration=2.5 M) and the mixture was incubated at RT for 18 hours. The precipitated material was then pelleted by centrifugation at 10,000×g for 45 minutes. The supernatant fluid was discarded and the pelleted material was dissolved in 100 ml of water.

Residual ammonium sulfate was removed from the EPI-HNE-3 preparation by batch ion exchange chromatography. The pH of the protein solution was adjusted to 3.0 with diluted (1/10) HOAc and the solution was then applied to a 10 ml bed volume Macroprep 50S column that had been equilibrated with 10 mM NaCitrate, pH=3.5. Following sample loading, the column was washed with 100 ml of 10 mM NaCitrate, pH=3.5 followed by 100 ml of $dH_2O$. EPI-HNE-3 was eluted from the column with 100 ml of 50 mM $NH_4CO_3$, pH=9.0. pH 9 fractions having the highest concentrations of EPI-HNE-3 were combined (60 mg) and stored at 4° C. for 7 days before lyophilization.

The lyophilized protein powder was dissolved in 26 ml $dH_2O$ and the solution was passed through a 0.2μ filter (#4912, Gelman Sciences, Ann Arbor, Mich.). The concentration of active inhibitor in the final stock solution was found to be 250 μM (1.5 mg/ml). This stock solution (EPI-HNE-3, Lot 1) has been stored as 1 ml aliquots at −70° C. for more than six months with no loss of activity. EPI-HNE-3 stored in water solution (without any buffering) deteriorated when kept at 4° C. After five months, about 70% of the material was active with a $K_i$ of about 12 pM.

Table 32 gives the yield and relative purity of EPI-HNE-3 at various steps in the purification procedure. A major purification step occurred at the first ion exchange chromatography procedure. The ammonium sulfate precipitation step provided only a small degree of further purification. Some loss of inhibitor activity occurred on incubation at pH=9 (See pH stability data). The production and purification of EPI-HNE-1 and EPI-HNE-4 were analogous to that of EPI-HNE-2 and EPI-HNE-3.

EXAMPLE 14

Tricine-PAGE Analysis of EPI-HNE-2 and EPI-HNE-3

The high resolution tricine gel system of Schagger and von Jagow (SCHA87) was used to analyze the purified proteins produced (vide supra). For good resolution of the low molecular weight EPI-HNE proteins we used a 16.5% resolving layer with 10% separating and 4% stacking layers. Following silver staining, we inspected a gel having:

Lane 1: EPI-HNE-2 25 ng,
Lane 2: EPI-HNE-2 50 ng,
Lane 3: EPI-HNE-2 100 ng,
Lane 4: EPI-HNE-2 200 ng,
Lane 5: EPI-HNE-3 25 ng,
Lane 6: EPI-HNE-3 50 ng,
Lane 7: EPI-HNE-3 100 ng,
Lane 8: EPI-HNE-3 200 ng, and
Lane 9: Molecular-weight standards: RPN 755, (Amersham Corporation, Arlington Heights, Ill.).

Stained proteins visible on the gel and their molecular weights in Daltons are: ovalbumin (46,000), carbonic anhydrase (30,000), trypsin inhibitor (21,500), lysozyme (14,300), and aprotinin (6,500). The amount of protein loaded was determined from measurements of hNE-inhibition. We found the following features. EPI-HNE-2, Lot 1 shows a single staining band of the anticipated size (ca. 6,700 D) at all loadings. Similarly, EPI-HNE-3, Lot 1 protein shows a single staining band of the anticipated size (ca. 6,200 D). At the highest loading, traces of the higher molecular weight (ca. 7,100 D) incorrectly processed form can be detected. On the basis of silver-stained high-resolution PAGE analysis, the purity of both protein preparations is assessed to be significantly greater than 95%.

IV. Properties of EPI-HNE-2 and EPI-HNE-3.

A. Inhibition of hNE.

EXAMPLE 15

Measured $K_D$s of EPI-HNE Proteins for hNE

Inhibition constants for the proteins reacting with hNE ($K_i$) were determined using RT measurements of hydrolysis of a fluorogenic substrate (N-methoxysuccinyl-Ala-Ala-Pro-Val-7-amino-4-methylcoumarin, Sigma M-9771) by hNE. For these measurements, aliquots of the appropriately diluted inhibitor stocks were added to 2 ml solutions of 0.847 nM hNE in reaction buffer (50 mM Tris-Cl, pH=8.0, 150 mM NaCl, 1 mM $CaCl_2$, 0.25% Triton-X-100) in plastic fluorescence cuvettes. The reactions were incubated at RT for 30 minutes. At the end of the incubation period, the fluorogenic substrate was added at a concentration of 25 µM and the time course for increase in fluorescence at 470 nm (excitation at 380 nm) due to enzymatic substrate cleavage was recorded using a spectrofluorimeter (Perkin-Elmer 650-15) and strip chart recorder. We did not correct for competition between substrate and inhibitor because ($S_0/K_m$) is 0.07 (where $S_0$ is the substrate concentration and $K_m$ is the binding constant of the substrate for hNE). $K_i$ is related to $K_{apparent}$ by $K_i = K_{apparent} \times (1/(1+(S_0/K_m)))$. The correction is small compared to the possible errors in $K_{apparent}$. Rates of enzymatic substrate cleavage were determined from the linear slopes of the recorded increases in fluorescence. The percent residual activity of hNE in the presence of the inhibitor was calculated as the percentage of the rate of fluorescence increase observed in the presence of the inhibitor to that observed when no added inhibitor was present.

We recorded data used to determine $K_i$ for EPI-HNE-2 and EPI-HNE-3 reacting with hNE. Data obtained as described above are recorded as percent residual activity plotted as a function of added inhibitor. Values for $K_i$ and for active inhibitor concentration in the stock are obtained from a least-squares fit program. From the data, $K_i$ values for EPI-HNE-2 and for EPI-HNE-3 reacting with hNE at RT were calculated to be 4.8 pM and 6.2 pM, respectively. Determinations of $K_i$ for EPI-HNE-2 and EPI-HNE-3 reacting with hNE are given in Table 36 and Table 37.

The kinetic on-rates for the inhibitors reacting with hNE ($k_{on}$) were determined from measurements of progressive inhibition of substrate hydrolytic activity by hNE following addition of inhibitor. For these experiments, a known concentration of inhibitor was added to a solution of hNE (0.847 nM) and substrate (25 µM) in 2 ml of reaction buffer in a plastic fluorescence cuvette. The change in fluorescence was recorded continuously following addition of the inhibitor. In these experiments, sample fluorescence did not increase linearly with time. Instead, the rate of fluorescence steadily decreased reflecting increasing inhibition of hNE by the added inhibitor. The enzymatic rate at selected times following addition of the inhibitor was determined from the slope of the tangent to the fluorescence time course at that time.

The kinetic constant $k_{on}$ for EPI-HNE-2 reacting with hNE was determined as follows. EPI-HNE-2 at 1.3 nM was added to buffer containing 0.867 nM hNE (I:E=1.5:1) at time 0. Measured percent residual activity was recorded as a function of time after addition of inhibitor. A least-squares fit program was used to obtain the value of $k_{on} = 4.0 \times 10^6$ $M^{-1}s^{-1}$.

The kinetic off rate, $k_{off}$, is calculated from the measured values of $K_i$ and $k_{on}$ as:

$$k_{off} = K_D \times k_{on}.$$

The values from such measurements are included in Table 30. The EPI-HNE proteins are small, high affinity, fast acting inhibitors of hNE.

B. Specificity.

EXAMPLE 16

Specificity of EPI-HNE Proteins

We attempted to determine inhibition constants for EPI-HNE proteins reacting with several serine proteases. The results are summarized in Table 33. In all cases except chymotrypsin, we were unable to observe any inhibition even when 10 to 100 µM inhibitor was added to enzyme at concentrations in the nM range. In Table 33, our calculated values for $K_i$ (for the enzymes other than chymotrypsin) are based on the conservative assumption of less than 10% inhibition at the highest concentrations of inhibitor tested. For chymotrypsin, the $K_i$ is about 10 µM and is probably not specific.

C. In Vitro Stability.

EXAMPLE 17

Resistance to Oxidative Inactivation

Table 39 shows measurements of the susceptibility of EPI-HNE proteins to oxidative inactivation as compared with that of two other natural protein hNE inhibitors: α1 Protease Inhibitor (API) and Secretory Leucocyte Protease Inhibitor (SLPI). API (10 µM), SLPI (8.5 µM), EPI-HNE-1 (5 µM), EPI-HNE-2 (10 µM), EPI-HNE-3 (10 µM), and EPI-HNE-4 (10 µM) were exposed to the potent oxidizing agent, Chloramine-T, at the indicated oxidant:inhibitor ratios in 50 mM phosphate buffer, pH=7.0 for 20 minutes at RT. At the end of the incubation period, the oxidation reactions were quenched by adding methionine to a final concentration of 4 mM. After a further 10 minute incubation, the quenched reactions were diluted and assayed for residual inhibitor activity in our standard hNE-inhibition assay.

Both API and SLPI are inactivated by low molar ratios of oxidant to inhibitor. The Chloramine-T:protein molar ratios required for 50% inhibition of API and SLPI are about 1:1 and 2:1, respectively. These ratios correspond well with the reported presence of two and four readily oxidized methionine residues in API and SLPI, respectively. In contrast, all four EPI-HNE proteins retain essentially complete hNE-inhibition activity following exposure to Chloramine-T at all molar ratios tested (up to 50:1, in the cases of EPI-HNE-3 and EPI-HNE-4). Neither EPI-HNE-3 nor EPI-HNE-4 contain any methionine residues. In contrast, EPI-HNE-1 and EPI-HNE-2 each contains two methionine residues (see Table 10). The resistance of these proteins to oxidative inactivation indicates that the methionine residues are either inaccessible to the oxidant or are located in a region of the protein that does not interact with hNE.

EXAMPLE 18 pH Stability

Table 38 shows the results of measurements of the pH stability of EPI-HNE proteins. The stability of the proteins to exposure to pH conditions in the range of pH 1 to pH 10 was assessed by maintaining the inhibitors in buffers of defined pH at 37° C. for 18 hours and determining the residual hNE inhibitory activity in the standard hNE-inhibition assay. Proteins were incubated at a concentration of 1 µM. The buffers shown in Table 4 were formulated as described (STOL90) and used in the pH ranges indicated:

TABLE 4

Buffers used in stability studies

| Buffer | Lowest pH | Highest pH |
|---|---|---|
| Glycine-HCl | 1 | 2.99 |
| Citrate-Phosphate | 3 | 7 |
| Phosphate | 7 | 8 |
| Glycine-NaOH | 8.5 | 10 |

Both BPTI-derived inhibitors, EPI-HNE-1 and EPI-HNE-2, are stable at all pH values tested. EPI-HNE-3 and EPI-HNE-4, the inhibitors derived from the human protein Kunitz-type domain, were stable when incubated at low pH, but showed some loss of activity at high pH. When incubated at 37° C. for 18 hours at pH=7.5, the EPI-HNE-3 preparation lost 10 to 15% of its hNE-inhibition activity. EPI-HNE-4 retains almost full activity to pH 8.5. Activity of the ITI-D2-derived inhibitor declined sharply at higher pH levels so that at pH 10 only 30% of the original activity remained. The sensitivity of EPI-HNE-3 to incubation at high pH probably explains the loss of activity of the protein in the final purification step noted previously.

EXAMPLE 19

Temperature Stability

The stability of EPI-HNE proteins to temperatures in the range 0° C. to 95° C. was assessed by incubating the inhibitors for thirty minutes at various temperatures and determining residual inhibitory activity for hNE. In these experiments, protein concentrations were 1 µM in phosphate buffer at pH=7. As is shown in Table 40, the four inhibitors are quite temperature stable.

EPI-HNE-1 and EPI-HNE-2 maintain full activity at all temperatures below about 90° C. EPI-HNE-3 and EPI-HNE-4 maintain full inhibitory activity when incubated at temperatures below 65° C. The activity of the protein declines somewhat at higher temperatures. However, all three proteins retain more than ≈50% activity even when incubated at 95° C. for 30 minutes.

EXAMPLE 20

Routes to Other hNE-Inhibitory Sequences

The present invention demonstrates that very high-affinity hNE inhibitors can be devised from Kunitz domains of human origin with very few amino-acid substitutions. It is believed that almost any Kunitz domain can be made into a potent and specific hNE inhibitor with eight or fewer substitutions. In particular, any one of the known human Kunitz domains could be remodeled to provide a highly stable, highly potent, and highly selective hNE inhibitor. There are at least three routes to hNE inhibitory Kunitz domains: 1) replacement of segments known to be involved in specifying hNE binding, 2) replacement of single residues thought to be important for hNE binding, and 3) use of libraries of Kunitz domains to select hNE inhibitors.

EXAMPLE 21

Substitution of Segments in Kunitz Domains

Table 10 shows the amino-acid sequences of 11 human Kunitz domains. These sequences have been broken into ten segments: 1:N terminus-residue 4; 2:residue 5; 3:6–9(or 9a); 4:10–13; 5:14; 6:15–21; 7:22–30; 8:31–36; 8:37–38; 9:39–42; and 10:43-C terminus (or 42a-C terminus).

Segments 1, 3, 5, 7, and 9 contain residues that strongly influence the binding properties of Kunitz domains and are double underscored in the Consensus Kunitz Domain of Table 10. Other than segment 1, all the segments are the same length except for TFPI-2 Domain 2 which carries an extra residue in segment 2 and two extra residues in segment 10.

It may be desirable to have an hNE inhibitor that is highly similar to a human protein to reduce the chance of immunogenicity. Candidate high-affinity hNE inhibitor protein sequences may be obtained by taking an aprotonin-type Kunitz domain that strongly or very strongly inhibits hNE, and replacing one, two, three, four or all of segments 2, 4, 6, 8, and 10 with the corresponding segment from a human Kunitz domain, such as those listed in Table 10, or other domain known to have relatively low immunogenicity in humans. (Each of segments 2, 4, 6, 8, and 10 may be taken from the same human domain, or they may be taken from different human domains.) Alternatively, a reduced immunogenicity, high hNE inhibiting domain may be obtained by taking one of the human aprotonin-type Kunitz domains and replacing one, two, three or all of segments 3, 5, 7 and 9 (and preferably also segment 1) with the corresponding segment from one or more aprotonin-like Kunitz domains that strongly or very strongly inhibit hNE. In making these humanized hNE inhibitors, one may, of course, use, rather than a segment identical to that of one of the aforementioned source proteins, a segment which differs from the native source segment by one or more conservative modifications. Such differences should, of course, be taken with due consideration for their possible effect on inhibitory activity and/or immunogenicity. In some cases, it may be advantageous that the segment be a hybrid of corresponding segments from two or more human domains (in the case of segments 2, 4, 6, 8 and 10) or from two or more strong or very strong hNE inhibitor domains (in the case of segments 3, 5, 7, and 9). Segment 1 may correspond to the segment 1 of a strong or very strong hNE inhibitor, or the segment 1 of a human aprotonin-like Kunitz domain, or be a chimera of segment 1's from both.

The proteins DPI.1.1, DPI.2.1, DPI.3.1, DPI.4.1, DPI.5.1, DPI.6.3, DPI.7.1, DPI.8.1, and DPI.9.1 were designed in this way. DPI.1.1 is derived from App-I by replacing segments 3, 5, 7, and 9 with the corresponding segments from EPI-HNE-1. DPI.2.1 is derived from TFPI2-D1 by replacing segments 3, 5, 7, and 9 with the corresponding residues from EPI-HNE-1. DPI.3.1 is derived from TFPI2-D2 by replacing residues 9a–21 with residues 10–21 of EPI-HNE-4 and replacing residues 31–42b with residues 31–42 of EPI-HNE-4. DPI.4.1 is derived from TFPI2-D3 by replacing segments 3, 5, 7, and 9 with the corresponding residues from MUTQE. DPI.5.1 is derived from LACI-D1 by replacing segments 3, 5, 7, and 9 with the corresponding residues from MUTQE. DPI.6.1 is derived from LACI-D2 by replacing segments 3, 5, 7, and 9 with the corresponding residues from MUTQE. DPI.7.1 is derived from LACI-D3 by replacing segments 3, 5, 7, 9 with the corresponding residues from EPI-HNE-4. DPI.8.1 is derived from the A3 collogen Kunitz domain by substitution of segments 3, 5, 7, and 9 from EPI-HNE-4. DPI.9.1 is derived from the HKI B9 domain by replacing segments 3, 5, 7, and 9 with the corresponding residues from EPI-HNE-4.

While the above-described chimera constitute preferred embodiments of the present invention, the invention is not limited to these chimera.

EXAMPLE 22

Point substitutions in Kunitz Domains

In this example, certain substitution mutations are discussed. It must be emphasized that this example describes preferred embodiments of the invention, and is not intended to limit the invention.

All of the protein sequences mentioned in this example are to be found in Table 10. Designed protease inhibitors are designated "DPI" and are derived from human Kunitz domains (also listed in Table 10). Each of the sequences designated DPI.i.2 (for i=1 to 9) is derived from the domain two above it in the table by making minimal point mutations. Each of the sequences designated DPI.i.3 (for i=1 to 9) is derived from the sequence three above it by more extensive mutations intended to increase affinity. For some parental domains, additional examples are given. The sequences designated DPI.i.1 are discussed in Example 21.

The most important positions are 18 and 15. Any Kunitz domain is likely to become a good hNE inhibitor if Val or Ile is at 15 (with Ile being preferred) and Phe is at 18. (However, these features are not necessarily required for such activity.)

If a Kunitz domain has Phe at 18 and either Ile or Val at 15 and is not a good hNE inhibitor, there may be one or more residues in the interface preventing proper binding.

The Kunitz domains having very high affinity for hNE herein disclosed (as listed in Table 10) have no charged groups at residues 10, 12 through 19, 21, and 32 through 42. At position 11, only neutral and positively charged groups have been observed in very high affinity hNE inhibitors. At position 31, only neutral and negatively charged groups have been observed in high-affinity hNE inhibitors. If a parental Kunitz domain has a charged group at any of those positions where only neutral groups have been observed, then each of the charged groups is preferably changed to an uncharged group picked from the possibilities in Table 46 as the next step in improving binding to hNE. Similarly, negatively charged groups at 11 and 19 and positively charged groups at 31 are preferably replaced by groups picked from Table 46.

At position 10, Tyr, Ser, and Val are seen in high-affinity hNE inhibitors. Asn or Ala may be allowed since this position may not contact hNE. At position 11, Thr, Ala, and Arg have been seen in high-affinity hNE inhibitors. Gln and Pro are very common at 11 in Kunitz domains and may be acceptable. Position 12 is almost always Gly. If 12 is not Gly, try changing it to Gly.

All of the high-affinity hNE inhibitors produced so far have $Pro_{13}$, but it has not been shown that this is required. Many (62.5%) Kunitz domains have $Pro_{13}$. If 13 is not Pro, then changing to Pro may improve the hNE affinity. Val, Ala, Leu, or Ile may also be acceptable here.

Position 14 is Cys. It is possible to make domains highly similar to Kunitz domains in which the 14–38 disulfide is omitted. Such domains are likely to be less stable than true Kunitz domains having the three standard disulfides.

Position 15 is preferably Ile or Val. Ile is more preferred.

Most Kunitz domains (82%) have either Gly or Ala at 16 and this may be quite important. If residue 16 is not Gly or Ala, change 16 to either Gly or Ala; Ala is preferred. Position 17 in very potent hNE inhibitors has either Phe or Met; those having Ile or Leu at 17 are less potent. Phe is preferred. Met should be used only if resistance to oxidation is not important. Position 18 is Phe.

It has been shown that high-affinity hNE inhibitors may have either Pro or Ser at position 19. Gln or Lys at position 19 may be allowed. At position 21, Tyr and Trp have been seen in very high affinity hNE inhibitors; Phe may also work.

At position 31, Gln, Glu, and Val have been observed in high affinity hNE inhibitors. Since this is on the edge of the binding interface, other types are likely to work well. One should avoid basic types (Arg and Lys). At position 32, Thr and Leu have been observed in high-affinity hNE inhibitors. This residue may not make direct contact and other uncharged types may work well. Pro is very common here. Ser has been seen and is similar to Thr. Ala has been seen in natural Kunitz domains and is unlikely to make any conflict. Position 33 is always Phe in Kunitz domains.

It appears that many amino acid types may be placed at position 34 while retaining high affinity for hNE; large hydrophobic residues (Phe, Trp, Tyr) are unfavorable. Val and Pro are most preferred at 34. Positions 35–38 contain the sequence Tyr-Gly-Gly-Cys. There is a little diversity at position 36 in natural Kunitz domains. In the BPTI-Trypsin complex, changing $Gly_{36}$ to Ser greatly reduces the binding to trypsin. Nevertheless, S36 or T36 may not interfere with binding to hNE and could even improve it. If residue 36 is not Gly, one should consider changing it to Gly.

Position 39 seems to tolerate a variety of types. Met and Gln are known to work in very high-affinity inhibitors. Either Ala or Gly are acceptable at position 40; Gly is preferred. At position 41, Asn is by far the most common type in natural Kunitz domains and may act to stabilize the domains. At position 42, Gly is preferred, but Ala is allowed.

Finally, positions that are highly conserved in Kunitz domains may be converted to the conserved type if needed. For example, the mutations X36G, X37G, X41N, and X12G may be desirable in those cases that do not already have these amino acids at these positions.

The above mutations are summarized in Table 41. Table 41 contains, for example, mutations of the form X15I which means change the residue at position 15 (whatever it is) to Ile or leave it alone if it is already Ile. A Kunitz domain that contains the mutation X18F and either X15I or X15V (X15I preferred) will have strong affinity for hNE. As from one up to about 8 of the mutations found in Table 41 are asserted, the affinity of the protein for hNE will increase so that the $K_i$ approaches the range 1–5 pM.

The sequence DPI.1.2 was constructed from the sequence of App-I by the changes R15I, I18F, and F34V and should be a potent hNE inhibitor. DPI.1.3 is likely to be a more potent inhibitor, having the changes R15I, M17F (to avoid sensitivity to oxidation), I18F, P32T, F34V, and G39M.

DPI.2.2 was derived from the sequence of TFPI2-D1 by the changes R15I, L18F, and L34V and should be a potent hNE inhibitor. DPI.2.3 may be more potent due to the changes Y11T, R15I, L17F, L18F, R31Q, Q32T, L34V, and E39M.

DPI.3.2 is derived from TFPI2-D2 by the changes E15I, T18F, S26A (to prevent glycosylation), K32T, and F34V and should be a potent hNE inhibitor. DPI.3.3 may be more potent by having the changes Δ9a, D11A, D12G, Q13P, E15I, S17F, T18F, E19K, K20R, N24A (to prevent glycosylation), K32T, F34V, and Δ42a–b 42b.

DPI.4.2 is derived from TFPI2-D3 by the changes S15I, N17F, and V18F and should be a potent inhibitor of hNE. DPI.4.3 may be more potent by having the changes E11T, L13P, S15I, N17F, V18F, A32T, T34V, and T36G.

DPI.5.2 is derived from LACI-D1 by the changes K15I and M18F and is likely to be a potent inhibitor of hNE. DPI.5.3 may be more potent due to the changes D10Y, D11T, K15I, I117F, M18F, and E32T. Other changes that may improve DPI.5.3 include F21W, I134V, E39M, and Q42G.

The sequence of DPI.6.2 was constructed from the sequence of human LACI-D2 by the mutations R15V and I18F. The rest of the sequence of LACI-D2 appears to be compatible with hNE binding. DPI.6.3 carries two further mutations that make it more like the hNE inhibitors here disclosed: Y17F and K34V. Other alterations that are likely to improve the hNE binding of LACI-D2 include I13P, R32T, and D10S. DPI.6.4 is derived from DPI.6.3 by the additional alteration N25A that will prevent glycosylation when the protein is produced in a eukaryotic cell. Other substitutions that would prevent glycosylation include: N25K, T27A, T27E, N25S, and N25S. DPI.6.5 moves further toward the ITI-D1, ITI-D2, and BPTI derivatives that are known to have affinity for hNE in the 1–5 pM range through the mutations I13P, R15V, Y17F, I18F, T19Q, N25A, K34V, and L39Q. In DPI.6.6, the T19Q and N25A mutations have been reverted. Thus the protein would be glycosylated in yeast or other eukaryotic cells at $N_{25}$. DPI.6.7 carries the alterations I13P, R15I, Y17F, I18F, T19P, K34V, and L39Q.

DPI.7.2 is derived from human LACI domain 3 by the mutations R15V and E18F. DPI.7.3 carries the mutations R15V, N17F, E18F, and T46K. The T46K mutation should prevent glycosylation at $N_{44}$. DPI.7.4 carries more mutations so that it is much more similar to the known high-affinity hNE inhibitors. The mutations are D10V, L13P, R15V, N17F, E18F, K34V, S36G, and T46K. DPI.7.5 carries a different set of alterations: L13P, R15I, N17F, E18F, N19P, F21W, R31Q, P32T, K34V, S36G, and T46K; DPI.7.5 should not be glycosylated in eukaryotic cells.

DPI.8.2 is derived from the sequence of the A3 collagen Kunitz domain by the changes R15I, D16A, I18F, and W34V and is expected to be a potent hNE inhibitor. DPI.8.3 is derived from the A3 collagen Kunitz domain by the changes T13P, R15I, D16A, I18F, K20R, and W34V.

DPI.9.2 is derived from the HKI B9 Kunitz domain by the changes Q15I, T16A, and M18F and is expected to be a potent hNE inhibitor. DPI.9.3 may be more potent due to the changes Q15I, T16A, M18F, T19P, E31V, and A34V.

EXAMPLE 23

Libraries of Kunitz Domains

Other Kunitz domains that can potently inhibit hNE may be derived from human Kunitz domains either by substituting hNE-inhibiting sequences into human domains or by using the methods of U.S. Pat. No. 5,223,409 and related patents. Table 42 shows a gene that will cause display of human LACI-D2 on M13 gIIIp; essentially the same gene could be used to achieve display on M13 gVIIIp or other anchor proteins (such as bacterial outer-surface proteins (OSPs)). Table 43 shows a gene to cause display of human LACI D1.

Table 44 and Table 45 give variegations of LACI-D1 and LACI-D2 respectively. Each of these is divided into variegation of residues 10–21 in one segment and residues 31–42 in another. In each case, the appropriate vgDNA is introduced into a vector that displays the parental protein and the library of display phage are fractionated for binding to immobilized hNE.

TABLE 13

BPTI Homologues (1–20)

| R # | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| −5 |   |   |   |   |   |   |   |   |   |   |   |   |   |   |   |   |   |   |   | — |
| −4 |   |   |   |   |   |   |   |   |   |   |   |   |   |   |   |   |   |   |   | — |
| −3 | — | — | — | F | — | — | — | — | — | — | — | — | — | — | — | — | Z | — | — | — |
| −2 | — | — | — | Q | T | — | — | — | — | — | — | Q | — | — | — | — | H | G | Z | — | Z |
| −1 | — | — | — | T | E | — | — | — | — | — | — | P | — | — | — | — | D | D | G | — | P |
| 1 | R | R | R | P | R | R | R | R | R | R | L | A | R | R | R | K | R | A | R |
| 2 | P | P | P | P | P | P | P | P | P | P | R | A | P | P | P | R | P | A | R |
| 3 | D | D | D | D | D | D | D | D | D | D | K | K | D | R | T | D | S | K | K |
| 4 | F | F | F | L | F | F | F | F | F | F | L | Y | F | F | F | I | F | Y | L |
| 5 | C | C | C | C | C | C | C | C | C | C | C | C | C | C | C | C | C | C | C |
| 6 | L | L | L | Q | L | L | L | L | L | L | I | K | E | E | N | R | N | K | I |
| 7 | E | E | E | L | E | E | E | E | E | E | L | L | L | L | L | L | L | L | L |
| 8 | P | P | P | P | P | P | P | P | P | P | H | P | P | P | P | P | P | P | H |
| 9 | P | P | P | Q | P | P | P | P | P | P | R | L | A | A | P | P | A | V | R |
| 10 | Y | Y | Y | A | Y | Y | Y | Y | Y | Y | N | R | E | E | E | E | E | R | N |
| 11 | T | T | T | R | T | T | T | T | T | T | P | I | T | T | S | Q | T | Y | P |
| 12 | G | G | G | G | G | G | G | G | G | G | G | G | G | G | G | G | G | G | G |
| 13 | P | P | P | P | P | P | P | P | P | P | R | P | L | L | R | P | P | P | R |
| 14 | C | T | A | C | C | C | C | C | C | C | C | C | C | C | C | C | C | C | C |
| 15 | K | K | K | K | K | V | G | A | L | I | K | Y | K | K | K | R | K | K | Y |

TABLE 13-continued

| 16 | A | A | A | A | A | A | A | A | A | A | Q | R | A | A | G | A | K | D |
| --- | --- | --- | --- | --- | --- | --- | --- | --- | --- | --- | --- | --- | --- | --- | --- | --- | --- | --- |
| 17 | R | R | R | A | A | R | R | R | R | R | K | K | Y | R | H | R | S | K | K |
| 18 | I | I | I | L | M | I | I | I | I | I | I | I | I | I | I | L | I | F | I |
| 19 | I | I | I | L | I | I | I | I | I | I | P | P | R | R | R | P | P | P | P |
| 20 | R | R | R | R | R | R | R | R | R | R | A | S | S | S | R | R | Q | S | A |
| 21 | Y | Y | Y | Y | Y | Y | Y | Y | Y | Y | F | F | F | F | I | Y | Y | F | F |
| 22 | F | F | F | F | F | F | F | F | F | F | F | Y | Y | H | H | Y | F | Y | Y |
| 23 | Y | Y | Y | Y | Y | Y | Y | Y | Y | Y | Y | Y | Y | Y | Y | Y | Y | Y | Y |
| 24 | N | N | N | N | N | N | N | N | N | N | N | K | N | N | N | N | N | N | N |
| 25 | A | A | A | S | A | A | A | A | A | A | A | Q | W | L | R | L | P | S | W | Q |
| 26 | K | K | K | T | K | K | K | K | K | K | K | K | A | A | E | A | K | K | K |
| 27 | A | A | A | S | A | A | A | A | A | A | K | A | A | S | S | S | S | A | K |
| 28 | G | G | G | N | G | G | G | G | G | G | K | K | Q | Q | N | R | G | K | K |
| 29 | L | L | L | A | F | L | L | L | L | L | L | Q | Q | Q | Q | K | M | G | Q | Q |
| 30 | C | C | C | C | C | C | C | C | C | C | C | C | C | C | C | C | C | C | C |
| 31 | Q | Q | Q | E | E | Q | Q | Q | Q | Q | E | L | L | L | K | E | Q | L | E |
| 32 | T | T | T | P | T | T | T | T | T | T | G | P | Q | E | V | S | Q | P | R |
| 33 | F | F | F | F | F | F | F | F | F | F | F | F | F | F | F | F | F | F | F |
| 34 | V | V | V | T | V | V | V | V | V | V | T | D | I | I | F | I | I | N | D |
| 35 | Y | Y | Y | Y | Y | Y | Y | Y | Y | Y | W | Y | Y | Y | Y | Y | Y | Y | W |
| 36 | G | G | G | G | G | G | G | G | G | G | S | S | G | G | G | G | G | S | S |
| 37 | G | G | G | G | G | G | G | G | G | G | G | G | G | G | G | G | G | G | G |
| 38 | C | T | A | C | C | C | C | C | C | C | C | C | C | C | C | C | C | C | C |
| 39 | R | R | R | Q | R | R | R | R | R | R | G | G | G | G | K | R | G | G | G |
| 40 | A | A | A | G | A | A | A | A | A | A | G | G | G | G | G | G | G | G | G |
| 41 | K | K | K | N | K | K | K | K | K | K | N | N | N | N | N | N | N | N | N |
| 42 | R | R | R | N | S | R | R | R | R | R | S | A | A | A | A | K | Q | A | S |
| 43 | N | N | N | N | N | N | N | N | N | N | N | N | N | N | N | N | N | N | N |
| 44 | N | N | N | N | N | N | N | N | N | N | R | R | R | R | N | N | R | R | R |
| 45 | F | F | F | F | F | F | F | F | F | F | F | F | F | F | F | F | F | F | F |
| 46 | K | K | K | E | K | K | K | K | K | K | K | K | K | K | E | K | D | K | K |
| 47 | S | S | S | T | S | S | S | S | S | S | S | T | T | T | T | T | T | T | T |
| 48 | A | A | A | T | A | A | A | A | A | A | A | I | I | I | I | R | K | I | I |
| 49 | E | E | E | E | E | E | E | E | E | E | E | D | D | D | D | A | Q | E | E |
| 50 | D | D | D | M | D | D | D | D | D | D | E | E | E | E | E | E | Q | E | E |
| 51 | C | C | C | C | C | C | C | C | C | C | C | C | C | C | C | C | C | C | C |
| 52 | M | M | M | L | M | M | M | M | M | M | E | R | R | H | R | V | Q | R | R |
| 53 | R | R | R | R | R | R | R | R | R | R | R | R | R | E | R | G | R | R | R |
| 54 | T | T | T | I | T | T | T | T | T | T | T | T | T | T | T | A | V | T | T |
| 55 | C | C | C | C | C | C | C | C | C | C | C | C | C | C | C | C | C | C | C |
| 56 | G | G | G | E | G | G | G | G | G | G | I | V | V | V | G | R | V | V | I |
| 57 | G | G | G | P | G | G | G | G | G | G | R | G | G | G | P | — | G | G | G |
| 58 | A | A | A | P | A | A | A | A | A | A | K | — | — | — | K | P | — | — | — |
| 59 | — | — | — | Q | — | — | — | — | — | — | — | — | — | — | — | E | — | — | — |
| 60 | — | — | — | Q | — | — | — | — | — | — | — | — | — | — | — | R | — | — | — |
| 61 | — | — | — | T | — | — | — | — | — | — | — | — | — | — | — | P | — | — | — |
| 62 | — | — | — | D | — | — | — | — | — | — | — | — | — | — | — | — | — | — | — |
| 63 | — | — | — | K | — | — | — | — | — | — | — | — | — | — | — | — | — | — | — |
| 64 | — | — | — | S | — | — | — | — | — | — | — | — | — | — | — | — | — | — | — |

BPTI Homologues (21–40)

| R # | 21 | 22 | 23 | 24 | 25 | 26 | 27 | 28 | 29 | 30 | 31 | 32 | 33 | 34 | 35 | 36 | 37 | 38 | 39 | 40 |
| --- | --- | --- | --- | --- | --- | --- | --- | --- | --- | --- | --- | --- | --- | --- | --- | --- | --- | --- | --- | --- |
| −5 | — | — | — | — | — | — | — | — | — | — | — | — | D | — | — | — | — | — | — | — |
| −4 | — | — | — | — | — | — | — | — | — | — | — | — | E | — | — | — | — | — | — | — |
| −3 | — | — | — | — | — | — | — | — | — | — | — | T | P | — | — | — | — | — | — | — |
| −2 | — | L | Z | R | K | — | — | — | R | R | — | E | T | — | — | — | — | — | — | — |
| −1 | — | Q | D | D | N | — | — | — | Q | K | — | R | T | — | — | — | Z | — | — | — |
| 1 | R | H | H | R | R | I | K | T | R | R | G | D | K | T | R | R | R | R | R | R |
| 2 | P | R | P | P | P | N | E | V | H | P | F | L | A | V | P | P | P | P | P | P |
| 3 | Y | T | K | K | T | G | D | A | R | P | L | P | D | E | D | D | D | D | D | D |
| 4 | A | F | F | F | F | D | S | A | D | F | D | I | S | A | F | F | F | F | F | F |
| 5 | C | C | C | C | C | C | C | C | C | C | C | C | C | C | C | C | C | C | C | C |
| 6 | E | K | Y | Y | N | E | Q | N | D | D | L | T | E | Q | N | L | L | L | L | L |
| 7 | L | L | L | L | L | L | L | L | K | K | E | S | Q | L | L | E | E | E | E | E |
| 8 | I | P | P | P | L | P | G | P | P | P | P | P | A | D | P | P | P | P | P | P |
| 9 | V | A | A | A | P | K | Y | V | P | P | P | P | FG | Y | I | P | P | P | P | P |

TABLE 13-continued

| | 1 | 2 | 3 | 4 | 5 | 6 | 7 | 8 | 9 | 10 | 11 | 12 | 13 |
|---|---|---|---|---|---|---|---|---|---|---|---|---|---|
| 10 | A | E | D | D | E | V | S | I | D | D | Y | V | D | 
| 11 | A | P | P | P | T | V | A | R | K | T | T | T | A |
| 12 | G | G | G | G | G | G | G | G | G | K | G | G | G |
| 13 | P | P | R | R | R | P | P | P | N | I | P | P | L |
| 14 | C | C | C | C | C | C | C | C | C | C | C | C | C |
| 15 | M | K | K | L | N | R | M | R | — | — | K | R | F |
| 16 | F | A | A | A | A | G | A | G | Q | A | A | G | G |
| 17 | F | S | H | Y | L | R | M | F | P | T | K | G | Y |
| 18 | I | I | I | M | I | F | T | I | V | V | M | F | M |
| 19 | S | P | P | P | P | P | S | Q | R | R | I | K | K |
| 20 | A | A | R | R | A | R | R | L | A | A | R | R | L |
| 21 | F | F | F | F | F | Y | Y | W | F | F | Y | Y | Y |
| 22 | Y | Y | Y | Y | Y | Y | F | A | Y | Y | F | N | S |
| 23 | Y | Y | Y | Y | Y | Y | Y | F | Y | Y | Y | Y | Y |
| 24 | S | N | D | N | N | N | N | D | D | K | N | N | N |
| 25 | K | W | S | P | S | S | S | G | A | T | P | A | T |
| 26 | G | A | A | A | H | S | T | V | R | S | K | R | E |
| 27 | A | A | S | S | L | S | S | S | K | L | A | A | T |
| 28 | N | K | N | N | H | K | M | G | K | K | G | K | K |
| 29 | K | K | K | K | K | R | A | K | T | R | F | Q | N |
| 30 | C | C | C | C | C | C | C | C | C | C | C | C | C |
| 31 | Y | Q | N | E | Q | E | E | V | K | V | E | E | E |
| 32 | P | L | K | K | K | K | T | L | A | Q | T | P | E |
| 33 | F | F | F | F | F | F | F | F | F | F | F | F | F |
| 34 | T | H | I | I | N | I | Q | P | Q | R | V | K | I |
| 35 | Y | Y | Y | Y | Y | Y | Y | Y | Y | Y | Y | Y | Y |
| 36 | S | G | G | G | G | G | G | G | R | G | G | G | G |
| 37 | G | G | G | G | G | G | G | G | G | G | G | G | G |
| 38 | C | C | C | C | C | C | C | C | C | C | C | C | C |
| 39 | R | K | P | R | G | G | M | Q | D | D | K | K | Q |
| 40 | G | G | G | G | G | G | G | G | G | G | A | G | G |
| 41 | N | N | N | N | N | N | N | N | D | D | K | N | N |
| 42 | A | A | A | A | A | A | A | G | G | H | H | S | G |
| 43 | N | N | N | N | N | N | N | N | G | G | N | N | N |
| 44 | R | R | N | N | N | N | K | N | N | N | R | R | N |
| 45 | F | F | F | F | F | F | F | F | F | F | F | Y | F |
| 46 | K | S | K | K | K | H | V | Y | K | K | R | K | S |
| 47 | T | T | T | T | T | T | T | S | T | S | S | S | T |
| 48 | I | I | W | W | I | L | E | E | E | D | A | E | L |
| 49 | E | E | D | D | D | E | K | K | T | H | E | Q | A |
| 50 | E | K | E | E | E | E | E | L | L | D | D | E | E |
| 51 | C | C | C | C | C | C | C | C | C | C | C | C | C |
| 52 | R | R | R | R | Q | E | L | R | R | M | L | E | L |
| 53 | R | H | Q | H | R | K | Q | E | C | C | R | D | Q |
| 54 | T | A | T | T | T | V | T | Y | E | E | T | A | K |
| 55 | C | C | C | C | C | C | C | C | C | C | C | C | C |
| 56 | V | V | G | V | A | G | R | G | L | E | G | S | I |
| 57 | V | G | A | A | A | V | — | V | V | L | G | G | N |
| 58 | — | — | S | S | K | R | — | P | Y | Y | A | F | — |
| 59 | — | — | A | G | Y | S | — | G | P | R | — | — | — |
| 60 | — | — | — | I | G | — | — | D | — | — | — | — | — |
| 61 | — | — | — | — | — | E | — | — | — | — | — | — | — |

Legand To Table 13
1  BPTI
2  Engineered BPTI From MARK87
3  Engineered BPTI From MARK87
4  Bovine Colostrum (DUFT85)
5  Bovine Serum (DUFT85)
6  Semisynthetic BPTI, TSCH87
7  Semisynthetic BPTI, TSCH87
8  Semisynthetic BPTI, TSCH87
9  Semisynthetic BPTI, TSCH87
10 Semisynthetic BPTI, TSCH87
11 Engineered BPTI, AUER87
12 *Dendroaspis polylepis polylepis* (Black mamba) venom I (DUFT85)
13 *Dendroaspis polylepis polylepis* (Black Mamba) venom K (DUFT85)

TABLE 13-continued

14  *Hemachatus hemachates* (Ringhals Cobra) HHV II (DUFT85)
15  *Naja nivea* (Cape cobra) NNV II (DUFT85)
16  *Vipera russelli* (Russel's Viper) RVV II (TAKA74)
17  Red sea turtle egg white (DUFT85)
18  Snail mucus (*Helix pomania*) (WAGN78)
19  *Dendroaspis angusticeps* (Eastern green mamba) C13 S1 C3 toxin (DUFT85)
20  *Dendroaspis angusticeps* (Eastern Green Mamba) C13 S2 C3 toxin (DUFT85)
21  *Dendroaspis polylepis polylepes* (Black mamba) B toxin (DUFT85)
22  *Dendroaspis polylepis polylepes* (Black Mamba) E toxin (DUFT85)
23  *Vipera ammodytes* TI toxin (DUFT85)
24  *Vipera ammodytes* CTI toxin (DUFT85)
25  *Bungarus fasciatus* VIII B toxin (DUFT85)
26  *Anemonia sulcata* (sea anemone) 5 II (DUFT85)
27  *Homo sapiens* HI-14 "inactive" domain (DUFT85)
28  *Homo sapiens* HI-8 "active" domain (DUFT85)
29  beta bungarotoxin B1 (DUFT85)
30  beta bungarotoxin B2 (DUFT85)
31  Bovine spleen TI II (FIOR85)
32  *Tachypleus tridentatus* (Horseshoe crab) hemocyte inhibitor (NAKA87)
33  *Bombyx mori* (silkworm) SCI-III (SASA84)
34  *Bos taurus* (inactive) BI-14
35  *Bos taurus* (active) BI-8
36: Engineered BPTI (KR15, ME52): Auerswald '88, Biol Chem Hoppe-Seyler, 369 Supplement, pp27–35.
37: Isoaprotinin G-1: Siekmann, Wenzel, Schroder, and Tschesche '88, Biol Chem Hoppe-Seyler, 369: 157–163.
38: Isoaprotinin 2: Siekmann, Wenzel, Schroder, and Tschesche '88, Biol Chem Hoppe-Seyler, 369: 157–163.
39: Isoaprotinin G-2: Siekmann, Wenzel, Schroder, and Tschesche '88, Biol Chem Hoppe-Seyler, 369: 157–163.
40: Isoaprotinin 1: Siekmann, Wenzel, Schroder, and Tschesche '88, Biol Chem Hoppe-Seyler, 369: 157–163.

Notes:
a) both beta bungarotoxins have residue 15 deleted.
b) *B. mori* has an extra residue between C5 and C14; we have assigned F and G to residue 9.
c) all natural proteins have C at 5, 14, 30, 38, 50, & 55.
d) all homologues have F33 and G37.
e) extra C's in bungarotoxins form interchain cystine bridges

TABLE 6

Tables: IIIsp::bpti::matureIII (initial fragment) fusion
gene. The DNA sequence has SEQ ID NO. 001; Amino-acid
sequence has SEQ ID NO. 002. The DNA is linear and is shown
on the lines that do not begin with "!". The DNA encoding
mature III is identical to the DNA found in M13mp18. The
amino-acid sequence is processed in vivo and disulfide bonds
form.

```
!    m   k   k   l   l   f   a   I   p   l              SEQ ID NO. 002
!    1   2   3   4   5   6   7   8   9   10
5'-gtg aaa aaa tta tta ttc gca att cct tta              SEQ ID NO. 001
!   |<---- gene III signal peptide--------
!
!                                    - cleavage site
!                                    |
!                                    ↓
!        v   v   p   f   y   s   G   A
!        11  12  13  14  15  16  17  18
         gtt gtt cct ttc tat tct GGc Gcc
!        ---------------------------->|
!
!                        |R |P |D |F |C |L |E |
!                        | 19| 20| 21| 22| 23| 24| 25|
                         |CGT|CCG|GAT|TTC|TGT|CTC|GAG|-
! M13/BPTI Jnct     ↑  |AccIII|           |XhoI  |(& AvaI)!
!
! |P |P |Y |T |G |P |C |K |A |R |
! | 26| 27| 28| 29| 30 31| 32| 33| 34| 35|
  |CCA|CCA|TAC|ACT|GGG|CCC|TGC|AAA|GCG|CGC|-
!       |PflMI      |       ||       |BssHII |
!                           | ApaI   |
!                           | DraII  | = PssI
!
! |I |I |R |Y |F |Y |N |A |K |A |
! | 36| 37| 38| 39| 40| 41| 42| 43| 44| 45|
```

TABLE 6-continued

Tables: *IIIsp::bpti::matureIII* (initial fragment) fusion gene. The DNA sequence has SEQ ID NO. 001; Amino-acid sequence has SEQ ID NO. 002. The DNA is linear and is shown on the lines that do not begin with "!". The DNA encoding mature III is identical to the DNA found in M13mp18. The amino-acid sequence is processed in vivo and disulfide bonds form.

```
 |ATC|ATC|CGC|TAT|TTC|TAC|AAT|GCT|AAA|GC|-
!
! | G | L | C | Q | T | F | V | Y | G | G |
! | 46| 47| 48| 49| 50| 51| 52| 53| 54| 55|
 A|GGC|CTG|TGC|CAG|ACC|TTT|GTA|TAC|GGT|GGT|-
!|_StuI_|                   |_XcaI__|( & AccI)
!
! | C | R | A | K | R | N | N | F | K |
! | 56| 57| 58| 59| 60| 61| 62| 63| 64|
  |TGC|CGT|GCT|AAG|CGT|AAC|AAC|TTT|AAA|-
!         |_EspI__|
!
! | S | A | E | D | C | M | R | T | C | G |
! | 65| 66| 67| 68| 69| 70| 71| 72| 73| 74|
  |TCG|GCC|GAA|GAT|TGC|ATG|CGT|ACC|TGC|GGT|-
!   |XmaIII|         |_SphI_|
!
!           BPTI/M13 boundary
! | G | A | A   E    (Residue numbers of mature III have had
! | 75| 76|119 120   118 added to the usual residue
numbers.)
  |GGC|GCC|gct gaa
! |_NarI__| (& KasI)
!
! 121 122 123 124 125 126 127 128 129 130 131 132 133 134
!  T   V   E   S   C   L   A   K   P   H   T   E   N   S ...
   act gtt gaa agt tgt tta gca aaa ccc cat aca gaa aat tca...
!
! The remainder of the gene is identical to the
corresponding part of iii in M13 mp18.
```

TABLE 7

*IIIsp::itiD1::matureIII* fusion gene.
DNA has SEQ ID NO. 003; amino-acid sequence has SEQ ID NO. 004.
The DNA is a linear segment and the amino-acid sequence is a protein that is processed in vivo and which contains disulfides.

```
 m   k   k   l   l   f   a   I   p   l   v   v   p   f   y     SEQ ID NO. 004
-18 -17 -16 -15 -14 -13 -12 -11 -10 -9  -8  -7  -6  -5  -4
5'-gtg aaa aaa tta tta ttc gca att cct tta gtt gtt cct ttc tat

|<---- gene III signal peptide --------------------------       SEQ ID NO. 003

- cleavage site
                |
 s   G   A   K   E   D   S   C   Q   L   G   Y   S   A   G
-3  -2  -1   1   2   3   4   5   6   7   8   9  10  11  12
tct GGc Gcc aaa gaa gaC tcT tGC CAG CTG GGC tac tCG GCC Ggt
--------->|                  |_BglI_____|   |EagI_|
    |_KasI_|

13  14  15  16  17  18  19  20  21  22  23  24  25  26
 P   C   M   G   M   T   S   R   Y   F   Y   N   G   T
ccc tgc atg gga atg acc agc agg tat ttc tat aat ggt aca 27  28  29  30  31  32  33  34  35  36  37  38  39  40  41
 S   M   A   C   E   T   F   Q   Y   G   G   C   M   G   N
tCC ATG Gcc tgt gag act ttc cag tac ggc ggc tgc atg ggc aac
|_NcoI_|
|_StyI_|

42  43  44  45  46  47  48  49  50  51  52  53  54  55  56
 G   N   N   F   V   T   E   K   E   C   L   Q   T   C   R
ggt aac aac ttc gtc aca gaa aag gag tgt CTG CAG acc tgc cga
                                         |_PstI__|
57  58      101 102 119 120
```

TABLE 7-continued

*IIIsp::itiD1::matureIII* fusion gene.
DNA has SEQ ID NO. 003; amino-acid sequence has SEQ ID NO. 004.
The DNA is a linear segment and the amino-acid sequence is a protein that is processed in vivo and which contains disulfides.

```
 T   V   g   a   A   E
act gtg ggc gcc gct gaa
    |BbeI  |         (Residue numbers of mature
    |NarI  |         III have had 118 added to
    |KasI  |         the usual residue numbers.)
121 122 123 124 125 126 127 128 129 130 131 132 133 134 135
 T   V   E   S   C   L   A   K   P   H   T   E   N   S   F..
act gtt gaa agt tgt tta gca aaa ccc cat aca gaa aat tca ttt..

The remainder of the gene is identical to the corresponding
part of gene iii in phage M13mp18.
```

TABLE 8

Affinity Classes of ITI-D1-derived hNE inhibitors

| Affinity Class | Estimated $K_D$ | Fraction of Input bound | pH Elution Maximum | Protein |
|---|---|---|---|---|
| WEAK | $K_D$ > 10 nM | <0.005% | >6.0 | ITI-D1 |
| MODERATE | 1 to 10 nM | 0.01% to 0.03% | 5.5 to 5.0 | BITI, ITI-D1E7 |
| STRONG | 10 to 1000 pM | 0.03% to 0.06% | 5.0 to 4.5 | BITI-E7, BITI-E7-1222, AMINO1, AMINO2, MUTP1 |
| VERY STRONG | <10 pM | >0.1% | ≤4.0 | BITI-E7-141, MUTT26A, MUTQE, MUT1619 |

TABLE 9

Definition of Class A, B and C mutations in PCT/US92/01501.

| Classes: | | |
|---|---|---|
| A | No major effect expected if molecular charge stays in range −1 to +1. | |
| B | Major effects not expected, but are more likely than in "A". | |
| C | Residue in the binding interface; any change must be tested. | |
| X | No substitution allowed. | |

| Res. Id. | EpiNE1 (SEQ ID NO:7) | Substitutions | Class |
|---|---|---|---|
| 1 | R | any | A |
| 2 | P | any | A |
| 3 | D | any | A |
| 4 | F | Y, W, L | B |
| 5 | C | C | X |
| 6 | L | non-proline | A |
| 7 | E | L, S, T, D, N, K, R | A |
| 8 | P | any | A |
| 9 | P | any | A |
| 10 | Y | non-proline prefr'd | B |
| 11 | T | any | C |
| 12 | G | must be G | X |
| 13 | P | any | C |
| 14 | C | C strongly preferred, any non-proline | C |
| 15 | I | V, A | C |
| 16 | A | any | C |
| 17 | F | L, I, M, Y, W, H, V | C |
| 18 | F | Y, W, H | C |
| 19 | P | any | C |
| 20 | R | non-proline prefr'd | C |
| 21 | Y | F & Y most prefr'd; W, I, L prefr'd; M, V allowed | C |
| 22 | F | Y & F most prefr'd; non-proline prefr'd | Y, F B |
| 23 | Y | Y & F strongly prefr'd | F, Y B |
| 24 | N | non-proline prefr'd | A |
| 25 | A | any | A |
| 26 | K | any | A |
| 27 | A | any | A |
| 28 | G | non-proline prefr'd | A |
| 29 | L | non-proline prefr'd | A |
| 30 | C | must be C | X |
| 31 | Q | non-proline prefr'd | B |
| 32 | T | non-proline prefr'd | B |
| 33 | F | F very strongly prefr'd; Y possible | X |
| 34 | V | any | C |
| 35 | Y | Y most prefr'd; W prefr'd; F allowed | B |
| 36 | G | G strongly prefr'd; S, A prefr'd; | C |
| 37 | G | must be G so long as 38 is C | X |
| 38 | C | C strongly prefr'd | X |
| 39 | M | any | C |
| 40 | G | A, S, N, D, T, P | C |
| 41 | N | K, Q, S, D, R, T, A, E | C |
| 42 | G | any | C |
| 43 | N | must be N | X |
| 44 | N | S, K, R, T, Q, D, E | B |
| 45 | F | Y | B |
| 46 | K | any non-proline | B |
| 47 | ST, N, A, G | | B |
| 48 | A | any | B |
| 49 | E | any | A |
| 50 | D | any | A |
| 51 | C | must be C | X |
| 52 | M | any | A |
| 53 | R | any | A |
| 54 | T | any | A |
| 55 | C | must be C | X |
| 56 | G | any | A |
| 57 | G | any | A |
| 58 | A | any | A | prefr'd stands for preferred.

TABLE 10

Sequences of Kunitz domains

| Name | Sequence<br>          1111111111222222222233333333334444 4444444555555555<br>123456789a0123456789012345678901234567890123456789012ab345678 | Parental domain | Seq Id No. |
|---|---|---|---|
| Consensus Kunitz Domain | RPDFCLLPA-ETGPGRAMTPRFYYNAKSGKCEPFTYGGCGGNA--NNFKTEEECRRTCGGA<br>   1          3      5          7   9<br>          2    4          6      8         10 | | 005 |
| BPTI (Genebank P00974) | RPDFCLEPP-YTGPCKARIIRYFYNAKAGLCQTFVYGGCRAKR--NNFKSAEDCMRTCGGA | BPTI | 006 |
| EPI-HNE-1 = EpiNE1 | rpdfclepp-ytgpcIaFFPryfynakaglcqtfvyggcCMGNG--nnfksaedcmrtcgga | BPTI | 007 |
| EPI-HNE-2 | EAEArpdfclepp-ytgpcIaFFPryfynakaglcqtfvyggcCMGNG--nnfksaedcmrtcgga | BPTI | 008 |
| EpiNE7 | rpdfclepp-ytgpcVaMFPryfynakaglcqtfvyggcMGNG--nnfksaedcmrtcgga | BPTI | 009 |
| EpiNE3 | rpdfclepp-ytgpcVGFFSryfynakaglcqtfvyggcMGNG--nnfksaedcmrtcgga | BPTI | 010 |
| EpiNE6 | rpdfclepp-ytgpcVGFFQryfynakaglcqtfvyggcMGNG--nnfksaedcmrtcgga | BPTI | 011 |
| EpiNE4 | rpdfclepp-ytgpcVaIFPryfynakaglcqtfvyggcMGNG--nnfksaedcmrtcgga | BPTI | 012 |
| EpiNE8 | rpdfclepp-ytgpcVaFFKrstynakaglcqtfvyggcMGNG--nnfksaedcmrtcgga | BPTI | 013 |
| EpiNE5 | rpdfclepp-ytgpcIaFFQryfynakaglcqtFVyggcMGNG--nnfksaedcmrtcgga | BPTI | 014 |
| EpiNE2 | rpdfclepp-ytgpcIaLFKryfynakaglcqtfvyggcMGNG--nnfksaedcmrtcgga | BPTI | 015 |
| ITI-D1 (Genebank P02760) | KEDSCQLGY-SAGPCMGMTSRYFYNGTSMACETFQYGGCMGNG--NNFVTEKDCLQTCRTV | ITI-D1 | 016 |
| BITI-E7-141 | RPdFcqlgy-sagpcVAmFPryfyngtsmacQtfVyggcmgng--nnfvtekdclqtcrga | ITI-D1 | 017 |
| MUTT26A | RPdFcqlgy-sagpcVAmEPryfyngAsmacQtfVyggcmgng--nnfvtekdclqtcrga | ITI-D1 | 018 |
| MUTQE | RPdFcqlgy-sagpcVAmEPryfyngtsmacetfVyggcmgng--nnfvtekdclqtcrga | ITI-D1 | 019 |
| MUT1619 | RPdFcqlgy-sagpcVgmFsryfyngtsmacQtfVyggcmgng--nnfvtekdclqtcrga | ITI-D1 | 020 |
| ITI-D1E7 | kedscqlgy-sagpcVAmFPryfyngtsmacetfqyggcmgng--nnfvtekdclqtcrga | ITI-D1 | 021 |
| AMINO1 | kedFcqlgy-sagpcVAmFPryfyngtsmacetfqyggcmgng--nnfvtekdclqtcrga | ITI-D1 | 022 |
| AMINO2 | kpdscqlgy-sagpcVAmFPryfyngtsmacetfqyggcmgng--nnfvtekdclqtcrga | ITI-D1 | 023 |
| MUTP1 | RPdFcqlgy-sagpclgmFsryfyngtsmacetfqyggcmgng--nnfvtekdclqtcrga | ITI-D1 | 024 |
| ITI-D2 (Genebank P02760) | TVAACNLPI-VRGPCRAFIQLWAFDAVKGKCVLFPYGGCQGNG--NKFSEKECGVP | ITI-D2 | 025 |
| EPI-HNE-3 | aacnlpi-vrgpcIafFPRwafdavkgkcvlfpyggcqgng--nkfysekecreycgvp | ITI-D2 | 026 |
| EPI-HNE-4 | Eacnlpi-vrgpcIafFPRwafdavkgkcvlfpyggcqgng--nkfysekecreycgvp | ITI-D2 | 027 |
| App-I (NCBI 105306) | VREVCSEQA-ETGPCRAMISRWYFDVTEGKCAPFFYGGCGGNR--NNFDTEEYCMAVCGSA | | 028 |
| DPI.1.1 | vrevcseqa-YtgpcIaFFPrYyfdvtegkcQTfvyggcMgnG--nnfdteeycmavcgsa | APP-I | 029 |
| DPI.1.2 | vrevcseqa-etgpcIamFsrwyfdvtegkcapfVyggcggnr--nnfdteeycmavcgsa | AAP-I | 030 |
| DPI.1.3 | vrevcseqa-etgpcIaFFsrwyfdvtegkcaTfVyggcMgnr--nnfdteeycmavcgsa | AAP-I | 031 |
| TFPI2-D1 (SPRE94) | NAEICLLPL-DYGPCRALLLRYYYDRYTQSCRQFLYGGCEGNA--NNFYTWEACDDACWRI | | 032 |
| DPI.2.1 | naeicllpl-YtgpcIaFFPryyydrtqscQTfVyggcMgna--nnfytweacddacwri | TFPI2-D1 | 033 |
| DPI.2.2 | naeicllpl-dygpcIalFlryyydrytgscrqfVyggcegna--nnfytweacddacwri | TFPI2-D1 | 034 |

TABLE 10-continued

Sequences of Kunitz domains

| Name | Sequence<br>          1111111111222222222233333333334444    4444444555555555<br>123456789a0123456789012345678901234567890012ab345678 | Parental domain | Seq Id No. |
|---|---|---|---|
| DPI.2.3 | naeicllpl-dTgpcIaFFlryyydrytqscQTfvyggcMgna--nnfytweacddacwri | TFPI2-D1 | 035 |
| TFPI2-D2 (SPRE94) | VPKVCRLQVSVDDQCEGSTEKYFFNLSSMTCEKFFSGGCHRNRIENRFPDEATCMGFCAPK | | 036 |
| DPI.3.1 | vpkvcrlqv-vRGPcIAFFPRWffnlssmtcvLfPYggcQGnG--nrfpdeatcmgfcapk | | 037 |
| DPI.3.2 | vpkvcrlqvsvddqcIgsFekyffnlAsmtceTfVsggchrnrienrfpdeatcmgfcapk | TFPI2-D1 | 038 |
| DPI.3.3 | vpkvcrlqv-vAGPcIgFFKRyffAlssmtceTfvsggchrnr--nrfpdeatcmgfcapk | TFPI2-D1 | 039 |
| TFPI2-D3 (SPRE94) | ipsfcyspk-deglcsanvtryyfnpryrtcdaftytgcggnd--nnfvsredckracaka | | 040 |
| DPI.4.1 | ipsfcyspk-SAgPcVaMFPryyfnpryrtcETfvyGgcMgnG--nnfvsredckracaka | TFPI2-D3 | 041 |
| DPI.4.2 | ipsfcyspk-deglcIavFtryyfnpryrtcdaftytgcggnd--nnfvsredckracaka | TFPI2-D3 | 042 |
| DPI.4.3 | ipsfcyspk-dTgPcIaFFtryyfnpryrtcdTfvyGgcggnd--nnfvsredckracaka | TFPI2-D3 | 043 |
| LACI-D1 (Genebank P10646) | mhsfcafka-ddgpckaimkrfffniftrqceefiyggcegnq--nrfesleeckkmctrd | | 044 |
| DPI.5.1 | mhsfcafka-SAgpcVaMFPryffniftrqceTfVyggcMgnG--nrfesleeckkmctrd | LACI-D1 | 045 |
| DPI.5.2 | mhsfcafka-ddgpcIaiFkrfffniftrqceefiyggcegnq--nrfesleeckkmctrd | LACI-D1 | 046 |
| DPI.5.3 | mhsfcafka-YTgpcIavvkrfffniftrqceTfiyggcegnq--nrfesleeckkmctrd | LACI-D1 | 047 |
| LACI-D2 (Genebank P10646) | KPDFCFLEE-DPGICRGYITRYFYNNQTKQCERFKYGGCLGNM--NNFETLEECKNICEDG | | 048 |
| DPI.6.1 | kpdfcflee-SAgPcVAMFPryfynnqtkqceTfVyggcMgnG--nnfetleecknicedg | LACI-D2 | 049 |
| DPI.6.2 | kpdfcflee-dpgicVgyFtryfynnqtkqcerfkyggclgnm--nnfetleecknicedg | LACI-D2 | 050 |
| DPI.6.3 | kpdfcflee-dpgicvgFFtryfynnqtkqcerfVyggclgnm--nnfetleecknicedg | LACI-D2 | 051 |
| DPI.6.4 | kpdfcflee-dpgicvgFFtryfynAqtkqcerfVyggclgnm--nnfetleecknicedg | LACI-D2 | 052 |
| DPI.6.5 | kpdfcflee-dpgPcVgFFQryfynAqtkqcerfVyggcQgnm--nnfetleecknicedg | LACI-D2 | 053 |
| DPI.6.6 | kpdfcflee-dpgPcVgFFtryfynnqtkqcerfVyggcQgnm--nnfetleecknicedg | LACI-D2 | 054 |
| DPI.6.7 | kpdfcflee-dpgPcIgFFPryfynnqtkqcerfvyggcQgnm--nnfetleecknicedg | LACI-D2 | 055 |
| LACI-D3 (Genebank P10646) | GPSWCLTPA-DRGLCRANENRFYYNSVIGKCRPFKYSGCGCNE--NNFTSKQECLRACKKG | | 056 |
| DPI.7.1 | gpswcltpa-VrgPcIaFFPrWyynsvigkcVLfpyGgcQgnG--nnftskqeclrackkg | LACI-D3 | 057 |
| DPI.7.2 | gpswcltpa-drglcVanFnrfyynsvigkcrpfkysgcggne--nnftskqeclrackkg | LACI-D3 | 058 |
| DPI.7.3 | gpswcltpa-drglcVaFFnrfyynsvigkcrpfkysgcggne--nnftskqeclrackkg | LACI-D3 | 059 |
| DPI.7.4 | gpswcltpa-VrgPcVaFFnrfyynsvigkcrpfkyGgcggne--nnftskqeclrackkg | LACI-D3 | 060 |
| DPI.7.5 | gpswcltpa-drgPcIaFFPrWyynsvigkcQTfVyGgcggne--nnftskqeclrackkg | LACI-D3 | 061 |
| A3 collagen (W093/14119) | ETDICKLPK-DEGTCRDFILKWYYDPNTKSCARFWYGGCGGNE--NKFGSQKECEKVCAPV | | 062 |
| DPI.8.1 | etdicklpk-VRgPcIAfFPRwyydpntkscVLfpyggcQgnG--nkfgsqkecekvcapv | A3 | 063 |
| DPI.8.2 | etdicklpk-degtcIAfFlkwyydpntkscarfVyggcggne--nkfgsqkecekvcapv | A3 collagen | 064 |

TABLE 10-continued

Sequences of Kunitz domains

| Name | Sequence<br>`          111111111122222222223333333333444  4444444555555555`<br>`123456789a012345678901234567890123456789012ab345678` | Parental domain | Seq Id No. |
|---|---|---|---|
| DPI.8.3 | etdicklpk-degPcIAfFlRwyydpntkscarfVyggcggne--nkfgsqkecekvcapv | A3 | 065 |
| HKI B9 Domain (NORR93) | LPNVCAFPM-EKGPCQTYMTRWFFNFETGECELFAYGGCGGNS--NNFLRKEKCEKFCKFT | | 066 |
| DPI.9.1 | lpnvcafpm-VRgpcIAFFPrwffnfetgecVlfVyggcQgnG--nnflrkekcekfckft | HKI B9 | 067 |
| DPI.9.2 | lpnvcafpm-ekgpcIAyFtrwffnfetgecelfayggcggns--nnflrkekcekfckft | HKI B9 | 068 |
| DPI.9.3 | lpnvcafpm-ekgpcIAyFPrwffnfetgecVlfVyggcggns--nnflrkekcekfckft | HKI B9 | 069 |

Sequences listed in Table 100 that strongly inhibit hNE are EPI-HNE-1 (= EpiNE1), EPI-HNE-2, EpiNE7, EpiNE3, EpiNE6, EpiNE4, EpiNE8, EpiNE2, BTTI-E7-141, MUTT26A, MUTQE, MUT1619, ITT-D1E7, AMINO1, AMINO2, MUTP1, and EPI-HNE-3, and EPI-HNE-4.
Sequences listed in Table 100 that are highly likely to strongly inhibit hNE are DPI.1.1, DPI.1.2, DPI.1.3, DPI.2.1, DPI.2.2, DPI.2.3, DPI.3.1, DPT.3.2, DPI.3.3, DPI.4.1, DPI.4.2, DPI.4.3, DPI.5.1, DPI.5.2, DPI.5.3, DPI.6.1, DPI.6.2, DPI.6.3, DPI.6.4, DPI.6.5, DPI.6.6, DPI.6.7, DPI.7.1, DPI.7.2, DPI.7.3, DPI.7.4, DPI.7.5, DPI.8.1, DPI.8.2, DPI.8.3, DPI.9.1, DPI.9.2, and DPI.9.3.
Human Kunitz domains listed in Table 100: ITI-D1, ITI-D2, App-I, TFPI2-D1, TFPI2-D2, TFPI2-D3, LACI-D1, LACI-D2, LACI-D3, A3 collagen Kunitz domain, and HKI B9 Domain.

TABLE 111

Restriction sites in plasmid pHIL-D2
pHIL-D2, 93-01-02 Ngene = 8157

Non-cutters

| AflII | ApaI | AscI | AvaI | AvrII | BamHI | BglII |
|---|---|---|---|---|---|---|
| Bsp120I | BsrGI | BssHII | BstEII | FseI | MluI | NruI |
| PacI | PmlI | RsrII | SacII | SexAI | SfiI | SgfI |
| SnaBI | SpeI | Sse8387I | | XhoI | | |
| XmaI | | | | (PaeR7I) | | |
| (SmaI) | | | | | | |

Cutters

| | | | |
|---|---|---|---|
| AatII GACGTc | | 1 | 5498 |
| AflIII Acrygt | | 1 | 7746 |
| AgeI Accggt | | 1 | 1009 |
| BlpI GCtnagc | | 1 | 597 |
| BspEI (BspMII,AccIII) Tccgga | | 1 | 3551 |
| BspMI gcaggt | | 1 | 4140 |
| Bst1107I GTAtac | | 1 | 7975 |
| BstBI (AsuII) TTcgaa | | 2 | 945   4780 |
| Bsu36I CCtnagg | | 1 | 1796 |
| Ec1136I GAGctc | | 1 | 216 |
| EcoRI Caattc | | 1 | 956 |
| EspI (Bpu1102I) GCtnagc | | 1 | 597 |
| HpaI GTTaac | | 1 | 1845 |
| NcoI Ccatgg | | 1 | 3339 |
| NdeI CAtatg | | 1 | 7924 |
| NsiI (Ppu10I) ATGCAt | | 1 | 684 |
| PflMI CCANNNNntgg | | 1 | 196 |
| PmeI GTTTaaac | | 1 | 420 |
| PstI CTGCAg | | 1 | 6175 |
| PvuI CGATcg | | 1 | 6049 |
| SapI gaagagc | | 1 | 7863 |
| SacI GAGCTc | | 1 | 216 |
| SalI Gtcgac | | 1 | 2885 |
| ScaI AGTact | | 1 | 5938 |
| SphI GCATGc | | 1 | 4436 |
| StuI AGGcct | | 1 | 2968 |
| SwaI ATTTaaat | | 1 | 6532 |
| Tth111I GACNnngtc | | 1 | 7999 |
| XbaI Tctaga | | 1 | 1741 |
| XcmI CCANNNNNnnnntgg | | 1 | 711 |
| Aox1 5' | 1 to about 950 | | |
| Aox1 3 | 950 to about 1250 | | |
| His4 | 1700 to about 4200 | | |
| Aox1 3' | 4500 to 5400 | | |
| bla | 5600 to 6400 | | |
| f1 ori | 6500 to 6900 | | |

TABLES 12-13 (merged)

SEQUENCES OF THE EpiNE CLONES IN THE P1 REGION

| CLONE IDENTIFIERS | SEQUENCE 1 1 1 1 1 1 1 2 2<br>3 4 5 6 7 8 9 0 1 | |
|---|---|---|
| BPTI (comp. only) | P C K A R I I R Y | (BPTI) (SEQ ID NO:132) |
|  | P C V A M F Q R Y | EpiNEα (SEQ ID NO:129) |
| 3, 9, 16, 17, 18, 19 | P C V G F F S R Y | EpiNE3 (SEQ ID NO:133) |
| 6 | P C V G F F Q R Y | EpiNE6 (SEQ ID NO:134) |
| 7, 13, 14, 15, 20 | P C V A M F P R Y | EpiNE7 (SEQ ID NO:135) |
| 4 | P C V A I F P R Y | EpiNE4 (SEQ ID NO:136) |
| 8 | P C V A I F K R S | EpiNE8 (SEQ ID NO:137) |
| 1, 10, 11, 12 | P C I A F F P R Y | EpiNE1 (SEQ ID NO:138) |
| 5 | P C I A F F Q R Y | EpiNE5 (SEQ ID NO:139) |
| 2 | P C I A L F K R Y | EpiNE2 (SEQ IDN O:140) |

Note:
The DNA sequences encoding these amino acid sequences are set forth in 08/133,031, previously incorporated by reference.

TABLE 14

Fractionation of EpiNE-7 and MA-ITI-D1 phage on hNE beads

| | | EpiNE-7 | | MA-ITI-D1 | |
|---|---|---|---|---|---|
| | | pfu | pfu/INPUT | pfu | pfu/INPUT |
| INPUT | | $3.3 \cdot 10^9$ | 1.00 | $3.4 \cdot 10^{11}$ | 1.00 |
| Final TBS-TWEEN Wash | | $3.8 \cdot 10^5$ | $1.2 \cdot 10^{-4}$ | $1.8 \cdot 10^6$ | $5.3 \cdot 10^{-6}$ |
| pH | 7.0 | $6.2 \cdot 10^5$ | $1.8 \cdot 10^{-4}$ | $1.6 \cdot 10^6$ | $4.7 \cdot 10^{-6}$ |
| | 6.0 | $1.4 \cdot 10^6$ | $4.1 \cdot 10^{-4}$ | $1.0 \cdot 10^6$ | $2.9 \cdot 10^{-6}$ |
| | 5.5 | $9.4 \cdot 10^5$ | $2.8 \cdot 10^{-4}$ | $1.6 \cdot 10^6$ | $4.7 \cdot 10^{-6}$ |
| | 5.0 | $9.5 \cdot 10^5$ | $2.9 \cdot 10^{-4}$ | $3.1 \cdot 10^5$ | $9.1 \cdot 10^{-7}$ |
| | 4.5 | $1.2 \cdot 10^6$ | $3.5 \cdot 10^{-4}$ | $1.2 \cdot 10^5$ | $3.5 \cdot 10^{-7}$ |
| | 4.0 | $1.6 \cdot 10^6$ | $4.8 \cdot 10^{-4}$ | $7.2 \cdot 10^4$ | $2.1 \cdot 10^{-7}$ |
| | 3.5 | $9.5 \cdot 10^5$ | $2.9 \cdot 10^{-4}$ | $4.9 \cdot 10^4$ | $1.4 \cdot 10^{-7}$ |
| | 3.0 | $6.6 \cdot 10^5$ | $2.0 \cdot 10^{-4}$ | $2.9 \cdot 10^4$ | $8.5 \cdot 10^{-8}$ |
| | 2.5 | $1.6 \cdot 10^5$ | $4.8 \cdot 10^{-5}$ | $1.4 \cdot 10^4$ | $4.1 \cdot 10^{-8}$ |
| | 2.0 | $3.0 \cdot 10^5$ | $9.1 \cdot 10^{-5}$ | $1.7 \cdot 10^4$ | $5.0 \cdot 10^{-8}$ |
| SUM | | $6.4 \cdot 10^6$ | $3 \cdot 10^{-3}$ | $5.7 \cdot 10^6$ | $2 \cdot 10^{-5}$ |

*SUM is the total pfu (or fraction of input) obtained from all pH elution fractions

TABLE 15

Abbreviated fractionation of display phage on hNE beads

| | Display phage | | | |
|---|---|---|---|---|
| | EpiNE-7 | MA-ITI-D1 2 | MA-ITI-D1E7 1 | MA-ITI-D1E7 2 |
| INPUT (pfu) | 1.00 ($1.8 \times 10^9$) | 1.00 ($1.2 \times 10^{10}$) | 1.00 ($3.3 \times 10^9$) | 1.00 ($1.1 \times 10^9$) |
| Wash | $6 \cdot 10^{-5}$ | $1 \cdot 10^{-5}$ | $2 \cdot 10^{-5}$ | $2 \cdot 10^{-5}$ |
| pH 7.0 | $3 \cdot 10^{-4}$ | $1 \cdot 10^{-5}$ | $2 \cdot 10^{-5}$ | $4 \cdot 10^{-5}$ |
| pH 3.5 | $3 \cdot 10^{-3}$ | $3 \cdot 10^{-6}$ | $8 \cdot 10^{-5}$ | $8 \cdot 10^{-5}$ |
| pH 2.0 | $1 \cdot 10^{-3}$ | $1 \cdot 10^{-6}$ | $6 \cdot 10^{-6}$ | $2 \cdot 10^{-5}$ |
| SUM | $4.3 \cdot 10^{-3}$ | $1.4 \cdot 10^{-5}$ | $1.1 \cdot 10^{-4}$ | $1.4 \cdot 10^{-4}$ |

Each entry is the fraction of input obtained in that component.
SUM is the total fraction of input pfu obtained from all pH elution fractions

TABLE 16

Fractionation of EpiNE-7 and MA-ITI-D1E7 phage on hNE beads

| | EpiNE-7 | | MA-ITI-D1E7 | |
|---|---|---|---|---|
| | Total pfu | Fraction of Input | Total pfu | Fraction of Input |
| INPUT | $1.8 \cdot 10^9$ | 1.00 | $3.0 \cdot 10^9$ | 1.00 |
| pH 7.0 | $5.2 \cdot 10^5$ | $2.9 \cdot 10^{-4}$ | $6.4 \cdot 10^4$ | $2.1 \cdot 10^{-5}$ |
| pH 6.0 | $6.4 \cdot 10^5$ | $3.6 \cdot 10^{-4}$ | $4.5 \cdot 10^4$ | $1.5 \cdot 10^{-5}$ |
| pH 5.5 | $7.8 \cdot 10^5$ | $4.3 \cdot 10^{-4}$ | $5.0 \cdot 10^4$ | $1.7 \cdot 10^{-5}$ |
| pH 5.0 | $8.4 \cdot 10^5$ | $4.7 \cdot 10^{-4}$ | $5.2 \cdot 10^4$ | $1.7 \cdot 10^{-5}$ |
| pH 4.5 | $1.1 \cdot 10^6$ | $6.1 \cdot 10^{-4}$ | $4.4 \cdot 10^4$ | $1.5 \cdot 10^{-5}$ |
| pH 4.0 | $1.7 \cdot 10^6$ | $9.4 \cdot 10^{-4}$ | $2.6 \cdot 10^4$ | $8.7 \cdot 10^{-6}$ |
| pH 3.5 | $1.1 \cdot 10^6$ | $6.1 \cdot 10^{-4}$ | $1.3 \cdot 10^4$ | $4.3 \cdot 10^{-6}$ |
| pH 3.0 | $3.8 \cdot 10^5$ | $2.1 \cdot 10^{-4}$ | $5.6 \cdot 10^3$ | $1.9 \cdot 10^{-6}$ |
| pH 2.5 | $2.8 \cdot 10^5$ | $1.6 \cdot 10^{-4}$ | $4.9 \cdot 10^3$ | $1.6 \cdot 10^{-6}$ |
| pH 2.0 | $2.9 \cdot 10^5$ | $1.6 \cdot 10^{-4}$ | $2.2 \cdot 10^3$ | $7.3 \cdot 10^{-7}$ |
| SUM | $7.6 \cdot 10^6$ | $4.1 \cdot 10^{-3}$ | $3.1 \cdot 10^5$ | $1.1 \cdot 10^{-4}$ |

*SUM is the total pfu (or fraction of input) obtained from all pH elution fractions.

TABLE 17

Fractionation of MA-EpiNE-7, MA-BITI and MA-BITI-E7 on hNE beads

| | MA-BITI | | MA-BITI-E7 | | MA-EpiNE7 | |
|---|---|---|---|---|---|---|
| | pfu | pfu/Input | pfu | pfu/Input | pfu | pfu/Input |
| INPUT | | | | | | |
| pH 2.0 | $10^{10}$ | 1.00 | $6.0 \; 10^9$ | 1.00 | $1.5 \; 10^9$ | 1.00 |
| 7.0 | $2.4 \; 10^5$ | $1.2 \; 10^{-5}$ | $2.8 \; 10^5$ | $4.7 \; 10^{-5}$ | $2.9 \; 10^5$ | $1.9 \; 10^{-4}$ |
| 6.0 | $2.5 \; 10^5$ | $1.2 \; 10^{-5}$ | $2.8 \; 10^5$ | $4.7 \; 10^{-5}$ | $3.7 \; 10^5$ | $2.5 \; 10^{-4}$ |
| 5.0 | $9.6 \; 10^4$ | $4.8 \; 10^{-6}$ | $3.7 \; 10^5$ | $6.2 \; 10^{-5}$ | $4.9 \; 10^5$ | $3.3 \; 10^{-4}$ |
| 4.5 | $4.4 \; 10^4$ | $2.2 \; 10^{-6}$ | $3.8 \; 10^5$ | $6.3 \; 10^{-5}$ | $6.0 \; 10^5$ | $4.0 \; 10^{-4}$ |
| 4.0 | $3.1 \; 10^4$ | $1.6 \; 10^{-6}$ | $2.4 \; 10^5$ | $4.0 \; 10^{-5}$ | $6.4 \; 10^5$ | $4.3 \; 10^{-4}$ |
| 3.5 | $8.6 \; 10^4$ | $4.3 \; 10^{-6}$ | $9.0 \; 10^4$ | $1.5 \; 10^{-5}$ | $5.0 \; 10^5$ | $3.3 \; 10^{-4}$ |
| 3.0 | $2.2 \; 10^4$ | $1.1 \; 10^{-6}$ | $8.9 \; 10^4$ | $1.5 \; 10^{-5}$ | $1.9 \; 10^5$ | $1.3 \; 10^{-4}$ |
| 2.5 | $2.2 \; 10^4$ | $1.1 \; 10^{-6}$ | $2.3 \; 10^4$ | $3.8 \; 10^{-6}$ | $7.7 \; 10^4$ | $5.1 \; 10^{-5}$ |
| 2.0 | $7.7 \; 10^3$ | $3.8 \; 10^{-7}$ | $8.7 \; 10^3$ | $1.4 \; 10^{-6}$ | $9.7 \; 10^4$ | $6.5 \; 10^{-5}$ |
| SUM | $8.0 \; 10^5$ | $3.9 \; 10^{-5}$ | $1.8 \; 10^6$ | $2.9 \; 10^{-4}$ | $3.3 \; 10^6$ | $2.2 \; 10^{-3}$ |

*SUM is the total pfu (or fraction of input) obtained from all PH elution fractions

TABLE 18

Fractionation of MA-BITI-E7 and MA-BITI-E7-1222 on hNE beads

| | | MA-BITI-E7 | | MA-BITI-E7-1222 | |
|---|---|---|---|---|---|
| | | pfu | pfu/INPUT | pfu | pfu/INPUT |
| INPUT | | $1.3 \cdot 10^9$ | 1.00 | $1.2 \cdot 10^9$ | 1.00 |
| pH | 7.0 | $4.7 \cdot 10^4$ | $3.6 \cdot 10^{-5}$ | $4.0 \cdot 10^4$ | $3.3 \cdot 10^{-5}$ |
| | 6.0 | $5.3 \cdot 10^4$ | $4.1 \cdot 10^{-5}$ | $5.5 \cdot 10^4$ | $4.6 \cdot 10^{-5}$ |
| | 5.5 | $7.1 \cdot 10^4$ | $5.5 \cdot 10^{-5}$ | $5.4 \cdot 10^4$ | $4.5 \cdot 10^{-5}$ |
| | 5.0 | $9.0 \cdot 10^4$ | $6.9 \cdot 10^{-5}$ | $6.7 \cdot 10^4$ | $5.6 \cdot 10^{-5}$ |
| | 4.5 | $6.2 \cdot 10^4$ | $4.8 \cdot 10^{-5}$ | $6.7 \cdot 10^4$ | $5.6 \cdot 10^{-5}$ |
| | 4.0 | $3.4 \cdot 10^4$ | $2.6 \cdot 10^{-5}$ | $2.7 \cdot 10^4$ | $2.2 \cdot 10^{-5}$ |
| | 3.5 | $1.8 \cdot 10^4$ | $1.4 \cdot 10^{-5}$ | $2.3 \cdot 10^4$ | $1.9 \cdot 10^{-5}$ |
| | 3.0 | $2.5 \cdot 10^3$ | $1.9 \cdot 10^{-6}$ | $6.3 \cdot 10^3$ | $5.2 \cdot 10^{-6}$ |
| | 2.5 | $<1.3 \cdot 10^3$ | $<1.0 \cdot 10^{-6}$ | $<1.3 \cdot 10^3$ | $<1.0 \cdot 10^{-6}$ |
| | 2.0 | $1.3 \cdot 10^3$ | $1.0 \cdot 10^{-6}$ | $1.3 \cdot 10^3$ | $1.0 \cdot 10^{-6}$ |
| SUM | | $3.8 \cdot 10^5$ | $2.9 \cdot 10^{-4}$ | $3.4 \cdot 10^5$ | $2.8 \cdot 10^{-4}$ |

SUM is the total pfu (or fraction of input) obtained from all pH elution fractions

TABLE 19

Fractionation of MA-EpiNE7 and MA-BITI-E7-141 on hNE beads

| | | MA-EpiNE7 | | MA-BITI-E7-141 | |
|---|---|---|---|---|---|
| | | pfu | pfu/INPUT | pfu | pfu/INPUT |
| INPUT | | $6.1 \cdot 10^8$ | 1.00 | $2.0 \cdot 10^9$ | 1.00 |
| pH | 7.0 | $5.3 \cdot 10^4$ | $8.7 \cdot 10^{-5}$ | $4.5 \cdot 10^5$ | $2.2 \cdot 10^{-4}$ |
| | 6.0 | $9.7 \cdot 10^4$ | $1.6 \cdot 10^{-4}$ | $4.4 \cdot 10^5$ | $2.2 \cdot 10^{-4}$ |
| | 5.5 | $1.1 \cdot 10^5$ | $1.8 \cdot 10^{-4}$ | $4.4 \cdot 10^5$ | $2.2 \cdot 10^{-4}$ |
| | 5.0 | $1.4 \cdot 10^5$ | $2.3 \cdot 10^{-4}$ | $7.2 \cdot 10^5$ | $3.6 \cdot 10^{-4}$ |
| | 4.5 | $1.0 \cdot 10^5$ | $1.6 \cdot 10^{-4}$ | $1.3 \cdot 10^6$ | $6.5 \cdot 10^{-4}$ |
| | 4.0 | $2.0 \cdot 10^5$ | $3.3 \cdot 10^{-4}$ | $1.1 \cdot 10^6$ | $5.5 \cdot 10^{-4}$ |
| | 3.5 | $9.7 \cdot 10^4$ | $1.6 \cdot 10^{-4}$ | $5.9 \cdot 10^5$ | $3.0 \cdot 10^{-4}$ |
| | 3.0 | $3.8 \cdot 10^4$ | $6.2 \cdot 10^{-5}$ | $2.3 \cdot 10^5$ | $1.2 \cdot 10^{-4}$ |
| | 2.5 | $1.3 \cdot 10^4$ | $2.1 \cdot 10^{-5}$ | $1.2 \cdot 10^5$ | $6.0 \cdot 10^{-5}$ |
| | 2.0 | $1.6 \cdot 10^4$ | $2.6 \cdot 10^{-5}$ | $1.0 \cdot 10^5$ | $5.0 \cdot 10^{-5}$ |
| SUM | | $8.6 \cdot 10^5$ | $1.4 \cdot 10^{-3}$ | $5.5 \cdot 10^6$ | $2.8 \cdot 10^{-3}$ |

SUM is the total pfu (or fraction of input) obtained from all pH elution fractions.

TABLE 20 pH Elution Analysis of hNE Binding by BITI-E7-141 Varient Display Phage

| | Input | Fraction of Input recovered at pH | | | Recovery | |
|---|---|---|---|---|---|---|
| Displayed protein | PFU ($\times 10^9$) | pH 7.0 | pH 3.5 $\times 10^{-4}$ | pH 2.0 $\times 10^{-4}$ | Total $\times 10^{-4}$ | Relative |
| AMINO1 (EE) | 0.96 | 0.24 | 2.3 | 0.35 | 2.9 | 0.11 |
| AMINO2 (AE) | 6.1 | 0.57 | 2.1 | 0.45 | 3.1 | 0.12 |
| BITI-E7-1222 (EE) | 1.2 | 0.72 | 4.0 | 0.64 | 5.4 | 0.21 |
| EpiNE7 (EE) | 0.72 | 0.44 | 6.4 | 2.2 | 9.0 | 0.35 |
| MUTP1 (AE) | 3.9 | 1.8 | 9.2 | 1.2 | 12.0 | 0.46 |
| MUT1619 (EE) | 0.78 | 0.82 | 9.9 | 0.84 | 12.0 | 0.46 |
| MUTQE (AE) | 4.7 | 1.2 | 16. | 5.3 | 22.0 | 0.85 |
| MUTT26A (EE) | 0.51 | 2.5 | 19.0 | 3.3 | 25.0 | 0.96 |
| BITI-E7-141 (AE) | 1.7 | 2.2 | 18.0 | 5.4 | 26.0 | 1.00 |
| BITI-E7-141 (EE) | 0.75 | 2.1 | 21. | 3.2 | 26.0 | 1.00 |

Notes:
EE Extended pH elution protocol
AE Abbreviated pH elution protocol
Total Total fraction of input = Sum of fractions collected at pH 7.0, pH 3.5, and pH 2.0.
Relative Total fraction of input recovered divided by total fraction of input recovered for BITI-E7-141

TABLE 23

Plasmid pHIL-D2 SEQ ID NO. 070
8157 base pairs. Only one strand is shown, but the DNA exists as double-stranded circular DNA in *vivo*.

```
              1          2          3          4          5
         1234567890 1234567890 1234567890 1234567890 1234567890

1     AgATCgCggC CgCgATCTAA CATCCAAAgA CgAAAggTTg AATgAAACCT

51     TTTTgCCATC CgACATCCAC AggTCCATTC TCACACATAA gTgCCAAACg

101     CAACAggAgg ggATACACTA gCAgCAgACC gTTgCAAACg CAggACCTCC

151     ACTCCTCTTC TCCTCAACAC CCACTTTTgC CATCgAAAAA CCAgCCCAgT

201     TATTgggCTT gATTggAgCT CgCTCATTCC AATTCCTTCT ATTAggCTAC

251     TAACACCATg ACTTTATTAg CCTgTCTATC CTggCCCCCC TggCgAggTC

301     ATgTTTgTTT ATTTCCgAAT gCAACAAgCT CCgCATTACA CCCgAACATC

351     ACTCCAgATg AgggCTTTCT gAgTgTggggg TCAAATAgTT TCATgTTCCC

401     AAATggCCCA AAACTgACAg TTTAAACgCT gTCTTggAAC CTAATATgAC

451     AAAAgCgTgA TCTCATCCAA gATgAACTAA gTTTggTTCg TTgAAAATgCT
```

TABLE 23-continued

Plasmid pHIL-D2 SEQ ID NO. 070
8157 base pairs. Only one strand is shown, but the DNA exists as double-stranded circular DNA in *vivo*.

```
 501 AACggCCAgT TggTCAAAAA gAAACTTCCA AAAgTCgCCA TACCgTTTgT

551 CTTgTTTggT ATTgATTgAC gAATgCTCAA AAATAATCTC ATTAATgCTT

601 AgCgCAgTCT CTCTATCgCT TCTgAACCCg gTggCACCTg TgCCgAAACg

651 CAAATggggA AACAACCCgC TTTTTggATg ATTATgCATT gTCCTCCACA

701 TTgTATgCTT CCAAgATTCT ggTgggAATA CTgCTgATAg CCTAACgTTC

751 ATgATCAAAA TTTAACTgTT CTAACCCCTA CTTgACAggC AATATATAAA

801 CAgAAggAAg CTgCCCTgTC TTAAACCTTT TTTTTTATCA TCATTATTAg

851 CTTACTTTCA TAATTgCgAC TggTTCCAAT TgACAAgCTT TTgATTTTAA

901 CgACTTTTAA CgACAACTTg AgAAgATCAA AAAACAACTA ATTATTCgAA
                                                      BstBI

951 ACgAggAATT CgCCTTAgAC ATgACTgTTC CTCAgTTCAA gTTgggCATT
           EcoRI

1001 ACgAgAAgAC CggTCTTgCT AgATTCTAAT CAAgAggATg TCAgAATgCC

1051 ATTTgCCTgA gAgATgCAgg CTTCATTTTT gATACTTTTT TATTTgTAAC

1101 CTATATAgTA TAggATTTTT TTTgTCATTT TgTTTCTTCT CgTACgAgCT

1151 TgCTCCTgAT CAgCCTATCT CgCAgCTgAT gAATATCTTg TggTAggggT

1201 TTgggAAAAT CATTCgAgTT TgATgTTTTT CTTggTATTT CCCACTCCTC

1251 TTCAgAgTAC AgAAgATTAA gTgAgAAgTT CgTTTgTgCA AgCTTATCgA

1301 TAAgCTTTAA TgCggTAgTT TATCACAgTT AAATTgCTAA CgCAgTCAgg

1351 CACCgTgTAT gAAATCTAAC AATgCgCTCA TCgTCATCCT CggCACCgTC

1401 ACCCTggATg CTgTAggCAT AggCTTggTT ATgCCggTAc TgCCgggCCT

1451 CTTgCgggAT ATCgTCCATT CCgACAgCAT CgCCAgTCAC TATggCgTgC

1501 TgCTAgCgCT ATATgCgTTg ATgCAATTTC TATgCgCACC CgTTCTCggA 1551 gCACTgTCCg ACCgCTTTgg CCgCCgCCCA gTCCTgCTCg CTTCgCTACT

1601 TggAgCCACT ATCgACTACg CgATCATggC gACCACACCC gTCCTgTggA

1651 TCTATCgAAT CTAAATgTAA gTTAAAATCT CTAPATAATT AAATAAgTCC

1701 CAgTTTCTCC ATACgAACCT TAACAgCATT gCggTgAgCA TCTAgACCTT

1751 CAACAgCAgC CAgATCCATC ACTgCTTggC CAATATgTTT CAgTCCCTCA 1801 ggAgTTACgT CTTgTgAAgT gATgAACTTC TggAAggTTg CAgTgTTAAC

1851 TCCgCTgTAT TgACgggCAT ATCCgTACgT TggCAAAgTg TggTTggTAC

1901 CggAggAgTA ATCTCCACAA CTCTCTggAg AgTAggCACC AACAAACACA 1951 gATCCAgCgT gTTgTACTTg ATCAACATAA gAAgAAgCAT TCTCgATTTg

2001 CAggATCAAg TgTTCAggAg CgTACTgATT ggACATTTCC AAAgCCTgCT

2051 CgTAggTTgC AACCgATAgg gTTgTAgAgT gTgCAATACA CTTgCgTACA

2101 ATTTCAACCC TTggCAACTg CACAgCTTgg TTgTgAACAg CATCTTCAAT

2151 TCTggCAAgC TCCTTgTCTg TCATATCgAC AgCCAACAgA ATCACCTggg

2201 AATCAATACC ATgTTCAgCT TgAgCAgAAg gTCTgAggCA ACgAAATCTg 2251 gATCAgCgTA TTTATCAgCA ATAACTAgAA CTTCAgAAgg CCCAgCAggC
```

TABLE 23-continued

Plasmid pHIL-D2 SEQ ID NO. 070
8157 base pairs. Only one strand is shown, but the DNA
exists as double-stranded circular DNA in *vivo*.

```
2301 ATgTCAATAC TACACAgggC TgATgTgTCA TTTTgAACCA TCATCTTggC

2351 AgCAgTAACg AACTggTTTC CTggACCAAA TATTTTgTCA CACTTAggAA

2401 CAgTTTCTgT TCCgTAAgCC ATAgCAgCTA CTgCCTgggC gCCTCCTgCT

2451 AgCACgATAC ACTTAgCACC AACCTTgTgg gCAACgTAgA TgACTTCTgg 2501 ggTAAgggTA CCATCCTTCT TAggTggAgA TgCAAAAACA ATTTCTTTgC 2551 AACCAgCAAC TTTggCAggA ACACCCAgCA TCAgggAAgT ggAAggCAgA 2601 ATTgCggTTC CACCAggAAT ATAgAggCCA ACTTTCTCAA TAggTCTTgC 2651 AAAACgAgAg CAgACTACAC CAgggCAAgT CTCAACTTgC AACgTCTCCg 2701 TTAgTTgAgC TTCATggAAT TTCCTgACgT TATCTATAgA gAgATCAATg 2751 gCTCTCTTAA CgTTATCTgg CAATTgCATA AgTTCCTCTg ggAAAggAgC 2801 TTCTAACACA 9gTgTCTTCA AAgCgACTCC ATCAAACTTg gCAgTTAgTT 2851 CTAAAAgggC TTTgTCACCA TTTTgAC9AA CATTgTCgAC AATTggTTTg 2901 ACTAATTCCA TAATCTgTTC CgTTTTCTgg ATAggACgAC gAAgggCATC 2951 TTCAATTTCT TgTgAggAgg CCTTAgAAAC gTCAATTTTg CACAATTCAA 3001 TACgACCTTC AgAAgggACT TCTTTAggTT TggATTCTTC TTTAggTTgT 3051 TCCTTggTgT ATCCTggCTT ggCATCTCCT TTCCTTCTAg TgACCTTTAg 3101 ggACTTCATA TCCAggTTTC TCTCCACCTC gTCCAACgTC ACACCgTACT 3151 TggCACATCT AACTAATgCA AAATAAAATA AgTCAgCACA TTCCCAggCT 3201 ATATCTTCCT TggATTTAgC TTCTgCAAgT TCATCAgCTT CCTCCCTAAT 3251 TTTAgCgTTC AACAAAACTT CgTCgTCAAA TAACCgTTTg gTATAAgAAC 3301 CTTCTggAgC ATTgCTCTTA CgATCCCACA AggTgCTTCC ATggCTCTAA 3351 gACCCTTTgA TTggCCAAAA CAggAAgTgC gTTCCAgTg ACAgAAACCA 3401 ACACCTgTTT gTTCAACCAC AAATTTCAAg CAgTCTCCAT CACAATCCAA 3451 TTCgATACCC AgCAACTTTT gAgTTCgTCC AgATgTAgCA CCTTTATACC 3501 ACAAACCgTg ACgACgAgAT TggTAgACTC CAgTTTgTgT CCTTATAgCC 3551 TCCggAATAg ACTTTTTggA CgAgTACACC AggCCCAACg AgTAATTAgA 3601 AgAgTCAgCC ACCAAAgTAg TgAATAgACC ATCggggCgg TCAgTAgTCA 3651 AAgACgCCAA CAAAATTTCA CTgACAgggA ACTTTTTgAC ATCTTCAgAA 3701 AgTTCgTATT CAgTAgTCAA TTgCCgAgCA TCAATAATgg ggATTATACC 3751 AgAAgCAACA gTggAAgTCA CATCTACCAA CTTTgCggTC TCAgAAAAAg 3801 CATAAACAgT TCTACTACCg CCATTAgTgA AACTTTTCAA ATCgCCCAgT 3851 ggAgAAgAAA AAggCACAgC gATACTAgCA TTAgCgggCA AggATgCAAC 3901 TTTATCAACC AgggTCCTAT AgATAACCCT AgCgCCTggg ATCATCCTTT 3951 ggACAACTCT TTCTgCCAAA TCTAggTCCA AAATCACTTC ATTgATACCA 4001 TTATACggAT gACTCAACTT gCACATTAAC TTgAAgCTCA gTCgATTgAg 4051 TgAACTTgAT CAggTTgTgC AgCTggTCAg CAgCATAggg AAACACggCT 4101 TTTCCTACCA AACTCAAggA ATTATCAAAC TCTgCAACAC TTgCgTATgC 4151 AggTAgCAAg ggAAATgTCA TACTTgAAgT CggACAgTgA gTgTAgTCTT
```

TABLE 23-continued

Plasmid pHIL-D2 SEQ ID NO. 070
8157 base pairs. Only one strand is shown, but the DNA
exists as double-stranded circular DNA in *vivo*.

```
4201 gAgAAATTCT gAAgCCgTAT TTTTATTATC AgTgAgTCAg TCATCAggAg
4251 ATCCTCTACg CCggACgCAT CgTggCCggc ATCACCggCg CCACAggTgC
4301 ggTTgCTggc gCCTATATCg CCgACATCAC CgATggggAA gATCgggCTC
4351 gCCACTTCgg gCTCATgAgC gCTTgTTTCg gCgTgggTAT ggTggCAggC
4401 CCCgTggCCg ggggACTgTT gggCgCCATC TCCTTgCATg CACCATTCCT
4451 TgCggCggcg gTgCTCAACg gCCTCAACCT ACTACTgggC TgCTTCCTAA
4501 TgCAggAgTC gCATAAgggA gAgCgTCgAg TATCTATgAT TggAAgTATg
4551 ggAATggTgA TACCCgCATT CTTCAgTgTC TTgAggTCTC CTATCAgATT
4601 ATgCCCAACT AAAgCAACCg gAggAggAgA TTTCATggTA AATTTCTCTg
4651 ACTTTTggTC ATCAgTAgAC TCgAACTgTg AgACTATCTC ggTTATgACA
4701 gCAgAAATgT CCTTCTTggA gACAgTAAAT gAAgTCCCAC CAATAAAgAA
4751 ATCCTTgTTA TCAggAACAA ACTTCTTgTT TCgAACTTTT TCggTgCCTT
4801 gAACTATAAA ATgTAgAgTg gATATgTCgg gTAggAATgg AgCgggCAAA
4851 TgCTTACCTT CTggACCTTC AAgAggTATg TAgggTTTgT AgATACTgAT
4901 gCCAACTTCA gTgACAACgT TgCTATTTCg TTCAAACCAT TCCgAATCCA
4951 gAgAAATCAA AgTTgTTTgT CTACTATTgA TCCAAgCCAg TgCggTCTTg
5001 AAACTgACAA TAgTgTgCTC gTgTTTTgAg gTCATCTTTg TATgAATAAA
5051 TCTAgTCTTT gATCTAAATA ATCTTgACgA gCCAAggCgA TAAATACCCA
5101 AATCTAAAAC TCTTTTAAAA CgTTAAAAgg ACAAgTATgT CTgCCTgTAT
5151 TAAACCCCAA ATCAgCTCgT AgTCTgATCC TCATCAACTT gAggggCACT
5201 ATCTTgTTTT AgAgAAATTT gCggAgATgC gATATCgAgA AAAAggTACg
5251 CTgATTTTAA ACgTgAAATT TATCTCAAgA TCgCggCCgC gATCTCgAAT
5301 AATAACTgTT ATTTTTCAgT gTTCCCgATC TgCgTCTATT TCACAATACC
5351 AACATgAgTC AgCTTATCgA TgATAAgCTg TCAAACATgA gAATTAATTC
5401 gATgATAAgC TgTCA[]ACAT gAgAAATCTT gAAgACgAAA gggC-
     CTCgTg
5451 ATACgCCTAT TTTTATAggT TAATgTCATg ATAATAATgg TTTCTTAgAC
5501 gTCAggTggC ACTTTTCggg gAAATgTgCg CggAACCCCT ATTTgTTTAT
5551 TTTTCTAAAT ACATTCAAAT ATgTATCCgC TCATgAgACA ATAACCCTgA
5601 TAAATgCTTC AATAATATTg AAAAAggAAg AgTATgAgTA TTCAACATTT
5651 CCgTgTCgCC CTTATTCCCT TTTTTgCggC ATTTTgCCTT CCTgTTTTTg
5701 CTCACCCAgA AACgCTggTg AAAgTAAAAg ATgCTgAAgA TCAgTTgggT
5751 gCACgAgTgg gTTACATCgA ACTggATCTC AACAgCggTA AgATCCTTgA
5801 gAgTTTTCgC CCCgAAgAAC gTTTTCCAAT gATgAgCACT TTTAAAgTTC
5851 TgCTATgTgg CgCggTATTA TCCCgTgTTg ACgCCgggCA AgAgCAACTC
5901 ggTCgCCgCA TACACTATTC TCAgAATgAC TTggTTgAgT ACTCACCAgT
5951 CACAgAAAAg CATCTTACgg ATggCATgAC AgTAAgAgAA TTATgCAgTg
6001 CTgCCATAAC CATgAgTgAT AACACTgCgg CCAACTTACT TCTgACAACg
```

TABLE 23-continued

Plasmid pHIL-D2 SEQ ID NO. 070
8157 base pairs. Only one strand is shown, but the DNA
exists as double-stranded circular DNA in *vivo*.

```
6051 ATCggAggAC CgAAggAgCT AACCgCTTTT TTgCACAACA TggggATCA

6101 TgTAACTCgC CTTgATCgTT gggAACCggA gCTgAATgAA gCCATACCAA

6151 ACgACgAgCg TgACACCACg ATgCCTgCAg CAATggCAAC AACgTTgCgC

6201 AAACTATTAA CTggCgAACT ACTTACTCTA gCTTCCCggC AACAATTAAT

6251 AgACTggATg gAggCggATA AAgTTgCAgg ACCACTTCTg CgCTCggCCC

6301 TTCCggCTgg CTggTTTATT gCTgATAAAT CTggAgCCgg TgAgCgTggg

6351 TCTCgCggTA TCATTgCAgC ACTggggCCA gATggTAAgC CCTCCCgTAT

6401 CgTAgTTATC TACACgACgg ggAgTCAggC AACTATggAT gAACgAAATA 6451 gACAgATCgC TgAgATAggT gCCTCACTgA TTAAgCATTg gTAACTgTCA 6501 gACCAAgTTT ACTCATATAT ACTTTAgATT gATTTAAATT gTAAACgTTA

6551 ATATTTTgTT AAAATTCgCg TTAAATTTTT gTTAAATCAg CTCATTTTTT

6601 AACCAATAgg CCgAAATCgg CAAAATCCCT TATAAATCAA AAgAATAgAC

6651 CgAgATAggg TTgAgTgTTg TTCCAgTTTg gAACAAgAgT CCACTATTAA

6701 AgAACgTggA CTCCAACgTC AAAgggCgAA AAACCgTCTA TCAgggCgAT 6751 ggCCCACTAC gTgAACCATC ACCCTAATCA AgTTTTTTgg ggTCgAggTg 6801 CCgTAAAgCA CTAAATCggA ACCCTAAAgg gAgCCCCCgA TTTAgAgCTT 6851 gACggggAAA gCCggCgAAC gTggCgAgAA AggAAgggAA gAAAgCgAAA 6901 ggAgCgggCg CTAgggCgCT ggCAAgTgTA gCggTCACgC TgCgCgTAAC 6951 CACCACACCC gCCgCgCTTA ATgCgCCgCT ACAgggCgCg TAAAAggATC 7001 TAggTgAAgA TCCTTTTTgA TAATCTCATg ACCAAAATCC CTTAACgTgA 7051 gTTTTCgTTC CACTgAgCgT CAgACCCCgT AgAAAAgATC AAAggATCTT 7101 CTTgAgATCC TTTTTTTCTg CgCgTAATCT gCTgCTTgCA AACAAAAAAA 7151 CCACCgCTAC CAgCggTggT TTgTTTgCCg gATCAAgAgC TACCAACTCT 7201 TTTTCCgAAg gTAACTggCT TCAgCAgAgC gCAgATACCA AATACTgTCC 7251 TTCTA9TgTA gCCgTAgTTA ggCCACCACT TCAAgAACTC TgTAgCACCg 7301 CCTACATACC TCgCTCTgCT AATCCTgTTA CCAgTggCTg CTgCCAgTgg 7351 CgATAAgTCg TgTCTTACCg ggTTggACTC AAgACgATAg TTACCggATA 7401 AggCgCAgCg gTCgggCTgA ACgggggggTT CgTgCACACA gCCCAgCTTg 7451 gAgCgAACgA CCTACACCgA ACTgAgATAC CTACAgCgTg AgCATTgAgA 7501 AAgCgCCACg CTTCCCgAAg ggAgAAAggC ggACAggTAT CCggTAAgCg 7551 gCAgggTCgg AACAggAgAg CgCACgAggg AgCTTCCAgg gggAAACgCC 7601 TggTATCTTT ATAgTCCTgT CgggTTTCgC CACCTCTgAC TTgAgCgTCg 7651 ATTTTTgTgA TgCTCgTCAg ggggCggAg CCTATggAAA AACgCCAgCA 7701 ACgCggCCTT TTTACggTTC CTggCCTTTT gCTggCCTTT TgCTCACATg 7751 TTCTTTCCTg CgTTATCCCC TgATTCTgTg gATAACCgTA TTACCgCCTT 7801 TgAgTgAgCT gATACCgCTC gCCgCAgCCg AACgACCgAg CgCAgCgAgT 7851 CAgTgAgCgA ggAAgCggAA gAgCgCCTgA TgCggTATTT TCTCCTTACg
```

TABLE 23-continued

Plasmid pHIL-D2 SEQ ID NO. 070
8157 base pairs. Only one strand is shown, but the DNA
exists as double-stranded circular DNA in *vivo*.

```
7901 CATCTgTgCg gTATTTCACA CCgCATATgg TgCACTCTCA gTACAATCTg

7951 CTCTgATgCC gCATAgTTAA gCCAgTATAC ACTCCgCTAT CgCTACgTgA

8001 CTgggTCATg gCTgCgCCCC gACACCCgCC AACACCCgCT gACgCgCCCT 8051 gACgggCTTg TCTgCTCCCg gCATCCgCTT ACAgACAAgC TgTgACCgTC 8101 TCCgggAgCT gCATgTgTCA gAggTTTTCA CCgTCATCAC CgAAACgCgC 8151 gAggCAg
```

TABLE 24 pHIL-D2(MFαPrePro::EPI-HNE-3) 8584 b.p.
DNA has SEQ ID NO. 071; Encoded polypeptide has SEQ ID NO.
072. DNA is circular and double stranded, only one strand is
shown. Translation of the protein to be expressed is shown.

```
              1          2          3          4          5
     1234567890 1234567890 1234567890 1234567890 1234567890

1 AgATCgCggC CgCgATCTAA CATCCAAAgA CgAAAggTTg AATgAAACCT

51 TTTTgCCATC CgACATCCAC AggTCCATTC TCACACATAA gTgCCAAACg

101 CAACAggAgg ggATACACTA gCAgCAgACC gTTgCAAACg CAggACCTCC

151 ACTCCTCTTC TCCTCAACAC CCACTTTTgC CATCgAAAAA CCAgCCCAgT

201 TATTgggCTT gATTggAgCT CgCTCATTCC AATTCCTTCT ATTAggCTAC

251 TAACACCATg ACTTTATTAg CCTgTCTATC CTggCCCCCC TggCgAggTC

301 ATgTTTgTTT ATTTCCgAAT gCAACAAgCT CCgCATTACA CCC9AACATC

351 ACTCCAgATg AgggCTTTCT gAgTgTgggg TCAAATAgTT TCATgTTCCC

401 AAATggCCCA AAACTgACAg TTTAAACgCT gTCTTggAAC CTAATATgAC

451 AAAAgCgTgA TCTCATCCAA gATgAACTAA gTTTggTTCg TTgAAATgCT

501 AACggCCAgT TggTCAAAAA 9AAACTTCCA AAgTCgCCA TACCgTTTgT

551 CTTgTTTggT ATTgATTgAC gAATgCTCAA AAATAATCTC ATTAATgCTT

601 AgCgCAgTCT CTCTATCgCT TCTgAACCCg gTggCACCTg TgCCgAAACg

651 CAAATggggA AACAACCCgC TTTTTggATg ATTATgCATT gTCCTCCACA

701 TTgTATgCTT CCAAgATTCT ggTgggAATA CTgCTgATAg CCTAACgTTC

751 ATgATCAAAA TTTAACTgTT CTAACCCCTA CTTgACAggC AATATATAAA

801 CAgAAggAAg CTgCCCTgTC TTAAACCTTT TTTTTTATCA TCATTATTAg

851 CTTACTTTCA TAATTgCgAC TggTTCCAAT TgACAAgCTT TTgATTTTAA

901 CgACTTTTAA CgACAACTTg AgAAgATCAA AAAACAACTA ATTATTCgAA
   |                                                  BstBI

ACg
```

```
    M   R   F   P   S   I   F   T   A   V   L   F   A
 13
    ATg AgA TTC CCA TCT ATC TTC ACT gCT gTT TTg TTC gCT
    |    | BsaBI |

A   S   S   A   L   A   A   P   V   N   T   T   T   E
 27
    gCT TCC TCT gCT TTg gCT gCT CCA gTT AAC ACC ACT ACT gAA
```

TABLE 24-continued

```
                         BpmI      HpaI              BbsI

D   E   T   A   Q   I   P   A   E   A   V   I   G   Y
 41
      gAC gAg ACT gCT CAA ATT CCT gCT gAg gCT gTC ATC ggT TAC
      BbsI

S   D   L   E   G   D   F   D   V   A   V   L   P   F
 55
      TCT gAC TTg gAA ggT gAC TTC gAC gTC gCT gTT TTg CCA TTC
                                      AatII

S   N   S   T   N   N   G   L   L   F   I   N   T   T
 69
      TCT AAC TCT ACT AAC AAC ggT TTg TTg TTC ATC AAC ACT ACC

I   A   S   I   A   A   K   E   E   G   V   S   L   D
 83
      ATC gCT TCT ATC gCT gCT AAg gAg gAA ggT gTT TCC TTg gAC

K   R       A   A   C   N   L   P
 91
      AAg AgA  |  gCT gCT TgT AAC TTg CCA
              ----- Site of cleavage I   V   R   G   P   C   I   A   F   F   P   R   W   A
105
      ATC gTC AgA ggT CCA TgC ATT gCT TTC TTC CCA AgA Tgg gCT
                          NsiI F   D   A   V   K   G   K   C   V   L   F   P   Y   G
119
      TTC gAC gCT gTT AAg ggT AAg TgC gTC TTg TTC CCA TAC ggT
                                                    |  PflMI G   C   Q   G   N   G   N   K   F   Y   S   E   K   E
133
  ggT TgT CAA ggT AAC ggT AAC AAg TTC TAC TCT gAg AAg gAg
      PflMI C   R   E   Y   C   G   V   P
141
  TgT AgA gAg TAC TgT ggT gTT CCA TAg TAA gAATTCgCCT
                                       EcoRI TAgACATg
 1401  ACTgTTCCTC AgTTCAAgTT gggCATTACg AgAAgACCgg TCTTgCTAgA
 1451  TTCTAATCAA gAggATgTCA gAATgCCATT TgCCTgAgAg ATgCAggCTT
 1501  CATTTTTgAT ACTTTTTTAT TTgTAACCTA TATAgTATAg gATTTTTTTT
 1551  gTCATTTTgT TTCTTCTCgT ACgAgCTTgC TCCTgATCAg CCTATCTCgC
 1601  AgCTgATgAA TATCTTgTgg TAggggTTTg ggAAAATCAT TCAgTTTgA
 1651  TgTTTTTCTT ggTATTTCCC ACTCCTCTTC AgAgTACAgA AgATTAAgTg
 1701  AgAAgTTCgT TTgTgCAAgC TTATCgATAA gCTTTAATgC ggTAgTTTAT
 1751  CACAgTTAAA TTgCTAACgC AgTCAggCAC CgTgTATgAA ATCTAACAAT
 1801  gCgCTCATCg TCATCCTCgg CACCgTCACC CTggATgCTg TAggCATAgg
 1851  CTTggTTATg CCggTACTgC CgggCCTCTT gCgggATATC gTCCATTCCg
 1901  ACAgCATCgC CAgTCACTAT ggCgTgCTgC TAgCgCTATA TgCgTTgATg
 1951  CAATTTCTAT gCgCACCCgT TCTCggAgCA CTgTCCgACC gCTTTggCCg
```

TABLE 24-continued

```
2001  CCgCCCAgTC CTgCTCgCTT CgCTACTTgg AgCCACTATC gACTACgCgA
2051  TCATggCgAC CACACCCgTC CTgTggATCT ATCgAATCTA AATgTAAgTT
2101  AAAATCTCTA AATAATTAAA TAAgTCCCAg TTTCTCCATA CgAACCTTAA
2151  CAgCATTgCg gTgAgCATCT AgACCTTCAA CAgCAgCCAg ATCCATCACT
2201  gCTTggCCAA TATgTTTCAg TCCCTCAggA gTTACgTCTT gTgAAgTgAT
2251  gAACTTCTgg AAggTTgCAg TgTTAACTCC gCTgTATTgA CgggCATATC
2301  CgTACgTTgg CAAAgTgTgg TTggTACCgg AggAgTAATC TCCACAACTC
2351  TCTggAgAgT AggCACCAAC AAACACAgAT CCAgCgTgTT gTACTTgATC
2401  AACATAAgAA gAAgCATTCT CgATTTgCAg gATCAAgTgT TCAggAgCgT
2451  ACTgATTggA CATTTCCAAA gCCTgCTCgT AggTTgCAAC CgATAgggTT
2501  gTAgAgTgTg CAATACACTT gCgTACAATT TCAACCCTTg gCAACTgCAC
2551  AgCTTggTTg TgAACAgCAT CTTCAATTCT ggCAAgCTCC TTgTCTgTCA
2601  TATCgACAgC CAACAgAATC ACCTgggAAT CAATACCATg TTCAgCTTgA
2651  gCAgAAggTc TgAggCAACg AAATCTggAT CAgCgTATTT ATCAgCAATA
2701  ACTAgAACTT CAgAAggCCC AgCAggCATg TCAATACTAC ACAgggCTgA
2751  TgTgTCATTT TgAACCATCA TCTTggCAgC AgTAACgAAC TggTTTCCTg
2801  9ACCAAATAT TTTgTCACAC TTAggAACAg TTTCTgTTCC gTAAgCCATA
2851  gCAgCTACTg CCTgggCgCC TCCTgCTAgC ACgATACACT TAgCACCAAC
2901  CTTgTgggCA ACgTAgATgA CTTCTgCgggT AAgggTACCA TCCTTCTTAg
2951  gTggAgATgC AAAAACAATT TCTTTgCAAC CAgCAACTTT ggCAggAACA
3001  CCCAgCATCA gggAAgTggA AggCA9AATT gCggTTCCAC CAggAATATA
3051  gAggCCAACT TTCTCAATAg gTCTTgCAAA ACgAgAgCAg ACTACACCAg
3101  ggCAAgTCTC AACTTgCAAC gTCTCCgTTA gTTgAgCTTC ATggAATTTc
3151  CTgACgTTAT CTATAgAgAg ATCAATggCT CTCTTAACgT TATCTggCAA
3201  TTgCATAAgT TCCTCTgggA AAggAgCTTC TAACACAggT gTCTTCAAAg
3251  CgACTCCATC AAACTTggCA gTTAgTTCTA AAAgggCTTT gTCACCATTT
3301  TgACgAACAT TgTCgACAAT TggTTTgACT AATTCCATAA TCTgTTCCgT
3351  TTTCTggATA ggACgACgAA gggCATCTTC AATTTCTTgT gAggAggCCT
3401  TAgAAACgTC AATTTTgCAC AATTCAATAC gACCTTCAgA AgggACTTCT
3451  TTAggTTTgg ATTCTTCTTT AggTTgTTcC TTggTgTATC CTggCTTggC
3501  ATCTCCTTTC CTTCTAgTgA CCTTTAgggA CTTCATATCC AggTTTCTCT
3551  CCACCTCgTC CAACgTCACA CCgTACTTgg CACATCTAAC TAATgCAAAA
3601  TAAAATAAgT CAgCACATTC CCAggCTATA TCTTCCTTgg ATTTAgCTTC
3651  TgCAAgTTCA TCAgCTTCCT CCCTAATTTT AgCgTTCAAC AAAACTTCgT
3701  CgTCAAATAA CCgTTTggTA TAAgAACCTT CTggAgCATT gCTCTTACgA
3751  TCCCACAAgg TgCTTCCATg gCTCTAAgAC CCTTTgATTg gCCAAAACAg
3801  gAAgTgCgTT CCAAgTgACA gAAACCAACA CCTgTTTgTT CAACCACAAA
3851  TTTCAAgCAg TCTCCATCAC AATCCAATTC gATACCCAgC AACTTTTgAg
3901  TTCgTCCAgA TgTAgCACCT TTATACCACA AACCgTgACg ACgAgATTgg
```

TABLE 24-continued

```
3951  TAgACTCCAg TTTgTgTCCT TATAgCCTCC ggAATAgACT TTTTggACgA
4001  gTACACCAgg CCCAACgAgT AATTAgAAgA gTCAgCCACC AAAgTAgTgA
4051  ATAgACCATC ggggCggTCA gTAgTCAAAg ACgCCAACAA AATTTCACTg
4101  ACAgggAACT TTTTgACATC TTCAgAAAgT TCgTATTCAg TAgTCAATTg
4151  CCgAgCATCA ATAATggggA TTATACCAgA AgCAACAgTg gAAgTCACAT
4201  CTACCAACTT TgCggTCTCA gAAAAAgCAT AAACAgTTCT ACTACCgCCA
4251  TTAgTgAAAC TTTTCAAATC gCCCAgTggA gAAgAAAAAg gCACAgCgAT
4301  ACTAgCATTA gCgggCAkgg ATgCAACTTT ATCAACCAgg gTCCTATAgA
4351  TAACCCTAgC gCCTgggATC ATCCTTTggA CAACTCTTTC TgCCAAATCT
4401  AggTCCAAAA TCACTTCATT gATACCATTA TACggATgAC TCAACTTgCA
4451  CATTAACTTg AAgCTCAgTC gATTgAgTgA ACTTgATCAg gTTgTgCAgC
4501  TggTCAgCAg CATAgggAAA CACggCTTTT CCTACCAAAC TCAAggAATT
4551  ATCAAACTCT gCAACACTTg CgTATgCAgg TAgCAAgggA AATgTCATAC
4601  TTgAAgTCgg ACAgTgAgTg TAgTCTTgAg AAATTCTgAA gCCgTATTTT
4651  TATTATCAgT gAgTCAgTCA TCAggAgATC CTCTACgCCg gACgCATCgT
4701  ggCCggCATC ACCggCgCCA CAggTgCggT TgCTggCgCC TATATCgCCg
4751  ACATCACCgA TggggAAgAT CgggCTCgCC ACTTCgggCT CATgAgCgCT
4801  TgTTTCggCg TgggTATggT ggCAggCCCC gTggCCgggg gACTgTTggg
4851  CgCCATCTCC TTgCATgCAC CATTCCTTgC ggCggCggTg CTCAACggCC
4901  TCAACCTACT ACTgggCTgC TTCCTAATgC AggAgTCgCA TAAgggAgAg
4951  CgTCgAgTAT CTATgATTgg AAgTATgggA ATggTgATAC CCgCATTCTT
5001  CAgTgTCTTg AggTCTCCTA TCAgATTATg CCCAACTAAA gCAACCggAg
5051  gAggAgATTT CATggTAAAT TTCTCTgACT TTTggTCATC AgTAgACTCg
5101  AACTgTgAgA CTATCTCggT TATgACAgCA gAAATgTCCT TCTTggAgAC
5151  AgTAAATgAA gTCCCACCAA TAAAgAAATC CTTgTTATCA ggAACAAACT
5201  TCTTgTTTCg AACTTTTTCg gTgCCTTgAA CTATAAAATg TAgAgTggAT
           BstBI
5251  ATgTCgggTA ggAATggAgC gggCAAATgC TTACCTTCTg gACCTTCAAg
5301  AggTATgTAg ggTTTgTAgA TACTgATgCC AACTTCAgTg ACAACgTTgC
5351  TATTTCgTTC AAACCATTCC gAATCCAgAg AAATCAAAgT TgTTTgTCTA
5401  CTATTgATCC AAgCCAgTgC ggTCTTgAAA CTgACAATAg TgTgCTCgTg
5451  TTTTgAg9TC ATCTTTgTAT gAATAAATCT AgTCTTTgAT CTAAATAATC
5501  TTgACgAgCC AAggCgATAA ATACCCAAAT CTAAAACTCT TTTAAAACgT
5551  TAAAAggACA AgTATgTCTg CCTgTATTAA ACCCCAAATC AgCTCgTAgT
5601  CTgATCCTCA TCAACTT9Ag gggCACTATC TTgTTTTAgA gAAATTTgCg
5651  gAgATgCgAT ATCgAgAAAA AggTACgCTg ATTTTAAACg TgAAATTTAT
5701  CTCAAgATCg CggCCgCgAT CTCgAATAAT AACTgTTATT TTTCAgTgTT
5751  CCCgATCTgC gTCTATTTCA CAATACCAAC ATgAgTCAgC TTATCgATgA
5801  TAAgCTgTCA AACATgAgAA TTAATTC9AT gATAAgCTgT CAAACATgAg
5851  AAATCTTgAA gACgAAAggg CCTCgTgATA CgCCTATTTT TATAggTTAA
```

TABLE 24-continued

| | | | | | |
|---|---|---|---|---|---|
| 5901 | TgTCATgATA | ATAATggTTT | CTTA<u>gACgTC</u> | AggTggCACT | TTTCggggAA |
| | | | AatII | | |
| 5951 | ATgTgCgCgg | AACCCCTATT | TgTTTATTTT | TCTAAATACA | TTCAAATATg |
| 6001 | TATCCgCTCA | TgAgACAATA | ACCCTgATAA | ATgCTTCAAT | AATATTgAAA |
| 6051 | AAggAAgAgT | ATgAgTATTC | AACATTTCCg | TgTCgCCCTT | ATTCCCTTTT |
| 6101 | TTgCggCATT | TTgCCTTCCT | gTTTTTgCTC | ACCCAgAAAC | gCTggTgAAA |
| 6151 | gTAAAAgATg | CTgAAgATCA | gTTgggTgCA | CgAgTgggTT | ACATCgAACT |
| 6201 | ggATCTCAAC | AgCggTAAgA | TCCTTgAgAg | TTTTCgCCCC | gAAgAACgTT |
| 6251 | TTCCAATgAT | gAgCACTTTT | AAAgTTCTgC | TATgTggCgC | ggTATTATCC |
| 6301 | CgTgTTgACg | CCgggCAAgA | gCAACTCggT | CgCCgCATAC | ACTATTCTCA |
| 6351 | gAATgACTTg | gTTgAgTACT | CACCAgTCAC | AgAAAAgCAT | CTTACggATg |
| 6401 | gCATgACAgT | AAgAgAATTA | TgCAgTgCTg | CCATAACCAT | gAgTgATAAC |
| 6451 | ACTgCggCCA | ACTTACTTCT | gACAACgATC | ggAggACCgA | AggAgCTAAC |
| 6501 | CgCTTTTTTg | CACAACATgg | gggATCATgT | AACTCgCCTT | gATCgTTggg |
| 6551 | AACCggAgCT | gAATgAAgCC | ATACCAAACg | ACgAgCgTgA | CACCACgATg |
| 6601 | CCTgCAgCAA | TggCAACAAC | gTTgCgCAAA | CTATTAACTg | gCgAACTACT |
| 6651 | TACTCTA9CT | TCCCggCAAC | AATTAATAgA | CTggATggAg | gCggATAAAg |
| 6701 | TTgCAggACC | ACTTCTgCgC | TCggCCCTTC | CggCTggCTg | gTTTATTgCT |
| 6751 | gATAAATCTg | gAgCCggTgA | gCgTgggTCT | CgCggTATCA | TTgCAgCACT |
| 6801 | ggggCCAgAT | ggTAAgCCCT | CCCgTATCgT | AgTTATCTAC | ACgACggggA |
| 6851 | gTCAggCAAC | TATggATgAA | CgAAATAgAC | AgATCgCTgA | gATAggTgCC |
| 6901 | TCACTgATTA | AgCATTggTA | ACTgTCAgAC | CAAgTTTACT | CATATATACT |
| 6951 | TTAgATTgAT | TTAAATTgTA | AACgTTAATA | TTTTgTTAAA | ATTCgCgTTA |
| 7001 | AATTTTTgTT | AAATCAgCTC | ATTTTTTAAC | CAATAggCCg | AAATCggCAA |
| 7051 | AATCCCTTAT | AAATCAAAAg | AATAgACCgA | gATAgggTTg | AgTgTTgTTC |
| 7101 | CAgTTTggAA | CAAgAgTCCA | CTATTAAAgA | ACgTggACTC | CAACgTCAAA |
| 7151 | gggCgAAAAA | CCgTCTATCA | gggCgATggC | CCACTACgTg | AACCATCACC |
| 7201 | CTAATCAAgT | TTTTTggggT | CgAggTgCCg | TAAAgCACTA | AATCggAACC |
| 7251 | CTAAAgggAg | CCCCCgATTT | AgAgCTTgAC | ggggAAAgCC | ggCgAACgTg |
| 7301 | gCgAgAAAgg | AAgggAAgAA | AgCgAAAggA | gCgggCgCTA | gggCgCTggC |
| 7351 | AAgTgTAgCg | gTCACgCTgC | gCgTAACCAC | CACACCCgCC | gCgCTTAATg |
| 7401 | CgCCgCTACA | gggCgCgTAA | AAggATCTAg | gTgAAgATCC | TTTTTgATAA |
| 7451 | TCTCATgACC | AAAATCCCTT | AACgTgAgTT | TTCgTTCCAC | TgAgCgTCAg |
| 7501 | ACCCCgTAgA | AAAgATCAAA | ggATCTTCTT | gAgATCCTTT | TTTTCTgCgC |
| 7551 | gTAATCTgCT | gCTTgCAAAC | AAAAAAACCA | CCgCTACCAg | CggTggTTTg |
| 7601 | TTTgCCggAT | CAAgAgCTAC | CAACTCTTTT | TCCgAAggTA | ACTggCTTCA |
| 7651 | gCAgAgCgCA | gATACCAAAT | ACTgTCCTTC | TAgTgTAgCC | gTAgTTAggC |
| 7701 | CACCACTTCA | AgAACTCTgT | AgCACCgCCT | ACATACCTCg | CTCTgCTAAT |
| 7751 | CCTgTTACCA | gTggCTgCTg | CCAgTggCgA | TAAgTCgTgT | CTTACCgggT |
| 7801 | TggACTCAAg | ACgATAgTTA | CCggATAAgg | CgCAgCggTC | gggCTgAACg |

TABLE 24-continued

```
7851  ggggTTCgT gCACACAgCC CAgCTTggAg CgAACgACCT ACACCgAACT
7901  gAgATACCTA CAgCgTgAgC ATTgAgAAAg CgCCACgCTT CCCgAAgggA
7951  gAAAggCggA CAggTATCCg gTAAgCggCA gggTCggAAC AggAgAgCgC
8001  ACgAgggAgC TTCCAggggg AAACgCCTgg TATCTTTATA gTCCTgTCgg
8051  gTTTCgCCAC CTCTgACTTg AgCgTCgATT TTTgTgATgC TCgTCAgggg
8101  ggCggAgCCT ATggAAAAAC gCCAgCAACg CggCCTTTTT ACggTTCCTg
8151  gCCTTTTgCT ggCCTTTTgC TCACATgTTC TTTCCTgCgT TATCCCCTgA
8201  TTCTgTggAT AACCgTATTA CCgCCTTTgA gTgAgCTgAT ACCgCTCgCC
8251  gCAgCCgAAC gACCgAgCgC AgCgAgTCAg TgAgCgAggA AgCggAAgAg
8301  CgCCTgATgC ggTATTTTCT CCTTACgCAT CTgTgCggTA TTTCACACCg
8351  CATATggTgC ACTCTCAgTA CAATCTgCTC TgATgCCgCA TAgTTAAgCC
8401  AgTATACACT CCgCTATCgC TACgTgACTg ggTCATggCT gCgCCCCgAC
8451  ACCCgCCAAC ACCCgCTgAC gCgCCCTgAC gggCTTgTCT gCTCCCggCA
8501  TCCgCTTACA gACAAgCTgT gACCgTCTCC gggAgCTgCA TgTgTCAgAg
8551  gTTTTCACCg TCATCACCgA AACgCgCgAg gCAg
```

Restriction map of pHIL-D2 (MFαPrePro::EPI-HNE-3)

Non-cutters

| | | | | |
|---|---|---|---|---|
| AflII | ApaI | AscI | AvaI | AvrII |
| BamBI | BglII | BssHII | BstEII | MluI |
| NruI | PacI | PmlI | RsrII | SacII |
| SfiI | SnaBI | SpeI | XhoI | XmaI |

Cutters, 3 or fewer sites

| | | | | | | |
|---|---|---|---|---|---|---|
| AatII | 2 | 1098 5925 | | ApaLI | 3 | 6176 7859 8357 |
| AflIII | 1 | 8173 | | AseI | 3 | 591 5820 6672 |
| AgeI | 1 | 1436 | | BglI | 3 | 284 2717 6724 |
| AlwNI | 3 | 2828 2852 7759 | | BsaAI | 2 | 7185 8421 |
| BsgI | 2 | 2545 4494 | | PvuI | 1 | 6476 |
| BsiWI | 2 | 1568 2301 | | PvuII | 2 | 1600 4497 |
| BspDI | 2 | 1723 5793 | | SacI | 1 | 216 |
| BspEI | 1 | 3978 | | SalI | 1 | 3312 |
| BspMI | 1 | 4576 | | ScaI | 2 | 1360 6365 |
| Bst1107I | 1 | 8402 | | SphI | 1 | 4863 |
| BstBI (AsuII) | 2 | 945 5207 | | SspI | 3 | 2806 6041 6977 |
| BstXI | 3 | 711 2765 2896 | | StuI | 1 | 3395 |
| Bsu36I | 1 | 2223 | | Tth111I | 1 | 8426 |
| DraIII | 2 | 3754 7182 | | XbaI | 1 | 2168 |
| EagI | 3 | 7 5711 8591 | | XcmI | 1 | 711 |
| Eam1105I | 2 | 5077 6843 | | | | |
| Ecl136I | 1 | 216 | | | | |
| Eco47III | 2 | 1932 4795 | | | | |
| EcoNI | 3 | 3433 4923 5293 | | | | |
| EcoRI | 1 | 1383 | | | | |
| EcoRV | 2 | 1885 5658 | | | | |
| EspI (BsaI) | 2 | 3120 8524 | | | | |
| EspI (Bpu1102I) | 1 | 597 | | | | |
| FspI | 2 | 1960 6623 | | | | |
| HindIII | 3 | 885 1717 1729 | | | | |
| HpaI | 2 | 1017 2272 | | | | |
| KpnI | 2 | 2323 2934 | | | | |
| MscI | 2 | 2204 3789 | | | | |
| NcoI | 1 | 3766 | | | | |
| NdeI | 1 | 8351 | | | | |
| NgoMI | 2 | 4702 7288 | | | | |
| NheI | 2 | 1929 2875 | | | | |
| NotI | 3 | 6 5710 8590 | | | | |
| NsiI | 2 | 684 1241 | | | | |
| PflMI | 2 | 196 1302 | | | | |
| PmeI | 1 | 420 | | | | |
| PpuMI | 2 | 142 4339 | | | | |
| PstI | 1 | 6602 | | | | |

TABLE 24-continued

Table 25: BstBI-AatII-EcoRI cassette for expression of EPI-HNE-4
DNA has SEQ ID NO. 073; amino-acid sequence has SEQ ID NO. 074

```
               M   R   P   P   S   T   F   T
    5'TTCgAA ACg ATg AgA TTC CCA TCT ATC TTC ACT
      BstBI        |  BsaBI  |

A   V   L   F   A   13
             gCT gTT TTg TTC gCT

A   S   S   A   L   A   A   P   V   N   T   T   T   E
27
     gCT TCC TCT gCT TTg gCT gCT CCA gTT AAC ACC ACT ACT gAA
                             BpmI    HpaI                Bbsi D   E   T   A   Q   I   P   A   E   A   V   I   G   Y
41
     gAC gAg ACT gCT OAA ATT CCT gCT gAg gCT gTC ATC ggT TAC
     BbsI S   D   L   E   G   D   F   D   V   A   V   L   P   F
55
     TCT gAC TTg gAA ggT gAC TTC gAC gTC gCT gTT TTg CCA TTC
                                 AatII S   N   S   T   N   N   G   L   L   F   I   N   T   T
69
     TCT AAC TCT ACT AAC AAC ggT TTg TTg TTC ATC AAC ACT ACC I   A   S   I   A   A   K   E   E   G   V   S   L   D
83
     ATC gCT TCT ATC gCT gCT AAg gAg gAA ggT gTT TCC TTg gAC K   R   E   A   C   N   L   P
91
     AAg AgA gAg gOT TgT AAC TTg CCA I   V   R   G   P   C   I   A   F   F   P   R   W   A
105
     ATC gTC AgA ggT CCA TgC ATT gCT TTC TTC CCA AgA Tgg gCT
                          NsiI F   D   A   V   K   C   K   C   V   L   F   P   Y   G
119
     TTC gAC gCT gTT AAg ggT AAg TgC gTC TTg TTC CCA TAC ggT
                                                 |  PflMI G   C   Q   C   N   G   N   K   F   Y   S   E   K   E
133
     ggT TgT CAA ggT AAC ggT AAC AAg TTC TAC TCT gAg AAg gAg
     PflMI C   R   E   Y   C   G   V   P   .   .
141
     TgT AgA gAg TAC TgT ggT gTT CCA TAg TAA gAATTC
                                              EcoRI
```

The DNA is a linear fragment that is double stranded *in vivo*, only one strand is shown.
The amino acid sequence is that of a disulfide-containing protein that is processed *in vivo*.

TABLE 26 pD2pick(MFαPrePro::EPI-HNE-3), 8590 bp, CIRCULAR dsDNA, one strand shown. pD2pick(MFαPrePro::EPI-HNE-3) DNA has SEQ ID NO. 075 Encoded protein has SEQ ID NO. 076

```
              1          2          3          4          5
     1234567890 1234567890 1234567890 1234567890 1234567890
   1 AgATCgCggC CgCgATCTAA CATCCAAAgA CgAAAggTTg AATgAAACCT

51 TTTTgCCATC CgACATCCAC AggTCCATTC TCACACATAA gTgCCAAACg

101 CAACAggAgg ggATACACTA gCAgCAgACC gTTgCAAACg CAggACCTCC

151 ACTCCTCTTC TCCTCAACAC CCACTTTTgC ATCgAAAAA  CCAgCCCAgT

201 TATTgggCTT gATTggAgCT CgCTCATTCC AATTCCTTCT ATTAggCTAC
                     SacI 251 TAACACCATg ACTTTATTAg CCTgTCTATC CTggCCCCCC TggCgAggTC 301 ATgTTTgTTT ATTTCCgAAT gCAACAAgCT CCgCATTACA CCCgAACATC 351 ACTCCAgATg AgggCTTTCT gAgTgTgggg TCAAATAgTT TCATgTTCCC 401 AAATggCCCA AAACTgACAg TTTAAACgCT gTCTTggAAC CTAATATgAC
                          PmeI 451 AAAAgCgTgA TCTCATCCAA gATgAACTAA gTTTggTTCg TTgAAATgCT 501 AACggCCAgT TggTCAAAAA gAAACTTCCA AAAgTCgCCA TACCgTTTgT 551 CTTgTTTggT ATTgATTgAC gAATgCTCAA AAATAATCTC ATTAATgCTTAgC
EspI 604 gCAgTCT CTCTATCgCT TCTgAACCCg gTggCACCTg TgCCgAAACg 651 CAAATggggA AACAACCCgC TTTTTggATg ATTATgCATT gTCCTCCACA 701 TTgTATgCTT CCAAgATTCT ggTgggAATA CTgCTgATAg CCTAACgTTC
                     XcmI 751 ATgATCAAAA TTTAACTgTT CTAACCCCTA CTTgACAggC AATATATAAA 801 CAgAAggAAg CTgCCCTgTC TTAAACCTTT TTTTTTATCA TCATTATTAg 851 CTTACTTTCA TAATTgCgAC TggTTCCAAT TgACAAgCTT TTgATTTTAA 901 CgACTTTTAA CgACAACTTg AgAAgATCAA AAAACAACTA ATTATTCgAA
                                                    BstBI 951 ACg M   R   F   P   S   I   F   T   A   V   L   F   A
 954    ATg AgA TTC CCA TCT ATC TTC ACT gCT gTT TTg TTC gCT A   S   S   A   L   A   A   P   V   N   T   T   T
 993    gCT TCC TCT gCT TTg gCT gCT CCA gTT AAC ACC ACT ACT E   D   E   T   A   Q   I   P   A   E   A   V   I
1032    gAA gAC gAg ACT gCT CAA ATT CCT gCT gAg gCT gTC ATC G   Y   S   D   L   E   G   D   F   D   V   A   V
1071    ggT TAC TCT gAC TTg gAA ggT gAC TTC gAC gTC gCT gTT
                                            AatII L   P   F   S   N   S   T   N   N   G   L   L   F
1110    TTg CCA TTC TCT AAC TCT ACT AAC AAC ggT TTg TTg TTC N   T   T   I   A   S   I   A   A   K   E   E
1149    ATC AAC ACT ACC ATC gCT TCT ATC gCT gCT Aag gAg gAA
```

TABLE 26-continued pD2pick(MFαPrePro::EPI-HNE-3), 8590 bp, CIRCULAR dsDNA, one strand shown. pD2pick(MFαPrePro::EPI-HNE-3) DNA has SEQ ID NO. 075 Encoded protein has SEQ ID NO. 076

```
           G   V   S   L   D   K   R   A   A   C   N   L   P
      1188 ggT gTT TCC TTg gAC AAg AgA gCT gCT TgT AAC TTg CCA

I   V   R   G   P   C   I   A   F   F   P   R   W
      1227 ATC gTC AgA ggT CCA TgC ATT gCT TTC TTC CCA AgA Tgg

A   F   D   A   V   K   G   K   C   V   L   F   P
      1266 gCT TTC gAC gCT gTT AAg ggT AAg TgC gTC TTg TTC CCA

Y   G   G   C   Q   G   N   G   N   K   F   Y   S
      1305 TAC ggT ggT TgT CAA ggT AAC ggT AAC AAg TTC TAC TCT

E   K   E   C   R   E   Y   C   G   V   P   .   .
      1344 gAg AAg gAg TgT AgA gAg TAC TgT ggT gTT CCA TAg TAA 1383 gAATTC                                         gC CTTAgACATg
           ECoRI

1401 ACTgTTCCTC AgTTCAAgTT gggCATTACg AgAAgACCgg TCTTgCTAgA
                                                       AegI 1451 TTCTAATCAA gAggATgTCA gAATgCCATT TgCCTgAgAg ATgCAggCTT 1501 CATTTTTgAT ACTTTTTTAT TTgTAACCTA TATAgTATAg gATTTTTTTT 1551 gTCATTTTgT TTCTTCTCgT ACgAgCTTgC TCCTgATCAg CCTATCTCgC 1601 AgCTgATgAA TATCTTgTgg TAggggTTTg ggAAAATCAT TCgAgTTTgA 1651 TgTTTTTCTT ggTATTTCCC ACTCCTCTTC AgAgTACAgA AgATTAAgTg 1701 AgAAgTTCgT TTgTgCAAgC TTATCgATAA gCTTAATgC ggTAgTTTAT 1751 CACAgTTAAA TTgCTAACgC AgTCAggCAC CgTgTATgAA ATCTAACAAT 1801 gCgCTCATCg TCATCCTCgg CACCgTCACC CTggATgCTg TAggCATAgg 1851 CTTggTTATg CCggTACTgC CgggCCTCTT CgggATATC gTCCATTCCg 1901 ACAgCATCgC CAgTCACTAT ggCgTgCTgC TAgCgCTATA TgCgTTgATg 1951 CAATTTCTAT gCgCACCCgT TCTCggAgCA CTgTCCgACC gCTTTggCCg 2001 CCgCCCAgTC CTgCTCgCTT CgCTACTTgg AgCCACTATC gACTACgCgA 2051 TCATggCgAC CACACCCgTC CTgTggATCT ATCgAATCTA AATgTAAgTT 2101 AAAATCTCTA AATAATTAAA TAAgTCCCAg TTTCTCCATA CgAACCTTAA 2151 CAgCATTgCg gTgAgCATCT AgACCTTCAA CAgCAgCCAg ATCCATCACT
                                  XbaI 2201 gCTTggCCAA TATgTTTCAg TCCCTCAggA gTTACgTCTT gTgAAgTgAT
                                   Bsu36I 2251 gAACTTCTgg AAggTTgCAg TgTTAACTCC gCTgTATTgA CgggCATATC 2301 CgTACgTTgg CAAAgTgTgg TTggTACCgg AggAgTAATC TCCACAACTC 2351 TCTggAgAgT AggCACCAAC AAACACAgAT CCAgCgTgTT gTACTTgATC 2401 AACATAAgAA gAAgCATTCT CgATTTgCAg gATCAAgTgT TCAggAgCgT 2451 ACTgATTggA CATTTCCAAA gCCTgCTCgT AggTTgCAAC CgATAgggTT 2501 gTAgAgTgTg CAATACACTT gCgTACAATT TCAACCCTTg CAACTgCAC 2551 AgCTTggTTg TgAACAgCAT CTTCAATTCT ggCAAgCTCC TTgTCTgTCA 2601 TATCgACAgC CAACAgAATC ACCTgggAAT CAATACCATg TTCAgCTTgA 2651 gCAgAAggTC TgAggCAACg AAATCTggAT CAgCgTATTT ATCAgCAATA
```

TABLE 26-continued pD2pick(MFαPrePro::EPI-HNE-3), 8590 bp, CIRCULAR
dsDNA, one strand shown. pD2pick(MFαPrePro::EPI-HNE-3) DNA
has SEQ ID NO. 075 Encoded protein has SEQ ID NO. 076

```
2701 ACTAgAACTT CAgAAggCCC AgCAggCATg TCAATACTAC ACAgggCTgA

2751 TgTgTCATTT TgAACCATCA TCTTggCAgC AgTAACgAAC TggTTTCCTg 2801 gACCAAATAT TTTgTCACAC TTAggAACAg TTTCTgTTCC gTAAgCCATA 2851 gCAgCTACTg CCTgggCgCC TCCTgCTAgC ACgATACACT TAgCACCAAC 2901 CTTgTgggCA ACgTAgATgA CTTCTggggT AAgggTACCA TCCTTCTTAg 2951 gTggAgATgC AAAAACAATT TCTTTgCAAC CAgCAACTTT ggCAggAACA 3001 CCCAgCATCA gggAAgTggA AggCAgAATT gCggTTCCAC CAggAATATA 3051 gAggCCAACT TTCTCAATAg gTCTTgCAAA ACgAgAgCAg ACTACACCAg 3101 ggCAAgTCTC AACTTgCAAC gTCTCCgTTA gTTgAgCTTC ATggAATTTC 3151 CTgACgTTAT CTATAgAgAg ATCAATggCT CTCTTAACgT TATCTggCAA 3201 TTgCATAAgT TCCTCTgggA AAggAgCTTC TAACACAggT gTCTTCAAAg 3251 CgACTCCATC AAACTTggCA gTTAgTTCTA AAAgggCTTT gTCACCATTT 3301 TgACgAACAT TgTCgACAAT TggTTTgACT AATTCCATAA TCTgTTCCgT 3351 TTTCTggATA ggACgACgAA gggCATCTTC AATTTCTTgT gAggAggCCT
                                                     StuI 3401 TAgAAACgTC AATTTTgCAC AATTCAATAC gACCTTCAgA AgggACTTCT 3451 TTAggTTTgg ATTCTTCTTT AggTTgTTCC TTggTgTATC CTggCTTggC 3501 ATCTCCTTTC CTTCTAgTgA CCTTTAgggA CTTCATATCC AggTTTCTCT 3551 CCACCTCgTC AACgTCACA CCgTACTTgg CACATCTAAC TAATgCAAAA 3601 TAAAATAAgT CAgCACATTC CCAggCTATA TCTTCCTTgg ATTTAgCTTC 3651 TgCAAgTTCA TCAgCTTCCT CCCTAATTTT AgCgTTCAAC AAAACTTCgT 3701 CgTCAAATAA CCgTTTggTA TAAgAACCTT CTggAgCATT gCTCTTACgA 3751 TCCCACAAgg TgCTTCCATg gCTCTAAgAC CCTTTgATTg gCCAAAACAg
                       NcoI 3801 gAAgTgCgTT CCAAgTgACA gAAACCAACA CCTgTTTgTT CAACCACAAA 3851 TTTCAAgCAg TCTCCATCAC AATCCAATTC gATACCCAgC AACTTTTgAg 3901 TTCgTCCAgA TgTAgCACCT TTATACCACA AACCgTgACg ACgAgATTgg 3951 TAgACTCCAg TTTgTgTCCT TATAgCCTCC ggAATAgACT TTTTggACgA
                                     BspEI 4001 gTACACCAgg CCCAACgAgT AATTAgAAgA gTCAgCCACC AAAgTAgTgA 4051 ATAgACCATC ggggCggTCA gTAgTCAAAg ACgCCAACAA AATTTCACTg 4101 ACAgggAACT TTTTgACATC TTCAgAAAgT TCgTATTCAg TAgTCAATTg 4151 CCgAgCATCA ATAATggggA TTATACCAgA AgCAACAgTg gAAgTCACAT 4201 CTACCAACTT TgCggTCTCA gAAAAAgCAT AAACAgTTCT ACTACCgCCA 4251 TTAgTgAAAC TTTTCAAATC gCCCAgTggA gAAgAAAAAg gCACAgCgAT 4301 ACTAgCATTA gCgggCAAgg ATgCAACTTT ATCAACCAgg gTCCTATAgA 4351 TAACCCTAgC gCCTgggATC ATCCTTTgA CAACTCTTTC TgCCAAATCT
```

TABLE 26-continued pD2pick(MFαPrePro::EPI-HNE-3), 8590 bp, CIRCULAR dsDNA, one strand shown. pD2pick(MFαPrePro::EPI-HNE-3) DNA has SEQ ID NO. 075 Encoded protein has SEQ ID NO. 076

```
4401 AggTCCAAAA TCACTTCATT gATACCATTA TACggATgAC TCAACTTgCA
4451 CATTAACTTg AAgCTCAgTC gATTgAgTgA ACTTgATCAg gTTgTgCAgC
4501 TggTCAgCAg CATAgggAAA CACggCTTTT CCTACCAAAC TCAAggAATT
4551 ATCAAACTCT gCAACACTTg CgTATgCAgg TAgCAAgggA AATgTCATAC
4601 TTgAAgTCgg ACAgTgAgTg TAgTCTTgAg AAATTCTgAA gCCgTATTTT
4651 TATTATCAgT gAgTCAgTCA TCAggAgATC CTCTACgCCg gACgCATCgT
4701 ggCCggCATC ACCggCgCCA CAggTgCggT TgCTggCgCC TATATCgCCg
4751 ACATCACCgA TggggAAgAT CgggCTCgCC ACTTCgggCT CATgAgCgCT
4801 TgTTTCggCg TgggTATggT ggCAggCCCC gTggCCgggg gACTgTTggg
4851 CgCCATCTCC TTgCATgCAC CATTCCTTgC ggCggCggTg CTCAACggCC
4901 TCAACCTACT ACTgggCTgC TTCCTAATgC AggAgTCgCA TAAgggAgAg
4951 CgTCgAgTAT CTATgATTgg AAgTATgggA ATggTgATAC CCgCATTCTT
5001 CAgTgTCTTg AggTCTCCTA TCAgATTATg CCCAACTAAA gCAACCggAg
5051 gAggAgATTT CATggTAAAT TTCTCTgACT TTTggTCATC AgTAgACTCg
5101 AACTgTgAgA CTATCTCggT TATgACAgCA gAAATgTCCT TCTTggAgAC
5151 AgTAAATgAA gTCCCACCAA TAAAgAAATC CTTgTTATCA ggAACAAACT
5201 TCTTgTTTCg CgAACTTTTT CggTgCCTTg AACTATAAAA TgTAgAgTgg
5251 ATATgTCggg TAggAATggA gCgggCAAAT gCTTACCTTC TggACCTTCA
5301 AgAggTATgT AgggTTTgTA gATACTgATg CCAACTTCAg TgACAACgTT
5351 gCTATTTCgT TCAAACCATT CCgAATCCAg AgAAATCAAA gTTgTTTgTC
5401 TACTATTgAT CCAAgCCAgT gCggTCTTgA AACTgACAAT AgTgTgCTCg
5451 TgTTTTgAgg TCATCTTTgT ATgAATAAAT CTAgTCTTTg ATCTAAATAA
5501 TCTTgACgAg CCAAggCgAT AAATACCCAA ATCTAAAACT CTTTTAAAAC
5551 gTTAAAAggA CAAgTATgTC TgCCTgTATT AAACCCCAAA TCAgCTCgTA
5601 gTCTgATCCT CATCAACTTg AggggCACTA TCTTgTTTTA gAgAAATTTg
5651 CggAgATgCg ATATCgAgAA AAAggTACgC TgATTTTAAA CgTgAAATTT
5701 ATCTCAAgAT CgCggCCgCg ATCTCgAATA ATAACTgTTA TTTTTCAgTg
5751 TTCCCgATCT gCgTCTATTT CACAATACCA ACATgAgTCA gCTTATCgAT
5801 gATAAgCTgT CAAACATgAg AATTAATTCg ATgATAAgCT gTCAAACATg
5851 AgAAATCTTg AAgACgAAAg ggCCTCgTgA TACgCCTATT TTTATAggTT
5901 AATgTCATgA TAATAATggT TTCTTAgACg TACgTCAggT ggCACTTTTC
5951 ggggAAATgT gCgCggAAcc CCTATTTgTT TATTTTTCTA AATACATTCA
6001 AATATgTATC CgCTCATgAg ACAATAACCC TgATAAATgC TTCAATAATA
6051 TTgAAAAAgg AAgAgTATgA gTATTCAACA TTTCCgTgTC gCCCTTATTC
6101 CCTTTTTTgC ggCATTTTgC CTTCCTgTTT TTgCTCACCC AgAAACgCTg
6151 gTgAAAgTAA AAgATgCTgA AgATCAgTTg ggTgCACgAg TgggTTACAT
6201 CgAACTggAT CTCAACAgCg gTAAgATCCT TgAgAgTTTT CgCCCCgAAg
6251 AACgTTTTCC AATgATgAgC ACTTTTAAAg TTCTgCTATg TggCgCggTA
```

TABLE 26-continued pD2pick(MFαPrePro::EPI-HNE-3), 8590 bp, CIRCULAR
dsDNA, one strand shown. pD2pick(MFαPrePro::EPI-HNE-3) DNA
has SEQ ID NO. 075 Encoded protein has SEQ ID NO. 076

```
6301 TTATCCCgTg TTgACgCCgg gCAAgAgCAA CTCggTCgCC gCATACACTA

6351 TTCTCAgAAT gACTTggTTg AgTACTCACC AgTCACAgAA AAgCATCTTA

6401 CggATggCAT gACAgTAAgA gAATTATgCA gTgCTgCCAT AACCATgAgT 6451 gATAACACTg CggCCAACTT ACTTCTgACA ACgATCggAg gACCgAAggA 6501 gCTAACCgCT TTTTTgCACA ACATgggggA TCATgTAACT CgCCTTgATC 6551 gTTgggAAcc ggAgCTgAAT gAAgCCATAC CAAACgACgA gCgTgACACC 6601 ACgATgCCTg CAgCAATggC AACAACgTTg CgCAAACTAT TAACTggCgA 6651 ACTACTTACT CTAgCTTCCC ggCAACAATT AATAgACTgg ATggAggCgg 6701 ATAAAgTTgC AggACCACTT CTgCgCTCgg CCCTTCCggC TggCTggTTT 6751 ATTgCTgATA AATCTggAgC CggTgAgCgT gggTCTCgCg gTATCATTgC 6801 AgCACTgggg CCAgATggTA AgCCCTCCCg TATCgTAgTT ATCTACACgA 6851 CggggAgTCA ggCAACTATg gATgAACgAA ATAgACAgAT CgCTgAgATA 6901 ggTgCCTCAC TgATTAAgCA TTggTAACTg TCAgACCAAg TTTACTCATA 6951 TATACTTTAg ATTgATTTAA ATTgTAAACg TTAATATTTT gTTAAAATTC 7001 gCgTTAAATT TTTgTTAAAT CAgCTCATTT TTTAACCAAT AggCCgAAAT 7051 CggCAAAATC CCTTATAAAT CAAAAgAATA gACCgAgATA gggTTgAgTg 7101 TTgTTCCAgT TTggAACAAg AgTCCACTAT TAAAAACgT ggACTCCAAC 7151 gTCAAAgggC gAAAAACCgT CTATCAgggC gATggCCCAC TACgTgAACC 7201 ATCACCCTAA TCAAgTTTTT TggggTCgAg gTgCCgTAAA gCACTAAATC 7251 ggAACCCTAA AgggAgCCCC CgATTTAgAg CTTgACgggg AAAgCCggCg 7301 AACgTggCgA gAAAggAAgg gAAgAAAgCg AAAggAgCgg gCgCTAgggC 7351 gCTggCAAgT gTAgCggTCA CgCTgCgCgT AACCACCACA CCCgCCgCgC 7401 TTAATgCgCC gCTACAgggC gCgTAAAAgg ATCTAggTgA AgATCCTTTT 7451 TgATAATCTC ATgACCAAAA TCCCTTAACg TgAgTTTTCg TTCCACTgAg 7501 CgTCAgACCC CgTAgAAAAg ATCAAAggAT CTTCTTgAgA TCCTTTTTTT 7551 CTgCgCgTAA TCTgCTgCTT gCAAACAAAA AAACCACCgC TACCAgCggT 7601 ggTTTgTTTg CCggATCAAg AgCTACCAAC TCTTTTTCCg AAggTAACTg 7651 gCTTCAgCAg AgCgCAgATA CCAAATACTg TCCTTCTAgT gTAgCCgTAg 7701 TTAggCCACC ACTTCAAgAA CTCTgTAgCA CCgCCTACAT ACCTCgCTCT 7751 gCTAATCCTg TTACCAgTgg CTgCTgCCAg TggCgATAAg TCgTgTCTTA 7801 CCgggTTggA CTCAAgACgA TAgTTACCgg ATAAggCgCA gCggTCgggC 7851 TgAACggggg gTTCgTgCAC ACAgCCCAgC TTggAgCgAA CgACCTACAC 7901 CgAACTgAgA TACCTACAgC gTgAgCATTg AgAAAgCgCC ACgCTTCCCg 7951 AAgggAgAAA ggCggACAgg TATCCggTAA gCggCAgggT CggAACAggA 8001 gAgCgCACgA gggAgCTTCC AgggggAAAC gCCTggTATC TTTATAgTCC 8051 TgTCgggTTT CgCCACCTCT gACTTgAgCg TCgATTTTTg TgATgCTCgT 8101 CAggggggCg gAgCCTATgg AAAAACgCCA gCAACgCggC CTTTTTACgg
```

TABLE 26-continued pD2pick(MFαPrePro::EPI-HNE-3), 8590 bp, CIRCULAR dsDNA, one strand shown. pD2pick(MFαPrePro::EPI-HNE-3) DNA has SEQ ID NO. 075 Encoded protein has SEQ ID NO. 076

```
8151 TTCCTggCCT TTTgCTggCC TTTTgCTCAC ATgTTCTTTC CTgCgTTATC

8201 CCCTgATTCT gTggATAACC gTATTACCgC CTTTgAgTgA gCTgATACCg

8251 CTCgCCgCAg CCgAACgACC gAgCgCAgCg AgTCAgTgAg CgAggAAgCg 8301 gAAgAgCgCC TgATgCggTA TTTTCTCCTT ACgCATCTgT gCggTATTTC

8351 ACACCgCATA TggTgCACTC TCAgTACAAT CTgCTCTgAT gCCgCATAgT

8401 TAAgCCAgTA TACACTCCgC TATCgCTACg TgACTgggTC ATggCTgCgC

8451 CCCgACACCC gCCAACACCC gCTgACgCgC CCTgACgggC TTgTCTgCTC

8501 CCggCATCCg CTTACAgACA AgCTgTgACC gTCTCCgggA gCTgCATgTg

8551 TCAgAggTTT TCACCgTCAT CACCgAAACg CgCgAggCAg
```

TABLE 27 restriction map of pD2pick(MFαPrePro::EPI-HNE-3)

Non-cutters

| AflII | ApaI | AscI | AvaI | AvrII |
| BamHI | BglII | BssHII | BstEII | MluI |
| PacI | PmlI | RsrII | SacII | SfiI |
| SnaBI | SpeI | XhoI | XmaI | |

Cutters, 3 or fewer sites

| AatII | 1 | 1098 | | | EcoRV | 2 | 1885 | 5660 | |
|---|---|---|---|---|---|---|---|---|---|
| AflIII | 1 | 8179 | | | Esp3I(BsaI) | 2 | 3120 | 8530 | |
| AgeI | 1 | 1436 | | | EspI(Bpu1102I) | 1 | 597 | | |
| AlwNI | 3 | 2828 | 2852 | 7765 | FspI | 2 | 1960 | 6629 | |
| ApaLI | 3 | 6182 | 7865 | 8363 | HindIII | 3 | 885 | 1717 | 1729 |
| AseI | 3 | 591 | 5822 | 6678 | HpaI | 2 | 1017 | 2272 | |
| BglI | 3 | 284 | 2717 | 6730 | KpnI | 2 | 2323 | 2934 | |
| BsaAI | 2 | 7191 | 8427 | | MacI | 2 | 2204 | 3789 | |
| BsgI | 2 | 2545 | 4494 | | NcoI | 1 | 3766 | | |
| BsiWI | 3 | 1568 | 2301 | 5929 | NdeI | 1 | 8357 | | |
| BspDI | 2 | 1723 | 5795 | | NgoMI | 2 | 4702 | 7294 | |
| BspEI | 1 | 3978 | | | NheI | 2 | 1929 | 2875 | |
| BspMI | 1 | 4576 | | | NotI | 3 | 6 | 5712 | 8596 |
| Bst1107I | 1 | 8408 | | | NruI | 1 | 5208 | | |
| BstBI(AsuII) | 1 | 945 | | | NsiI | 2 | 684 | 1241 | |
| BstXI | 3 | 711 | 2765 | 2896 | PflMI | 2 | 196 | 1302 | |
| Bsu36I | 1 | 2223 | | | PmeI | 1 | 420 | | |
| DraIII | 2 | 3754 | 7188 | | PpuMI | 2 | 142 | 4339 | |
| EagI | 3 | 7 | 5713 | 8597 | PstI | 1 | 6608 | | |
| Eam1105I | 2 | 5077 | 6849 | | PvuI | 1 | 6482 | | |
| Ecl136I | 1 | 216 | | | PvuII | 2 | 1600 | 4497 | |
| Eco47III | 2 | 1932 | 4795 | | SacI | 1 | 216 | | |
| EcoNI | 3 | 3433 | 4923 | 5295 | SalI | 1 | 3312 | | |
| EcoRI | 1 | 1383 | | | ScaI | 2 | 1360 | 6371 | |
| SphI | 1 | 4863 | | | | | | | |
| SspI | 3 | 2806 | 6047 | 6983 | | | | | |
| StuI | 1 | 3395 | | | | | | | |
| Tth111I | 1 | 8432 | | | | | | | |
| XbaI | 1 | 2168 | | | | | | | |
| XcmI | 1 | 711 | | | | | | | |

TABLE 28

Amino-acid Sequence of ITI light chain (SEQ ID NO. 077)
```
           111111 111122
  12345 6789012345 678901
  avlpq eeegsggggl vtevtk
```

TABLE 28-continued

Amino-acid Sequence of ITI light chain

```
2222222223333333333444444444455555555556666666666777777
2345678901234567890123456789012345678901234567890123456
KEDSCQLGYSAGPCMGMTSRYFYNGTSMACETFQYGGCMGNGNNFVTEKECLQTC
    |_____|
        |_____|
                  |_____|
                                        |_____

77788
78901
rtvaa 1111111111111111111111111111111111
888888888999999999900000000001111111111222222222233333
234567890123456789012345678901234567890123456789012345
CNLPIVRGPCRAFIQLWAFDAVKGKCVLFPYGGCQGNGNKFYSEKECREYCGVP
_____|
        |_____|
    |_____|
                |_____|
                        |_____|
                                         |_____|

111111111111
                                     333344444444
                                     678901234567
                                     gdgdeellrfsn
```

ITI-D1 comprises residues 22–76 and optionally one of residue 77, residues 77 and 78, or residues 77–79.
ITI-D2 comprises residues 80–135 and optionally one of residue 79 or residues 78–79.
The lines under the sequences represent disulfides.

TABLE 30

Physical properties of hNE inhibitors derived from Kunitz domains

| Protein | Parent | # Residues | Mol Wt | Predicted pI | $K_D$ (pM) | $k_{on}$ ($10^6$/M/s) | $k_{off}$ ($10^{-6}$/s) |
|---|---|---|---|---|---|---|---|
| EPI-HNE-1 | BPTI | 58 | 6359 | 9.10 | 2.0 | 3.7 | 7.4 |
| EPI-HNE-2 | BPTI | 62 | 6759 | 4.89 | 4.9 | 4.0 | 20. |
| EPI-HNE-3 | ITI-D2 | 56 | 6179 | 10.04 | 6.2 | 8.0 | 50. |
| EPI-HNE-4 | ITI-D2 | 56 | 6237 | 9.73 | 4.6 | 10.6 | 49. |

The constants $K_D$ and $k_{on}$ above were measured with [hNE] = $8.47 \times 10^{-10}$ molar; $k_{off}$ was calculated from $k_{off} = K_D \times k_{on}$.

TABLE 31

SUMMARY OF PURIFICATION OF EPI-HNE-2

| STAGE | Volume (ml) | Concentration (mg/ml) | Total (mg) | Activity (mg/$A_{280}$) |
|---|---|---|---|---|
| HARVEST | 3,300 | 0.70 | 2.31 | <0.01 |
| 30K ULTRA-FILTRATION FILTRATE | 5,000 | 0.27 | 1.40 | <0.01 |
| 5K ULTRA-FILTRATION RETENTATE | 1,000 | 1.20 | 1.20 | 0.63 |
| AMMONIUM SULFATE PRECIPITATE | 300 | 2.42 | 0.73 | 1.05 |
| IEX pH 6.2 ELUATE | 98 | 6.88 | 0.67 | 1.03 |
| EPI-HNE-3, LOT 1 | 50 | 13.5 | 0.68 | 1.04 |

TABLE 32

SUMMARY OF PURIFICATION OF EPI-HNE-3

| STAGE | VOLUME (ml) | CONCENTRATION (mg/ml) | TOTAL (mg) | ACTIVITY (mg/$A_{280}$) |
|---|---|---|---|---|
| HARVEST | 3,100 | 0.085 | 263 | nd |
| 30K ULTRA-FILTRATION FILTRATE | 3,260 | 0.055 | 179 | 0.007 |
| FIRST IEX: pH 6.2 ELUATE | 180 | 0.52 | 94 | 0.59 |
| AMMONIUM SULFATE PRECIPITATE | 100 | 0.75 | 75 | 0.59 |
| IEX pH 9 ELUATE | 60 | 1.01 | 60 | 0.59 |
| EPI-HNE-3, LOT 1 | 26 | 1.54 | 40 | 0.45 |

TABLE 33

$K_I$ VALUES OF EPI-HNE PROTEINS FOR VARIOUS HUMAN SERUM SERINE PROTEASES

| | Inhibitor: | | | |
|---|---|---|---|---|
| Enzyme | EPI-HNE-1 | EPI-HNE-2 | EPI-HNE-3 | EPI-HNE-4 |
| Human Neutrophil Elastase | 2 pM | 5 pM | 6 pM | 5 pM |
| Human Serum Plasmin | >6 µM | >100 µM | >100 µM | >90 µM |
| Human Serum Kallikrein | >10 µM | >100 µM | >100 µM | >90 µM |
| Human Serum Thrombin | >90 µM | >100 µM | >100 µM | >90 µM |
| Human Urine Urokinase | >90 µM | >100 µM | >100 µM | >90 µM |
| Human Plasma Factor $X_a$ | >90 µM | >100 µM | >100 µM | >90 µM |
| Human Pancreatic | ~10 µM | ~10 µM | ~30 µM | ~10 µM |

TABLE 33-continued

K_I VALUES OF EPI-HNE PROTEINS FOR VARIOUS HUMAN SERUM SERINE PROTEASES

| | Inhibitor: | | | |
|---|---|---|---|---|
| Enzyme | EPI-HNE-1 | EPI-HNE-2 | EPI-HNE-3 | EPI-HNE-4 |
| Chymotrypsin | | | | |

TABLE 34

PEY-33 which produces EPI-HNE-2

| Elapse Fermenter Time Hours:minutes | Cell Density ($A_{600}$) | Activity in supernatant (mg/l) |
|---|---|---|
| 41:09 | 89 | 28 |
| 43:08 | 89 | 57 |
| 51:54 | 95 | 92 |
| 57:05 | 120 | 140 |
| 62:43 | 140 | 245 |
| 74:45 | 160 | 360 |
| 87:56 | 170 | 473 |
| 98:13 | 190 | 656 |
| 102:25 | 200 | 678 |
| 109:58 | 230 | 710 |

Fermenter culture growth and EPI-HNE protein secretion by *P. pastoris* strains PEY-33. Time course is shown for fermenter cultures following initiation of methanol-limited feed growth phase. Increase in cell mass is estimated by $A_{600}$. Concentration of inhibitor protein in the fermenter culture medium was determined from measurements of hNE inhibition by diluted aliquots of cell-free CM obtained at the times indicated and stored at −20° C. until assay.

TABLE 35

PEY-43 Which produces EPI-HNE-3

| Elapse Fermenter Time Hours:minutes | Cell Density ($A_{600}$) | Activity in supernatent (mg/l) |
|---|---|---|
| 44:30 | 107 | 0.63 |
| 50:24 | 70 | 9.4 |
| 52:00 | 117 | 14. |
| 62:00 | 131 | 28. |
| 76:00 | 147 | 39. |
| 86:34 | 200 | 56. |
| 100:27 | 185 | 70. |
| 113:06 | 207 | 85. |

Fermenter culture growth and EPI-HNE protein secretion by *P. pastoris* strains PEY-43. Time course is shown for fermenter cultures following initiation of methanol-limited feed growth phase. Increase in cell mass is estimated by $A_{600}$. Concentration of inhibitor protein in the fermenter CM was determined by assays of hNE inhibition by diluted aliquots of cell-free CM obtained at the times indicated and stored at −20° C. until assay.

TABLE 36

Inhibitory properties of EPI-HNE-2

| μl of EPI-HNE-2 solution added | Percent residual hNE activity |
|---|---|
| 0. | 101.1 |
| 0. | 100.0 |
| 0. | 100.0 |
| 0. | 100.0 |
| 0. | 100.0 |
| 0. | 98.9 |
| 10. | 82.9 |
| 20. | 71.8 |

TABLE 36-continued

Inhibitory properties of EPI-HNE-2

| μl of EPI-HNE-2 solution added | Percent residual hNE activity |
|---|---|
| 30. | 59.5 |
| 40. | 46.2 |
| 50. | 39.2 |
| 55. | 32.2 |
| 60. | 22.5 |
| 65. | 23.5 |
| 70. | 15.0 |
| 75. | 10.4 |
| 80. | 8.6 |
| 85. | 4.8 |
| 90. | 1.4 |
| 95. | 2.0 |
| 100. | 2.5 |
| 120. | 0.2 |
| 150. | 0.2 |
| 200. | 0.04 |

TABLE 37 hNE inhibitory properties of EPI-HNE-3

| μl of EPI-HNE-2 solution added | Percent residual hNE activity |
|---|---|
| 0. | 101.2 |
| 0. | 100.0 |
| 0. | 100.0 |
| 0. | 100.0 |
| 0. | 100.0 |
| 0. | 98.8 |
| 10. | 81.6 |
| 20. | 66.9 |
| 30. | 53.4 |
| 40. | 38.0 |
| 50. | 27.6 |
| 55. | 21.5 |
| 60. | 13.0 |
| 65. | 11.0 |
| 70. | 7.9 |
| 75. | 3.8 |
| 80. | 3.3 |
| 85. | 2.1 |
| 90. | 1.8 |
| 100. | 1.6 |
| 110. | 0.8 |
| 120. | 0.7 |
| 160. | 0.6 |
| 200. | 0.2 |

TABLE 38 pH stability of Kunitz-domain hNE inhibitors

| | Percent Residual hNE Inhibitory Activity | | | |
|---|---|---|---|---|
| Incubation pH | EPI-HNE-1 | EPI-HNE-2 | EPI-HNE-3 | EPI-HNE-4 |
| 1.0 | 102 | 98 | 97 | 98 |
| 2.0 | 100 | 97 | 97 | 100 |
| 2.6 | 101 | | | |
| 3.0 | 100 | 101 | 100 | 96 |
| 4.0 | 98 | 101 | 102 | 94 |
| 5.0 | 100 | | | |
| 5.5 | | 99 | 99 | 109 |
| 6.0 | 100 | | 103 | 99 |
| 6.5 | | | 99 | 100 |
| 7.0 | 93 | 103 | 103 | 93 |
| 7.5 | | | 87 | 109 |
| 8.0 | 96 | | 84 | 83 |

TABLE 38-continued pH stability of Kunitz-domain hNE inhibitors

Percent Residual hNE Inhibitory Activity

| Incubation pH | EPI-HNE-1 | EPI-HNE-2 | EPI-HNE-3 | EPI-HNE-4 |
|---|---|---|---|---|
| 8.5 |  | 104 | 68 | 86 |
| 9.4 | 100 |  | 44 | 40 |
| 10.0 | 98 | 102 | 27 | 34 |

Proteins were incubated at 37° C. for 18 hours in buffers of defined pH (see text). In all cases protein concentrations were 1 µM. At the end of the incubation period, aliquots of the reactions were diluted and residual hNE-inhibition activity determined.

TABLE 39

Stability of hNE inhibitory proteins to oxidation by Chloramine-T

Table 620

| CHL-T: Inhibitor Molar Ratio | EPI-HNE-1 | EPI-HNE-2 | EPI-HNE-3 | EPI-HNE-4 | α1 anti trypsin | SLPI |
|---|---|---|---|---|---|---|
| 0 | 100 | 100 | 100 | 100 | 100 | 100 |
| 0.25 |  | 94 |  |  |  |  |
| 0.29 |  |  |  |  |  | 93 |
| 0.30 |  |  |  |  | 97 |  |
| .48 | 102 |  |  |  |  |  |
| .50 |  | 102 | 97 | 100 | 85 |  |
| .59 |  |  |  |  |  | 82 |
| .88 |  |  |  |  |  | 73 |
| .95 | 100 |  |  |  |  |  |
| 1.0 |  | 102 | 97 | 100 | 41 |  |
| 1.2 |  |  |  |  |  | 65 |
| 1.4 | 98 |  |  |  |  |  |
| 1.5 |  | 95 |  |  |  |  |
| 1.9 | 102 |  |  |  |  |  |
| 2.0 |  | 102 |  |  |  |  |
| 2.1 |  |  |  |  | 7 |  |
| 2.4 |  |  |  |  |  | 48 |
| 3.0 |  |  | 97 | 100 |  |  |
| 3.8 | 94 |  |  |  |  |  |
| 4.0 |  | 95 |  |  |  |  |
| 5.0 |  |  | 94 | 100 |  |  |
| 5.2 |  |  |  |  | 7 |  |
| 5.9 |  |  |  |  |  | 18 |
| 9.5 | 95 |  |  |  |  |  |
| 10. |  | 98 | 97 | 104 |  |  |
| 10.4 |  |  |  |  | >5 |  |
| 12. |  |  |  |  |  | 15 |
| 19. | 92 |  |  |  |  |  |
| 30. |  |  | 100 | 100 |  |  |
| 50. |  |  | 94 | 100 |  |  |

Inhibitors were incubated in the presence of Chloramine-T at the molar ratios indicated for 20 minutes at RT. Oxidation reactions were quenched by adding methionine to a final concentration of 4 mM. Residual hNE-inhibition activity remaining in the quenched reactions is shown as a percentage of the activity observed with no added oxidant. Proteins and concentrations in the oxidation reactions are: EPI-HNE-1, (5 µM); EPI-HNE-2, (10 µM); EPI-HNE-3, (10 µM); EPI-HNE-4, (10 µM); API, (10 µM); and SLPI, (8.5 µM).

TABLE 40

Temperature stability of EPI-HNE proteins

| Temperature (° C.) | EPI-HNE-1 | EPI-HNE-2 | EPI-HNE-3 | EPI-HNE-4 |
|---|---|---|---|---|
| 0 | 97 | 101 | 96 | 100 |
| 23 | 100 | 103 | 105 | 103 |
| 37 | 100 | 97 | 99 | 98 |
| 45 | 103 |  |  |  |
| 52 |  | 101 | 100 |  |
| 55 | 99 |  |  | 98 |
| 65 | 94 | 95 | 87 |  |
| 69 |  |  |  | 82 |
| 75 | 100 |  |  |  |
| 80 |  | 101 | 79 |  |
| 85 | 106 |  |  | 63 |
| 93 |  | 88 | 57 |  |
| 95 | 64 |  |  | 48 |

Proteins were incubated at the stated temperature for 18 hours in buffer at pH 7.0. In all cases protein concentrations were 1 µM. At the end of the incubation period, aliquots of the reactions were diluted and residual hNE-inhibition activity determined.

TABLE 41

Mutations that are likely to improve the affinity of a Kunitz domain for hNE

Most Preferred

X18F;
[X15I (preferred), X15V];
Highly Preferred

[X16A (Preferred), X16G];
[X17F (preferred), X17M, X17L, X17I, X17L];
[{X19P, X19S} (equally preferred), X19K, X19Q];
X37G;
X12G;
Preferred X13P;
X20R;
X21Y; X21W;
[X34V (preferred), X34P];
[X39Q, X39M];
[X32T, X32L];
[X31Q, X31E, X31V];
[X11T, X11A, X11R];
[X10Y, X10S, X10V];
[X40G, X40A];
X36G;

TABLE 42

M13_III signal::Human_LACI-D2::mature_M13_III
DNA has SEQ ID NO. 078, amino-acid sequence has
SEQ ID NO. 079. DNA is linear and in vivo it is
double stranded. Amino-acid sequence is of a
protein that is processed in vivo by cleavage
after Ala$_{-1}$; the entire gene encodes an
amino-acid sequence that continues to give a
functional M13 III protein.

```
 M   K   K   L   L   F
-18 -17 -16 -15 -14 -13
|atg|aaG|aaG|ctt|ctc|ttc|
   |_____|
    HindIII A   I   P   L   V   V   P   F   Y   S   G   A
-12 -11 -10 -9  -8  -7  -6  -5  -4  -3  -2  -1
|gcc|att|cct|ctg|gt|gta|cct|ttc|tat|tcc|ggc
|  BstXI    |  KpnI  |              |  KasI  |
|    XcmI        |
```

TABLE 42-continued

M13_III signal::Human_LACI-D2::mature_M13_III
DNA has SEQ ID NO. 078, amino-acid sequence has
SEQ ID NO. 079. DNA is linear and in vivo it is
double stranded. Amino-acid sequence is of a
protein that is processed in vivo by cleavage
after Ala$_{-1}$; the entire gene encodes an
amino-acid sequence that continues to give a
functional M13 III protein.

```
  K    P    D    F    C    F    L    E    E    D    P
  1    2    3    4    5    6    7    8    9   10   11
|gcc|aag|cct|gac|ttc|tgc|ttc|ctc|gag|gag|gat|ccc|
                    | XhoI  |         | XmaI  |

G    I    C    R    G    Y    I    T    R    Y    F
 12   13   14   15   16   17   18   19   20   21   22
|ggg|att|tgc|cgc|ggt|tat|att|acg|cgt|tat|ttc|
            | SacII|         | MluI  |

Y    N    N    Q    T    K    Q    C    E    R
 23   24   25   26   27   28   29   30   31   32
|tat|aat|aac|cag|act|aag|caa|tgt|gag|cgg|
                         | BsrDI| BsrI  |

F    K    Y    G    G    C    L    G    N    M
 33   34   35   36   37   38   39   40   41   42
|ttc|aag|tat|ggt|ggt|tgc|cta|ggt|aat|atg|
                              | AvrII |

N    N    F    E    T    L    E    E    C    K
 43   44   45   46   47   48   49   50   51   52
|aac|aac|ttc|gag|act|cta|gaa|gag|tgt|aag|
                    | XbaI  |

N    I    C    E    D    G    G    A
 53   54   55   56   57   58  100  101
|aac|ata|tgt|gag|gat|ggt|ggt|gct|
 | NdeI |

E    T    V    E    S
102  103  104  105  106
|gag|act|gtt|gag|tct|
 |   DrdI        |
```

Ala$_{101}$ is the first residue of mature M13 III.

TABLE 43

Synthetic laci-d1 with sites for cloning into
display vector

DNA has SEQ ID NO. 080, amino-acid sequence has
SEQ ID NO.081

```
       A    A    E    M    H    S    F    C    A    F    K    A
            1    2    3    4    5    6    7    8    9
5'-gcg|gcc|gag|atg|cat|tcc|ttc|tgc|gct|ttc|aaa|gct|
   |EagI   | NsiI  |

D    D    G    P    C    K    A    I    M    K    R
 10   11   12   13   14   15   16   17   18   19   20
|gat| |gaC|ggT|ccG|tgt|aaa|gct|atc|atg|aaa|cgt|
         | RsrII    |              | BspHI |

F    F    F    N    I    F    T    R    Q    C
 21   22   23   24   25   26   27   28   29   30
|ttc|ttc|ttc|aac|att|ttc|acG|cgt|cag|tgc|
                              | MluI  |

E    E    F    I    Y    G    G    C    E    G    N    Q
 31   32   33   34   35   36   37   38   39   40   41   42
|gag|gaA|ttC|att|tac|ggt|ggt|tgt|gaa|ggt|aac|cag|
         | EcoRI |                        | BstEII |

N    R    F    E    S    L    E    E
 43   44   45   46   47   48   49   50
|aac|cgG|ttc|gaa|tct|ctA|gag|gaa|
       | BstBI |    | XbaI  |
```

TABLE 43-continued

Synthetic laci-d1 with sites for cloning into
display vector

```
         | AgeI  |
  C    K    K    M    C    T    R    D    G    A
 51   52   53   54   55   56   57   58   59  101
|tgt|aag|aag|atg|tgc|act|cgt|gac|ggc|gcc|
                                   | KasI  |
```

Ala$_{101}$ is the first residue of mature M13 III.

TABLE 44

LACI-D1 hNE Library

DNA has SEQ ID NO. 082, amino-acid sequence has
SEQ ID NO. 083

```
       A    A    E    M    H    S    F    C    A    F    K
            1    2    3    4    5    6    7    8
5'-gcg|gcc|gag|atg|cat|tcc|ttc|tgc|gct|ttc|aaa|
   |EagI   | NsiI  |

S
           T|N                           T|N
     C|R   K|R                           I|M
     S|G   S|A                           Q|H
     Y|H   E|G            H|R       F|L  L|P
  A  D|N   D    G   P|L   C   V|I  A|G  I|V   F   K|R   R
  9   10   11   12   13   14   15   16   17   18  19   20
|gct|NRt|RVS|ggT|cNt|tgt|Rtt|gSt|Ntc|ttc|MNS|cgt|

C
  Y|W
  F|L   F    F    N    I    F    T    R    Q    C
  21   22   23   24   25   26   27   28   29   30
|tDS|ttc|ttc|aac|att|ttc|acG|cgt|cag|tgc|
                                   | MluI  |

Q                    Q                   Q
         L|P                  L|P                 L|P
         T|K                  T|K                 T|K
  L|Q    V|I            V|E            V|M             E|G
  E|V    E|A   F   I|A  Y    G    G    C   E|A  G|A    N   Q|R
  31    32   33   34   35   36   37   38   39   40   41  42
|SWG|VHA|ttC|VHA|tac|ggt|ggt|tgt|VHG|gSt|aac|SRG|

N    R    F    E    S    L    E    E
 43   44   45   46   47   48   49   50
|aac|cgG|ttc|gaa|tct|ctA|gag|gaa|
       | BstBI |    | XbaI  |
       | AgeI  |

C    K    K    M    C    T    R    D    G    A
 51   52   53   54   55   56   57   58   59  101
|tgt|aag|aag|atg|tgc|act|cgt|gac|ggc gcc|
                                   | KasI  |
```

Variegation at 10, 11, 13, 15, 16, 17, 19, and 20
gives rise to 253,400 amino-acid sequences and 589,
824 DNA sequences. Variegation at 31, 32, 34, 39,
40, and 42 gives 23,328 amino-acid and DNA
sequences. There are about $5.9 \times 10^9$ protein
sequences and $1.4 \times 10^{10}$ DNA sequences.
Ala$_{101}$ would be the first residue of mature M13 III.

TABLE 45

LACI-D2 hNE Library

DNA has SEQ ID NO. 084; amino-acid sequence has
SEQ ID NO. 085

```
                                               C|R
                                               S|G
```

TABLE 45-continued

LACI-D2 hNE Library

```
                                             Y|H
  G   A   K   P   D   F   C   F   L   E   E  D|N
 -2  -1   1   2   3   4   5   6   7   8   9  10
|ggc|gcc|aag|cct|gac|ttc|tgc|ttc|ctc|gag|gag|NRt|
|  KasI |                     | XhoI  |

P|H
 T|N                           I|N
 K|R    H|R            F|L    Q|M
 S|A    P|L            I|V    L|H      C
 E|G    N|S            Y|H    K|P     F|L
 D|Q  G I|T C V|I G|A N|D  F T|R  R Y|W  F
  11  12  13  14  15  16  17  18  19  20  21  22
|VVS|ggg|MNt|tgc|Rtt|gSt|NWt|ttt|MNS|cgt|tDS|ttc|

Q|G
                                     L|P
                                     T|K
                                     V|I
                                 L|Q E|A
  Y   N   N   Q   A   K   Q   C  E|V  R
  23  24  25  26  27  28  29  30  31  32
|tat|aat|aac|cag|Gct|aag|caa|tgt|SWg|VNA|
                    |       | BsrDI|
                    | EspI    |

Q|L                Q|P
     P|T                T|K        R|G
     V|E                V|M        K|E
     I|A                E|A        L|Q
  F   K   Y   G   G   C   L  G|A  N M|V
  33  34  35  36  37  38  39  40  41  42
|ttc|VHA|tat|ggt|ggt|tgc|VHG|gSt|aat|VBg|

N   N   F   E   T   L   E   E   C   K
  43  44  45  46  47  48  49  50  51  52
|aac|aac|ttc|gag|act|cta|gaa|gag|tgt|aag|
                      | XbaI |

N   I   C   E   D   G   G   A
  53  54  55  56  57  58 100 101
|aac|ata|tgt|gag|gat|ggt|ggt|gct|
   | NdeI |

E   T   V   E   S
 102 103 104 105 106
|gag|act|gtt|gag|tct|
   |  DrdI        |
```

$6.37 \times 10^{10}$ amino acid sequences; $1.238 \times 10^{11}$ DNA sequences

TABLE 46

| Amino acids preferred in hNE-inhibiting Kunitz domains | |
|---|---|
| Position | Allowed amino acids |
| 5 | C |
| 10 | YSV, (NA) |
| 11 | TAR, (QP) |
| 12 | G |
| 13 | P, (VALI) |
| 14 | C |
| 15 | IV |
| 16 | AG |
| 17 | FM, ILV (A) |
| 18 | F |
| 19 | PS, QK |
| 20 | R |
| 21 | YW, (F) |
| 30 | C |
| 31 | QEV, (AL) |
| 32 | TL, (PSA) |
| 33 | F |
| 34 | VP |
| 35 | Y |
| 36 | G |
| 37 | G |
| 38 | C |
| 39 | MQ |
| 40 | G, A |
| 41 | N highly preferred |
| 42 | G preferred, A allowed |
| 45 | F |
| 51 | C |
| 55 | C |

CITATIONS

ALBR83a: Albrecht et al., Hoppe-Seyler's Z Physiol Chem (1983), 364:1697–1702.
ALBR83b: Albrecht et al., Hoppe-Seyler's Z Physiol Chem (1983), 364:1703–1708.
ALTM91: Altman et al., Protein Engineering 4(5)593–600 (1991).
AUER87: Auerswald et al., Biol Chem Hoppe-Seyler (1987), 368:1413–1425.
AUER88: Auerswald et al., Bio Chem Hoppe-Seyler (1988), 369(Supplement):27–35.
AUER89: Auerswald et al., UK Patent Application GB 2,208,511 A.
AUER90: Auerswald et al., U.S. Pat. No. 4,894,436 (16 Jan. 1990).
AUSU87: Ausubel et al., Editors. Current Protocols in Molecular Biology, Greene Publishing Associates and Wiley-Interscience, Publishers: John Wiley & Sons, New York, 1987.
BERN93: Berndt et al., J Mol Biol (1993) 234 (3) p 735–50.
BRIN90: Biol Chem Hoppe-Seyler (1990) 371(Suppl)43–52. Brinkmann and Tschesche.
BRIN91: Eur J Biochem (1991) 202(1)95–99. Brinkmann et al.
CAMP82: J Clin Invest 70:845–852 (1982) Campbell et al.
CAMP88: J Cell Biol 106:667–676 (1988) Campbell et al.
CANT89: Cantor JO, and GM Turino, pp. 159–168 in Elastin and Elastase, Vol. II,

| CITATIONS | |
|---|---|
| | Editors L Robert and W Hornebeck, CRC Press, Boca Raton, Fla., 1989. |
| DIAR90: | Diarra-Mehrpour et al., Eur J Biochem (1990), 191:131–139. |
| DIGA89: | Digan et al., (1989) Bio/Technology 7:160ff. |
| ENGH89: | Enghild et al., J Biol Chem (1989), 264:15975–15981. |
| GEBH86: | Gebhard, W, and K Hochstrasser, pp. 389–401 in Barret and Salvesen (eds.) Protease Inhibitors (1986) Elsevier Science Publishers BV (Biomedical Division). |
| GEBH90: | Gebhard et al., Biol Chem Hoppe-Seyler (1990), 371, suppl 13–22. |
| GOLD86 | Am Rev Respir Dis 134:49–56 (1986) Goldstein, W, and G Doering. |
| GREG93: | Gregg et al., Bio/Technology (1993) 11:905–910. |
| HEID86 | Heidtmann, H, and J Travis, pp. 441–446 in Proteinase Inhibitors, Editors Barrett and Salvesen, Elsevier Science Publishers BV, Amsterdam, 1986. |
| HYNE90: | Hynes et al., Biochemistry (1990), 29:10018–10022. |
| KAUM86: | Kaumerer et al., Nucleic Acids Res (1986), 14:7839–7850. |
| MCEL91 | The Lancet 337:392–4 (1991) McElvaney et al. |
| MCWH89 | Biochem 28:5708–5714 (1989) McWherter et al. |
| NORR93: | Norris et al., WIPO Application 93/14123. |
| ODOM90: | Odom, L, Int J Biochem (1990), 22:925–930. |
| ROBE92: | Roberts et al., (1992) Proc Natl Acad Sci USA 89(6)2429–33. |
| SALI90 | TIBS 15:435–9 (November 1990) Salier, J-P. |
| SAMB89: | Sambrook et al., Molecular Cloning, A Laboratory Manual, Second Edition, Cold Spring Harbor Laboratory, 1989. |
| SCHA87: | Schagger, H. and G. von Jagow (1987) Analytical Biochemistry 166:368ff. |
| SCHE67: | Schecter and Berger, Biochem Biophys Res Comm (1967) 27:157–162. |
| SELL87: | Selloum et al., Biol Chem Hoppe-Seyler (1987), 368:47–55. |
| SKAR92: | Skarzynski, T, J Mol Biol (1992) 224(3)671–83. |
| SPRE94: | Sprecher et al., Proc Natl Acad Sci USA 91:3353–3357 (1994). |
| STOL90: | Stoll and Blanchard (1990) Methods in Enzymology 182:24ff. |
| SWAI88: | Swaim, MW, and SV Pizzo, Biochem J (1988), 254:171–178. |
| TRAB86: | Traboni, C, R Cortese, Nucleic Acids Res (1986), 14(15)6340. |
| TRAV88 | Am J Med 84(6A)37–42 (1988) Travis. |
| VEDV91: | Vedvick et al., J Ind Microbiol (1991) 7:197–201. |
| WAGN92: | Wagner et al., Biochem Biophys Res Comm (1992) 186:1138–1145. |

The invention claimed is:

1. A polypeptide which inhibits human neutrophil elastase, and which comprises a Kunitz domain comprising at least two modifications of the amino acid sequence of the carboxyl-proximal Kunitz domain of the human Inter-α-Trypsin-Inhibitor (ITI-D2) set forth in SEQ ID NO:25 wherein the modifications are amino acid substitutions selected from the group of substitutions consisting of:
   (a) a substitution of the residue corresponding to position 3 of SEQ ID NO:25 with Glu,
   (b) a substitution of the residue corresponding to position 15 of SEQ ID NO:25 with Ile,
   (c) a substitution of the residue corresponding to position 18 of SEQ ID NO:25 with Phe,
   (d) a substitution of the residue corresponding to position 19 of SEQ ID NO:25 with Pro, and
   (e) a substitution of the residue corresponding to position 20 of SEQ ID NO:25 with Arg.

2. The polypeptide of claim 1, which comprises the amino acid substitutions stated in each of clauses (b) through (d).

3. The polypeptide of claim 1, wherein the polypeptide comprises the amino acid sequence set forth in SEQ ID NO:27 (Epi-HNE-4).

4. The polypeptide of claim 1, wherein the polypeptide comprises the amino acid sequence set forth in SEQ ID NO:26 (Epi-HNE-3).

5. The polypeptide of claim 1 which has an affinity for human neutrophil elastase such that its $K_D$ is less than 5 pM.

6. The polypeptide of claim 1 which has an affinity for human neutrophil elastase such that its $K_D$ is less than 7 pM.

7. A method of inhibiting human neutrophil elastase which comprises contacting human neutrophil elastase with an inhibitory effective amount of a polypeptide of any one of claims 1–6.

8. A method of inhibiting harmful human neutrophil elastase activity in a subject which comprises administering to the subject an inhibitory effective amount of polypeptide of any one of claims 1–6.

9. A method of treating emphysema in a subject which comprises administering to the subject a therapeutically effective amount of a polypeptide of any one of claims 1–6.

10. A method of treating cystic fibrosis in a subject which comprises administering to the subject a therapeutically effective amount of a polypeptide of any one of claims 1–6.

* * * * *